US010837005B2

(12) United States Patent
Lee et al.

(10) Patent No.: US 10,837,005 B2
(45) Date of Patent: Nov. 17, 2020

(54) RECOMBINANT MICROORGANISM CAPABLE OF PRODUCING METHYL ANTHRANILATE AND METHOD OF PRODUCING METHYL ANTHRANILATE USING THE SAME

(71) Applicant: KOREA ADVANCED INSTITUTE OF SCIENCE AND TECHNOLOGY, Daejeon (KR)

(72) Inventors: Sang Yup Lee, Daejeon (KR); Zi Wei Luo, Daejeon (KR); Jae Sung Cho, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/792,229

(22) Filed: Feb. 15, 2020

(65) Prior Publication Data
US 2020/0270587 A1     Aug. 27, 2020

(30) Foreign Application Priority Data

Feb. 26, 2019 (KR) .................. 10-2019-0022379

(51) Int. Cl.
| | |
|---|---|
| *A23L 3/00* | (2006.01) |
| *A23L 2/56* | (2006.01) |
| *A23L 29/212* | (2016.01) |
| *A23L 29/244* | (2016.01) |
| *C12N 15/67* | (2006.01) |
| *C12N 9/10* | (2006.01) |
| *C12P 13/00* | (2006.01) |
| *C12N 15/70* | (2006.01) |
| *C12N 15/77* | (2006.01) |
| *C12N 1/20* | (2006.01) |

(52) U.S. Cl.
CPC ............. *C12N 9/1007* (2013.01); *C12N 1/20* (2013.01); *C12N 15/70* (2013.01); *C12N 15/77* (2013.01); *C12P 13/001* (2013.01)

(58) Field of Classification Search
CPC ........... A61K 8/411; A61K 8/36; C12N 15/00
See application file for complete search history.

(56) References Cited

FOREIGN PATENT DOCUMENTS

KR     1020180111680 A     10/2018

OTHER PUBLICATIONS

Blin, K., et al, "CRISPy-web: An online resource to design sgRNAs for CRISPR applications", "Synthetic and Systems Biotechnology", 2016, pp. 118-121, vol. 1, Publisher: ScienceDirect.

Cho, S.C., et al., "CRISPR/Cas9-coupled recombineering for metabolic engineering of Corynebacterium glutamicum", "Metabolic Engineering", 2017, Page(s) http://dx.doi.org/10.1016/j.ymben.2017.06.010, Publisher: Elsevier.

Datsenko, K., et al., "One-step inactivation of chromosomal genes in *Escherichia coli* K-12 using PCR products", "PNAS", 2000, pp. 6640-6645, vol. 97, No. 12.

Du, J., et al., "Metabolic engineering of *Escherichia coli* for the production of indirubin from glucose", "Journal of Biotechnology", 2018, pp. 19-28, vol. 267, Publisher: Elsevier.

Gross, B., et al., "Production of methylanthranilate by the basidiomycee *Pycnoporus cinnabarinus* (Karst.)", "Appliec Microbiology and Biotechnology", 1990, pp. 387-391, vol. 24, Publisher: Springer-Verlag.

Hernandez, V.E., et al., "Metabolic engineering for improving anthranilate synthesis from glucose in *Escherichia coli*", "Microbial Cell Factories", Apr. 2, 2009, p. doi:10.1186/1475-2859-8-19, vol. 8, No. 19, Publisher: BioMed Central.

Kim, S.Y., et al., "Metabolic Engineering of Corynebacterium glutamicum for the Production of L-Ornithine", "Biotechnology and Bioengineering", 2014, p. DOI 10.1002/bit.25440, vol. 9999, Publisher: Wiley Periodicals, Inc.

Lee, Y., et al., "Enhanced Production of Poly (3-hydroxybutyrate) by Filamentation-Suppressed Recombinant *Escherichia coli* Defined Medium", "Journal of Environmental Polymer Degradation", 1996, pp. 131-134, vol. 4, No. 2, Publisher: 1996 Plenum Publishing Corporation.

Lee, S.Y., "High cell-density culture of *Escherichia coli*", "IBTECH", Mar. 1996, pp. 98-105, vol. 14, Publisher: Elsevier.

Park, S.H., et al., "Metabolic engineering of Corynebacterium glutamicum for L-arginine production", "Nature communications", Aug. 5, 2014, p. DOI:10.1038/NCOMMS5618, Publisher Macmillan Publishers Limited.

"Registry of Standard Biological Parts, Promoters/Cagalog/Constitutive", , Page(s) http://parts.igem.org.

Song, C.W., et al., "Combining rational metabolic engineering and flux optimization strategies for efficient production of fumaric acid", "Appl Microbiol Biotechnol", Jul. 21, 2015, p. DOI 10.1007/s00253-015-6816-6, Publisher: Springer.

Yanofsky, C., et al., "Polarity and Enzyme Functions in Mutants of the First Three Genes of the Tryptophan Operon of *Escherichia Coli*", "Genetics", Dec. 1971, pp. 409-433, vol. 69, Publisher: Stanford University.

Berger, R.G., et al., "Microbial Sources of Flavour Compounds", "Bioflavour '87", 1988, pp. 415-434, Publisher: Ed. by P. Schreier.

(Continued)

Primary Examiner — Maryam Monshipouri
(74) Attorney, Agent, or Firm — Hultquist, PLLC; Steven J. Hultquist

(57) ABSTRACT

Disclosed are a recombinant microorganism capable of producing methyl anthranilate, wherein the recombinant microorganism is obtained by introducing an aamt1 gene into a microorganism having the capacity to produce anthranilic acid (ANT), and a method of producing methyl anthranilate using the same. The recombinant microorganism is capable of producing methyl anthranilate using only a purely biological process from renewable carbon-circulating biomass without chemical catalytic reaction, thus having an advantage of enabling mass production of high value-added methyl anthranilate in a very economical manner based on an environmentally friendly and simple production process.

19 Claims, 18 Drawing Sheets

Specification includes a Sequence Listing.

(56) References Cited

OTHER PUBLICATIONS

Cao, M., et al., "Building Microbial Factories for the Production of Aromatic Amino Acid Pathway Derivatives: From Commodity Chemicals to Plant-Sourced Natural Products", "Metabolic Engineering", 2019, pp. 1-127.

Lee, H.L., et al.; "Synthesis of Methylated Anthranilate Derivatives Using Engineered Strains of *Escherichia coli*", "J. Microbiol. Biotechnol.", 2019, pp. 839-844, vol. 29, No. 6.

Noda, S., et al., "Recent Advances in Microbial Production of Aromatic Chemicals and Derivatives", "Trends in Biotechnology", Aug. 2017, pp. 785-796, vol. 35, No. 8.

Rodriguez, A., et al., "Engineering *Eschericia coli* to Overproduce Aromatic Amino Acids and Derived Compounds", "Microbial Cell Factories", 2014, pp. 1-15, vol. 13, No. 126.

RECOMBINANT MICROORGANISM CAPABLE OF PRODUCING METHYL ANTHRANILATE AND METHOD OF PRODUCING METHYL ANTHRANILATE USING THE SAME

CROSS-REFERENCE TO RELATED APPLICATION

The priority under 35 USC § 119 of Korean Patent Application 10-2019-0022379 filed Feb. 26, 2019 is hereby claimed. The disclosure of Korean Patent Application 10-2019-0022379 is hereby incorporated herein by reference, in its entirety, for all purposes.

TECHNICAL FIELD

The present invention relates to a recombinant microorganism capable of producing methyl anthranilate and a method of producing methyl anthranilate using the same, and more particularly to a recombinant microorganism capable of producing methyl anthranilate, wherein the recombinant microorganism is obtained by introducing an aamt1 gene into a microorganism having the capacity to produce anthranilic acid (ANT), and a method of producing methyl anthranilate using the same.

BACKGROUND ART

Methyl anthranilate (MANT), which gives a grape scent and flavor, has been extensively used as a flavor enhancer in flavored foods (e.g., candy, chewing gum or soft drinks), cosmetics (perfume or masks), pharmaceuticals and the like. MANT is used as an important additive especially in perfumes and cosmetics owing to the pleasant aroma thereof. In addition, MANT has various industrial applications as a bird and goose repellent for crop protection, as an oxidation inhibitor or a UV radiation-blocking agent, and as an intermediate for the synthesis of a wide range of chemicals, dyes and pharmaceuticals.

MANT is a natural metabolite giving the characteristic odor of Concord grapes, and is contained in several essential oils (e.g., neroli, ylang-ylang and jasmine). However, it is economically infeasible to directly extract MANT from plants due to the low yield thereof. Currently, MANT is being commercially manufactured through petroleum-based chemical processes, which mainly rely on esterification of anthranilic acid (ANT) with methanol or isatoic anhydride with methanol, using homogeneous acids as catalysts. However, these processes have drawbacks, for example, the requirement of acid catalysts in large quantities and problems with disposal of toxic liquid acids after the reaction. Moreover, MANT produced by such chemical methods is classified as an "artificial flavor" which does not meet the increasing demand by consumers for natural flavors. Taking another important flavoring agent, vanillin, as an example, market preference for natural vanillin has led to a far higher price of $1,200-$4,000/kg, compared to $15/kg for artificial vanillin. However, it is currently difficult to supply sufficient MANT from natural substances. In order to obtain substitutes to natural MANT, biotransformation approaches using several enzymes and microbes have been attempted for MANT production by esterification of ANT or N-demethylation of N-methyl ANT. These biotransformation procedures are considered more ecofriendly than chemical synthesis, but the use thereof to date is limited due to low yields, long reaction times and formation of byproducts. In addition, the chemical and biotransformation processes mentioned above depend on petroleum-based substrates.

MANT biosynthesis based on biotransformation methods known to date is disclosed in only two reports describing the process of MANT biosynthesis in monosaccharide (maltose) using the wild fungi *Poria cocos* and *Pycnoporus cinnabarinus* nearly 30 years ago [Berger, R. G. et al., Microbial sources of flavour compounds. (Berlin, Germany; 415-434, 1988), Gross, B. et al. *Appl. Microbiol. Biotechnol.* 34, 387-391, 1990]. Unfortunately, the MANT productivity achieved in these two studies was extremely low (the concentration of MANT produced after 5 days of culture was 18.7 mg/L), and the underlying biosynthetic mechanisms including biosynthesis genes, enzymes and pathways in these two fungal species have not been elucidated. For this reason, it was not easy to improve these fungal species.

Thus, the present inventors have made efforts to establish a variety of metabolic engendering pathways leading to the biosynthesis of MANT from simple carbon sources (e.g., glucose) in order to develop mutant microorganisms capable of efficiently producing MANT based on reconstituted biosynthetic pathways and to produce 100% biologically based natural MANT in an environmentally friendly manner through fermentation of renewable raw materials (e.g. glucose). As a result, the present inventors have found that MANT can be produced easily by recombinant microorganisms expressing anthranilic acid methyltransferase (AAMT1) derived from *Zea mays*, which converts ANT to MANT, have significantly improved the production of MANT through additional metabolic and fermentation engineering approaches, and have identified that food-grade MANT suitable for human consumption can be produced by the method described above, thereby completing the present invention.

DISCLOSURE

Technical Problem

Therefore, the present invention has been made in view of the above problems, and it is an object of the present invention to produce a recombinant microorganism capable of producing high value-added methyl anthranilate through biotransformation using a simple carbon source such as glucose, and to provide a method of producing methyl anthranilate using the same.

Technical Solution

In accordance with an aspect of the present invention, the above and other objects can be accomplished by the provision of a recombinant microorganism obtained by introducing a gene encoding anthranilate O-methyltransferase into a microorganism having the capacity to produce anthranilic acid (ANT), the recombinant microorganism having the capacity to produce methyl anthranilate (MANT).

In accordance with another aspect of the present invention, there is provided a method of producing methyl anthranilate including (a) culturing the recombinant microorganism to produce methyl anthranilate and (b) recovering the methyl anthranilate.

Advantageous Effects

The recombinant microorganism according to the present invention is capable of producing methyl anthranilate using only a purely biological process from renewable carbon-circulating biomass without a chemical catalytic reaction, thus having an advantage of enabling mass-production of high value-added methyl anthranilate in a very economical manner based on an environmentally friendly and simple production process and thus being variously applicable to the food and cosmetic industries.

BRIEF DESCRIPTION OF DRAWINGS

The above and other objects, features and other advantages of the present invention will be more clearly understood from the following detailed description taken in conjunction with the accompanying drawings, in which:

FIG. 3 in part b shows strain growth (white), ANT concentration (gray) and MANT concentration (black) depending on whether pTrcAAMT is introduced into an E. coli strain (W3110 trpD9923) overproducing ANT;

DETAILED DESCRIPTION OF THE INVENTION

Figure 1:
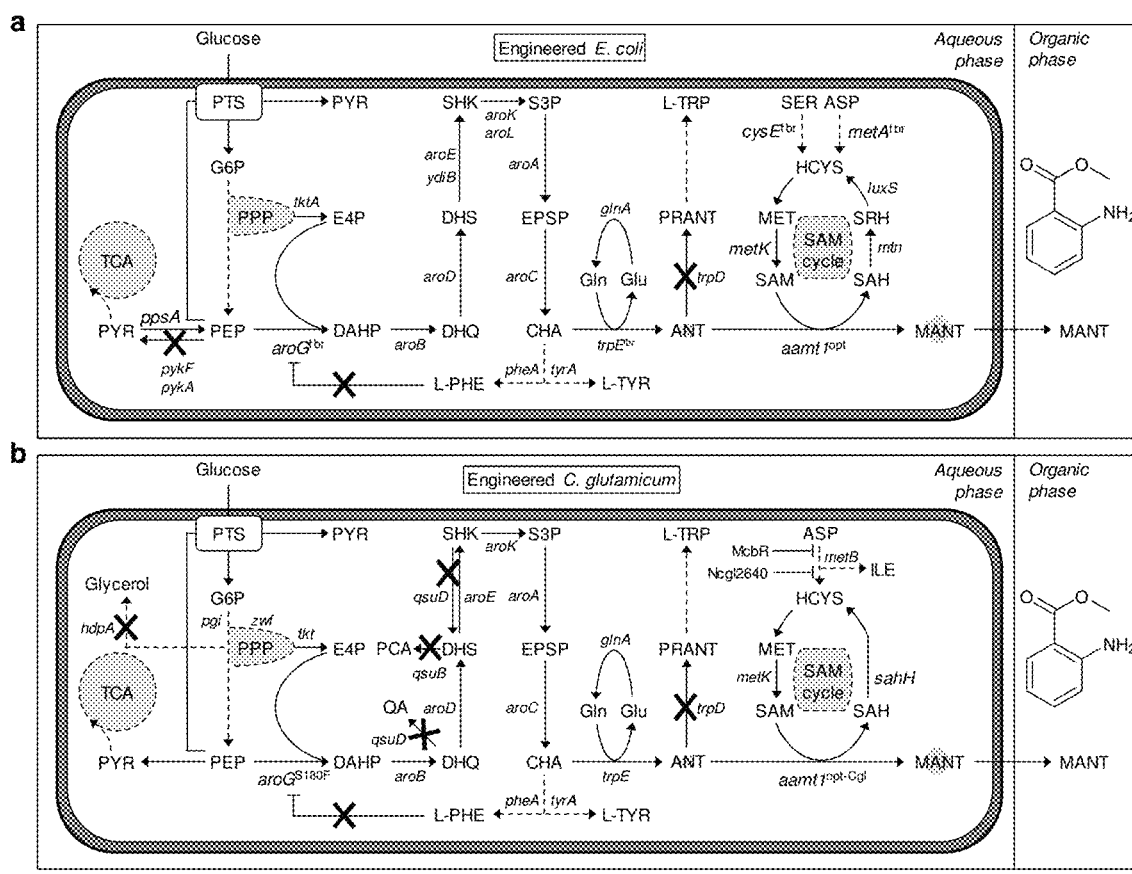
FIG. 1 is a schematic diagram illustrating E. coli (a) and C. glutamicum (b) metabolic circuits associated with MANT biosynthesis and important metabolic engineering strategies used in the present invention.

Unless defined otherwise, all technical and scientific terms used herein have the same meanings as appreciated by those skilled in the field to which the present invention pertains. In general, the nomenclature used herein is well-known in the art and is ordinarily used.

The present invention is based on the identification that a recombinant microorganism having the capacity to produce methyl anthranilate can be produced by introducing a gene encoding anthranilic acid methyltransferase into a microorganism having no capacity to produce methyl anthranilate, and that the capacity to produce methyl anthranilate can be significantly improved by introducing additional metabolic engineering methods into the pathway of producing anthranilic acid, which is a precursor of methyl anthranilate, and the pathway of conversion from anthranilic acid to methyl anthranilate.

Therefore, in one aspect, the present invention provides a recombinant microorganism obtained by introducing a gene encoding anthranilate O-methyltransferase into a microorganism having the capacity to produce anthranilic acid (ANT), the recombinant microorganism having the capacity to produce methyl anthranilate (MANT).

According to the present invention, the gene encoding anthranilate O-methyltransferase may be aamt1, aamt2 or aamt3, but is not limited thereto.

In the present invention, the aamt1 gene may be derived from corn (Zea mays), but is not limited thereto. The aamt1 gene may be represented by SEQ ID NO: 1, but is not limited thereto. That is, in the present invention, the recombinant microorganism having the capacity to produce methyl anthranilate may be prepared by introducing an aamt1 gene derived from microorganisms or organisms other than corn (Zea mays), and the aamt1 gene may be codon-optimized to be suitable for a host microorganism. For example, in an embodiment of the present invention, the recombinant microorganism is prepared using E. coli and C. glutamicum strains as the host microorganism, and the aamt1 gene may be codon-optimized to be suitable for each of E. coli and C. glutamicum strains before use and how to codon-optimize is well known in the art.

```
Sequence of Aamt1 gene derived from Zea mays
                                          <SEQ ID NO: 1>
atgccgatgagaatcgagcgtgatctccacatggccatagggaacggag aaactagctacacaaaaaattctaggattcaagagaaagctatgtttca gatgaagtcggtccttgaggaggccactagagcagtatgcacaactctc ctcccacaaaccatggttgtggccgacttaggctgctcatcagggccta acacactgcgcttcgtcactgaggtgactagaatcatagctcaccattg caagctggagcacaaccgacgacatgaccacctgccgcagcttcagttc tttctgaatgacctgcctggtaacgacttcaacaatctcttccagctca tcgagcagttcaataagtcatcgacgacacaagggagatgcagcaac tgaggcactacagcctccttgctatatctccggattgccgggctcctac tacactaggatcttccctagcgaaagcgttcatcttttccactctctgt
```

-continued
```
tctgccttcagtggcgctctcaggcaccagagcaactgaagggcaccca aaaatcatgcctagatatctacatcacaaagactatgtcaccatcgatg gtgaagttgtttcaacagcagtttcagaaggacttctccctcttcctca ggctacgctatgaggaactcgtgtctggtggccaaatggttctaacatt tattggaaggaagcatgaggatgtgttcactggagagtccaaccatctt tacggattgcttgcgcagtcactgaaatccctagttgatgagggtcttg tggagaaagaaaaacttgagtcattctatcttccgatctactcaccgtc ggttggtgaagtggaggcgatagtgaagcaacttgggttgttcaacatg aatcatgttaaagtatttgagataaattgggatccctacgatgactcag aaggtgatgatgtgcataacagtattgagagtggtgaaaatgttgctaa gtgcctacgcgcagttatggagccgctggtcgcaagccaatttggagaa cgcatactcgacgagttattcaaagagtacgctcgccgtgttgccaaac accttgagaatgagaaaaccaagcatgctgttcttgtcctatccatcga gaaagcaataattcatgtgtga
```

In the present invention, anthranilic acid methyltransferase gene such as aamt1 gene may be introduced along with a promoter selected from the group consisting of lac, lacUV5, trc, tac, trp, araBAD, T3, T5, T7, L10, I16, H30, H36, sod, tuf, eftu, Pm and Ptet, but is not limited thereto.

In the present invention, the capacity to produce anthranilic acid may be inherent in the microorganism, or may be introduced from an external origin, but is not limited thereto. Anthranilic acid, which is a precursor of methyl anthranilate, maybe added from an external source to a culture medium during culture of the recombinant microorganism, which can be used for the production of methyl anthranilate.

In the present invention, the microorganism having the capacity to produce anthranilic acid is selected from the group consisting of bacteria, archaea, yeast, fungi, protozoa (such as mastigophora, amoebozoa, choanoflagellate, rhizaria and chromalveolata) and microalgae, and is preferably selected from the group consisting of *Escherichia coli*, *Corynebacterium* sp., *Bacillus* sp., *Lactobacillus* sp., *Lactococcus* sp., *Pseudomonas* sp., *Anacystis* sp., *Anabena* sp., *Chlorobium* sp., *Chloroflexus* sp., *Clostridium* sp., *Methanobacterium*, *Propionibacterium* sp., *Rhodopsuedomonas* sp., *Rhodobacter* sp., *Rhodovulum* sp., *Streptococcus* sp., *Saccharomyces* sp., and *Aspergillus* sp., and is more preferably selected from the group consisting of *Escherichia coli*, *Corynebacterium glutamicum*, *Bacillus subtilis*, *Lactobacillus brevis*, *Lactobacillus casei*, *Lactobacillus reuteri*, *Lactococcus lactis*, *Aspergillus niger*, *Saccharomyces cerevisiae* and *Saccharomyces pombe*, but is not limited thereto.

In the present invention, the recombinant microorganism may be characterized in that SAM recycling capacity is further enhanced.

In the present invention, the recombinant microorganism introduced with the aamt1 gene may further include at least one of the following additional mutations:

The recombinant microorganism may be characterized in that at least one gene selected from the group consisting of trpD, pykA and pykF is deleted or inhibited.

The recombinant microorganism may be characterized in that at least one feedback resistance gene selected from the group consisting of aroG$^{fbr}$, MetA$^{fbr}$, cysE$^{fbr}$ and trpE$^{fbr}$ is introduced or amplified. The aroG$^{fbr}$ gene may be aroG$^{D146N}$ or aroG$^{S180F}$, but is not limited thereto.

The recombinant microorganism may be characterized in that at least one gene selected from the group consisting of ppsA, aroL, tktA, metK, mtn and luxS is introduced or amplified.

In the present invention, the recombinant microorganism may be characterized in that aamt1, aroG$^{fbr}$, metA$^{fbr}$, cysE$^{fbr}$ and ppsA genes are introduced or amplified, and trpD and pykF genes are deleted or inhibited, but is not limited thereto. The recombinant microorganism may be characterized in that a tktA and/or metK gene is further introduced or amplified, but is not limited thereto. The recombinant microorganism may be *Escherichia coli* (*E. coli*), but is not limited thereto.

In one embodiment of the present invention, the host microorganism for producing the recombinant microorganism is *Escherichia coli*, for example, a mutant strain W3110 trpD9923 already having suppressed trpD activity. For W3110 trpD9923, the 8$^{th}$ codon of trpD is mutated from GAA to TAA, the stop codon (Balderas-Hernáandez, V. E. et al. *Microb. Cell Fact.* 8, 19, 2009).

In one embodiment of the present invention, the recombinant microorganism may be a recombinant microorganism in which the aamt1 gene is introduced into the W3110 trpD9923 strain, and the aamt1 gene may be codon-optimized (aamt1$^{opt}$) to be suitable for *Escherichia coli*. The aamt1 (or aamt1$^{opt}$) gene can be introduced along with a Trc promoter or a Tac promoter so that expression can be regulated by the promoter.

In the present invention, an aroG$^{fbr}$ gene may be further introduced into the recombinant microorganism in which the aamt1 (aamt1$^{opt}$) gene is introduced into the W3110 trpD9923 strain. In this case, the aroG$^{fbr}$ gene can be regulated by various intensities of promoters, and is preferably introduced along with a lac promoter. A tktA gene may be further introduced into the recombinant microorganism or amplified, and the tktA gene may be introduced into the recombinant microorganism as one vector together with the aroG$^{fbr}$ gene, but is not limited thereto.

In another embodiment of the present invention, the W3110 trpD9923 strain may be produced and used as a ZW4 strain in which a promoter of an intrinsic ppsA gene is substituted with a Trc promoter and a pykE gene is deleted. In the ZW4 strain, the aroL gene and the trpE$^{fbr}$ gene may be overexpressed in the presence of the Tac promoter so that the production of the precursor metabolite anthranilic acid can be maximized.

In another embodiment of the present invention, the aamt1 (or aamt1$^{opt}$) gene is introduced into the ZW4 strain, and the aroG$^{fbr}$ gene is further introduced into the ZW4 strain, and/or the tktA gene is further introduced or amplified, so that the production of methyl anthranilate can be improved.

In another embodiment of the present invention, the aamt1 (or aamt1$^{opt}$) gene is introduced into the ZW4 strain, and the aroG$^{fbr}$, metA$^{fbr}$, and cysE$^{fbr}$ gene is further introduced into the ZW4 strain, and/or the tktA gene is further introduced or amplified, so that the production of methyl anthranilate can be improved.

In another embodiment of the present invention, the aamt1 (or aamt1$^{opt}$) gene is introduced into the ZW4 strain, and the aroG$^{fbr}$ gene is further introduced into the ZW4 strain, and/or the tktA gene and metK gene are further introduced or amplified, so that the production of methyl anthranilate can be improved.

In the present invention, the recombinant microorganism introduced with the aamt1 gene may further include at least one of the following additional mutations:

The recombinant microorganism may be characterized in that at least one gene selected from the group consisting of trpD, qsuB, qsuD and hdpA is deleted or inhibited.

The recombinant microorganism may be characterized in that at least one gene selected from the group consisting of aroK, aroB, tkt, metK, aroG and sahH is introduced or amplified. The aroG gene may be aroG$^{fbr}$ having feedback resistance, for example, aroG$^{D146N}$ or aroG$^{S180F}$, but is not limited thereto.

The recombinant microorganism may be characterized in that an aamt1 gene is introduced or amplified and trpD, qsuB, qsuD and hdpA genes are deleted or inhibited, but is not limited thereto. The recombinant microorganism may be *Corynebacterium glutamicum* (*C. glutamicum*), but is not limited thereto.

In one embodiment of the present invention, the host microorganism for producing the recombinant microorganism may be *Corynebacterium glutamicum* (*C. glutamicum*), for example, *C. glutamicum* ATCC 13032.

In one embodiment of the present invention, the recombinant microorganism for producing methyl anthranilate may be a recombinant microorganism in which the aamt1 gene is introduced into the *C. glutamicum* ATCC 13032 strain, and the aamt1 gene may be codon-optimized (aamt1$^{opt}$), preferably codon-optimized to be suitable for *C. glutamicum* (aamt1$^{opt-cgl}$). The aamt1 (or aamt1$^{opt}$, aamt1$^{opt-cgl}$) gene may be introduced with a Tac or H36 promoter so that expression can be regulated by the promoter.

In another embodiment of the present invention, the aamt1 (or aamt1$^{opt}$, aamt1$^{opt-cgl}$) gene is introduced into a YTM1 strain, which is a *C. glutamicum* ATCC 13032 strain from which a trpD gene has been deleted, or a YTM2 strain, which is a *C. glutamicum* ATCC 13032 strain from which all of trpD, qsuB and qsuD genes have been deleted, so that the production of methyl anthranilate can be improved.

In another embodiment of the present invention, in addition to the aamt1 (or aamt1$^{opt}$, aamt1$^{opt-cgl}$) gene, an aroG$^{S180F}$ gene is further introduced into the YTM2 strain, so that the production of methyl anthranilate can be improved.

In another embodiment of the present invention, in addition to the aamt1 (or aamt1$^{opt}$, aamt1$^{opt-cgl}$) gene and the aroG$^{S180F}$ gene, a metK gene is further introduced into the YTM2 strain or amplified, so that the production of methyl anthranilate can be improved.

In another embodiment of the present invention, in addition to the aamt1 (or aamt1$^{opt}$, aamt1$^{opt-cgl}$) gene and the aroG$^{S180F}$ gene, a sahH gene is further introduced into the YTM2 strain or amplified, so that the production of methyl anthranilate can be improved.

In another embodiment of the present invention, in addition to the aamt1 (or aamt1$^{opt}$, aamt1$^{opt-cgl}$) gene and the aroG$^{S180F}$ gene, a sahH gene is further introduced into the YTM2 strain or amplified, and a hdpA gene is further deleted or inhibited, so that the production of methyl anthranilate can be improved.

In various embodiments of the present invention, the start codon of some genes is modified from ATG to GTG so that the production of methyl anthranilate can be improved.

Meanwhile, in the present invention, when the recombinant microorganism is cultured, methyl anthranilate can be produced. In this case, by using a medium containing both an aqueous phase and an organic phase, the recombinant microorganism can be protected from the cytotoxicity of the produced methyl anthranilate, and thus production of methyl anthranilate can be increased. The effects of improving productivity through the addition of methionine and of removing a byproduct (succinic acid) due to increase in the amount of dissolved oxygen can be further identified.

Therefore, in another aspect, the present invention provides a method of producing methyl anthranilate comprising (a) culturing the recombinant microorganism to produce methyl anthranilate and (b) recovering the methyl anthranilate.

In the present invention, the culture is a culture in two phases, namely an aqueous phase and an organic phase, wherein the organic phase (i) is biocompatible and thus does not inhibit microbial cell growth, (2) is non-bioavailable and thus is not available for catabolism by microbial cells, and (3) may be any organic phase with high MANT solubility without limitation and preferably includes an organic substance such as tributyrin, silicon oil or 2-undecanone, but is not limited thereto.

In the present invention, the recombinant microorganism may be cultured in a medium supplemented with methionine.

In the present invention, the recombinant microorganism may be cultured while maintaining the amount of dissolved oxygen in the culture solution in the range from 40 to 60% in step (a).

In the present invention, the recombinant microorganism may be cultured in a medium supplemented with anthranilic acid in step (a)

In the present invention, "a gene is introduced or amplified" includes that, not only it is artificially expressed in the host microorganism to provide the activity of the enzyme or protein when an enzyme or protein produced by the gene is not present in a host microorganism, but also an enzyme or protein produced by the gene is modified in order for the enzyme or protein to have enhanced activity compared to the intrinsic activity thereof.

In the present invention, "modified to have enhanced activity compared to intrinsic activity" means a state in which the activity of the microorganism after manipulation is increased compared to the activity of the microorganism before the manipulation, such as the introduction of genes exhibiting activity or an increased number of copies of the corresponding gene (for example, expression using a plasmid introduced with the gene), and deletion of the inhibitory regulatory factors of the gene expression or modification of expression regulation sequences, for example, the use of enhanced promoters.

In the present invention, "enhancement in enzymatic activity" includes not only having effects beyond original functions through new introduction of activity of enzymes or amplification thereof, but also increased enzymatic activity based on an increase in endogenous gene activity, amplification of endogenous genes due to internal or external factors, deletion of inhibitory regulatory factors of the gene expression, an increase in the number of copies of genes, introduction of genes from external sources, modification of expression regulation sequences, in particular, promoter replacement or modification, and increased enzymatic activity due to gene mutations.

In the present invention "a gene is deleted or inhibited" includes not only removal of an enzyme or protein produced by the gene from a host microorganism, but also modification of the enzyme or protein produced by the gene such that the activity of the enzyme or protein is attenuated compared to the intrinsic activity thereof.

In the present invention, "modified to have attenuated activity compared to intrinsic activity" means a state in which the activity of the microorganism after the manipulation is decreased compared to the activity of the microorganism before the manipulation, such as deletion or inactivation of genes exhibiting activity (for example, substitution with mutant genes), attenuated gene expression (e.g., substitution with weak promoters, introduction of siRNA, gRNA, sRNA and the like, replacement of start codon from ATG to GTG), and inhibition of activity of the enzyme expressed by the gene (for example, addition of non-competitive or competitive inhibitors).

As used herein, the term "intrinsic activity" refers to the activity of an enzyme or the like that a microorganism innately has in an unmodified state, the term "modified to have enhanced activity compared to the intrinsic activity" means that an activity is newly introduced or improved compared to the enzyme activity before modification, and the term "modified to have attenuated activity compared to intrinsic activity" means that the present activity is lost or reduced compared to the enzyme activity before modification.

In the present invention, the term "deletion" encompasses cases in which a gene is not expressed through a method of mutation, replacement or deletion of a part or the entirety of the base of the gene and in which the enzymatic activity thereof is not expressed even though the gene is expressed, and includes all operations for blocking biosynthetic pathways that the enzyme of the corresponding gene mediates.

In the present invention, the term "overexpression" refers to expression at a level higher than the level at which the corresponding gene in the cell is expressed in a normal state, and includes increases in expression levels by replacing promoters of genes present on the genome with stronger promoters or cloning the corresponding gene into the expression vector to transform cells therewith.

As used herein, the term "vector" means a DNA product containing a base sequence of a polynucleotide encoding a target protein operably linked to a suitable control sequence so as to express the target protein in a suitable host. The control sequence includes a promoter capable of initiating transcription, any operator sequence for controlling such transcription, a sequence encoding a suitable mRNA ribosomal binding site, and a sequence for controlling termination of transcription and translation. After the vector is transformed into a suitable host cell, it may be replicated or perform functions independent of the host genome, and may be integrated with the genome.

The vector that can be used in the present invention may be at least one selected from the group consisting of pTac15K, pBBR1MCS, pEKEx1 and pCES208, but is not limited thereto.

Hereinafter, the present invention will be described in more detail with reference to examples. However, it will be obvious to those skilled in the art that these examples are provided only for illustration of the present invention and should not be construed as limiting the scope of the present invention.

In particular, it will be obvious to those skilled in the art that *E. coli* and *Corynebacterium glutamicum* are used as host microorganisms in the following examples, but other bacteria, yeasts and fungi may also be used. In addition, in the following examples, it will be apparent to those skilled in the art that genes to be introduced are exemplified only by genes derived from specific strains, but there are no limitations on the strains derived as long as they are introduced into host cells and exhibit the same activity. In addition, it will be understood that variations in the nucleotide sequence that can be translated into the same amino acid used in the following examples may be easily substituted by those skilled in the art, and therefore fall within the scope of the present invention.

Figure 3:
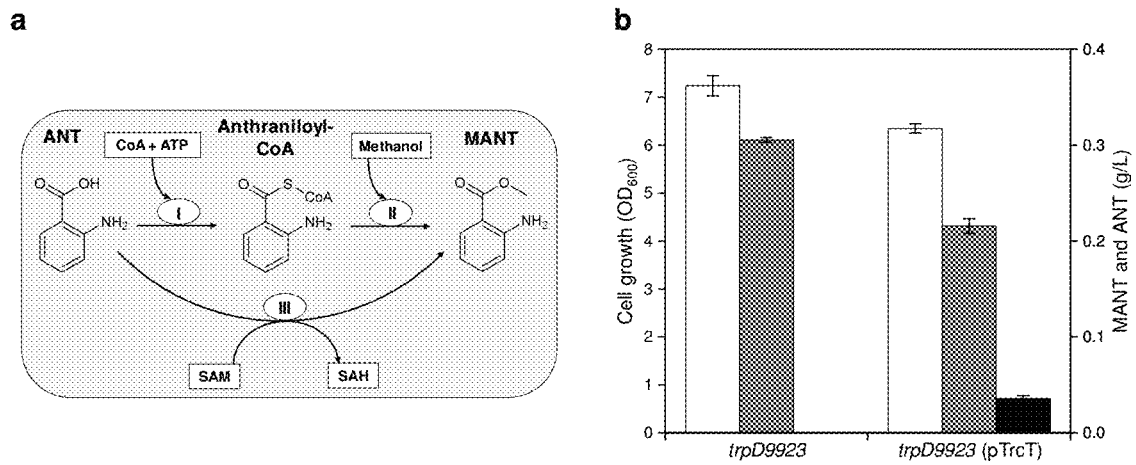
FIG. 3 in part a shows two biosynthetic pathways from ANT to MANT, wherein the first pathway is a two-step conversion from ANT to MANT via anthraniloyl-CoA catalyzed by an anthraniloyl-CoA-linking enzyme (a) and anthraniloyl-CoA:methanol acyltransferase (b), and CoA, ATP and methanol are involved in this conversion process, and the second pathway is a single-step conversion from ANT to MANT catalyzed by SAM-dependent methyltransferase for co-converting SAM to SAH.

Example 1 Construction of MANT Biosynthesis Pathway 1-1. Selection of Metabolic Circuit from ANT to MANT Research commenced based on mechanisms of MANT biosynthesis in plants due to the lack of sufficient research on MANT metabolism in *E. coli* and *C. glutamicum* strains used in the present invention. Two different enzymes, anthraniloyl-CoA:methanol acyltransferase and SAM-dependent methyltransferase, are reported to mediate biosynthesis of MANT from anthranilate in plants (FIG. 3 in part a). Both routes share the same precursor metabolite ANT, which is derived from the L-tryptophan (L-TRP) biosynthesis pathway in plants. The present invention focuses on selection of SAM-dependent methyltransferase encoded by aamt1 rather than anthraniloyl-CoA:methanol acyltransferase in designing metabolic pathways for MANT biosynthesis for the following reasons. First, anthraniloyl-CoA: methanol acyltransferase requires two steps (CoA activation and acyl transfer) for production of MANT from anthranilate, while the SAM-dependent methyltransferase route requires only single-step conversion from ANT to MANT. Second, in order to form MANT by transferring a methyl group to ANT for anthraniloyl-CoA:methanol acyltransferase-based MANT production, methanol is required as a co-substrate. However, because *E. coli* is not capable of naturally producing methanol, methanol supplementation from an external source is required, complicating the entire microorganism production system. Therefore, the present invention focuses on research on the latter route because it does not require methanol which is toxic. The SAM-dependent anthranilic acid methyltransferase used for MANT biosynthesis was anthranilic acid methyltransferase) (AAMT1, aamt1) derived from maize (*Zea mays*).

1-2. Vector Production for Construction of Metabolic Circuit from ANT to MANT and MANT Biosynthesis Verification MANT is the carboxymethyl ester of anthranilate, which is an intermediate in the L-tryptophan production metabolic pathway. In *E. coli* and many other organisms, the carbon flow of anthranilate biosynthesis may be derived from polymerization of D-erythrose 4-phosphate (E4P) and phosphoenolpyruvate (PEP) to produce 3-deoxy-D-arabino-heptulosonic acid 7-phosphate (DAHP) (FIG. 1). Six additional reactions result in the synthesis of chorismate, leading to the beginning of biosynthetic pathways for L-tryptophan, L-tyrosine and L-phenylalanine production. In *E. coli*, the trpD gene has additional activity due to being fused with the trpG gene encoding anthranilate phosphoribosyltransferase. Thus, inactivation of trpD is key to blocking the carbon flow from anthranilate to phosphoribosyl anthranilate (PRANT) for the preferential use of anthranilate for MANT production. Initial research on the polarity of an L-tryptophan operon in *E. coli* has identified mutants that secrete anthranilate and has shown that one of those mutant strains (W3110 trpD9923), obtained through UV mutagenesis, includes a trpD gene mutation. This strain was used in the present invention.

The vector pTrcT capable of expressing a MANT biosynthesis gene was produced in *E. coli* strain W3110 trpD9923 (Yanofsky et al., *Genet.* 69, 409-433, 1971) overproducing ANT through the following process. The gene aamt1 was codon-optimized in *E. coli*, designated as aamt1$^{opt}$ (SEQ ID NO: 1), and synthesized at GenScript (New Jersey, USA). The aamt1$^{opt}$ was amplified using primers of SEQ ID NO: 2 and SEQ ID NO: 3 and inserted into the vector pTrc99A cleaved with ecoRI and PstI to construct the vector pTrcT. ANT and MANT production was identified through shake flask culture using glucose as a single carbon source in MR medium (6.67 g/L of $KH_2PO_4$, 4 g/L of $(NH_4)_2HPO_4$, 0.8 g/L of $MgSO_4 \cdot 7H_2O$, 0.8 g/L of citric acid, and 5 mL of a trace metal solution (Lee et al., *J. Environ. Polym. Degrad.* 4, 131-134, 1996)).

The flask culture conditions are as follows: *E. coli* strains were inoculated into 5 mL of LB medium (10 g/L of tryptone, 5 g/L of yeast extract, 10 g/L of NaCl) from −80° C. glycerol stock and incubated at 37° C. and 200 rpm for 12 hours. After 12 hours, 1 mL of the strain incubated in LB medium was inoculated into 50 mL of MR medium (supplemented with 20 mg/L of L-tryptophan and 10 mg/L of thiamine) in a 300 mL baffle flask and cultured at 37° C. and 200 rpm. Six hours after inoculation, when $OD_{600}$ reached 0.6 to 0.8, 1 mM of IPTG was added. Flask culture was performed for 60 hours after strain inoculation.

The W3110 trpD9923 strain having pTrcT successfully produced 35.8±3.0 mg/L of MANT and 215.5±7.5 mg/L of ANT (FIG. 3 in part b). On the other hand, a base strain introduced with an empty vector did not produce MANT at all.

TABLE 1

| SEQ ID NO | Base sequence |
|---|---|
| SEQ ID NO: 2 | 5′-AGACAGGAATTCATGCCGATGCGTATTGAG-3′ |
| SEQ ID NO: 3 | 5′-AGACAGCTGCAGTCACACATGGATAATCGC-3′ |

Example 2 MANT Toxicity Test on *E. Coli* and Two-Phase Extraction Flask Culture 2-1. Test of MANT Toxicity on *E. Coli*

Figure 4:
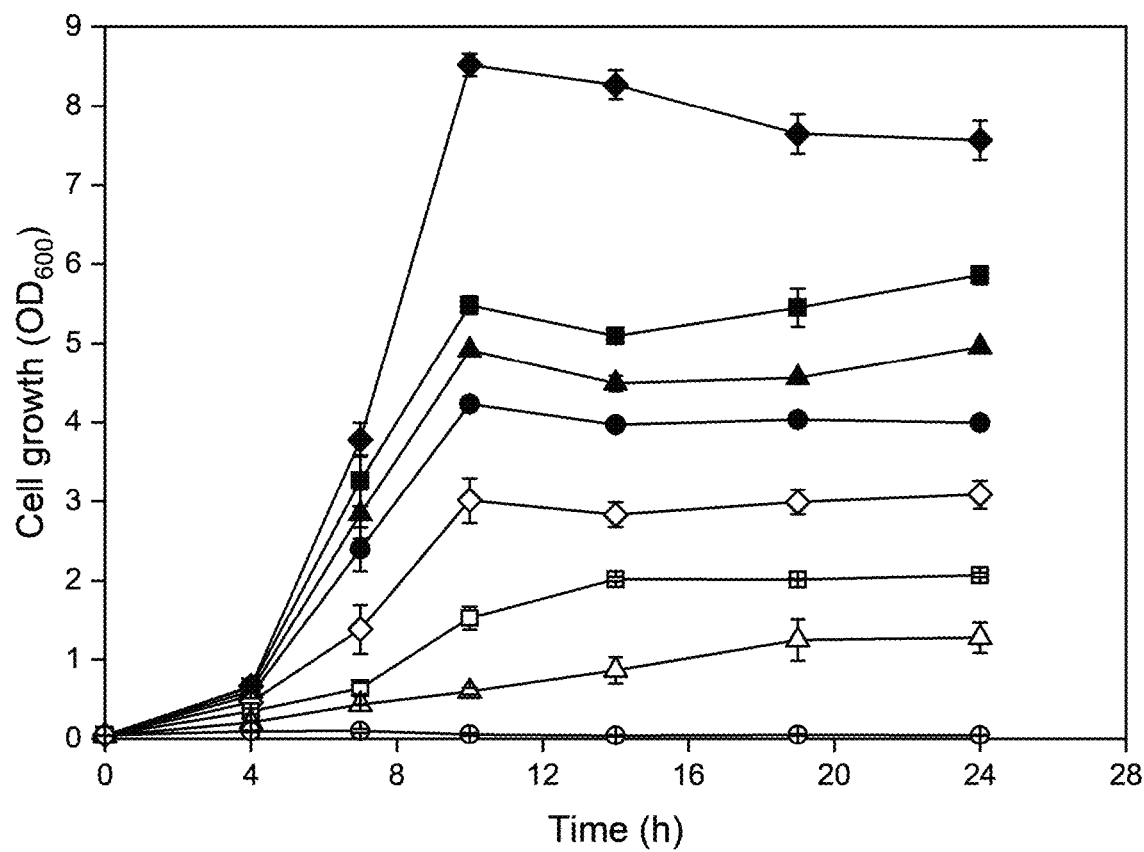
FIG. 4 shows the resistance of E. coli to various concentrations of MANT (black diamond, 0 g/L; black square, 0.1 g/L; black triangle, 0.2 g/L; black circle, 0.3 g/L; white diamond, 0.5 g/L; white square, 0.7 g/L; white triangle, 0.8 g/L; white circle, 1.0 g/L)

Prior to further manipulation for MANT production in ANT-producing strains, a MANT toxicity test was first conducted on *E. coli*. MANT has low solubility in water (2.85 g/L at 25° C.) and an octanol/water partition coefficient (log Kow) of 1.88. It is known that, as the polarity in *E. coli* increases, the octanol/water partition coefficient decreases and the toxicity of the solvent increases. Thus, MANT was expected to be toxic to *E. coli*. As a result of exposing *E. coli* to various concentrations of MANT up to 1 g/L, the final $OD_{600}$ value was significantly reduced. The MANT toxicity test on *E. coli* showed that *E. coli* can withstand MANT up to 0.5 g/L. The final $OD_{600}$ value when exposed to 0.5 g/L of MANT was found to be about one third of that of the base strain not exposed to MANT (FIG. 4). The low resistance of *E. coli* to MANT could adversely affect *E. coli* mutations that produce MANT at high concentrations. Thus, *E. coli* was cultured in a modified culture system.

2-2. Two-Phase Extraction Flask Culture of *E. Coli*

Figure 5:
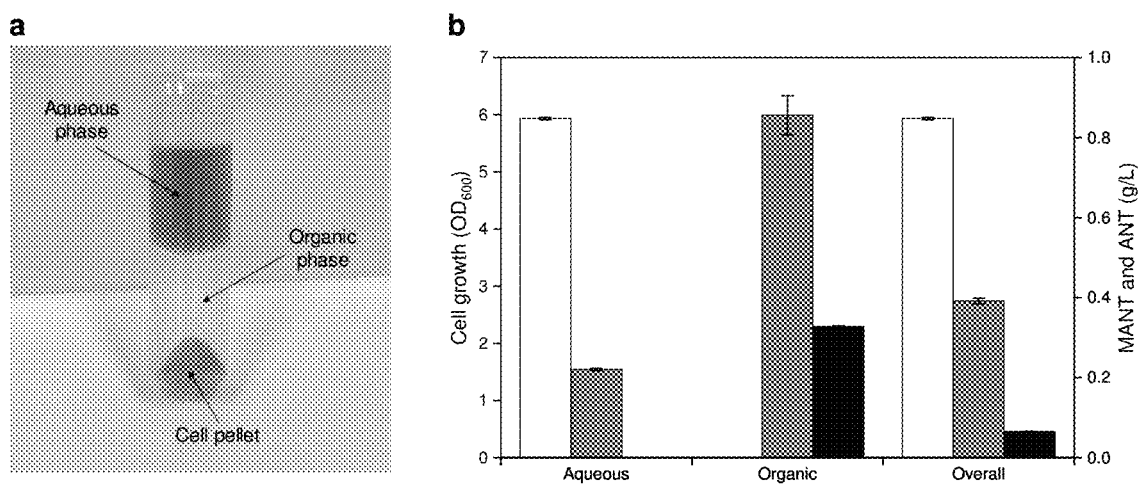
FIG. 5 shows (a) two-phase culture medium containing tributyrin as an organic solvent and cells and (b) strain growth (white), ANT concentration (gray) and MANT concentration (black) in aqueous, organic and the overall phase during two-phase flask culture.

In order to solve the problem of toxicity of MANT, a two-phase aqueous organic culture system was used in the present invention (FIG. 5 in part a). Tributyrin was used as an organic solvent to extract MANT from the culture medium. Tributyrin extraction capacity was determined by measuring the partition coefficient between the aqueous medium of MANT and tributyrin, the solvent, and the result is shown in Table 2. Tributyrin is also capable of extracting ANT, but the amount of ANT extracted is very small compared to the amount of MANT and thus is negligible. As a result of using a two-phase flask culture at a ratio of the aqueous phase to the organic phase of 5:1, it was found that MANT production increased to 65.6±0.4 mg/L, which is an increase of 83.2% compared to the single-phase flask culture (FIG. 5 in part b). The culture was carried out under the same conditions as in Example 1-2, except that, when IPTG was added, 10 mL of tributyrin was added therewith. MANT productivity was calculated on an aqueous phase basis (that is, Titer=$C_{aq} \cdot V_{aq} + C_{org} \cdot V_{org})/V_{aq}$)).

TABLE 2

Partition coefficient of MANT and ANT between aqueous-phase culture medium and organic-phase tributyrin

| Substance | Aqueous phase state | Partition coefficient |
|---|---|---|
| MANT | Carbon-free MR minimum medium, pH 7.0 | 420.1 ± 7.6 |
| Anthranilate | Carbon-free MR minimum medium, pH 5.0 | 4.7 ± 0.2 |
| Anthranilate | Carbon-free MR minimum medium, pH 7.0 | 0.1 ± 0.0 |
| Anthranilate | Carbon-free MR minimum medium, pH 9.0 | Very low |

Example 3 Optimization of AAMT1 Expression Level to Improve MANT Production in E. Coli The MANT production pathway was constructed in *E. coli* and optimization of the expression level of AAMT1 was attempted in order to enhance MANT production. In order to obtain AAMT1 at various levels of expression, the aamt1 gene expressing AAMT1 was introduced into two different expression vectors, pTac15K-derived vector (low copy number) and pTrc99A-derived vector (medium copy number). The two vectors each have a series of synthetic promoters with varying transcription intensities (see Table 3, BBa_J23177, BBa_J23114, BBa_J23105, BBa_J23118, BBa_J23101, BBa_J23100).

TABLE 3

Sequences and relative intensities of synthetic promoters

| Name | Relative intensity | Sequence (5'-3') |
|---|---|---|
| BBa_J23100 | 1 | TTGACGGCTAGCTCAGTCCTAGGTACAGTGCTAGC |
| BBa_J23101 | 0.70 | TTTACAGCTAGCTCAGTCCTAGGTATTATGCTAGC |
| BBa_J23118 | 0.56 | TTGACGGCTAGCTCAGTCCTAGGTATTGTGCTAGC |
| BBa_J23105 | 0.24 | TTTACGGCTAGCTCAGTCCTAGGTACTATGCTAGC |
| BBa_J23114 | 0.10 | TTTATGGCTAGCTCAGTCCTAGGTACAATGCTAGC |
| BBa_J23117 | 0.06 | TTGACAGCTAGCTCAGTCCTAGGGATTGTGCTAGC |

The gene aamt1$^{opt}$ was amplified with SEQ ID NO: 4 and SEQ ID NO: 5 and inserted into pSynPPC1, pSynPPC2, pSynPPC3, pSynPPC4, pSynPPC5, pSynPPC6, pSynPPC13, pSynPPC14, pSynPPC15, pSynPPC16, pSynPPC17, and pSynPPC18 (Song & Lee, Appl. Microbiol. Biotechnol. 99, 8455-8464, 2015), and the amplification products and the vectors were cleaved with EcoRI and SacI and the cleaved amplification product was inserted at positions cleaved with EcoRI and SacI by Gibson assembly to finally produce pSynT1, pSynT2, pSynT3, pSynT4, pSynT5, pSynT6, pSynT7, pSynT8, pSynT9, pSynT10, pSynT11, and pSynT12. Specifically, pSynT1 to pSynT6 were obtained by introducing six intensities of promoters (sequentially, BBa_J23117, BBa_J23114, BBa_J23105, BBa_J23118, BBa_J23101, and BBa_J23100) into the medium-copy pTrc99A vector, and pSynT7 to pSynT12 were obtained by introducing six intensities of promoters (sequentially, BBa_J23117, BBa_J23114, BBa_J23105, BBa_J23118, BBa_J23101, and BBa_J23100) into the low-copy pTac15K vector.

Further, pTac15K-derived vectors, pTacT and pT5T, having tac and T5 promoters, respectively, were constructed. In the case of the vector pTacT, the aamt1$^{opt}$ gene was amplified with SEQ ID NO: 2 and SEQ ID NO: 3 and inserted into pTac15K cleaved with restriction enzymes EcoRI and PstI to finally produce pTacT. In the case of vector pT5T, the aamt1$^{opt}$ gene was amplified with SEQ ID NO: 6 and SEQ ID NO: 7, was assembled to the vector pQE-30 (Qiagen, USA) amplified with SEQ ID NO:8 and SEQ ID NO: 9 by Gibson-assembly to produce the vector pQE-aamt1$^{opt}$, and T5-aamt1$^{opt}$ was amplified from pQE-aamt1$^{opt}$ with SEQ ID NO: 10 and SEQ ID NO: 11 and inserted into pTac15K cleaved with restriction enzyme NheI to finally produce pT5T.

TABLE 4

| SEQ ID NO: | Base sequence |
|---|---|
| SEQ ID NO: 4 | 5' AGACAGGAATTCTCACACAGGAAACAGACCATGCCGATGCGTATTGAG-3' |
| SEQ ID NO: 5 | 5' AGACAGGAGCTCTCACACATGGATAATCGC-3' |
| SEQ ID NO: 6 | 5' TTAAAGAGGAGAAATTAACTATGCCGATGCGTATTGAGCG-3' |
| SEQ ID NO: 7 | 5' CTATCAACAGGAGTCCAAGCTCACACATGGATAATCGCCT-3' |
| SEQ ID NO: 8 | 5' AGGCGATTATCCATGTGTGAGCTTGGACTCCTGTTGATAG-3' |
| SEQ ID NO: 9 | 5' CGCTCAATACGCATCGGCATAGTTAATTTCTCCTCTTTAA-3' |
| SEQ ID NO: 10 | 5' GTGCCAACATAGTAAGCCAGTATACACTCCGTCATAAAAAATTTATTTGC-3' |
| SEQ ID NO: 11 | 5' TGGCCGGGGGACTGTTGGGCGCCATCTCCTTGATTCTCACCAATAAAAAACG-3' |

Figure 6:
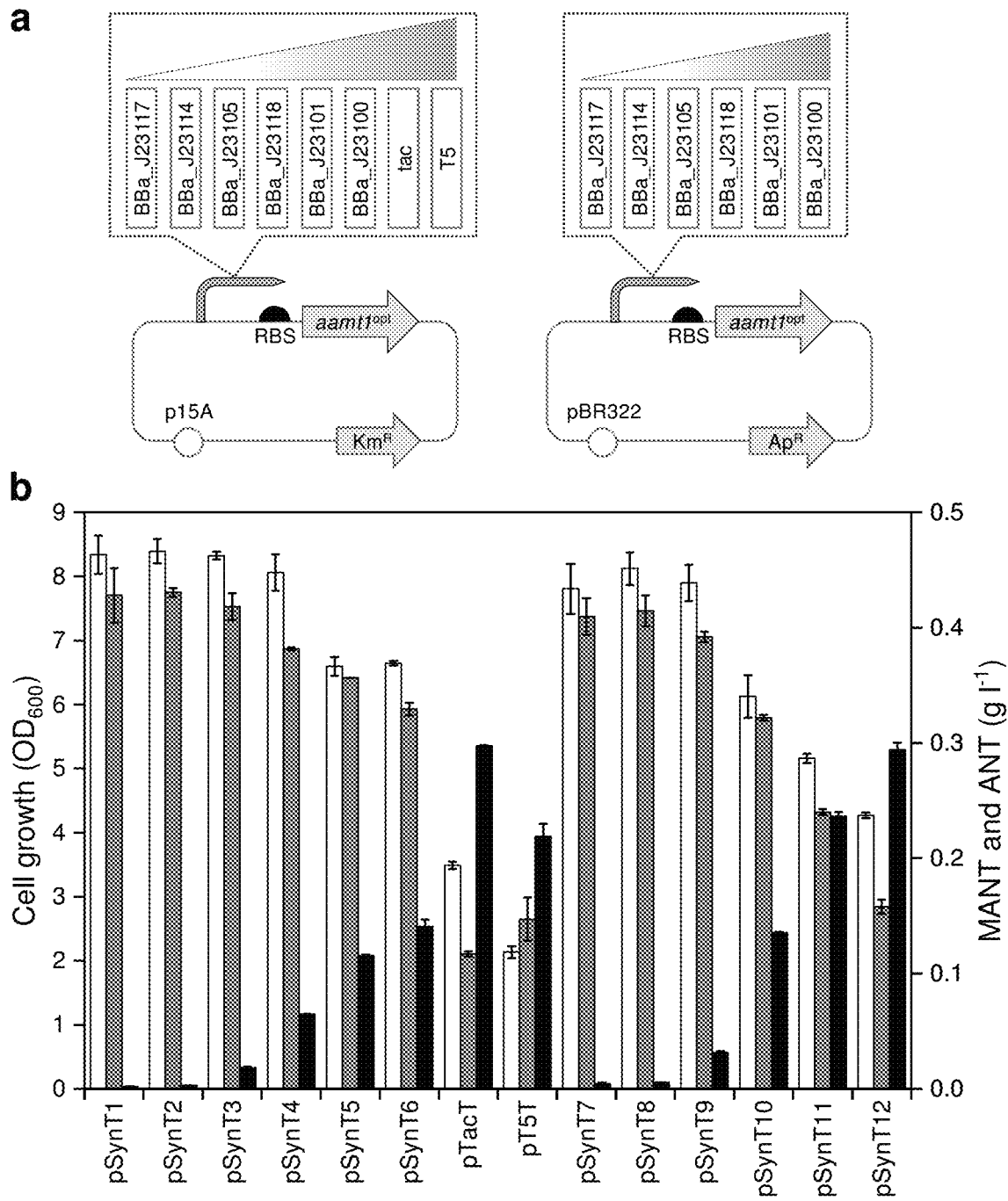
FIG. 6 shows (a) a strategy for optimizing the expression level of aamt1$^{opt}$ using a combination of the numbers of copies of various promoters and plasmids to increase the production of MANT and (b) strain growth (white), ANT concentration (gray) and MANT concentration (black) resulting therefrom.

When the aamt1 gene was expressed in vectors having various promoters, a correlation between the expression level of the aamt1 gene and the production of MANT was identified. In particular, the W3110 trpD9923 strain, in which the aamt1 gene is expressed in the presence of the tac promoter, showed the highest production of 297.3±0.7 mg/L of MANT, which corresponds to a 3.5-fold increase over the first strain in two-phase flask culture (FIG. 6 in part b). The pSynT recombinant vector also exhibited high MANT production, but also exhibited increased ANT production. Thus, pTacT was used in subsequent experiments.

Example 4 Re-Manipulation of Supply of Precursor ANT to Improve MANT Production in E. Coli

4-1. Overexpression of Variants of Feedback-Resistant DHAP Synthetic Genes

The present invention focused on increasing the intracellular supply of the precursor ANT in order to further increase MANT production. ANT is a metabolite that appears as an intermediate in the L-tryptophan-producing metabolic circuit in E. coli and other organisms. The mutant of the feedback-resistant DAHP synthetic gene expressed by aroG$^{fbr}$ promotes the first step involved in the polymerization of E4P and PEP in the shikimate pathway (SHK pathway). The first strategy to increase the supply of ANT is to overexpress the mutant of the feedback-resistant DAHP synthetic gene. PTrcG$^{fbr}$ (strong trc promoter, medium copy number) and pBBR1G$^{fbr}$ (relatively weak lac promoter, low copy number) were constructed for ANT production and compared with two different aroG$^{fbr}$ gene expression levels.

The vector pTrcG$^{fbr}$ was produced by amplifying pTyr-a (Na, D. et al., *Nat. Biotechnol.* 31, 170-174, 2013) with SEQ ID NO: 12 and SEQ ID NO: 13 and assembling the amplification product to pTrC99A amplified with SEQ ID NO: 14 and SEQ ID NO: 15 by Gibson assembly. pBBR1G$^{fbr}$ was produced by amplifying pTyr-a with SEQ ID NO: 16 and SEQ ID NO: 17 and assembling the amplification product to pBBR1MCS amplified with SEQ ID NO: 18 and SEQ ID NO: 19 by Gibson assembly.

TABLE 5

| SEQ ID NO: | Base sequence |
| --- | --- |
| SEQ ID NO: 12 | 5'TCACACAGGAAACAGACCATATGAATTATCAGAACGACGATTTAC-3' |
| SEQ ID NO: 13 | 5'GGGTACCGAGCTCGAATTCCTTACCCGCGACGCGCTTTTA-3' |
| SEQ ID NO: 14 | 5'TAAAAGCGCGTCGCGGGTAAGGAATTCGAGCTCGGTACCC-3' |
| SEQ ID NO: 15 | 5'TCGTCGTTCTGATAATTCATATGGTCTGTTTCCTGTGTGA-3' |
| SEQ ID NO: 16 | 5'TTCACACAGGAAACAGCTATGAATTATCAGAACGACG-3' |
| SEQ ID NO: 17 | 5'AGCTTATCGATACCGTCGACTTACCCGCGACGCGCTTTTA-3' |
| SEQ ID NO: 18 | 5'TAAAAGCGCGTCGCGGGTAAGTCGACGGTATCGATAAGCT-3' |
| SEQ ID NO: 19 | 5'CGTCGTTCTGATAATTCATAGCTGTTTCCTGTGTGAA-3' |

The W3110 trpD9923 introduced with pBBR1G$^{fbr}$ during flask culture produced 731.7±7.4 mg/L of ANT, which is 2.3 times higher than the W3110 trpD9923 introduced with pTrcG$^{fbr}$, and is 1.4 times higher than W3110 trpD9923 not introduced with a vector.

4-2. Increase in Availability of E4P and PEP

Following overexpression of the aroG$^{fbr}$ gene, the present invention focused on increasing the availability of E4P and PEP, two important aromatic precursors for ANT production. In order to increase E4P, pBBR1G$^{fbr}$-A was constructed to overexpress the tktA gene. The Vector pBBR1G$^{fbr}$-A was produced by amplifying RBS-tktA from the E. coli W3110 genome using SEQ ID NO: 20 and SEQ ID NO: 21 and inserting an amplification product into a pBBR1Gfbr vector cleaved with BamHI by GiBson assembly. The W3110 trpD9923 introduced with pBBR1G$^{fbr}$-A produced 760.4±12.5 mg/L of ANT.

TABLE 6

| SEQ ID NO: | Base sequence |
| --- | --- |
| SEQ ID NO: 20 | 5'CTTGATATCGAATTCCTGCAGCCCGGGGACAGGAAACAGACCATATGTCCTCACGTAAAGAG-3' |
| SEQ ID NO: 21 | 5'ACCGCGGTGGCGGCCGCTCTAGAACTAGTGTTACAGCAGTTCTTTTGC-3' |

Next, in order to increase the amount of PEP, four strains, that is, ZWA1 (ppsA overexpression using trc promoter), ZWA2 (pykA gene deletion), ZWA3 (pykF and pykA gene deletion), ZWA4 (ppsA gene overexpression using trc promoter, pykF gene deletion), all of which were derived from W3110 trpD9923, were constructed.

Gene deletion and intrachromosomal promoter exchange of E. coli were conducted by producing strains using a one-step homologous recombination-mediated method (Datsenko & Wanner, *Proc. Natl. Acad. Sci. USA*, 97, 6640-6645, 2000). The trc promoter to be used for ppsA overexpression was amplified with pMtrc9 as a template using SEQ ID NO: 22 and SEQ ID NO: 23 and was further amplified with SEQ ID NO: 24 and SEQ ID NO: 25. The gene pykF was amplified with SEQ ID NO: 26 and SEQ ID NO: 27 and further amplified with SEQ ID NO: 28 and SEQ ID NO: 29. The gene pykA was amplified with SEQ ID NO: 30 and SEQ ID NO: 31 and was further amplified with SEQ ID NO: 32 and SEQ ID NO: 33.

Figure 7:
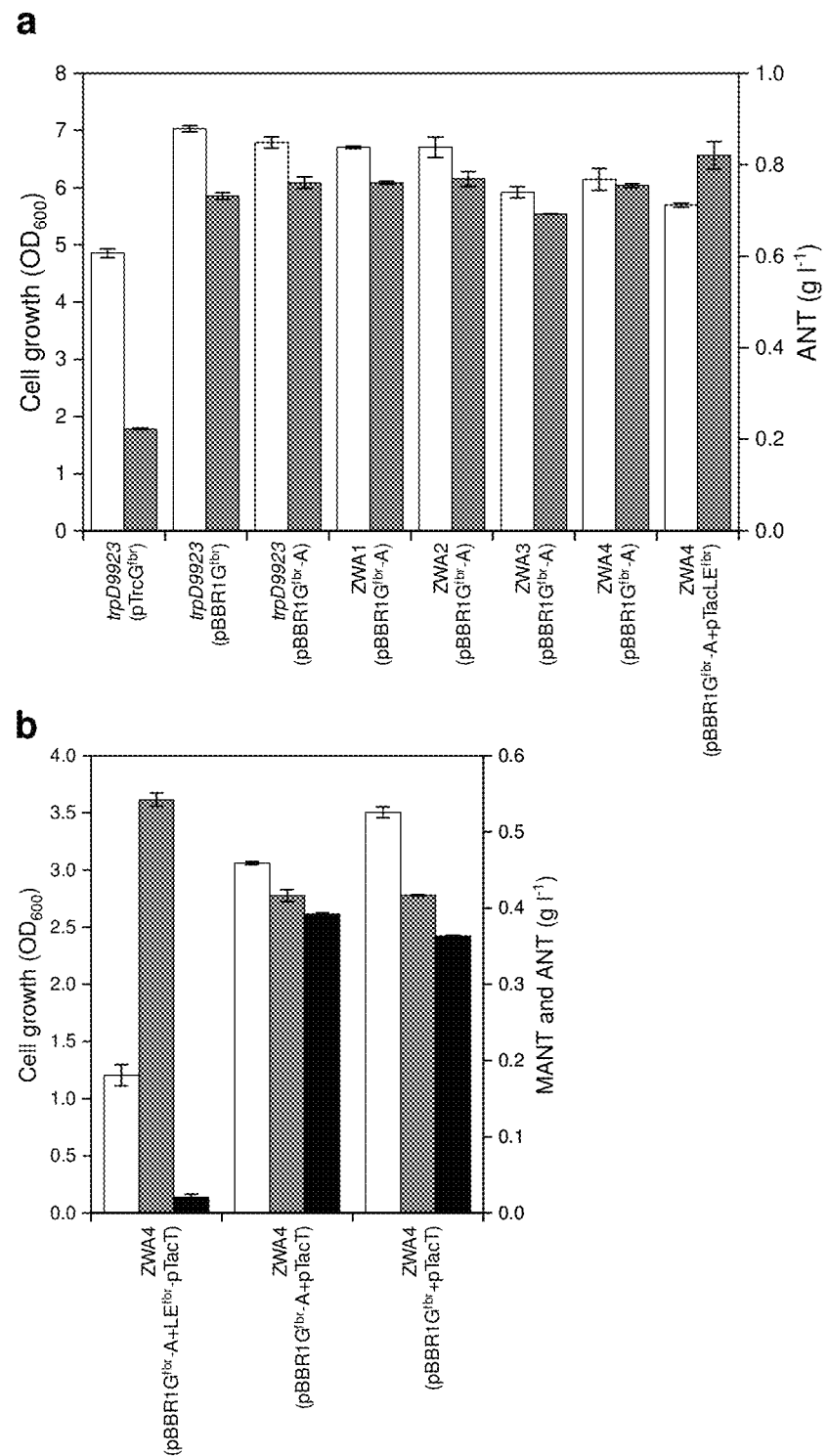
FIG. 7 shows (a) strain growth (white) in variously engineered strains and ANT production (gray) from glucose to increase the supply of precursor ANT and (b) MANT production (black) from glucose when using a strain overproducing ANT, for improvement of the productivity of MANT, wherein white represents strain growth, gray represents ANT production and black represents MANT production.

The ZWA1, ZWA2, ZWA3 and ZWA4 strains were produced from these amplified sequences in the same manner as presented in Datsenko & Wanner (*Proc. Natl. Acad. Sci. USA*, 97, 6640-6645, 2000). However, the result of flask culture of the four strains thus produced showed that there was no further improvement in the production of ANT (FIG. 7 in part a).

TABLE 7

| SEQ ID NO: | Base sequence |
| --- | --- |
| SEQ ID NO: 22 | 5'GCATTTCATTTTTATGGTTTCGTTTATACCGATGGTTTATGTGGAAATTGCGCGTCATACACATACGATT-3' |
| SEQ ID NO: 23 | 5'ATGCCGAGTTGGTTATACCAAAGCACCAGCGGTGACGAGCCATTGTTGGACATGGTCTGTTTCCTGTGTG-3' |
| SEQ ID NO: 24 | 5'-TTATGTCTGGTTTATAAAATGAACCTTCAATTTTATTTTTTATGAAAACAGCATTTCATTTTTATGGT-3' |
| SEQ ID NO: 25 | 5'-TCATTTCACCCAGGGAGGCATTTTTGCCCCCAACCCTGTCTACATCATTCATGCCGAGTTGGTTATAC-3' |
| SEQ ID NO: 26 | 5'-GAAAGCAAGTTTCTCCCATCCTTCTCAACTTAAAGACTAAGACTGTCATGTAGGTGACACATAGAACGCG-3' |
| SEQ ID NO: 27 | 5'-GATATACAAATTAATTCACAAAAGCAATATTACAGGACGTGAACAGATGCTAGTGGATCTGATGGGTACC-3' |
| SEQ ID NO: 28 | 5'-AGGCACCACCACTTTCGTAATACCGGATTCGCTTTCCGGCAGTGCGCCCAGAAAGCAAGTTTCTCCCATC-3' |
| SEQ ID NO: 29 | 5'-ATTGCTTCTGGTTATCGATTAAATAAAAAAAGCGCCCATCAGGGCGCTTCGATATACAAATTAATTCACA-3' |
| SEQ ID NO: 30 | 5'-TTATTTCATTCGGATTTCATGTTCAAGCAACACCTGGTTGTTTCAGTCAACGGAGTATTACATTAGGTGACACTATAGAACGCG-3' |

TABLE 7-continued

| SEQ ID NO: | Base sequence |
|---|---|
| SEQ ID NO: 31 | 5'-GTTGAACTATCATTGAACTGTAGGCCGGATGTGGCGTTT TCGCCGCATCCGGCAACGTACTAGTGGATCTGATGGGTACC-3' |
| SEQ ID NO: 32 | 5'-CCTAATCTTATACGACATCCGAATGAGATTAATTTATCG CCATCGCGGCGTTATTTCATTCGGATTTC-3' |
| SEQ ID NO: 33 | 5'-GGCCTTCGCCTGATGATAAGTTCAAGTTTGCTTCAGAAT ATTCGAAATCTGTTGAACTATCATTGAAC-3' |

In addition, pTacLE$^{fbr}$, which overexpresses the aroL gene helping improve L-tryptophan production flow and the feedback-resistant trpE$^{fbr}$ gene, was constructed.

The vector pTacLE$^{fbr}$ was produced by amplifying pTac-E (Du, et al., *J. Biotechnol.* 267, 19-28, 2018) using SEQ ID NO: 34 and SEQ ID NO: 35 and then assembling the amplification product to a pTac-AroL (Du, et al., *J. Biotechnol.* 267, 19-28, 2018) vector cleaved with PstI by Gibson assembly.

TABLE 8

| SEQ ID NO: | Base sequence |
|---|---|
| SEQ ID NO: 34 | 5'AGCGCCCTGGCACAGACGATCAATTGTTGACTGCATCACA CAGGAAACAGACCATGCAAACACAAAAACCG -3' |
| SEQ ID NO: 35 | 5'TCATCCGCCAAAACAGCCAAGCTTGCATGCCTGCATCAGA AGTCTCCTGTGC -3' |

The ZWA4 strain introduced with pBBR1G$^{fbr}$-A and pTacLE$^{fbr}$ produced 820.5±30.3 mg/L of ANT, which is 8.7% higher than the amount produced by the ZWA4 strain introduced with pBBR1G$^{fbr}$-A.

The vector pTacT optimized for MANT production was assembled to engineered strains with increased production of ANT mentioned above. First, plasmids pTacT and pTacLE$^{fbr}$ were assembled with one expression vector LE$^{fbr}$-pTacT.

The vector LE$^{fbr}$-pTacT was produced by amplifying tac-aroL-RBS-trpE$^{fbr}$ from pTacLE$^{fbr}$ using SEQ ID NO: 36 and SEQ ID NO: 37 and assembling the amplification product to the pTacT vector cleaved with NheI by Gibson assembly.

TABLE 9

| SEQ ID NO: | Base sequence |
|---|---|
| SEQ ID NO: 36 | 5'ATCAGTGCCAACATAGTAAGCCAGTATACACTCCGTGAGC TGTTGACAATTAATC -3' |
| SEQ ID NO: 37 | 5'CCGTGGCCGGGGGACTGTTGGGCGCCATCTCCTTGGCAAC GTTCAAATCCGCTC -3' |

Unexpectedly, the flask culture of ZWA4 introduced with pBBR1G$^{fbr}$-A and LE$^{fbr}$-pTacT produced only 20.8±3.9 mg/L of MANT (FIG. 7 in part b). Thus, two recombinant strains, namely ZWA4 further introduced with pBBR1G$^{fbr}$-A and pTacT, and ZWA4 further introduced with pBBR1G$^{fbr}$ and pTacT, were produced. As the result of the two-phase extraction flask culture, the former produced 392.0±1.7 mg/L of MANT and the latter produced 363.5±0.8 mg/L of MANT (FIG. 7 in part b). Both strains exhibited increased MANT production compared to the initial strain, W3110 trpD9923 introduced with pTacT.

Example 5 Manipulation of Availability of Co-Substrate SAM to Improve MANT Production 5-1. Manipulation of Availability of Co-Substrate SAM In order to increase the production of MANT from the produced ANT, an attempt was made to improve the availability of SAM as a co-substrate. First, in order to increase the availability of SAM, the mutants of homoserine O-succinyltransferase expressed by the metA$^{fbr}$ gene and the L-serine O-acetyltransferase expressed by the cysE$^{fbr}$ gene, which are feedback-resistant were overexpressed, and the result was observed.

For this purpose, a pBBR1G$^{fbr}$A$^{fbr}$E$^{fbr}$ vector was constructed. First, RBS-metA$^{fbr}$ (encoding MetA$^{R27C, \, I296S, \, P298L}$) was amplified with SEQ ID NO: 38 and SEQ ID NO: 39 and then inserted into vector pBBR1G$^{fbr}$ cleaved with HindIII and PstI to produce a vector pBBR1G$^{fbr}$A$^{fbr}$. Next, RBS-cysE$^{fbr}$ (encoding CysE$^{V95R, \, D96P}$) was amplified with SEQ ID NO: 40 and SEQ ID NO: 41 and inserted into the vector pBBR1G$^{fbr}$A$^{fbr}$ cleaved with BamHI to produce a vector pBBR1G$^{fbr}$A$^{fbr}$E$^{fbr}$. In addition, RBS-metK was amplified from the *E. coli* W3110 genome with SEQ ID NO: 42 and SEQ ID NO: 43 and then inserted into the pTacT vector cleaved with SphI by Gibson assembly to produce a pTacTK vector.

TABLE 10

| SEQ ID NO: | Base sequence |
|---|---|
| SEQ ID NO: 38 | 5'AGACAGAAGCTTACAGGAAACAGCTATGCCGATTCGTGTG CCG -3' |
| SEQ ID NO: 39 | 5'AGACAGCTGCAGTTAATCCAGCGTTGGATTC -3' |
| SEQ ID NO: 40 | 5'-CACATGAATCCAACGCTGGATTAACTGCAGCCCGGGGACAGG AAACAGCTATGTCGTGTGAAGAACTG-3' |
| SEQ ID NO: 41 | 5'-AATTGGAGCTCCACCGCGGTGGCGGCCGCTCTAGAACTAGTG TTAGATCCCATCCCCATAC-3' |
| SEQ ID NO: 42 | 5'-AGGCGATTATCCATGTGTGACTGCAGGCATGACACAGGAAAC AGACCATATGGCAAAACACCTTTTTACG-3' |
| SEQ ID NO: 43 | 5'-CTCTCATCCGCCAAAACAGCCAAGCTTGCATGTTACTTCAGA CGGCAG CCATC-3' |

Figure 8:
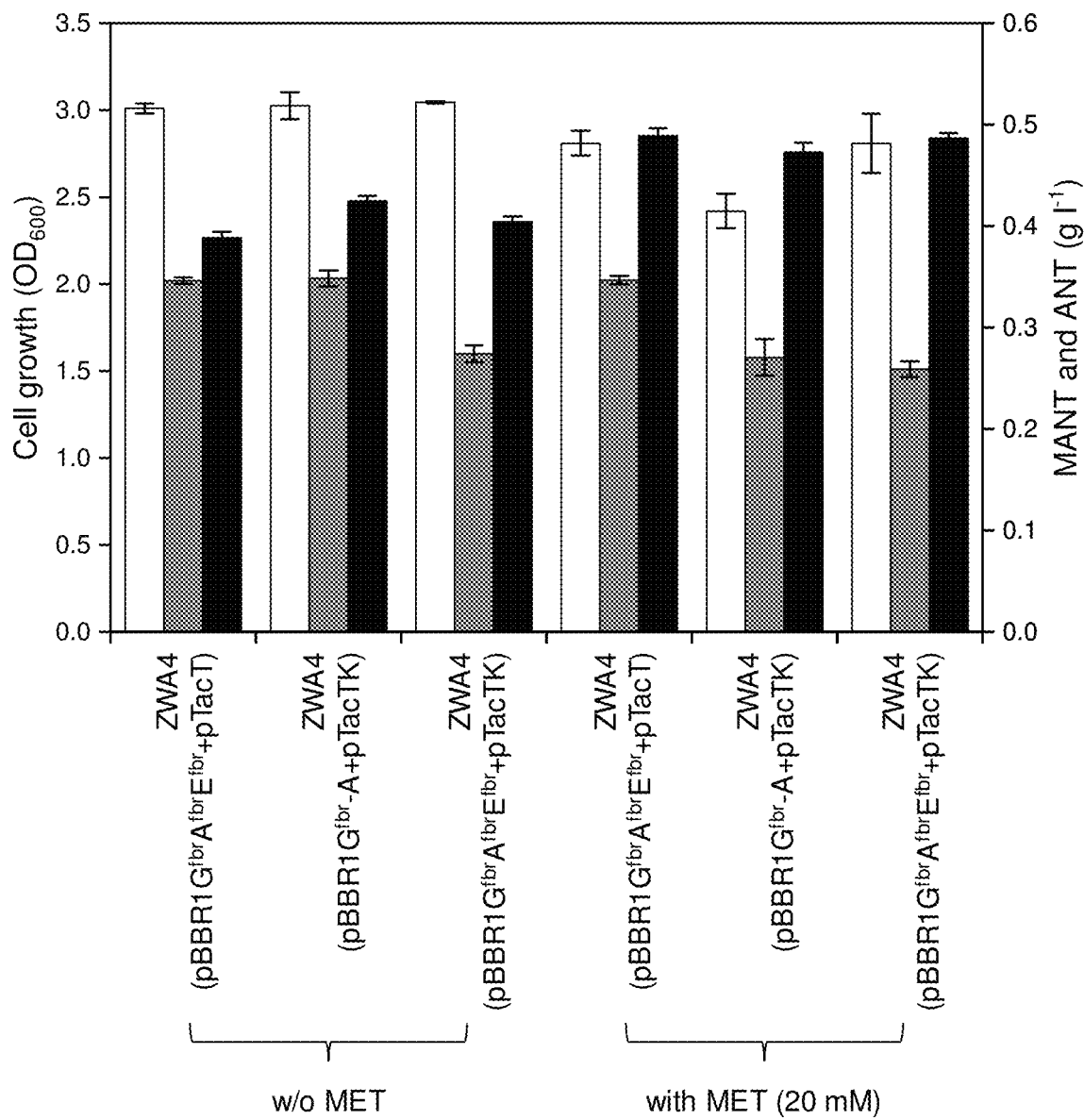
FIG. 8 shows strain growth (white), ANT concentration (gray) and MANT concentration (black) upon overexpression of metA$^{fbr}$, cysE$^{fbr}$ and metK genes and the addition of L-methionine (20 mM) for production of MANT from glucose.

As a result, ZWA4 introduced with pBBR1G$^{fbr}$A$^{fbr}$E$^{fbr}$ and pTacT produced 388±6.0 mg/L of MANT and 346.3±3.3 mg/L of ANT (FIG. 8). The ZWA4 introduced with pBBR1G$^{fbr}$-A and pTacTK produced 424.8±5.0 mg/L of MANT and 348.3±7.8 mg/L of ANT (FIG. 8). The ZWA4 introduced with pBBR1G$^{fbr}$A$^{fbr}$E$^{fbr}$ and pTacTK produced smaller amounts of 404.3±5.4 mg/L of MANT and 274.2±8.4 mg/L of ANT (FIG. 8).

In addition to the manipulation of SAM using the aforementioned gene manipulation, an attempt was made to improve SAM production through additional supplementation of L-methionine, a precursor of SAM. All three SAM engineered strains were recultured in a two-phase flask supplemented with 20 mM of L-methionine. As a result, the ZWA4 introduced with pBBR1G$^{fbr}$A$^{fbr}$E$^{fbr}$ and pTacT produced 489.0±7.4 mg/L of MANT, which corresponds to an increase of 25.9% compared with the case of no addition of L-methionine (388.3 mg/L). In this case, the amount of ANT was 346.7±4.2 mg/L (FIG. 8). In addition, the ZWA4 introduced with pBBR1G$^{fbr}$A$^{fbr}$E$^{fbr}$ and pTacTK produced a similar level of MANT (486.8±4.8 mg/L), but a much smaller amount of ANT (258.9±7.6 mg/L) was observed (FIG. 8). Therefore, these two strains were evaluated in a fed-batch fermentation environment.

Example 6 Two-Phase Extraction Fed-Batch Fermentation for MANT Production Using Manipulated E. Coli 6-1. Two-Phase Extraction Fed-Batch Fermentation Conditions The fed-batch fermentation of the two engineered strains mentioned above was carried out using glucose minimal medium in a two-phase manner. A pH-stat feeding strategy was used for nutrient supply, $(NH_4)_2SO_4$ was added as an additional nitrogen source and 20 mM of L-methionine was added to increase the availability of SAM.

E. coli two-phase extraction fed-batch fermentation was conducted in a 6.6 L fermenter (Bioflo 3000; New Brunswick Scientific Co., Edison, N.J.) containing 1.8 L MR medium supplemented with 20 g/L of glucose, 20 mM MET, 3 g/L $(NH_4)_2SO_4$, 40 mg/L of L-TRP, and 10 mg/L of thiamine. First, strains inoculated in a LB medium in a 2 mL test tube were cultured at 37° C. for at least 12 hours. The preculture solution was inoculated into two 250 mL flasks each containing 100 mL of the same medium and incubated at 37° C. and 200 rpm for 10 hours. This preculture solution (200 mL) was inoculated into the fermenter (starting $OD_{600}$~0.3). In fed-batch fermentation, the pH was maintained at 7.0 using ammonia water (28%, Junsei Chemical Co., Ltd., Tokyo, Japan) and the temperature was maintained at 37° C. in P-I-D (proportional-integral-derivative) mode. The aeration rate was maintained at 1 vvm, agitation was conducted at 200 to 1,000 rpm to maintain the dissolved oxygen (DO) at 40%, and oxygen was injected together when the agitation rate was higher than 1,000 rpm. IPTG was added when the $OD_{600}$ of the strains reached about 5, and 500 mL of tributyrin was added to the medium at a rate of 250 ml/h. For fed-batch fermentation, a pH-stat feeding strategy (Lee, S Y Trends Biotechnol. 14, 98-105, 1996), wherein, when the pH was higher than 7.02, a feed solution was added until the pH was lower than 7.02, was used. The feed solution consisted of 700 g/L of glucose, 8 g/L of $MgSO_4 \cdot 7H_2O$, 20 mM of MET, 30 g/L of $(NH_4)_2SO_4$, 100 mg/L of L-TRP, 10 mg/L of thiamine, 5 ml/L of a trace metal solution, and 1 mM IPTG. At 24 and 48 hours, 20 mL of L-TRP (4 g/L) was added to the medium.

Figure 9:
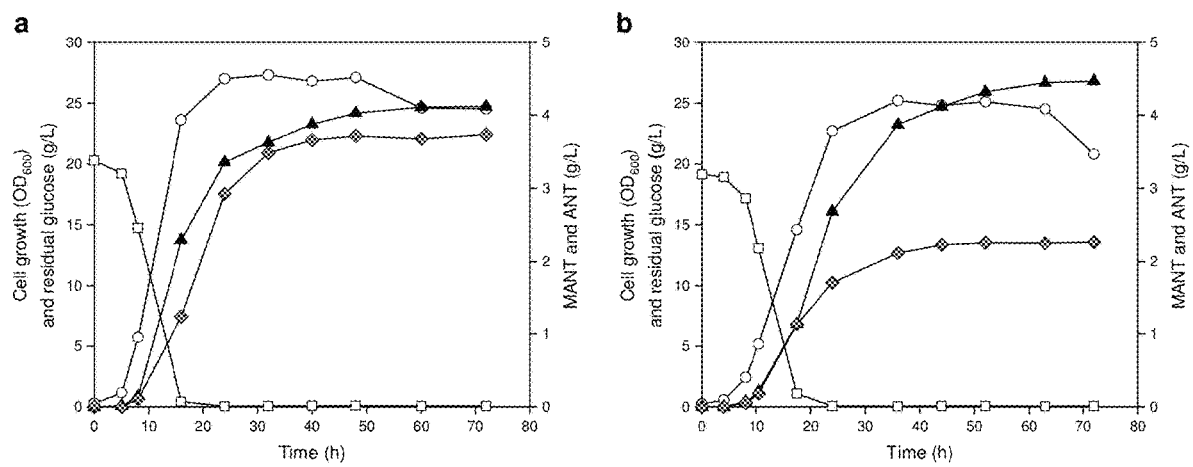
FIG. 9 shows strain growth, ANT concentration and MANT concentration upon two-phase extraction fed-batch fermentation of (a) a ZWA4 strain introduced with pBBR1G$^{fbr}$A$^{fbr}$E$^{fbr}$ and pTacTK and (b) a ZWA4 strain introduced with pBBR1G$^{fbr}$A$^{fbr}$E$^{fbr}$ and pTacT, wherein the circles represent cell growth (OD$_{600}$), the squares represent residual glucose concentration (g/L), the gray diamonds represent ANT concentration (g/L), and the black triangles represent MANT concentration (g/L)

As a result, the ZWA4 introduced with pBBR1G$^{fbr}$A$^{fbr}$E$^{fbr}$ and pTacTK produced 4.12 g/L of MANT and 3.74 g/L of ANT (FIG. 9 in part a). On the other hand, the ZWA4 introduced with pBBR1G$^{fbr}$A$^{fbr}$E$^{fbr}$ and pTacT produced a higher amount of 4.47 g/L of MANT and a smaller amount of 2.26 g/L of ANT, and exhibited 0.045 g/g of glucose yield and 0.062 g/L/h of productivity (FIG. 9 in part b). Almost all of the produced MANT was extracted in the organic phase and most of the ANT remained as the aqueous phase because the pH was kept neutral during the two-phase fermentation, so the production of ANT during fed-batch fermentation could not be considered a by-product.

Example 7 Selection of C. Glutamicum as Host for Food-Grade MANT Production

Figure 2:
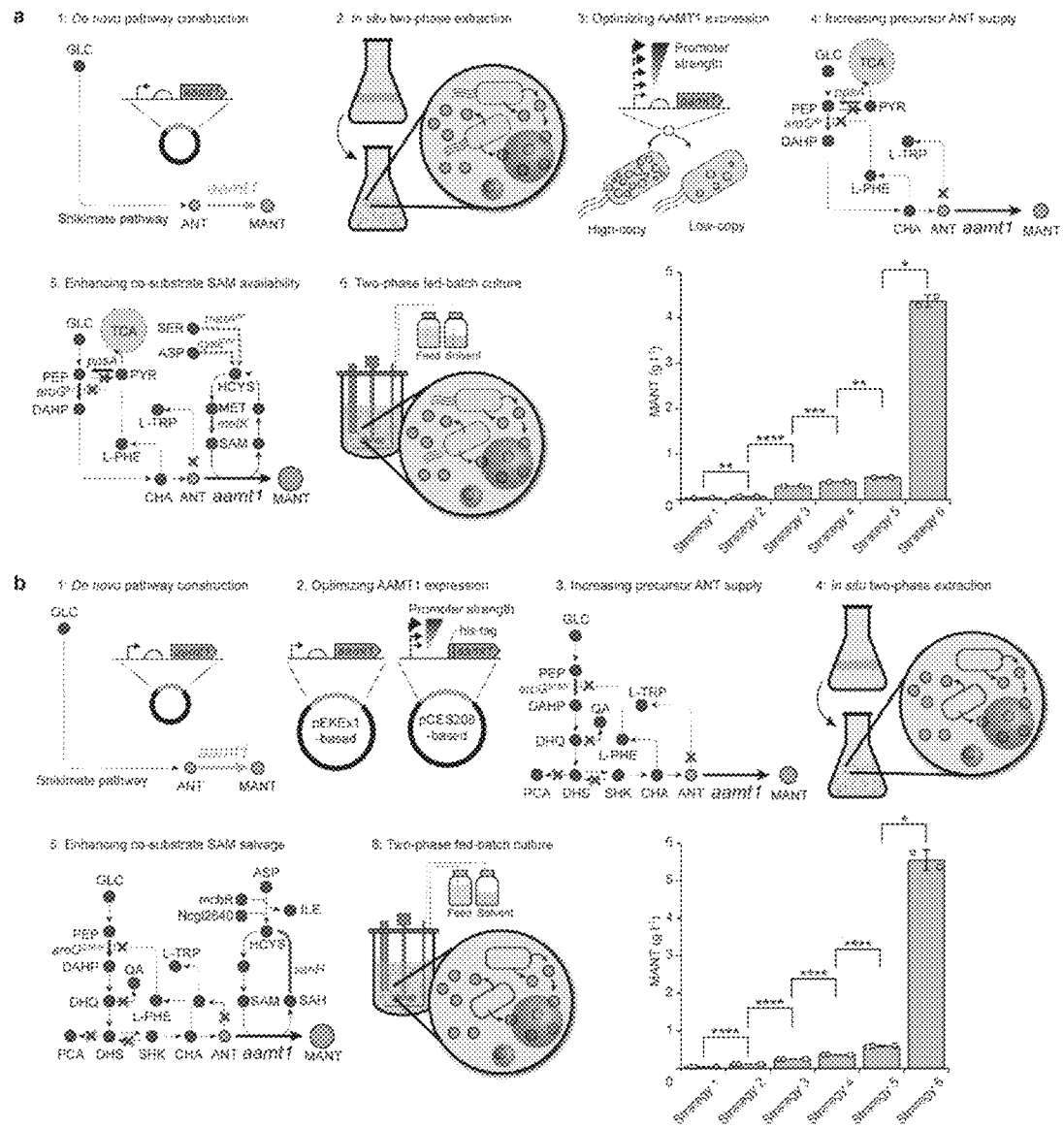
FIG. 2 shows an overview of the overall engineering strategy for optimizing MANT production in E. coli (a) and C. glutamicum (b)
Figure 10:
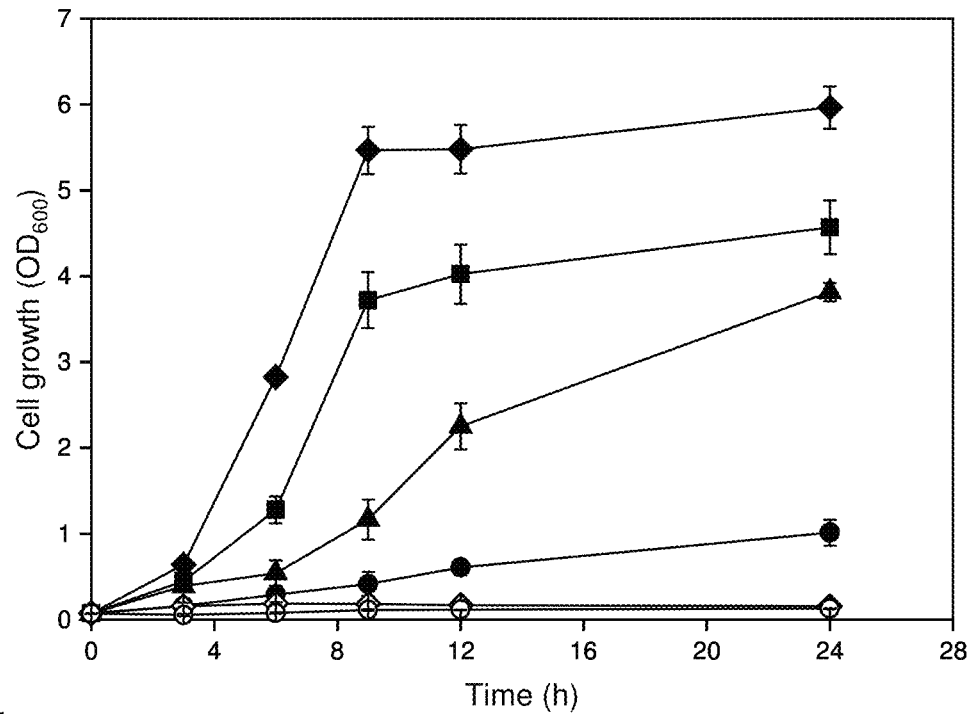
FIG. 10 shows the toxicity of MANT concentrations to (a) P. putida KT2440 and (b) C. glutamicum (black diamond, 0 g/L; black square, 0.1 g/L; black triangle, 0.3 g/L; black circle, 0.5 g/L; white diamond, 0.75 g/L; white circle, 1.0 g/L)
Figure 10:
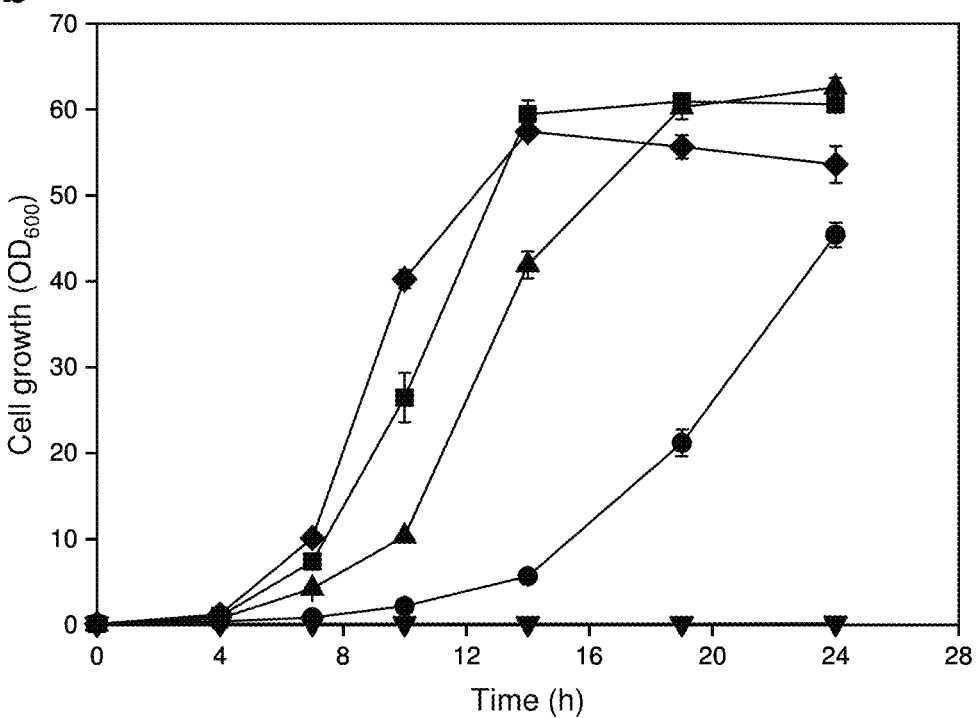

After the production capacity of MANT by E. coli from glucose was demonstrated, food-grade MANT was produced using other industrial GRAS microorganisms because MANT is mainly applied to the food and cosmetic industries. The potential for producing MANT was investigated by comparing the MANT toxicity between Pseudomonas putida KT2440 (Gram-negative) and C. glutamicum ATCC 13032 (Gram-positive), which are typical GRAS microorganisms. The results of toxicity tests showed that both strains had growth profiles having concentration-dependent inhibition. However, the P. Putida KT2440 strain was not capable of growing in the presence of 1.0 g/L MANT (FIG. 10 in part a), whereas the growth of C. glutamicum was completely inhibited in the presence of MANT at a concentration of 2.0 g/L (FIG. 10 in part b). The results show that C. glutamicum is more resistant to MANT than P. putida or E. coli. Therefore, C. glutamicum was selected as a host for food-grade MANT production (FIG. 1 in part b), and similar metabolic engineering strategies were applied to optimize MANT production of C. glutamicum (FIG. 2 in part b).

Example 8 Strategies for Improving MANT Production in C. Glutamicum 8-1. Optimization of AAMT1 Expression Level to Improve MANT Production In order to establish the MANT synthetic pathway, the AAMT1 expression vectors of pEKT, pL10T, pI16T, pH36T, pL10HT, pI16HT and pH36HT were constructed and the expression levels thereof were optimized to express the aamt1$^{opt-Cgl}$ gene in wild-type C. glutamicum ATCC 13032.

The pEKT vector was prepared by amplifying the aamt1$^{opt}$ gene with SEQ ID NO: 44 and SEQ ID NO: 45, cleaving the amplified sequence with EcoRI and PstI, and inserting the resulting product into the pEKEx1 vector cleaved with the same restriction enzyme. The pL10T, pI16T and pH36T vectors were produced by amplifying the aamt1$^{opt}$ gene with SEQ ID NO: 46 and SEQ ID NO: 47, cleaving the amplified sequences with BamHI and NotI, and then inserting the resulting product into pCES-L10-M18, pCES-I16-M18 and pCES-H36-M18 vectors (Yim S S, et al., Biotechnol Bioeng, 110:2959, 2013) cleaved with the same restriction enzyme. The pL10HT, pI16HT and pH36HT vectors were produced by amplifying the aamt1$^{opt}$ gene with SEQ ID NO: 48 and SEQ ID NO: 49, cleaving the amplified sequence with BamHI and NotI and inserting the resulting product into pCES-L10-M18, pCES-I16-M18 and pCES-H36-M18 vectors cleaved with the same restriction enzyme.

TABLE 11

| SEQ ID NO: | Base sequence |
|---|---|
| SEQ ID NO: 44 | 5'-AGACAGGAATTCATGCCGATGCGTATTGAG-3' |
| SEQ ID NO: 45 | 5'-AGACAGCTGCAGTCACACATGGATAATCGC-3' |
| SEQ ID NO: 46 | 5'-AGACAGGGATCCATGCCGATGCGTATTGAG-3' |
| SEQ ID NO: 47 | 5'-AGACAGGCGGCCGCTCACACATGGATAATCGC-3' |

TABLE 11-continued

| SEQ ID NO: | Base sequence |
|---|---|
| SEQ ID NO: 48 | 5'-AGACAGGGATCCATGCATCACCATCACCATCATCCGATGCGTATTGAG-3' |
| SEQ ID NO: 49 | 5'-AGACAGGCGGCCGCTCACACATGGATAATCGC-3' |

Figure 11:
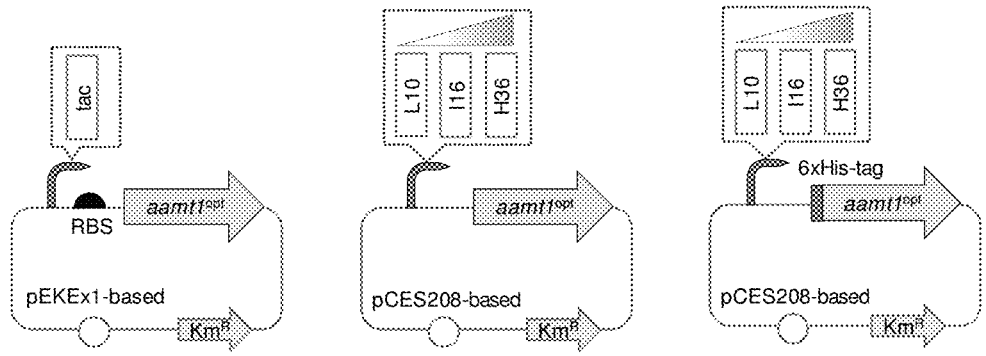
FIG. 11 is (a) a schematic diagram showing the production of a vector having a variety of promoters for regulating aamt1$^{opt}$ gene expression in C. glutamicum, and shows (b) strain growth (white) and MANT production (black) resulting therefrom.
Figure 11:
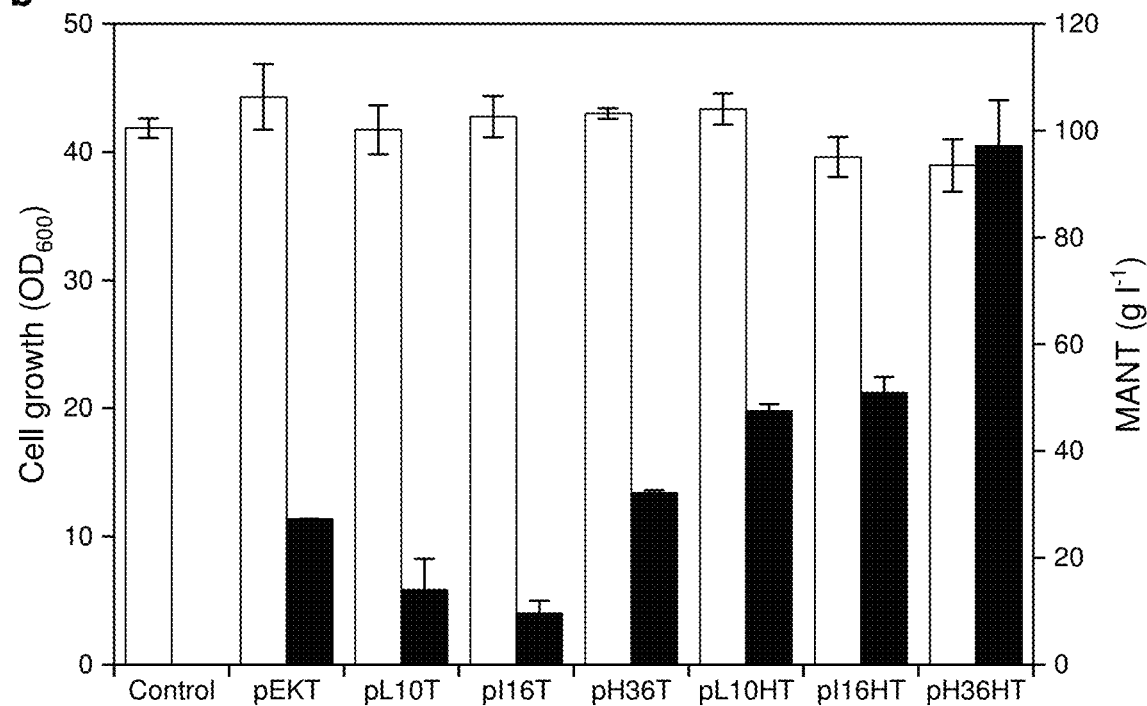

*C. glutamicum* strains introduced with the produced vectors were added with 0.8 g/L of ANT and flask-cultured in CGXII medium (40 g/L of glucose, 20 g/L of $(NH_4)_2SO_4$, 5 g/L of urea, 1 g/L of $KH_2PO_4$, 1 g/L of $K_2HPO_4$, 0.25 g/L of $MgSO_4.7H_2O$, 42 g/L of 3-morpholinopropanesulfonic acid (MOPS), 13 mg/L of $CaCl_2.2H_2O$, 10 mg/L of $FeSO_4.7H_2O$, 14 mg/L of $MnSO_4.5H_2O$, 1 mg/L of $ZnSO_4.7H_2O$, 0.3 mg/L of $CuSO_4.5H_2O$, 0.02 mg/L of $NiCl_2.6H_2O$, 0.5 mg/L of biotin, 30 mg/L of protocatechuic acid and 0.5 mg/L of thiamine). The result showed that the *C. glutamicum* strain having the vector pH36HT produced the highest amount of 97.2±8.6 mg/L of MANT (FIG. 11). The base strain did not produce any MANT at all.

8-2. Metabolic Engineering Strategies to Improve MANT Production

In order to improve ANT production capacity, competitive metabolic circuits in ANT production were deleted. Here, genes encoding qsuB and qusD enzymes along with the trpD enzyme leading L-tryptophan production were deleted (FIG. 1 in part b). In order to delete the genes encoding the trpD, qsuB and qusD enzymes, strains transformed with pTacCC1-HrT vector in *C. glutamicum* were first produced (Cho et al., *Metabolic Engineering*, 42: 157-167, 2017). Then, for the produced *C. glutamicum* strain, i) pCG9ts-series each including sgRNA sequences of three types of genes, and ii) ssODNs each binding to the three types of genes were produced to delete the genes for *C. glutamicum*.

8-3. Production of pCG9ts-Series Vectors Including sgRNA Guide Sequences of Genes First, the optimal guide sequence with a low off-target effect was selected as follows using the online program CRISPy-web (Blin et al., *Synthetic and Systems Biotechnology*, 1(2):118-121, 2016), which analyzes nonspecific targets of sgRNA guide sequences and provides the optimal sgRNA guide sequence (Table 12).

TABLE 12 sgRNA guide sequence using CRISPy-web

| Guide sequence | Target gene | sgRNA guide sequence |
|---|---|---|
| SEQ ID NO: 50 | trpD | CTGCTCACCGCGAGTACGGA |
| SEQ ID NO: 51 | qsuB | CTGGCCAAGACGGGTTATGA |
| SEQ ID NO: 52 | qsuD | GCACTGATTACTACCCAAAT |

DNA fragments that target the trpD gene and encode the sgRNA-T1/TE sequence (Korean Patent Application No. 2017-0042124; Cho et al., *Metabolic Engineering*, 42: 157-167, 2017) were amplified using, as a template, the PUC19-sgRNA vector (Korean Patent Application No. 2017-0042124; Cho et al., *Metabolic Engineering*, 42: 157-167, 2017, SEQ ID NO: 55) and using the primers of SEQ ID NOS: 53 and 56, in order to produce pCG9ts-series vectors including the sgRNA guide sequences (SEQ ID NOS: 50 to 52). The amplified DNA fragments were further amplified once again by PCR using the primers of SEQ ID NOS: 54 and 55. After the pEKts-Cas9 vector (Korean Patent Application No. 2017-0042124; Cho et al., *Metabolic Engineering*, 42: 157-167, 2017, SEQ ID NO: 66) was treated with the enzyme of StuI, and pCG9ts-trpD vector expressing sgRNA targeting the trpD gene along with Cas9 protein was finally produced by Gibson assembly using the amplified fragment. Then, fragments targeting genes encoding a total of three random enzymes were produced in the same manner (SEQ ID NOS: 53, 54 and 55 are the same, and PCR was conducted in the order of SEQ ID NOS: 56 to 58 on each gene) to produce pCG9ts-trpD, pCG9ts-qsuB and pCG9ts-qsuD vectors.

TABLE 13

Primers for amplifying sgRNA-T1/TE fragments

| SEQ ID NO: | Base sequence |
|---|---|
| SEQ ID NO: 53 | TATAGATATCCCGCGGTATATTAATTAATATAAACGCAGAAAGGCCC |
| SEQ ID NO: 54 | TGGATGATGGGGCGATTCAGGtatagatatcTTGACAATTAATCTCATCGG |
| SEQ ID NO: 55 | AAGGTGTTGCTGACTCATACCAGGTATAGATATCCCGCGGTATA |

TABLE 14

Primers for producing pCG9ts-series vectors

| SEQ ID NO: | Gene | Base sequence |
|---|---|---|
| SEQ ID NO: 56 | trpD | ttgacaattaatcatcggctcgtataatgtgtggCTGCTCACCGCGAGTACGGAgttttagagctagaaatagcaagt |
| SEQ ID NO: 57 | qsuB | ttgacaattaatcatcggctcgtataatgtgtggCTGGCCAAGACGGGTTATGAgttttagagctagaaatagcaagt |
| SEQ ID NO: 58 | qsuD | ttgacaattaatcatcggctcgtataatgtgtggCCTCGCGCAGGGACGTGCGAgttttagagctagaaatagcaagt |

8-4. Production of ssODN Each Binding to Gene

The ssODN for deleting target genes was selected such that the position where the sgRNA guide sequence binds was located in the section between the two binding sequences of ssODN, and the length thereof was designed to be 80 nucleotides in total (Table 15). In this case, the ssODN consists of a 5'-homology arm and a 3'-homology arm, and each homology arm had 40 base pairs and was designed such that the ssODN could bind to both ends of the target gene region including a sequence complementary to the sgRNA guide sequence. When ssODN bound to the target, a loop structure was formed and this region was deleted. The length of the deletion region was designed to have 100 base pairs so that deletion of the target gene could be easily identified through PCR.

TABLE 15 ssODN sequence binding to gene

| SEQ ID NO: | Target gene | Base sequence |
|---|---|---|
| SEQ ID NO: 59 | trpD | TGTGTCGAACAGCTTCTCGCGAACTAATAAAAAAAG GATTTGATAGGTTTGCTAGATTCCGCTGGTACTGGT GGCGACGGTGCCAACA |
| SEQ ID NO: 60 | qsuB | TCAGTTAGCGGATGCGCCGAAGCTGAGCATGGACAT TTTGCTTTGGAGATCTTCAACGATTCCTTCCGCAAG GCCGAGGT |
| SEQ ID NO: 61 | qsuD | CTGGCAAATCTCAAAAAGTAGAAAGCCCAAAAATAT GAACACAGGCGCATCGACACGCTTGGGTCGCGTGCT TCCGGGCA |

8-5. Production of *C. Glutamicum* with Improved ANT Production Capacity

The PCG9ts-trpD vector and ssODN produced for deletion of the gene from the genome were transformed into wild-type *Corynebacterium glutamicum* (ATCC 13032). Then, the pTacCC1-HrT vector (Korean Patent Application No. 2017-0042124; Cho et al., *Metabolic Engineering*, 42: 157-167, 201, SEQ ID NO: 57) and the pCG9ts-trpD vector were removed from the transformed mutant *C. glutamicum* by curing on the 37° C. BHI plate. This step was sequentially performed using pCG9ts-qsuB and pCG9ts-qsuD to produce trpD-deleted YTM1 strains, and trpD, qsuB and qsuD-deleted YTM2 strains.

8-6. Production of *C. Glutamicum* with Improved MANT Production Capacity

Figure 12:
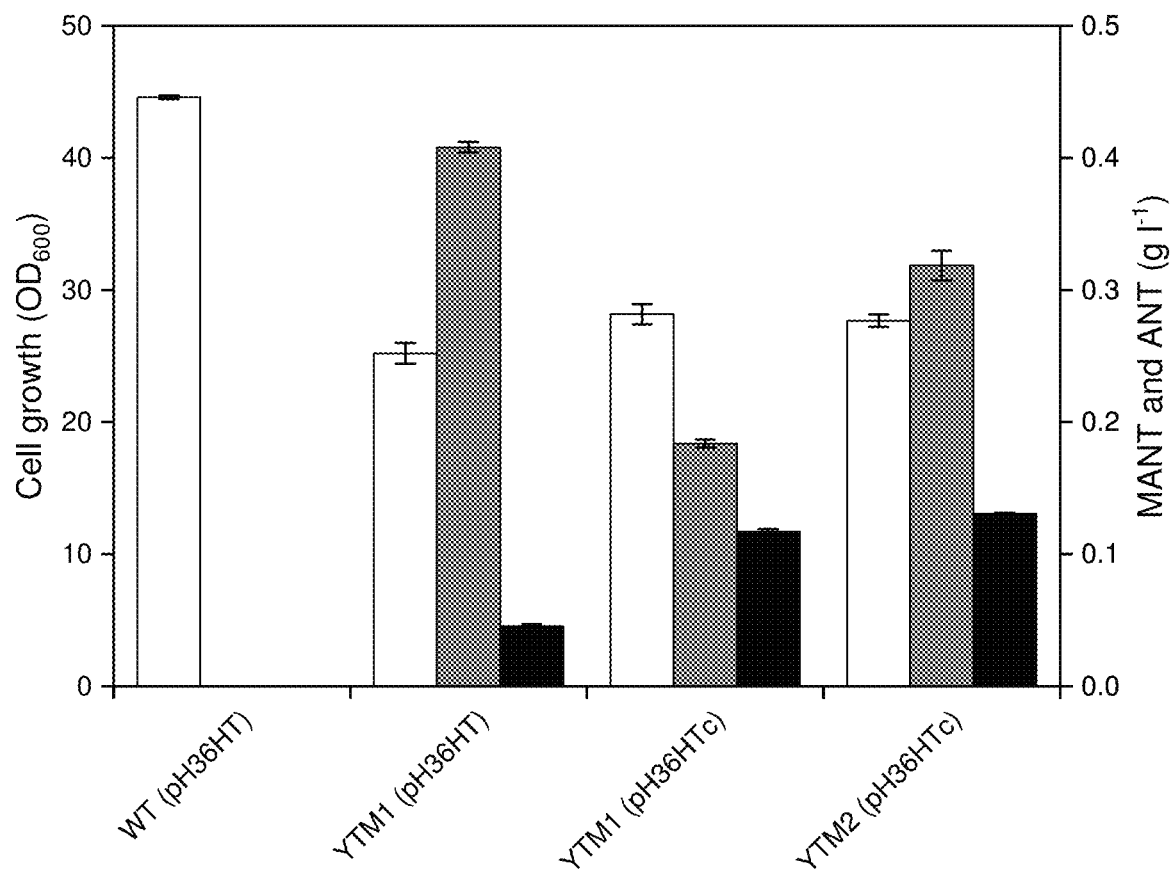
FIG. 12 shows the effects of deletion of trpD, qsuB and qsuD genes and codon optimization of aamt1 in a C. glutamicum strain on MANT productivity, wherein white represents strain growth, gray represents ANT production and black represents MANT production.

The codon-optimized aamt1$^{opt-cgl}$ gene in *C. glutamicum* was amplified with SEQ ID NO: 62 and SEQ ID NO: 63, and the amplified sequence was cleaved with BamHI and NotI and then inserted into the pCES-H36-M18 vector cleaved with the same restriction enzyme to produce a pH36HTc vector. The previously produced pH36HT vector and the newly produced pH36HTc vector were separately inserted into the YTM1 strain and were compared by flask culture. The result showed that the YTM1 strain having the vector pH36HTc exhibited higher MANT productivity of 117.1±2.0 mg/L. Further, introduction of the pH36HTc vector into the YTM2 strain exhibited improved MANT productivity of 130.4±0.8 mg/L (FIG. 12).

TABLE 16

| SEQ ID NO: | Base sequence |
|---|---|
| SEQ ID NO: 62 | 5'AGACAGGGATCCATGCATCACCATCACCATCATCCTATGC GTATCGAACG -3' |
| SEQ ID NO: 63 | 5'AGACAGGCGGCCGCTCAGACGTGGATGATAGC -3' |

Example 9 Re-Manipulation of Supply of Precursor ANT to Improve MANT Production in *C. Glutamicum*

9-1. Metabolic Pathways Involved in ANT Overproduction in *C. Glutamicum*

Metabolic engineering approaches were used to improve the production of ANT, the precursor of MANT, in *C. glutamicum*. ANT production has been reported in *E. coli* and *P. putida*, but ANT production has not been reported in *C. glutamicum*. Various genes needed to be manipulated to produce ANT. aroG, aroB and aroK are known as genes involved in the shikimate pathway, and pgi, zwf, tkt, opcA, pgl and tal are reported to be involved in the metabolic flow of the pentose phosphate pathway. Vectors were produced as follows to manipulate the genes.

9-2. Vector for Production of *C. Glutamicum* Capable of Overproducing ANT

The genes were manipulated by previously reported methods (Park, S. H. et al., *Nat. Commun* 5, 4618, 2018). In order to convert an aroK promoter into a sod promoter (SEQ ID NO: 64), the sod promoter was first amplified from the *C. glutamicum* ATCC13032 genome with SEQ ID NO: 65 and SEQ ID NO: 66. In addition, the upstream (left arm), the homologous arm, was amplified from the *C. glutamicum* ATCC13032 genome with SEQ ID NO: 67 and SEQ ID NO: 68, and the downstream (right arm) was amplified from the *C. glutamicum* ATCC13032 genome with SEQ ID NO: 69 and SEQ ID NO: 70. These three amplified sequences were subjected to overlapping PCR with SEQ ID NO: 67 and SEQ ID NO: 70 and inserted by Gibson assembly into pK19mob-sacB cleaved with BamHI and PstI to produce the final vector pK19-msb-aroK.

Sod promoter
<SEQ ID NO: 64>
aaccctacttagctgccaattattccgggcttgtgacccgctacccga taaataggtcggctgaaaaatttcgttgcaatatcaacaaaaaggcct atcattgggaggtgtcgcaccaagtactttgcgaagcgccatctgac ggattttcaaaagatgtatatgctcggtgcggaaacctacgaaaggat tttttaccc In order to convert an aroB promoter into a sod promoter (SEQ ID NO: 64), the sod promoter was first amplified from the *C. glutamicum* ATCC13032 genome with SEQ ID NO: 65 and SEQ ID NO: 66 in the same manner as described above. In addition, the upstream (left arm), the homologous arm, was amplified from the *C. glutamicum* ATCC13032 genome with SEQ ID NO: 71 and SEQ ID NO: 72, and the downstream (right arm) was amplified from the *C. glutamicum* ATCC13032 genome with SEQ ID NO: 73 and SEQ ID NO: 74. These three amplified sequences were subjected to overlapping PCR with SEQ ID NO: 71 and SEQ ID NO: 74 and inserted by Gibson assembly into pK19mob-sacB cleaved with BamHI and PstI to produce the final vector pK19-msb-aroB.

TABLE 17

| SEQ ID NO: | Base sequence |
|---|---|
| SEQ ID NO: 65 | 5'-AACCCTACTTAGCTGCCAAT-3' |
| SEQ ID NO: 66 | 5'- GGGTAAAAAATCCTTTCGTAGG-3' |
| SEQ ID NO: 67 | 5'- CCAAGCTTGCATGCCTGCAGTTTGGGCTCACACATTT CTG-3' |
| SEQ ID NO: 68 | 5'- ATTGGCAGCTAAGTAGGGTTCCTCTAAACCTTCGAAT TTC-3' |
| SEQ ID NO: 69 | 5'- TACGAAAGGATTTTTTACCCATGGAGCGTAATGAAGT GAA-3' |
| SEQ ID NO: 70 | 5'- AGCTCGGTACCCGGGGATCCTAGGTTGCCACCTCTTC GTA-3' |

TABLE 17-continued

| SEQ ID NO: | Base sequence |
|---|---|
| SEQ ID NO: 71 | 5'- CCAAGCTTGCATGCCTGCAGAACACTGAACTCGTCGACTCCG-3' |
| SEQ ID NO: 72 | 5'- ATTGGCAGCTAAGTAGGGTTGGGGCACGTTGCCTTTCGCT-3' |
| SEQ ID NO: 73 | 5'- TACGAAAGGATTTTTTACCCATGAGCGCAGTGCAGATTTT-3' |
| SEQ ID NO: 74 | 5'- AGCTCGGTACCCGGGGATCCAATACTGCGTCAGGCTCGTG-3' |

9-3. Vector for Production of *C. Glutamicum* Capable of Overproducing ANT

In order to convert aroK and aroB into potent sod promoters, a YTM3 strain was produced by sequential insertion of pK19-msb-aroK and pK19-msb-aroB into the YTM2 strain by the previously reported method (Park, S. H. et al., *Nat. Commun.* 5, 4618, 2018). In addition, the previously reported vectors pSY04 and pSY05 (Kim, et al., *Biotechnol. Bioeng.* 112, 416-421, 2015) were inserted into the YTM3 strain to convert the first codon of the pgi gene from ATG to GTG and convert the first codon of the zwf gene from GTG to ATG to thereby produce a YTM4 strain. Finally, the vector pSY06 (Kim, et al., *Biotechnol. Bioeng.* 112, 416-421, 2015) was inserted into the YTM4 strain to convert the existing tkt promoter into a potent sod promoter and thereby to produce a YTM5 strain.

9-4. Overexpression of Feedback-Resistant DHAP Synthesis Gene in Mutant *C. Glutamicum*

As shown in Example 4-1, the mutant of the feedback-resistant DAHP synthesis gene expressed by aroG$^{fbr}$ promotes the first step involved in the polymerization of E4P and PEP in the shikimate pathway (SHK pathway). In order to overexpress the variant of the feedback-resistant DAHP synthesis gene, a pEKG vector overexpressing aroG$^{S180F}$, that is, a feedback-resistant aroG, was produced. aroG$^{S180F}$ was produced in *E. coli* W3110 by an overlapping PCR method. aroG$^{S180F}$ was amplified with SEQ ID NO: 75 and SEQ ID NO: 76 and inserted into pEKEx1 vector cut with EcoRI and BamHI to produce a pEKG vector.

TABLE 18

| SEQ ID NO: | Base sequence |
|---|---|
| SEQ ID NO: 75 | 5'-AGACAGGAATTCATGAATTATCAGAACGACG-3' |
| SEQ ID NO: 76 | 5'-AGACAGGGATCCTTACCCGCGACGCGCTTT-3' |

9-5. Production of pSH36HTc Vector

Both the pH36HTc and pEKG vectors produced before have kanamycin markers. Therefore, pSH36HTc was produced by converting the marker of pH36HTc into spectinomycin. For this purpose, the aamt1$^{opt-Cgl}$ sequence was amplified from pH36HTc using SEQ ID NO: 77 and SEQ ID NO: 78 and inserted into the pCES208S vector cleaved with BamHI and NotI.

TABLE 19

| SEQ ID NO: | Base sequence |
|---|---|
| SEQ ID NO: 77 | 5'- AGACAGGGATCCATGCATCACCATCACCATCATCCTATGCGTATCGAACG -3' |
| SEQ ID NO: 78 | 5'- AGACAGGCGGCCGCTCAGACGTGGATGATAGC -3' |

9-6. Flask Culture of *C. Glutamicum*

Figure 13:
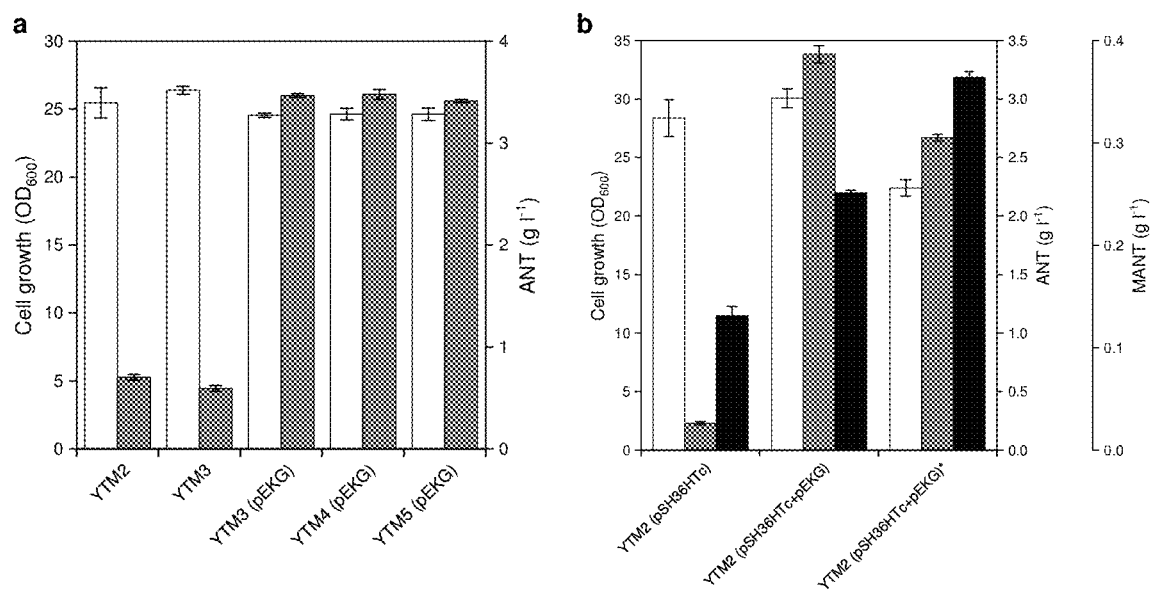
FIG. 13 shows the change of MANT productivity depending on the increase in ANT production by overexpression of feedback-resistant aroG$^{S180F}$ in a C. glutamicum mutant strain according to an embodiment of the present invention, wherein white represents strain growth, gray represents ANT production, black represents MANT production and represents two-phase culture.

The newly produced pEKG vector was inserted into the previously produced YTM2, YTM3, YTM4 and YTM5 strains and ANT production was first observed. The result showed that ANT production was more effective through pEKG insertion than through genome manipulation (FIG. 13 in part a). Therefore, in the case of MANT, the introduction of pEKG and pSH36HTc overexpressing aroG$^{S180F}$ into the YTM2 strain resulted in higher MANT productivity of 251.2±2.5 mg/L, and 2-phase extraction flask culture resulted in higher MANT productivity of 364.1±5.4 mg/L (FIG. 13 in part b).

Example 10 Manipulation of Availability of Co-Substrate SAM to Improve Production in *C. Glutamicum*

10-1. MetK Overexpression to Improve Production of Co-Substrate SAM

First, metK was overexpressed to over-produce SAM as a co-substrate in *C. glutamicum*.

First, metK$^{G1A}$ was amplified from the *C. glutamicum* ATCC13032 genome using SEQ ID NO: 79 and SEQ ID NO: 80, and was inserted into a pTac15K vector cut with EcoRI and PstI to produce a pTac-metK (Cgl) vector. Then, the tac-metK$^{G1A}$-terminator cassette was amplified with SEQ ID NO: 81 and SEQ ID NO: 82 and inserted into a pEKG vector cut with DraI to produce a pEKGK vector.

TABLE 20

| SEQ ID NO: | Base sequence |
|---|---|
| SEQ ID NO: 79 | 5'-AGACAGGAATTCATGGCTCAGCCAACCGCCGTC-3' |
| SEQ ID NO: 80 | 5'-AGACAGCTGCAGTTAGGCCAACTTGAGGGCTG-3' |
| SEQ ID NO: 81 | 5'- GTTTTCGCCCCGAAGAACGTTTTCCAATGATGAGCACTTTTGAGCTGTTGACAATTAATC -3' |
| SEQ ID NO: 82 | 5'- CGTCAACACGGGATAATACCGCGCCACATAGCAGAACTTTTTAGGCCAACTTGAGGGC -3' |

Figure 14:
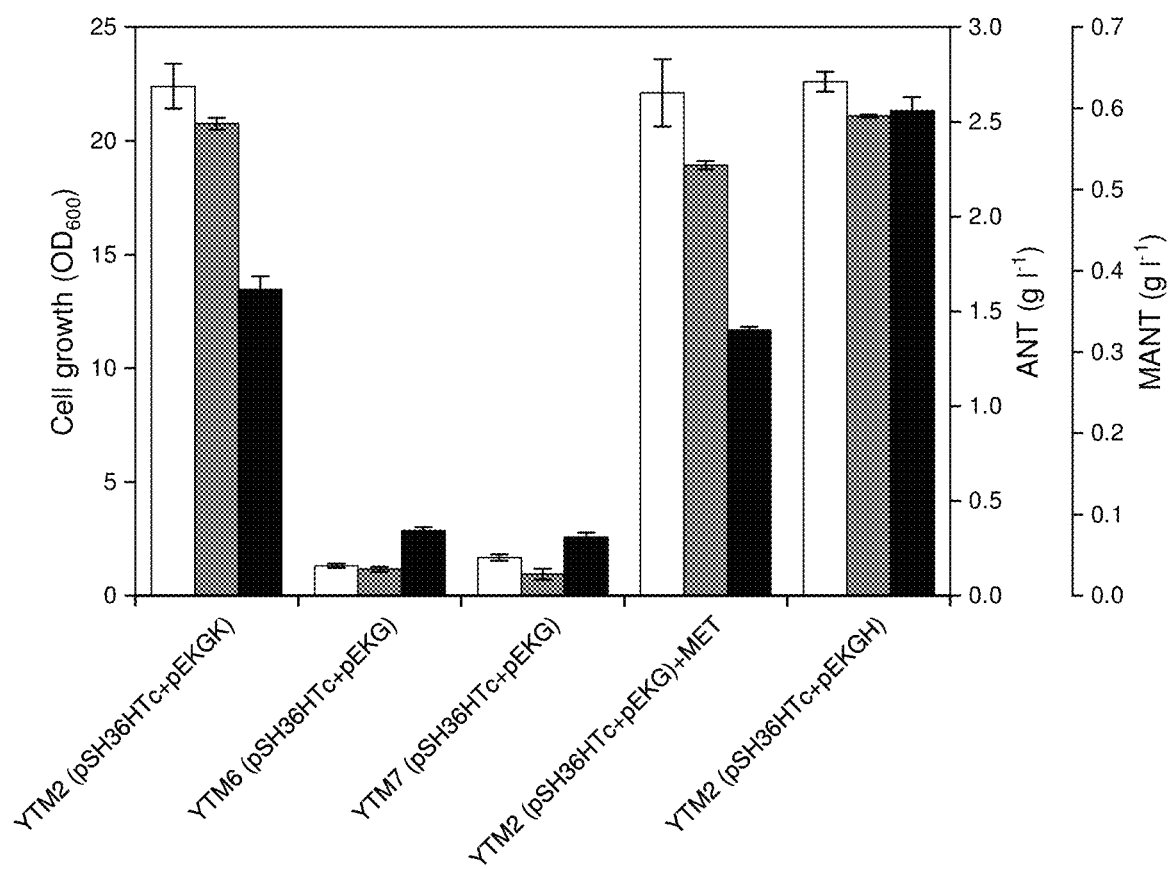
FIG. 14 shows the effect of manipulation of availability of co-substrate SAM in the C. glutamicum mutant strain according to an embodiment of the present invention on MANT productivity, wherein white represents strain growth, gray represents ANT production and black represents MANT production.

The pEKGK vector and the previously produced pSH36HTc vector were inserted into the YTM2 strain and the production of MANT was then observed. As a result, the production of MANT through two-phase flask culture could be further improved to 377.0±16.2 mg/L (FIG. 14).

10-2. Production of Vector for Deletion of Transcription Regulator to Improve Production of Co-Substrate SAM The following vectors were produced to delete the mcbR and Ncgl2640 genes known to be involved in MET biosynthesis.

For the mcbR deletion, the upstream (left arm), a homologous arm, was amplified from the *C. glutamicum* ATCC13032 genome with SEQ ID NO: 83 and SEQ ID NO:

84, and the downstream (right arm) was amplified from the *C. glutamicum* ATCC13032 genome with SEQ ID NOs: 85 and SEQ ID NO: 86. In addition, these two amplified sequences were subjected to overlapping PCR with SEQ ID NO: 83 and SEQ ID NO: 86 and were assembled to pK19mob-sacB cleaved with BamHI and PstI by Gibson assembly to produce the final vector pK19-msb-mcbR.

For Ncgl2640 deletion, the upstream (left arm), a homologous arm, was amplified from the *C. glutamicum* ATCC13032 genome with SEQ ID NO: 87 and SEQ ID NO: 88, and the downstream (right arm) was amplified from the *C. glutamicum* ATCC13032 genome with SEQ ID NO: 89 and SEQ ID NO: 90. These two amplified sequences were subjected to overlapping PCR with SEQ ID NO: 83 and SEQ ID NO: 86 and were assembled to pK19mob-sacB cleaved with BamHI and PstI by Gibson assembly to produce the final vector pK19-msb-Ncgl2640.

In addition, the following vector was produced to further delete the metB gene encoding cystathionine-γ in L-isoleucine biosynthesis, which is involved in the competitive circuit.

For metB deletion, the upstream (left arm), a homologous arm, was amplified from the *C. glutamicum* ATCC13032 genome with SEQ ID NO: 91 and SEQ ID NO: 92, and the downstream (right arm) was amplified from the *C. glutamicum* ATCC13032 genome with SEQ ID NO: 93 and SEQ ID NO: 94. In addition, these two amplified sequences were subjected to overlapping PCR with SEQ ID NO: 91 and SEQ ID NO: 92 and were assembled to pK19mob-sacB cleaved with BamHI and PstI by Gibson assembly to produce the final vector pK19-msb-metB.

TABLE 21

| SEQ ID NO: | Base sequence |
|---|---|
| SEQ ID NO: 83 | 5'- CCAAGCTTGCATGCCTGCAGCGCAAATACCCAC TTACCGA-3' |
| SEQ ID NO: 84 | 5'- AAGAGTAAAAGCTGTTGGTGTTCCTTGATG-3' |
| SEQ ID NO: 85 | 5'- CACCAACAGCTTTTACTCTTGCCTGAAGCG-3' |
| SEQ ID NO: 86 | 5'- AGCTCGGTACCCGGGGATCCCACCGAAAGAAAA GGAGAAC-3' |
| SEQ ID NO: 87 | 5'- CCAAGCTTGCATGCCTGCAGTTCTTTCGGAAGA AGAATCC-3' |
| SEQ ID NO: 88 | 5'- GATGTTGATTCTTGAACTTGTGTTGGAAAT-3' |
| SEQ ID NO: 89 | 5'- CAAGTTCAAGAATCAACATCTGGTTTCCCC-3' |
| SEQ ID NO: 90 | 5'- AGCTCGGTACCCGGGGATCCAGGCAAAGATGCC CTCGTTT-3' |
| SEQ ID NO: 91 | 5'- CCAAGCTTGCATGCCTGCAGAGGTTATTGAGGG CCTGCTC-3' |
| SEQ ID NO: 92 | 5'- ATTCACGCTGAACGACCAGGAAATGGACGA-3' |
| SEQ ID NO: 93 | 5'- CCTGGTCGTTCAGCGTGAATCGATGCAGTG-3' |
| SEQ ID NO: 94 | 5'- AGCTCGGTACCCGGGGATCCAAAAAGCCCGCAC CCTGATT-3' | pK19-msb-mcbR and pK19-msb-Ncgl2640 were sequentially inserted into the YTM2 strain, and the mcbR and Ncgl2640 genes were deleted by the reported method (Park, S. H. et al., *Nat. Commun.* 5, 4618, 2018) to produce a YTM6 strain. In addition, pK19-msb-metB was inserted into the YTM6 strain and the metB gene was deleted therefrom in the same manner as above to produce a YTM7 strain.

10-3. MANT Productivity of Transcription Regulator-Deleted Strain to Improve Production of Co-Substrate SAM The pSH36HTc and pEKG vectors were inserted into the produced YTM6 and YTM7 strains, respectively, and MANT productivity was observed through two-phase extraction flask culture. As a result, these two strains exhibited severely inhibited cell growth, more particularly, YTM6 having pSH36HTc and pEKG vectors exhibited MANT productivity of 80.0±4.2 mg/L, and YTM7 having pSH36HTc and pEKG vectors exhibited MANT productivity of 72.3±5.5 mg/L (FIG. 14).

10-4. Addition of MET to Improve Production of Co-Substrate SAM

It had been observed before that the addition of MET, the precursor of SAM, had a positive effect on the production of MANT in *E. coli*. Thus, 10 mM of MET was added to the *C. glutamicum* YTM2 strain having the vectors pSH36HTc and pEKG that produced the highest amounts of MANT, and two-phase extraction flask culture was conducted. Unfortunately, the result showed a MANT productivity of 326.8±3.9 mg/L, which was lower than when there was no addition of MET (FIG. 14).

10-5. Improvement of SAM Recycling Pathways to Improve Production of Co-Substrate SAM The strategy to recycle S-ribosyl-l-homocysteine (SAH), obtained as a reaction product of the SAM reaction, to the SAM biosynthesis pathway was established (FIG. 1 in part b). First, in order to amplify sahH encoding SAH hydrolase, a vector was prepared as follows. The sahH gene was amplified from the *C. glutamicum* ATCC13032 genome with SEQ ID NO: 95 and SEQ ID NO: 96 and inserted into the pEKG vector cleaved with PstI to produce a pEKGH vector.

The pSH36HTc and pEKGH vectors were inserted into YTM2 strain, two-phase flask culture was conducted, and MANT productivity was observed. The result showed that a high MANT productivity of 596.9±16.7 mg/L was obtained.

TABLE 22

| SEQ ID NO: | Base sequence |
|---|---|
| SEQ ID NO: 95 | 5'-AAAGCGCGTCGCGGGTAAGGATCCGTCGACCTGCAAG AAGGAGATATACCATGGCACAGGTTATGGAC-3' |
| SEQ ID NO: 96 | 5'-TCTCTCATCCGCCAAAACAGCCAAGCTTGGCTGCATT AGTAGCGGTAGTGCTC-3' |

Example 11 Fed-Batch Fermentation Using *C. Glutamicum*

11-1. Production of MANT in *C. Glutamicum* Through Single-Phase Fed-Batch Fermentation First, the MANT productivity of YTM2 introduced with pSH36HTc and pEKGH vectors was observed using single-phase fed-batch fermentation. The fed-batch fermentation was conducted as follows.

Stock cells stored in a deep freezer at −80° C. were melted, was spread in BHIS plate medium (containing 37 g/L of brain heart infusion (BHI), 91 g/L of sorbitol 15 g/L of agar) supplemented with kanamycin and spectinomycin and incubated for 48 hours at 30° C. Then, a fresh colony was inoculated in 5 mL of BHIS medium (containing 37 g/L of brain heart infusion (BHI) and 91 g/L of sorbitol) in a 50 mL Falcon tube and incubated at 30° C. for 16 to 24 hours. 1 mL of the preculture solution was inoculated in 50 mL of CGXII medium (containing 20 g/L of $(NH_4)_2SO_4$, 5 g/L of urea, 1 g/L of $KH_2PO_4$, 1 g/L of $K_2HPO_4$, 0.25 g/L of $MgSO_4.7H_2O$, 42 g/L of 3-morpholinopropanesulfonic acid (MOPS), 13 mg/L of $CaCl_2.2H_2O$, 10 mg/L of $FeSO_4.7H_2O$, 14 mg/L of $MnSO_4.5H_2O$, 1 mg/L of $ZnSO_4.7H_2O$, 0.3 mg/L of $CuSO_4.5H_2O$, 0.02 mg/L of $NiCl_2.6H_2O$, 0.5 mg/L of biotin, 30 mg/L of protocatechuic acid and 0.5 mg/L of thiamine) in each of four 250 mL baffle flasks (fermenter seed) and then cultured in a 200 rpm shaking incubator at 30° C. for 24 hours. At this time, the initial glycerol concentration in the CGXII medium was set to 40 g/L, 10 g/L of a yeast extract was added thereto, and MOPS was excluded. Next, a total of 200 mL of the preculture solution was inoculated in 1.8 L of a CGXII fermentation medium (total volume 6 L fermenter) (starting $OD_{600}$=5.0-6.0), starting glucose was added in an amount of 80 g/L, L-tryptophan was added in an amount of 10 mg/L, and the MOPS was excluded. In addition, $MgSO_4$-$7H_2O$, biotin, thiamine, protocatechuic acid, kanamycin and spectinomycin were separately produced by filtering and then added. In addition, treatment with 1 mM of IPTG was performed when $OD_{600}$>=40 after at least 13 hours.

Figure 15:
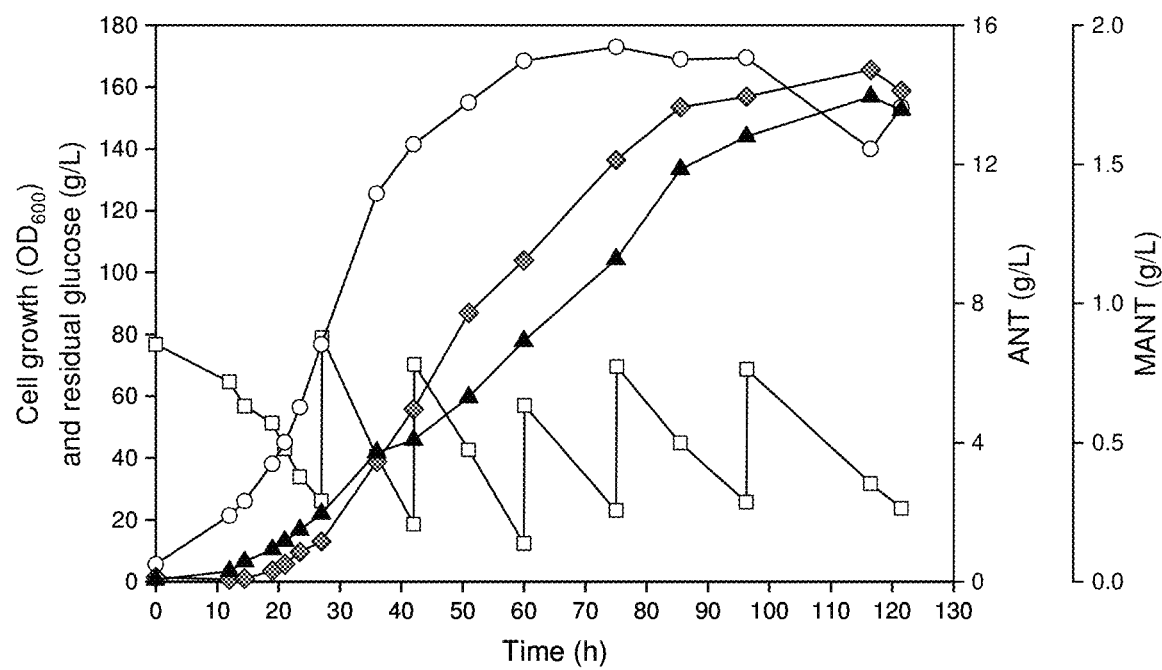
FIG. 15 shows the production of MANT through single-phase fed-batch fermentation in the C. glutamicum mutant strain according to an embodiment of the present invention, wherein the white circles represent cell growth (OD$_{600}$), the white squares represent residual glucose concentration (g/L), the gray diamonds represent ANT concentration (g/L) and the black triangles represent MANT concentration (g/L)

In fed-batch fermentation, the pH was maintained at 7.0 using ammonia water (28%, Junsei Chemical Co., Ltd., Tokyo, Japan), and temperature and agitation were maintained at 30° C. and 600 rpm, respectively, in a P-I-D mode (proportional-integral-derivative). Oxygen was injected along with air to maintain dissolved oxygen at 30%. The aeration rate was maintained at 1 vvm and foam that formed during culture was removed by treatment with antifoam 204 (Sigma-Aldrich). The feeding solution has the same composition as CGXII except 700 g/L of glucose and urea, MOPS, $K_2HPO_4$ and $KH_2PO_4$, and 150 mL of this was added when the residual glucose concentration was decreased to 10 g/L. The result of culture showed that 1.70 g/L of MANT production and 14.11 g/L of ANT production occurred (FIG. 15).

Figure 16:
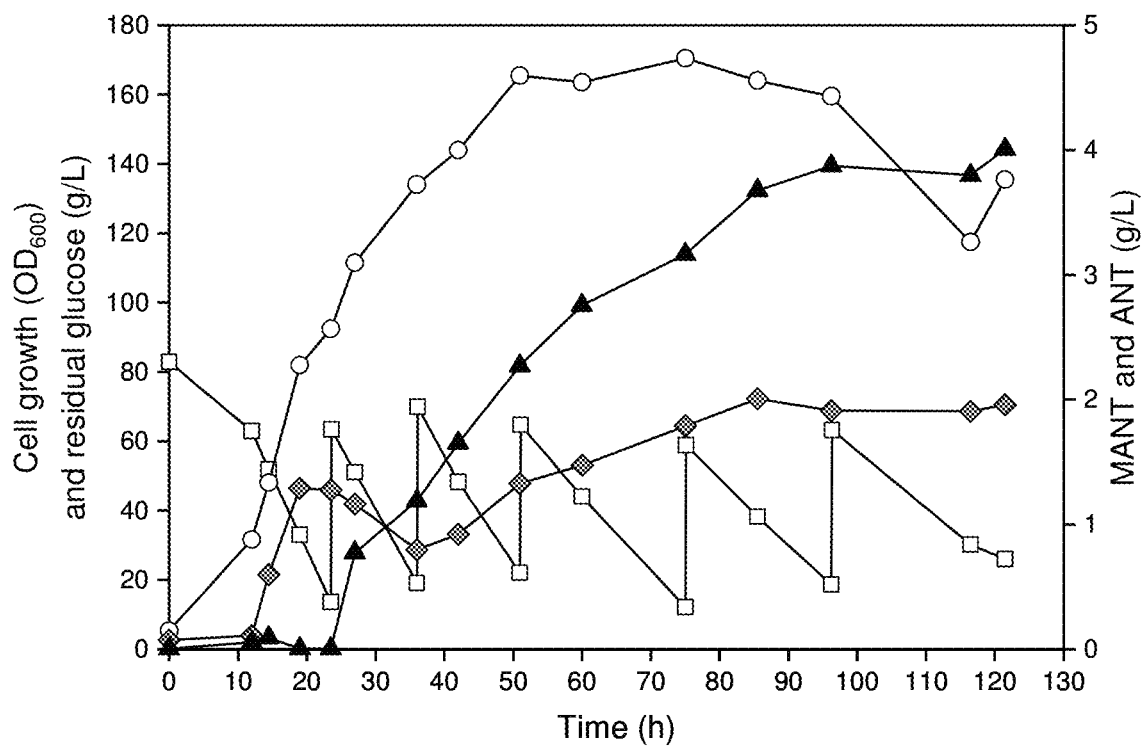
FIG. 16 shows MANT production through two-phase extraction fed-batch fermentation in the C. glutamicum mutant strain according to an embodiment of the present invention, wherein the white circles represent cell growth (OD$_{600}$), the white squares represent residual glucose concentration (g/L), the gray diamonds represent ANT concentration (g/L), and the black triangles represent MANT concentration (g/L)

11-2. MANT Production in *C. Glutamicum* Through Two-Phase Extraction Fed-Batch Fermentation MANT production was observed through two-phase fed batch fermentation using the same strain as in Example 11-1. The two-phase fed-batch fermentation was carried out under the same fermentation conditions as in Example 11-1, except that, during treatment with IPTG, 500 mL of tributyrin was added to the medium at a rate of 0.83 ml/min. As a result, MANT production of 4.01 g/L and ANT production of 1.96 g/L were obtained (FIG. 16). 10.06 g/L of succinic acid was also produced.

Figure 17:
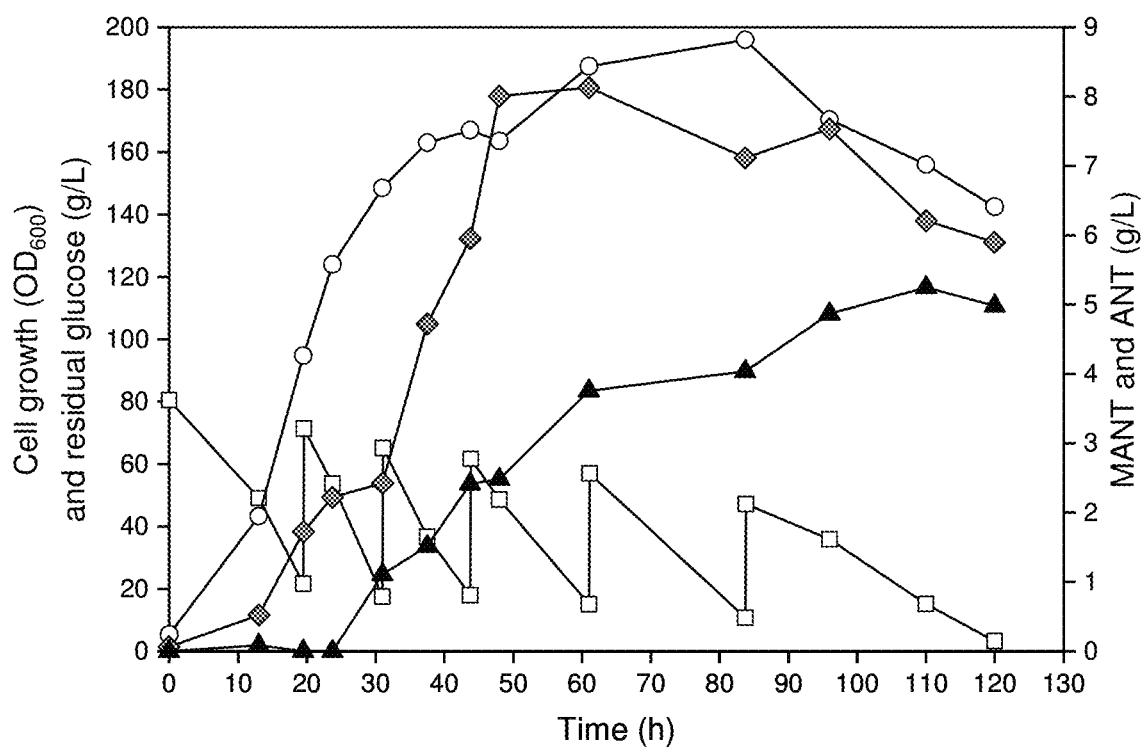
FIG. 17 shows MANT production through two-phase extraction fed-batch fermentation in the C. glutamicum mutant strain according to an embodiment of the present invention, wherein the white circles represent cell growth (OD$_{600}$), the white squares represent residual glucose concentration (g/L), the gray diamonds represent ANT concentration (g/L) and the black triangles represent MANT concentration (g/L)

11-3. Production of MANT in *C. Glutamicum* Through Two-Phase Extraction Fed-Batch Fermentation with Increased Dissolved Oxygen 10.06 g/L of succinic acid was also produced in Example 11-2. The reason for this was considered that an emulsion-like environment formed in the two-phase culture prevented the oxygen from being transferred to the cells. In order to solve this problem, fermentation conditions were changed as follows. Dissolved oxygen was increased from 30% to 50%. For this purpose, the agitation rate was increased up to 1,000 rpm from 600 rpm during fermentation. The remaining fermentation conditions were the same as in Example 11-2. As a result, 5.25 g/L of MANT was produced at 100 hours (FIG. 17).

11-4. MANT Production in *C. Glutamicum* Through Two-Phase Extraction Fed-Batch Fermentation of hdpA-Deficient Strain As a result of the fermentation in Example 11-3, glycerol was also produced. In order to reduce this, the hdpA gene encoding the main enzyme of the glycerol biosynthetic pathway was deleted.

For hdpA deletion, the upstream (left arm), the homologous arm, was amplified from the *C. glutamicum* ATCC13032 genome with SEQ ID NO: 97 and SEQ ID NO: 98, and the downstream (right arm) was amplified from the *C. glutamicum* ATCC13032 genome with SEQ ID NO: 99 and SEQ ID NO: 100. In addition, these two amplified sequences were subjected to overlapping PCR with SEQ ID NO: 97 and SEQ ID NO: 100 and were assembled to pK19mob-sacB cleaved with BamHI and PstI by Gibson assembly to produce the final vector pK19-msb-hdpA.

TABLE 23

Figure 18:
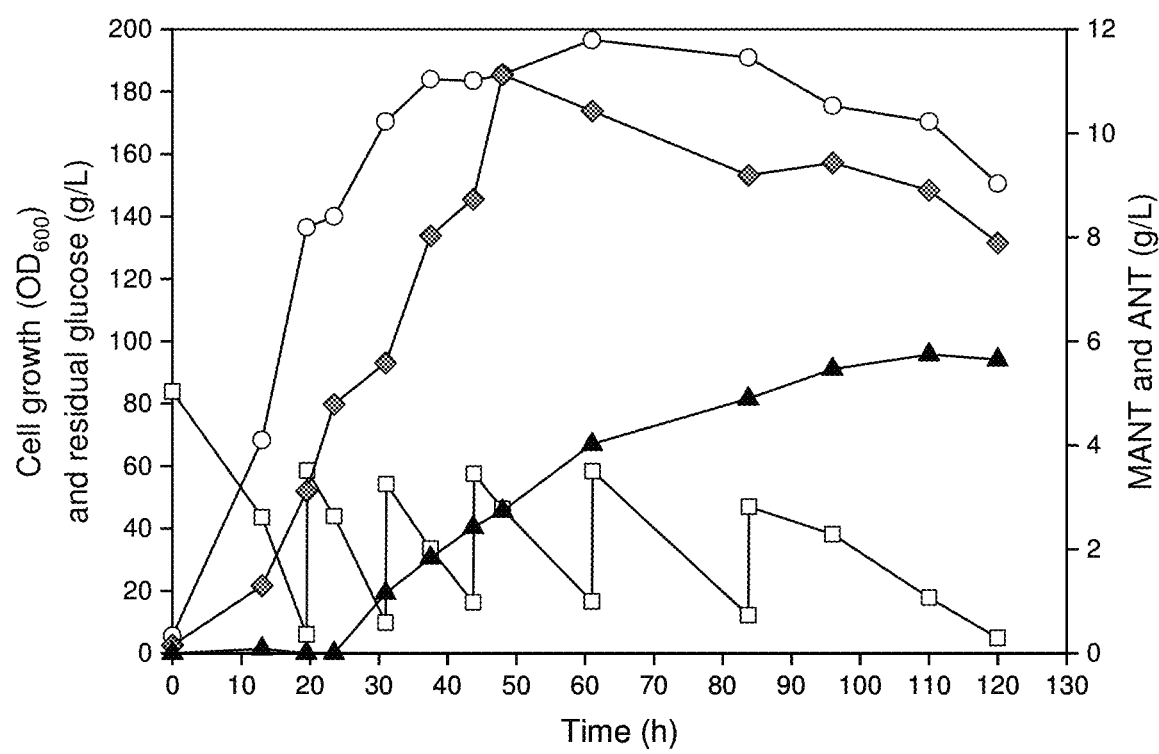
FIG. 18 shows MANT production through fed-batch fermentation in the C. glutamicum strain {YTM8 (pSH36HTc and pEKGH)} according to an embodiment of the present invention, wherein the white circles represent cell growth (OD$_{600}$), the white squares represent residual glucose concentration (g/L), the gray diamonds represent ANT concentration (g/L), and the black triangles represent MANT concentration (g/L)
Figure 19:
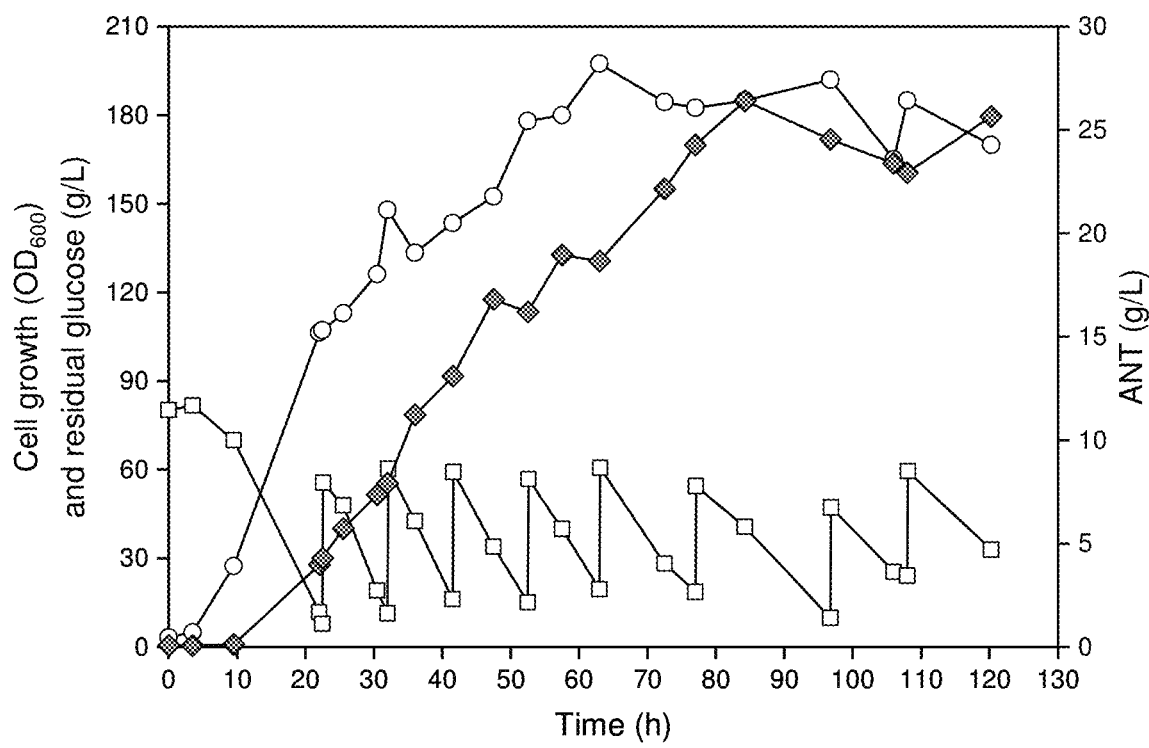
FIG. 19 shows ANT production through fed-batch fermentation in the C. glutamicum strain according to an embodiment of the present invention, wherein the white circles represent cell growth (OD$_{600}$), the white squares represent residual glucose concentration (g/L) and the gray diamonds represent ANT concentration (g/L).

| SEQ ID NO: | Base sequence |
|---|---|
| SEQ ID NO: 97 | 5'-CCAAGCTTGCATGCCTGCAGGTACGGTTTTTGCTAAATGC-3' |
| SEQ ID NO: 98 | 5'-CTACAGAATAAACACCATTGTCCCTGTTTT-3' |
| SEQ ID NO: 99 | 5'-CAATGGTGTTTATTCTGTAGGTCATGGCAT-3' |
| SEQ ID NO: 100 | 5'-AGCTCGGTACCCGGGGATCCTGTCGGAGATGAGTCCGATT-3' | pK19-msb-hdpA was inserted into the YTM2 strain and the hdpA gene was deleted therefrom by the reported method (Park, S. H. et al., *Nat. Commun* 5, 4618, 2018) to produce a YTM8 strain. The PSH36HTc and pEKGH vectors were inserted into the YTM8 strain, and MANT was produced under the same fermentation conditions as in Example 11-3. The result showed that MANT productivity of a high concentration of 5.74 g/L was obtained and that ANT was also produced at 7.89 g/L (FIG. 18)

Example 12 *C. Glutamicum* Fed-Batch Fermentation for ANT Production 12-1. Co-Production Through Two-Phase Extraction Fed-Batch Fermentation Many efforts have been made through bio-processes to produce ANT, which is an industrially useful chemical. In the present invention, when two-phase extraction fed-batch fermentation was performed at a neutral pH, all MANT was extracted with tributyrin and almost all ANT was extracted from an aqueous phase (96.9% for *E. coli* and 98.4% for *C. glutamicum*). Therefore, MANT and ANT can be co-produced using the two-phase extraction process of the present invention.

12-2. Production of Only ANT Through Single-Phase Fed-Fermentation

Meanwhile, in order to determine ANT production capacity alone, ANT production was observed through fed-batch fermentation using the ANT-overproducing strain (i.e., *C. glutamicum* YTM5 strain having PEKG) developed in the present invention. The fermentation conditions were the same as above except for the antibiotic spectinomycin in the medium of Example 11-1. As a result, ANT was produced at a high concentration of 26.4 g/L at 84 hours. This reports not only the first production of ANT in *C. glutamicum*, but also higher ANT productivity than that of ANT obtained from all microbial hosts to date.

Example 13 Additional Sequence Information

13-1. ammt1

Zea mays ammt1 original gene sequence
<SEQ ID NO: 1>
atgccgatgagaatcgagcgtgatctccacatggccatagggaacggaga
aactagctacacaaaaaattctaggattcaagagaaagctatgtttcaga
tgaagtcggtccttgaggaggccactagagcagtatgcacaactctcctc
ccacaaaccatggttgtggccgacttaggctgctcatcagggcctaacac
actgcgcttcgtcactgaggtgactagaatcatagctcaccattgcaagc
tggagcacaaccgacgacatgaccacctgccgcagcttcagttctttctg
aatgacctgcctggtaacgacttcaacaatctcttccagctcatcgagca
gttcaataagtcatcgacgacacacaagggagatgcagcaactgaggcac
tacagcctccttgctatatctccggattgccgggctcctactacactagg
atcttccctagcgaaagcgttcatcttttccactctctgttctgccttca
gtggcgctctcaggcaccagagcaactgaagggcacccaaaaatcatgcc
tagatatctacatcacaaagactatgtcaccatcgatggtgaagttgttt
caacagcagtttcagaaggacttctccctcttcctcaggctacgctatga
ggaactcgtgtctggtggccaaatggttctaacatttattggaaggaagc
atgaggatgtgttcactggagagtccaaccatctttacggattgcttgcg
cagtcactgaaatccctagttgatgagggtcttgtggagaaagaaaaact
tgagtcattctatcttccgatctactcaccgtcggttggtgaagtggagg
cgatagtgaagcaacttgggttgttcaacatgaatcatgttaaagtatttt
gagataaattgggatccctacgatgactcagaaggtgatgatgtgcataa
cagtattgagagtggtgaaaatgttgctaagtgcctacgcgcagttatgg
agccgctggtcgcaagccaatttggagaacgcatactcgacgagttattc
aaagagtacgctcgccgtgttgccaaacacccttgagaatgagaaaccaa
gcatgctgttcttgtcctatccatcgagaaagcaataattcatgtgtga Zea mays AMMT1 original amino acid sequence
<SEQ ID NO: 101>
MPMRIERDLHMAIGNGETSYTKNSRIQEKAMFQMKSVLEEATRAVCTTLL
PQTMVVADLGCSSGPNTLRFVTEVTRIIAHHCKLEHNRRHDHLPQLQFFL
NDLPGNDFNNLFQLIEQFNKSSTTHKGDAATEALQPPCYISGLPGSYYTR
IFPSESVHLFHSLFCLQWRSQAPEQLKGTQKSCLDIYITKTMSPSMVKLF
QQQFQKDFSLFLRLRYEELVSGGQMVLTFIGRKHEDVFTGESNHLYGLLA
QSLKSLVDEGLVEKEKLESFYLPIYSPSVGEVEAIVKQLGLFNMNHVKVF
EINWDPYDDSEGDDVHNSIESGENVAKCLRAVMEPLVASQFGERILDELF
KEYARRVAKHLENEKTKHAVLVLSIEKAIIHV E. coli codon-optimized sequence of Zea mays
derived aamt1 gene
<SEQ ID NO: 102>
atgccgatgcgtattgagcgcgacctgcacatggcgatcggtaatggcga
gaccagctacaccaagaacagccgtatccaagaaaagcgatgttccaga
tgaaaagcgtgctggaggaagcgaccgtgcggtttgcaccaccctgctg
ccgcaaaccatggttgttgcggacctgggttgcagcagcggtccgaacac cctgcgttttgtgaccgaggttacccgtatcattgcgcaccactgcaagc
tggaacacaaccgtcgtcacgatcacctgccgcaactgcaattctttctg
aacgacctgccgggtaacgatttcaacaacctgtttcaactgatcgagca
gttcaacaagagcagcaccacccataaaggtgatgcggcgaccgaagcgc
tgcaaccgccgtgctacatcagcggtctgccgggtagctactatacccgt
atttttccgagcgagagcgtgcacctgttccacagcctgttttgcctgca
atggcgtagccaggcgccggaacaactgaagggtacccagaagagctgcc
tggacatctacattaccaagaccatgagcccgagcatggttaaactgttc
cagcaacagtttcagaaggatttcagcctgtttctgcgtctgcgttatga
ggaactggtgagcggtggccaaatggttctgaccttcattggtcgtaaac
acgaggacgtgtttaccggtgaaagcaaccacctgtatggcctgctggcg
cagagcctgaagagcctggtggatgagggcctggttgagaaggaaaaact
ggaaagcttctacctgccgatctatagcccgagcgtgggtgaggttgaag
cgattgttaaacaactgggcctgttcaacatgaaccacgtgaaggttttt
gagatcaactgggacccgtacgacgatagcgaaggtgacgatgtgcacaa
cagcattgagagcggcgaaaacgttgcgaaatgcctgcgtgcggtgatgg
agccgctggttgcgagccagttcggcgaacgtatcctggatgagctgttt
aaagaatgcgcgtcgtgtggcgaagcacctggagaacgaaaagaccaa
acacgcggttctggttctgagcattgaaaaggcgattatccatgtgtga E. coli codon-optimized sequence of Zea mays
derived aamt1 gene
<SEQ ID NO: 103>
atgcctatgcgtatcgaacgtgacctccacatggctatcggtaacggcga
aacctcttacaccaaaaactctcgtattcaggaaaaagccatgttccaga
tgaaagtccgttctggaagaggccacccgcgcagtgtgcaccaccctgctg
ccacagaccatggttgttgctgatctgggctgctcctccggtccaaacac
cctgcgcttcgtcaccgaagttacccgcatcatcgcacaccactgcaagc
tggagcacaaccgtcgccacgaccacctgccacagctccagttcttcctg
aacgatctgccaggcaacgacttcaacaacctgttccagctgatcgaaca
gttcaacaagtcctccaccacccacaagggtgatgcagctaccgaggcac
tccagccaccatgctatatctccggcctgccaggttcctactacacccgc
atcttcccatccgaatccgtgcacctgttccactccctgttctgcctcca
gtggcgctcccaggctccagagcagctgaagggcacccagaagtcctgcc
tggatatctacatcaccaagaccatgtcccatccatggtcaagctgttc
cagcagcagttccagaaggacttctccctgttcctgcgcctgcgctacga
agagctggtgtccggcggtcagatggtcctgaccttcatcggccgcaagc
acgaagatgttttcaccggcgagtccaaccacctgtacggtctgctggct
cagtccctgaagtccctggttgacgaaggtctggtggaaaaggagaagct
ggagtccttctacctgccaatctactccccatccgtgggcgaagtcgagg
ccatcgtgaagcagctgggtctgttcaacatgaaccacgttaaggtgttc
gaaatcaactgggatccatacgatgactccgagggcgatgacgtccacaa
ctccatcgaatccggcgagaacgttgcaaagtgcctgcgcgctgtcatgg -continued aaccactggttgcttcccagttcggcgagcgcatcctggacgaactgttc aaggagtacgctcgtcgcgtcgccaagcacctggaaaacgaaaaaaccaa acacgcagtgcttgtgctgtccattgaaaaggctatcatccacgtctga 13-2. Promoters The sequence information of the promoters used in the present invention can be obtained from the following website:

http://parts.igem.org/Promoters/Catalog/Constitutive.

13-3. Sequence Information Used for E. Coli Recombinant Strains trpD gene sequence
<SEQ ID NO: 104>
atggctgacattctgctgctcgataatatcgactcttttacgtacaacctggca gatcagttgcgcagcaatgggcataacgtggtgatttaccgcaaccatattccggcgcaa accttaattgaacgcctggcgaccatgagcaatccggtgctgatgctttctcctggcccc ggtgtgccgagcgaagccggttgtatgccggaactcctcacccgcttgcgtggcaagctg cccattattggcatttgcctcggacatcaggcgattgtcgaagcttacgggggctatgtc ggtcaggcgggcgaaattctccacggtaaagcctccagcattgaacatgacggtcaggcg atgtttgccggattaacaaacccgctgccggtggcgcgttatcactcgctggttggcagt aacattccggccggtttaaccatcaacgcccatttttaatggcatggtgatggcagtacgt cacgatgcggatcgcgtttgtggattccagttccatccggaatccattctcaccacccag ggcgctcgcctgctggaacaaacgctggcctgggcgcagcagaaactagagccagccaac acgctgcaaccgattctggaaaaactgtatcaggcgcagacgcttagccaacaagaaagc caccagctgttttcagcggtggtgcgtggcgagctgaagccggaacaactggcggcggcg ctggtgagcatgaaaattcgcggtgagcacccgaacgagatcgccggggcagcaaccgcg ctactggaaaacgcagcgccgttcccgcgcccggattatctgtttgctgatatcgtcggt actggcggtgacggcagcaacagtatcaatatttctaccgccagtgcgtttgtcgccgcg gcctgtgggctgaaagtggcgaaacacggcaaccgtagcgtctccagtaaatctggttcg tccgatctgctggcggcgttcggtattaatcttgatatgaacgccgataaatcgcgccag gcgctggatgagttaggtgtatgtttcctctttgcgccgaagtatcacaccggattccgc cacgcgatgccggttcgccagcaactgaaaacccgcaccctgttcaatgtgctggggcca ttgattaacccggcgcatccgccgctggcgttaattggtgtttatagtccggaactggtg ctgccgattgccgaaaccttgcgcgtgctggggtatcaacgcgcggcggtggtgcacagc ggcgggatggatgaagtttcattacacgcgccgacaatcgttgccgaactgcatgacggc gaaattaaaagctatcagctcaccgcagaagactttggcctgacaccctaccaccaggag caactggcaggcggaacaccggaagaaaaccgtgacattttaacacgtttgttacaaggt aaaggcgacgccgcccatgaagcagccgtcgctgcgaacgtcgccatgttaatgcgcctg catggccatgaagatctgcaagccaatgcgcaaaccgttcttgaggtactgcgcagtggt tccgcttacgacagagtcaccgcactggcggcacgagggtaa trpD amino acid sequence
<SEQ ID NO: 105>
MADILLLDNIDSFTYNLADQLRSNGHNVVIYRNHIPAQTLIERLATMSNPVLML

SPGPGVPSEAGCMPELLTRLRGKLPIIGICLGHQAIVEAYGGYVGQAGEILHGKASSIEH

DGQAMFAGLTNPLPVARYHSLVGSNIPAGLTINAHFNGMVMAVRHDADRVCGFQFHPESI

LTTQGARLLEQTLAWAQQKLEPANTLQPILEKLYQAQTLSQQESHQLFSAVVRGELKPEQ

LAAALVSMKIRGEHPNEIAGAATALLENAAPFPRPDYLFADIVGTGGDGSNSINISTASA

FVAAACGLKVAKHGNRSVSSKSGSSDLLAAFGINLDMNADKSRQALDELGVCFLFAPKYH

TGFRHAMPVRQQLKTRTLFNVLGPLINPAHPPLALIGVYSPELVLPIAETLRVLGYQRAA

```
                                                     -continued
VVHSGGMDEVSLHAPTIVAELHDGEIKSYQLTAEDFGLTPYHQEQLAGGTPEENRDILTR

LLQGKGDAAHEAAVAANVAMLMRLHGHEDLQANAQTVLEVLRSGSAYDRVTALAARG pykA gene sequence
                                                      <SEQ ID NO: 106>
atgtccagaaggcttcgcagaacaaaaatcgttaccacgttagcccagcaaca gatcgcgataataatcttgaaaaagttatcgcggcgggtgccaacgttgtacgtatgaac tttctcacggctcgcctgaagatcacaaaatgcgcgcggataaagttcgtgagattgcc gcaaaactggggcgtcatgtggctattctgggtgacctccaggggcccaaaatccgtgta tccacctttaaagaaggcaaagttttcctcaatattggggataaattcctgctcgacgcc aacctgggtaaaggtgaaggcgacaaagaaaaagtcggtatcgactacaaaggcctgcct gctgacgtcgtgcctggtgacatcctgctgctggacgatggtcgcgtccagttaaaagta ctggaagttcagggcatgaaagtgttcaccgaagtcaccgtcggtggtcccctctccaac aataaaggtatcaacaaacttggcggcggtttgtcggctgaagcgctgaccgaaaaagac aaagcagacattaagactgcggcgttgattggcgtagattacctggctgtctccttccca cgctgtggcgaagatctgaactatgcccgtcgcctggcacgcgatgcaggatgtgatgcg aaaattgttgccaaggttgaacgtgcggaagccgtttgcagccaggatgcaatggatgac atcatcctcgcctctgacgtggtaatggttgcacgtggcgacctcggtgtggaaattggc gacccggaactggtcggcattcagaaagcgttgatccgtcgtgcgcgtcagctaaaccga gcggtaatcacggcgacccagatgatggagtcaatgattactaacccgatgccgacgcgt gcagaagtcatggacgtagcaaacgccgttctggatggtactgacgctgtgatgctgtct gcagaaactgccgctgggcagtatccgtcagaaaccgttgcagccatggcgcgcgtttgc ctgggtgcggaaaaaatcccgagcatcaacgtttctaaacaccgtctggacgttcagttc gacaatgtggaagaagctattgccatgtcagcaatgtacgcagctaaccacctgaaaggc gttacggcgatcatcaccatgaccgaatcgggtcgtaccgcgctgatgacctcccgtatc agctctggtctgccaattttcgccatgtcgcgccatgaacgtacgctgaacctgactgct ctctatcgtggcgttacgccggtgcactttgatagcgctaatgacggcgtagcagctgcc agcgaagcggttaatctgctgcgcgataaaggttacttgatgtctggtgacctggtgatt gtcacccagggcgacgtgatgagtaccgtgggttctactaataccacgcgtattttaacg gtagagtaa pykA amino acid sequence
                                                      <SEQ ID NO: 107>
MSRRLRRTKIVTTLGPATDRDNNLEKVIAAGANVVRMNFSHGSPEDHKMRADKV

REIAAKLGRHVAILGDLQGPKIRVSTFKEGKVFLNIGDKFLLDANLGKGEGDKEKVGIDY

KGLPADVVPGDILLLDDGRVQLKVLEVQGMKVFTEVTVGGPLSNNKGINKLGGGLSAEAL

TEKDKADIKTAALIGVDYLAVSFPRCGEDLNYARRLARDAGCDAKIVAKVERAEAVCSQD

AMDDIILASDVVMVARGDLGVEIGDPELVGIQKALIRRARQLNRAVITATQMMESMITNP

MPTRAEVMDVANAVLDGTDAVMLSAETAAGQYPSETVAAMARVCLGAEKIPSINVSKHRL

DVQFDNVEEAIAMSAMYAANHLKGVTAIITMTESGRTALMTSRISSGLPIFAMSRHERTL

NLTALYRGVTPVHFDSANDGVAAASEAVNLLRDKGYLMSGDLVIVTQGDVMSTVGSTNTT

RILTVE pykF gene sequence
                                                      <SEQ ID NO: 108>
atgaaaaagaccaaaattgtttgcaccatcggaccgaaaaccgaatctgaagag atgttagctaaaatgctggacgctggcatgaacgttatgcgtctgaacttctctcatggt
```

-continued

```
gactatgcagaacacggtcagcgcattcagaatctgcgcaacgtgatgagcaaaactggt aaaaccgccgctatcctgcttgataccaaaggtccggaaatccgcaccatgaaactggaa ggcggtaacgacgtttctctgaaagctggtcagacctttactttcaccactgataaatct gttatcggcaacagcgaaatggttgcggtaacgtatgaaggtttcactactgacctgtct gttggcaacaccgtactggttgacgatggtctgatcggtatggaagttaccgccattgaa ggtaacaaagttatctgtaaagtgctgaacaacggtgacctgggcgaaaacaaaggtgtg aacctgcctggcgtttccattgctctgccagcactggctgaaaaagacaaacaggacctg atctttggttgcgaacaaggcgtagactttgttgctgcttcctttattcgtaagcgttct gacgttatcgaaatccgtgagcacctgaaagcgcacggcggcgaaaacatccacatcatc tccaaaatcgaaaaccaggaaggcctcaacaacttcgacgaaatcctcgaagcctctgac ggcatcatggttgcgcgtggcgacctgggtgtagaaatcccggtagaagaagttatcttc gcccagaagatgatgatcgaaaaatgtatccgtgcacgtaaagtcgttatcactgcgacc cagatgctggattccatgatcaaaaacccacgcccgactcgcgcagaagccggtgacgtt gcaaacgccatcctcgacggtactgacgcagtgatgctgtctggtgaatccgcaaaaggt aaatacccgctggaagcggtttctatcatggcgaccatctgcgaacgtaccgaccgcgtg atgaacagccgtctcgagttcaacaatgacaaccgtaaactgcgcattaccgaagcggta tgccgtggtgccgttgaaactgctgaaaaactggatgctccgctgatcgtggttgctact cagggcggtaaatctgctcgcgcagtacgtaaatacttcccggatgccaccatcctggca ctgaccaccaacgaaaaaacggctcatcagttggtactgagcaaaggcgttgtgccgcag cttgttaaagagatcacttctactgatgatttctaccgtctgggtaaagaactggctctg cagagcggtctggcacacaaaggtgacgttgtagttatggtttctggtgcactggtaccg agcggcactactaacaccgcatctgttcacgtcctgtaa
``` pykF amino acid sequence
<SEQ ID NO: 109>
```
MKKTKIVCTIGPKTESEEMLAKMLDAGMNVMRLNFSHGDYAEHGQRIQNLRNVM

SKTGKTAAILLDTKGPEIRTMKLEGGNDVSLKAGQTFTFTTDKSVIGNSEMVAVTYEGFT

TDLSVGNTVLVDDGLIGMEVTAIEGNKVICKVLNNGDLGENKGVNLPGVSIALPALAEKD

KQDLIFGCEQGVDFVAASFIRKRSDVIEIREHLKAHGGENIHIISKIENQEGLNNFDEIL

EASDGIMVARGDLGVEIPVEEVIFAQKMMIEKCIRARKVVITATQMLDSMIKNPRPTRAE

AGDVANAILDGTDAVMLSGESAKGKYPLEAVSIMATICERTDRVMNSRLEFNNDNRKLRI

TEAVCRGAVETAEKLDAPLIVVATQGGKSARAVRKYFPDATILALTTNEKTAHQLVLSKG

VVPQLVKEITSTDDFYRLGKELALQSGLAHKGDVVVMVSGALVPSGTTNTASVHVL
``` aroG$^{fbr}$ gene sequence
<SEQ ID NO: 110>
```
atgaattatcagaacgacgatttacgcatcaaagaaatcaaagagttacttcct cctgtcgcattgctggaaaaattccccgctactgaaaatgccgcgaatacggttgcccat gcccgaaaagcgatccataagatcctgaaaggtaatgatgatcgcctgttggttgtgatt ggcccatgctcaattcatgatcctgtcgcggcaaaagagtatgccactcgcttgctggcg ctgcgtgaagagctgaaagatgagctggaaatcgtaatgcgcgtctattttgaaaagccg cgtaccacggtgggctggaagggctgattaacgatccgcatatggataatagcttccag atcaacgacggtctgcgtatagcccgtaaattgctgcttgatattaacgacagcggtctg ccagcggcaggtgagtttctcaatatgatcacccccacaatatctcgctgacctgatgagc tggggcgcaattggcgcacgtaccaccgaatcgcaggtgcaccgcgaactggcatcaggg
```

```
ctttcttgtccggtcggcttcaaaaatggcaccgacggtacgattaaagtggctatcgat gccattaatgccgccggtgcgccgcactgcttcctgtccgtaacgaaatgggggcattcg gcgattgtgaataccagcggtaacggcgattgccatatcattctgcgcggcggtaaagag cctaactacagcgcgaagcacgttgctgaagtgaaagaagggctgaacaaagcaggcctg ccagcacaggtgatgatcgatttcagccatgctaactcgtccaaacaattcaaaaagcag atggatgtttgtgctgacgtttgccagcagattgccggtggcgaaaaggccattattggc gtgatggtggaaagccatctggtggaaggcaatcagagcctcgagagcggggagccgctg gcctacggtaagagcatcaccgatgcctgcatcggctgggaagataccgatgctctgtta cgtcaactggcgaatgcagtaaaagcgcgtcgcgggtaa
``` aroG<sup>fbr</sup> amino acid sequence
<SEQ ID NO: 111>

```
MNYQNDDLRIKEIKELLPPVALLEKFPATENAANTVAHARKAIHKILKGNDDRL

LVVIGPCSIHDPVAAKEYATRLLALREELKDELEIVMRVYFEKPRTTVGWKGLINDPHMD

NSFQINDGLRIARKLLLDINDSGLPAAGEFLNMITPQYLADLMSWGAIGARTTESQVHRE

LASGLSCPVGFKNGTDGTIKVAIDAINAAGAPHCFLSVTKWGHSAIVNTSGNGDCHIILR

GGKEPNYSAKHVAEVKEGLNKAGLPAQVMIDFSHANSSKQFKKQMDVCADVCQQIAGGEK

AIIGVMVESHLVEGNQSLESGEPLAYGKSITDACIGWEDTDALLRQLANAVKARRG
``` metA<sup>fbr</sup> gene sequence
<SEQ ID NO: 112>

```
atgccgattcgtgtgccggacgagctacccgccgtcaatttcttgcgtgaagaa aacgtctttgtgatgacaacttcttgcgtctggtcaggaaattcgtccacttaaggtt ctgatccttaacctgatgccgaagaagattgaaactgaaaatcagtttctgcgcctgctt tcaaactcacctttgcaggtcgatattcagctgttgcgcatcgattcccgtgaatcgcgc aacacgcccgcagagcatctgaacaacttctactgtaactttgaagatattcaggatcag aactttgacggtttgattgtaactggtgcgccgctgggcctggtggagtttaatgatgtc gcttactggccgcagatcaaacaggtgctggagtggtcgaaagatcacgtcacctcgacg ctgtttgtctgctgggcggtacaggccgcgctcaatatcctctacggcattcctaagcaa actcgcaccgaaaaactctctggcgtttacgagcatcatattctccatcctcatgcgctt ctgacgcgtggctttgatgattcattcctggcaccgcattcgcgctatgctgactttccg gcagcgttgattcgtgattacaccgatctggaaattctggcagagacggaagaaggggat gcatatctgtttgccagtaaagataagcgcattgcctttgtgacgggccatcccgaatat gatgcgcaaacgctggcgcaggaattttccgcgatgtggaagccggactagacccggat gtaccgtataactatttcccgcacaatgatccgcaaaatacaccgcgagcgagctggcgt agtcacggtaatttactgtttaccaactggctcaactattacgtctaccagagcacgcta tacgatctacggcacatgaatccaacgctggattaa
``` metA<sup>fbr</sup> amino acid sequence
<SEQ ID NO: 113>

```
MPIRVPDELPAVNFLREENVFVMTTSCASGQEIRPLKVLILNLMPKKIETENQF

LRLLSNSPLQVDIQLLRIDSRESRNTPAEHLNNFYCNFEDIQDQNFDGLIVTGAPLGLVE

FNDVAYWPQIKQVLEWSKDHVTSTLFVCWAVQAALNILYGIPKQTRTEKLSGVYEHHILH

PHALLTRGFDDSFLAPHSRYADFPAALIRDYTDLEILAETEEGDAYLFASKDKRIAFVTG

HPEYDAQTLAQEFFRDVEAGLDPDVPYNYFPHNDPQNTPRASWRSHGNLLFTNWLNYYVY

QSTLYDLRHMNPTLD-
``` cysE^fbr gene sequence
<SEQ ID NO: 114>
atgtcgtgtgaagaactggaaattgtctggaacaatattaaagccgaagccaga acgctggcggactgtgagccaatgctggccagttttaccacgcgacgctactcaagcac gaaaaccttggcagtgcactgagctacatgctggcgaacaagctgtcatcgccaattatg cctgctattgctatccgtgaagtggtggaagaagcctacgccgctgacccggaaatgatc gcctctgcggcctgtgatattcaggcggtgcgtacccgcgacccggcaagacccaaatac tcaaccccgttgttatacctgaagggttttcatgccttgcaggcctatcgcatcggtcac tggttgtggaatcaggggcgtcgcgcactggcaatctttctgcaaaaccaggtttctgtg acgttccaggtcgatattcacccggcagcaaaaattggtcgcggtatcatgcttgaccac gcgacaggcatcgtcgttggtgaaacggcggtgattgaaaacgacgtatcgattctgcaa tctgtgacgcttggcggtacgggtaaatctggtggtgaccgtcacccgaaaattcgtgaa ggtgtgatgattggcgcgggcgcgaaaatcctcggcaatattgaagttgggcgcggcgcg aagattggcgcaggttccgtggtgctgcaaccggtgccgccgcataccaccgccgctggc gttccggctcgtattgtcggtaaaccagacagcgataagccatcaatggatatggaccag catttcaacggtattaaccatacatttgagtatggggatgggatctaa cysE^fbr amino acid sequence
<SEQ ID NO: 115>
MSCEELEIVWNNIKAEARTLADCEPMLASFYHATLLKHENLGSALSYMLANKLS

SPIMPAIAIREVVEEAYAADPEMIASAACDIQAVRTRDPARPKYSTPLLYLKGFHALQAY

RIGHWLWNQGRRALAIFLQNQVSVTFQVDIHPAAKIGRGIMLDHATGIVVGETAVIENDV

SILQSVTLGGTGKSGGDRHPKIREGVMIGAGAKILGNIEVGRGAKIGAGSVVLQPVPPHT

TAAGVPARIVGKPDSDKPSMDMDQHFNGINHTFEYGDGItrpE^fbr gene sequence
<SEQ ID NO: 116>
atgcaaacacaaaaaccgactctcgaactgctaacctgcgaaggcgcttatcgc gacaatcccaccgcgcttttcaccagttgtgtggggatcgtccggcaacgctgctgctg gaattcgcagatatcgacagcaaagatgatttaaaaagcctgctgctggtagacagtgcg ctgcgcattacagctttaggtgacactgtcacaatccaggcactttccggcaacggcgaa gccctcctggcactactggataacgccctgcctgcgggtgtggaaagtgaacaatcacca aactgccgtgtgctgcgcttcccccctgtcagtccactgctggatgaagacgcccgctta tgctcccttcggttttttgacgctttccgtttattgcagaatctgttgaatgtaccgaag gaagaacgagaagccatgttcttcggcggcctgttctcttatgaccttgtggcgggattt gaagatttaccgcaactgtcagcggaaaataactgccctgatttctgttttttatctcgct gaaacgctgatggtgattgaccatcagaaaaaaagcacccgtattcaggccagcctgttt gctccgaatgaagaagaaaacaacgtctcactgctcgcctgaacgaactacgtcagcaa ctgaccgaagccgccgccgctgccagtggtttccgtgccgcatatgcgttgtgaatgt aatcagagcgatgaagagttcggtggcgtagtgcgtttgttgcaaaaagcgattcgcgct ggagaaattttccaggtggtgccatctcgccgtttctctctgccctgcccgtcaccgctg gcggcctattacgtgctgaaaaagagtaatcccagcccgtacatgtttttttatgcaggat aatgatttcaccctatttggcgcgtcgccggaaagctcgctcaagtatgatgccaccagc cgccagattgagatctacccgattgccggaacacgcccacgcggtcgtcgcgccgatggt tcactggacagagatctcgacagccgtattgaactggaaatgcgtaccgatcataaagag ctgtctgaacatctgatgctggttgatctcgcccgtaatgatctggcacgcatttgcacc -continued

```
cccggcagccgctacgtcgccgatctcaccaaagttgaccgttattcctatgtgatgcac ctcgtctctcgcgtagtcggcgaactgcgtcacgatcttgacgccctgcacgcttatcgc gcctgtatgaatatggggacgttaagcggtgcgccgaaagtacgcgctatgcagttaatt gccgaggcggaaggtcgtcgccgcggcagctacggcggcgcggtaggttatttcaccgcg catggcgatctcgacacctgcattgtgatccgctcggcgctggtggaaaacggtatcgcc accgtgcaagcgggtgctggtgtagtccttgattctgttccgcagtcggaagccgacgaa acccgtaacaaagcccgcgctgtactgcgcgctattgccaccgcgcatcatgcacaggag actttctga
``` trpE<sup>fbr</sup> amino acid sequence
<SEQ ID NO: 117>
```
MQTQKPTLELLTCEGAYRDNPTALFHQLCGDRPATLLLEFADIDSKDDLKSLLL

VDSALRITALGDTVTIQALSGNGEALLALLDNALPAGVESEQSPNCRVLRFPPVSPLLDE

DARLCSLSVFDAFRLLQNLLNVPKEEREAMFFGGLFSYDLVAGFEDLPQLSAENNCPDFC

FYLAETLMVIDHQKKSTRIQASLFAPNEEEKQRLTARLNELRQQLTEAAPPLPVVSVPHM

RCECNQSDEEFGGVVRLLQKAIRAGEIFQVVPSRRFSLPCPSPLAAYYVLKKSNPSPYMF

FMQDNDFTLFGASPESSLKYDATSRQIEIYPIAGTRPRGRRADGSLDRDLDSRIELEMRT

DHKELSEHLMLVDLARNDLARICTPGSRYVADLTKVDRYSYVMHLVSRVVGELRHDLDAL

HAYRACMNMGTLSGAPKVRAMQLIAEAEGRRRGSYGGAVGYFTAHGDLDTCIVIRSALVE

NGIATVQAGAGVVLDSVPQSEADETRNKARAVLRAIATAHHAQETF-
``` ppsA gene sequence
<SEQ ID NO: 118>
```
atgtccaacaatggctcgtcaccgctggtgctttggtataaccaactcggcatg aatgatgtagacagggttgggggcaaaaatgcctccctgggtgaaatgattactaatctt tccggaatgggtgtttccgttccgaatggtttcgccacaaccgccgacgcgtttaaccag tttctggaccaaagcggcgtaaaccagcgcatttatgaactgctggataaaacggatatt gacgatgttactcagcttgcgaaagcgggcgcgcaaatccgccagtggattatcgacact cccttccagcctgagctggaaaacgccatccgcgaagcctatgcacagctttccgccgat gacgaaaacgcctcttttgcggtgcgctcctccgccaccgcagaagatatgccggacgct tcttttgccggtcagcaggaaaccttcctcaacgttcagggttttgacgccgttctcgtg gcagtgaaacatgtatttgcttctctgtttaacgatcgcgccatctcttatcgtgtgcac cagggttacgatcaccgtggtgtggcgctctccgccggtgttcaacggatggtgcgctct gacctcgcatcatctggcgtgatgttctccattgataccgaatccggctttgaccaggtg gtgtttatcacttccgcatggggccttggtgagatggtcgtgcagggtgcggttaacccg gatgagttttacgtgcataaaccgacactggcggcgaatcgcccggctatcgtgcgccgc accatggggtcgaaaaaaatccgcatggtttacgcgccgacccaggagcacggcaagcag gttaaaatcgaagacgtaccgcaggaacagcgtgacatcttctcgctgaccaacgaagaa gtgcaggaactggcaaaacaggccgtacaaattgagaaacactacggtcgcccgatggat attgagtgggcgaaagatggccacaccggtaaactgttcattgtgcaggcgcgtccggaa accgtgcgctcacgcggtcaggtcatggagcgttatacgctgcattcacagggtaagatt atcgccgaaggccgtgctatcggtcatcgcatcggtgcgggtccggtgaaagtcatccat gacatcagcgaaatgaaccgcatcgaacctggcgacgtgctggttactgacatgaccgac ccggactgggaaccgatcatgaagaaagcatctgccatcgtcaccaaccgtggcggtcgt acctgtcacgcggcgatcatcgctcgtgaactgggcattccggcggtagtgggctgtgga
```

-continued

```
gatgcaacagaacggatgaaagacggtgagaacgtcactgtttcttgtgccgaaggtgat accggttacgtctatgcggagttgctggaatttagcgtgaaaagctccagcgtagaaacg atgccggatctgccgttgaaagtgatgatgaacgtcggtaacccggaccgtgctttcgac ttcgcctgcctaccgaacgaaggcgtgggccttgcgcgtctggaatttatcatcaaccgt atgattggcgtccacccacgcgcactgcttgagtttgacgatcaggaaccgcagttgcaa aacgaaatccgcgagatgatgaaaggttttgattctccgcgtgaattttacgttggtcgt ctgactgaagggatcgcgacgctgggtgccgcgttttatccgaagcgcgtcattgtccgt ctctctgattttaaatcgaacgaatatgccaacctggtcggtggtgagcgttacgagcca gatgaagagaacccgatgctcggcttccgtggcgcgggccgctatgtttccgacagcttc cgcgactgtttcgcgctggagtgtgaagcagtgaaacgtgtgcgcaacgacatgggactg accaacgttgagatcatgatcccgttcgtgcgtaccgtagatcaggcgaaagcggtggtt gaagaactggcgcgtcaggggctgaaacgtggcgagaacgggctgaaaatcatcatgatg tgtgaaatcccgtccaacgccttgctggccgagcagttcctcgaatatttcgacggcttc tcaattggctcaaacgatatgacgcagctggcgctcggtctggaccgtgactccggcgtg gtgtctgaattgttcgatgagcgcaacgatgcggtgaaagcactgctgtcgatggctatc cgtgccgcgaagaaacagggcaaatatgtcgggatttgcggtcagggtccgtccgaccac gaagactttgccgcatggttgatggaagaggggatcgatagcctgtctctgaacccggac accgtggtgcaaacctggttaagcctggctgaactgaagaaataa
``` ppsA amino acid sequence <SEQ ID NO: 119>

MSNNGSSPLVLWYNQLGMNDVDRVGGKNASLGEMITNLSGMGVSVPNGFATTAD

AFNQFLDQSGVNQRIYELLDKTDIDDVTQLAKAGAQIRQWIIDTPFQPELENAIREAYAQ

LSADDENASFAVRSSATAEDMPDASFAGQQETFLNVQGFDAVLVAVKHVFASLFNDRAIS

YRVHQGYDHRGVALSAGVQRMVRSDLASSGVMFSIDTESGFDQVVFITSAWGLGEMVVQG

AVNPDEFYVHKPTLAANRPAIVRRTMGSKKIRMVYAPTQEHGKQVKIEDVPQEQRDIFSL

TNEEVQELAKQAVQIEKHYGRPMDIEWAKDGHTGKLFIVQARPETVRSRGQVMERYTLHS

QGKIIAEGRAIGHRIGAGPVKVIHDISEMNRIEPGDVLVTDMTDPDWEPIMKKASAIVTN

RGGRTCHAAIIARELGIPAVVGCGDATERMKDGENVTVSCAEGDTGYVYAELLEFSVKSS

SVETMPDLPLKVMMNVGNPDRAFDFACLPNEGVGLARLEFIINRMIGVHPRALLEFDDQE

PQLQNEIREMMKGFDSPREFYVGRLTEGIATLGAAFYPKRVIVRLSDFKSNEYANLVGGE

RYEPDEENPMLGFRGAGRYVSDSFRDCFALECEAVKRVRNDMGLTNVEIMIPFVRTVDQA

KAVVEELARQGLKRGENGLKIIMMCEIPSNALLAEQFLEYFDGFSIGSNDMTQLALGLDR

DSGVVSELFDERNDAVKALLSMAIRAAKKQGKYVGICGQGPSDHEDFAAWLMEEGIDSLS

LNPDTVVQTWLSLAELKKaroL gene sequence <SEQ ID NO: 120>

```
atgacacaacctctttttctgatcgggcctcggggctgtggtaaaacaacggtc ggaatggcccttgccgattcgcttaaccgtcggtttgtcgataccgatcagtggttgcaa tcacagctcaatatgacggtcgcggagatcgtcgaaagggaagagtgggcgggatttcgc gccagagaaacggcggcgctggaagcggtaactgcgccatccaccgttatcgctacaggc ggcggcattattctgacggaatttaatcgtcacttcatgcaaaataacgggatcgtggtt tatttgtgtgcgccagtatcagtcctggttaaccgactgcaagctgcaccggaagaagat ttacggccaaccttaacgggaaaaccgctgagcgaagaagttcaggaagtgctggaagaa
```

-continued cgcgatgcgctatatcgcgaagttgcgcatattatcatcgacgcaacaaacgaacccagc caggtgatttctgaaattcgcagcgccctggcacagacgatcaattgttga aroL amino acid sequence
<SEQ ID NO: 121>
MTQPLFLIGPRGCGKTTVGMALADSLNRRFVDTDQWLQSQLNMTVAEIVEREEW

AGFRARETAALEAVTAPSTVIATGGGIILTEFNRHFMQNNGIVVYLCAPVSVLVNRLQAA

PEEDLRPTLTGKPLSEEVQEVLEERDALYREVAHIIIDATNEPSQVISEIRSALAQTINC tktA gene sequence
<SEQ ID NO: 122>
atgtcctcacgtaaagagcttgccaatgctattcgtgcgctgagcatggacgca gtacagaaagccaaatccggtcacccgggtgcccctatgggtatggctgacattgccgaa gtcctgtggcgtgatttcctgaaacacaacccgcagaatccgtcctgggctgaccgtgac cgcttcgtgctgtccaacggccacggctccatgctgatctacagcctgctgcacctcacc ggttacgatctgccgatggaagaactgaaaaacttccgtcagctgcactctaaaactccg ggtcacccggaagtgggttacaccgctggtgtggaaccaccaccggtccgctgggtcag ggtattgccaacgcagtcggtatggcgattgcagaaaaaacgctggcggcgcagtttaac cgtccgggccacgacattgtcgaccactacacctacgccttcatgggcgacggctgcatg atggaaggcatctcccacgaagtttgctctctggcgggtacgctgaagctgggtaaactg attgcattctacgatgacaacggtatttctatcgatggtcacgttgaaggctggttcacc gacgacaccgcaatgcgtttcgaagcttacggctggcacgttattcgcgacatcgacggt catgacgcggcatctatcaaacgcgcagtagaagaagcgcgcgcagtgactgacaaacct tccctgctgatgtgcaaaaccatcatcggtttcggttccccgaacaaagccggtacccac gactccacggtgcgccgctgggcgacgctgaaattgccctgacccgcgaacaactgggc tggaaatatgcgccgttcgaaatcccgtctgaaatctatgctcagtgggatgcgaaagaa gcaggccaggcgaaagaatccgcatggaacgagaaattcgctgcttacgcgaaagcttat ccgcaggaagccgctgaatttacccgccgtatgaaaggcgaaatgccgtctgacttcgac gctaaagcgaaagagttcatcgctaaactgcaggctaatccggcgaaaatcgccagccgt aaagcgtctcagaatgctatcgaagcgttcggtccgctgttgccggaattcctcggcggt tctgctgacctggcgccgtctaacctgaccctgtggtctggttctaaagcaatcaacgaa gatgctgcgggtaactacatccactacggtgttcgcgagttcggtatgaccgcgattgct aacggtatctcctgcacggtggcttcctgccgtacacctccaccttcctgatgttcgtg gaatacgcacgtaacgccgtacgtatggctgcgctgatgaaacagcgtcaggtgatggtt tacacccacgactccatcggtctgggcgaagacggcccgactcaccagccggttgagcag gtcgcttctctgcgcgtaaccccgaacatgtctacatggcgtccgtgtgaccaggttgaa tccgcggtcgcgtggaaatacggtgttgagcgtcaggacggcccgaccgcactgatcctc tcccgtcagaacctggcgcagcaggaacgaactgaagagcaactggcaaacatcgcgcgc ggtggttatgtgctgaaagactgcgccggtcagccggaactgattttcatcgctaccggt tcagaagttgaactggctgttgctgcctacgaaaaactgactgccgaaggcgtgaaagcg cgcgtggtgtccatgccgtctaccgacgcatttgacaagcaggatgctgcttaccgtgaa tccgtactgccgaaagcggttactgcacgcgttgctgtagaagcgggtattgctgactac tggtacaagtatgttggcctgaacggtgctatcgtcggtatgaccaccttcggtgaatct gctccggcagagctgctgtttgaagagttcggcttcactgttgataacgttgttgcgaaa gcaaaagaactgctgtaa tktA amino acid sequence <SEQ ID NO: 123>

MSSRKELANAIRALSMDAVQKAKSGHPGAPMGMADIAEVLWRDFLKHNPQNPSW
ADRDRFVLSNGHGSMLIYSLLHLTGYDLPMEELKNFRQLHSKTPGHPEVGYTAGVETTTG
PLGQGIANAVGMAIAEKTLAAQFNRPGHDIVDHYTYAFMGDGCMMEGISHEVCSLAGTLK
LGKLIAFYDDNGISIDGHVEGWFTDDTAMRFEAYGWHVIRDIDGHDAASIKRAVEEARAV
TDKPSLLMCKTIIGFGSPNKAGTHDSHGAPLGDAEIALTREQLGWKYAPFEIPSEIYAQW
DAKEAGQAKESAWNEKFAAYAKAYPQEAAEFTRRMKGEMPSDFDAKAKEFIAKLQANPAK
IASRKASQNAIEAFGPLLPEFLGGSADLAPSNLTLWSGSKAINEDAAGNYIHYGVREFGM
TAIANGISLHGGFLPYTSTFLMFVEYARNAVRMAALMKQRQVMVYTHDSIGLGEDGPTHQ
PVEQVASLRVTPNMSTWRPCDQVESAVAWKYGVERQDGPTALILSRQNLAQQERTEEQLA
NIARGGYVLKDCAGQPELIFIATGSEVELAVAAYEKLTAEGVKARVVSMPSTDAFDKQDA
AYRESVLPKAVTARVAVEAGIADYWYKYVGLNGAIVGMTTFGESAPAELLFEEFGFTVDN
VVAKAKELLmetK gene sequence <SEQ ID NO: 124> atggcaaaacaccttttttacgtccgagtccgtctctgaagggcatcctgacaaa
attgctgaccaaatttctgatgccgttttagacgcgatcctcgaacaggatccgaaagca
cgcgttgcttgcgaaacctacgtaaaaaccggcatggttttagttggcggcgaaatcacc
accagcgcctgggtagacatcgaagagatcacccgtaacaccgttcgcgaaattggctat
gtgcattccgacatgggctttgacgctaactcctgtgcggttctgagcgctatcggcaaa
cagtctcctgacatcaaccagggcgttgaccgtgccgatccgctggaacagggcgcgggt
gaccagggtctgatgtttggctacgcaactaatgaaaccgacgtgctgatgccagcacct
atcacctatgcacaccgtctggtacagcgtcaggctgaagtgcgtaaaaacggcactctg
ccgtggctgcgcccggacgcgaaaagccaggtgacttttcagtatgacgacggcaaaatc
gttggtatcgatgctgtcgtgctttccactcagcactctgaagagatcgaccagaaatcg
ctgcaagaagcggtaatggaagagatcatcaagccaattctgcccgctgaatggctgact
tctgccaccaaattcttcatcaacccgaccggtcgtttcgttatcggtggcccaatgggt
gactgcggtctgactggtcgtaaaattatcgttgatacctacggcggcatggcgcgtcac
ggtggcggtgcattctctggtaaagatccatcaaaagtggaccgttccgcagcctacgca
gcacgttatgtcgcgaaaaacatcgttgctgctggcctggccgatcgttgtgaaattcag
gtttcctacgcaatcggcgtggctgaaccgacctccatcatggtagaaactttcggtact
gagaaagtgccttctgaacaactgaccctgctggtacgtgagttcttcgacctgcgccca
tacggtctgattcagatgctggatctgctgcacccgatctacaaagaaaccgcagcatac
ggtcactttggtcgtgaacatttcccgtgggaaaaaccgacaaagcgcagctgctgcgc
gatgctgccggtctgaagtaa metK amino acid sequence <SEQ ID NO: 125>

MAKHLFTSESVSEGHPDKIADQISDAVLDAILEQDPKARVACETYVKTGMVLVG
GEITTSAWVDIEEITRNTVREIGYVHSDMGFDANSCAVLSAIGKQSPDINQGVDRADPLE
QGAGDQGLMFGYATNETDVLMPAPITYAHRLVQRQAEVRKNGTLPWLRPDAKSQVTFQYD
DGKIVGIDAVVLSTQHSEEIDQKSLQEAVMEEIIKPILPAEWLTSATKFFINPTGRFVIG
GPMGDCGLTGRKIIVDTYGGMARHGGGAFSGKDPSKVDRSAAYAARYVAKNIVAAGLADR

-continued

CEIQVSYAIGVAEPTSIMVETFGTEKVPSEQLTLLVREFFDLRPYGLIQMLDLLHPIYKE

TAAYGHFGREHFPWEKTDKAQLLRDAAGLKmtn gene sequence <SEQ ID NO: 126>
atgaaaatcggcatcattggtgcaatggaagaagaagttacgctgctgcgtgac aaaatcgaaaaccgtcaaactatcagtctcggcggttgcgaaatctataccggccaactg aatggaaccgaggttgcgcttctgaaatcgggcatcggtaaagtcgctgcggcgctgggt gccactttgctgttggaacactgcaagccagatgtgattattaacaccggttctgccggt ggcctggcaccaacgttgaaagtgggcgatatcgttgtctcggacgaagcacgttatcac gacgcggatgtcacggcatttggttatgaataccggtcagttaccaggctgtccggcaggc tttaaagctgacgataaactgatcgctgccgctgaggcctgcattgccgaactgaatctt aacgctgtacgtggcctgattgttagcggcgacgctttcatcaacggttctgttggtctg gcgaaaatccgccacaacttcccacaggccattgctgtagagatggaagcgacggcaatc gcccatgtctgccacaatttcaacgtcccgtttgttgtcgtacgcgccatctccgacgtg gccgatcaacagtctcatcttagcttcgatgagttcctggctgttgccgctaaacagtcc agcctgatggttgagtcactggtgcagaaacttgcacatggctaa mtn amino acid sequence <SEQ ID NO: 127>
MKIGIIGAMEEEVTLLRDKIENRQTISLGGCEIYTGQLNGTEVALLKSGIGKVA

AALGATLLLEHCKPDVIINTGSAGGLAPTLKVGDIVVSDEARYHDADVTAFGYEYGQLPG

CPAGFKADDKLIAAAEACIAELNLNAVRGLIVSGDAFINGSVGLAKIRHNFPQAIAVEME

ATAIAHVCHNFNVPFVVVRAISDVADQQSHLSFDEFLAVAAKQSSLMVESLVQKLAHGluxS gene sequence <SEQ ID NO: 128>
atgccgttgttagatagcttcacagtcgatcatacccggatggaagcgcctgcagttcgg gtggcgaaaacaatgaacaccccgcatggcgacgcaatcaccgtgttcgatctgcgcttc tgcgtgccgaacaaagaagtgatgccagaaagagggatccatacccctggagcacctgttt gctggttttatgcgtaaccatcttaacggtaatggtgtagagattatcgatatctcgcca atgggctgccgcaccggttttatatgagtctgattggtacgccagatgagcagcgtgtt gctgatgcctggaaagcggcaatggaagacgtgctgaaagtgcaggatcagaatcagatc ccggaactgaacgtctaccagtgtggcacttaccagatgcactcgttgcaggaagcgcag gatattgcgcgtagcattctggaacgtgacgtacgcatcaacagcaacgaagaactggca ctgccgaaagagaagttgcaggaactgcacatctag luxS amino acid sequence <SEQ ID NO: 129>
MPLLDSFTVDHTRMEAPAVRVAKTMNTPHGDAITVFDLRFCVPNKEVMPERGIH

TLEHLFAGFMRNHLNGNGVEIIDISPMGCRTGFYMSLIGTPDEQRVADAWKAAMEDVLKV

QDQNQIPELNVYQCGTYQMHSLQEAQDIARSILERDVRINSNEELALPKEKLQELHI- 13-4. Gene Information Used for *C. Glutamicum* Recombinant Strains trpD gene sequence <SEQ ID NO: 130>
atgacttctccagcaacactgaaagttctcaacgcctacttggataaccccact ccaaccctggaggaggcaattgaggtgttcaccccgctgaccgtgggtgaatacgatgac gtgcacatcgcagcgctgcttgccaccatccgtactcgcggtgagcagttcgctgatatt -continued

```
gccggcgctgccaaggcgttcctcgcggcggctcgtccgttcccgattactggcgcaggt ttgctagattccgctggtactggtggcgacggtgccaacaccatcaacatcaccaccggc gcatccctgatcgcagcatccggtggagtgaagctggttaagcacggcaaccgttcggtg agctccaagtccggctccgccgatgtgctggaagcgctgaatattcctttgggccttgat gtggatcgtgctgtgaagtggttcgaagcgtccaacttcaccttcctgttcgcacctgcg tacaaccctgcgattgcgcatgtgcagccggttcgccaggcgctgaaattccccaccatc ttcaacacgcttggaccattgctgtccccggcgcgcccggagcgtcagatcatgggcgtg gccaatgccaatcatggacagctcatcgccgaggtcttccgcgagttgggccgtacacgc gcgcttgttgtgcatggcgcaggcaccgatgagatcgcagtccacggcaccaccttggtg tgggagcttaaagaagacggcaccatcgagcattacaccatcgagcctgaggaccttggc cttggccgctacacccttgaggatctcgtaggtggcctcggcactgagaacgccgaagct atgcgcgctactttcgcgggcaccggccctgatgcacaccgtgatgcgttggctgcgtcc gcaggtgcgatgttctacctcaacggcgatgtcgactccttgaaagatggtgcacaaaag gcgctttccttgcttgccgacggcaccacccaggcatggttggccaagcacgaagagatc gattactcagaaaaggagtcttccaatgactag
``` trpD amino acid sequence <SEQ ID NO: 131>

MTSPATLKVLNAYLDNPTPTLEEAIEVFTPLTVGEYDDVHIAALLATIRTRGEQ

FADIAGAAKAFLAAARPFPITGAGLLDSAGTGGDGANTINITTGASLIAASGGVKLVKHG

NRSVSSKSGSADVLEALNIPLGLDVDRAVKWFEASNFTFLFAPAYNPAIAHVQPVRQALK

FPTIFNTLGPLLSPARPERQIMGVANANHGQLIAEVFRELGRTRALVVHGAGTDEIAVHG

TTLVWELKEDGTIEHYTIEPEDLGLGRYTLEDLVGGLGTENAEAMRATFAGTGPDAHRDA

LAASAGAMFYLNGDVDSLKDGAQKALSLLADGTTQAWLAKHEEIDYSEKESSNDqsuB gene sequence <SEQ ID NO: 132>

```
atgcgtacatccattgccactgtttgtttgtccggaactcttgctgaaaagctg cgcgcagctgcagatgctggatttgatggtgtggaaatcttcgagcaggacttggtggtt tccccgcattcggcagagcagattcgtcagcgggctcaggatttgggattaaccctggat ctgttccagccgtttcgagatttcgaaggtgtggaagaagagcagtttctgaagaatctg caccgcttggaagagaagttcaagctgatgaacaggcttggcattgagatgatcttgttg tgttccaatgtgggcaccgcgaccatcaatgatgatgacctttcgtggagcagttgcat cgtgcagcagatttggctgagaagtacaacgtcaagattgcttatgaagcgttggcgtgg ggcaagtttgtcaatgattttgagcatgcgcatgcacttgtggagaaggtgaatcacaag gcgctgggaacctgcttggatacgttccatattctttcccgtggttgggaaaccgacgag gtggagaacatccctgcggagaagatcttctttgttcagttagcggatgcgccgaagctg agcatggacattttgtcctggtcgcgtcaccaccgtgttttccctggtgaaggcgatttc gatctggtgaaattcatggttcatctggccaagacgggttatgatggcccgatttctttg gagatcttcaacgattccttccgcaaggccgaggttggtcgcaccgcgattgatgggttg cgttcttcgcgttggttggaagatcagacctggcatgcgctaaatgctgaggatcgtcca agcgctcttgaactgcgtgcacttcctgaggtcgcggaacctgagggtgttgatttcatt gagatcgccactggacgtttgggtgagaccattcgggttcttcatcaattgggtttccgc ttgggtggtcatcactgcagtaagcaggattaccaggtatggacccagggcgatgtgcgc attgtggtgtgtgatcgtggggtcaccggggctccaaccacgatctctgcgatgggcttt
```

-continued

```
gacaccccgatccagaagctgctcatgcccgtgcggaattgctgcgggctcagacaatt gatcgtccccacatcgagggcgaagttgacctaaaaggtgtgtacgcaccggatggggtg gagctgttttcgcggggccgagcccgatggaatgcccgagtggctgccggaattcggc gtcgaaaagcaagaagctggtctcattgaagccatcgaccacgtcaatttcgcccagccg tggcaacattttgatgaggcagtgctgttttacaccgcgctgatggcgttggagactgtg cgtgaggatgagttcccgagcccaattggtttggtgcgcaatcaggtgatgcgttcgccg aatgatgcggtgcggttgctgctcagcgtggcgccggaggacggtgagcagggagatttc ctcaacgcggcctaccggagcacattgcgttggccacggcggacatcgtggcggtggct gaacgtgcgcgcaaacgaggcctggatttcttgcccgtcccagagaattactacgacgat gtgcaggcgcgttttgatttgccgcaggaattcttggacacactcaaggaaaaccacctg ctttacgaccgcgacgagaacggcgaattcctccacttttacacccgcacgttgggcacg ctgttcttcgaagtggtggaacgccgcggcggttttgcaggttggggcgaaacaaacgct ccggtgcggttggcggcgcagtatcgtgaggtgcgggacctcgagcggggaatcccaaac tag
``` qsuB amino acid sequence
<SEQ ID NO: 133>
```
MRTSIATVCLSGTLAEKLRAAADAGFDGVEIFEQDLVVSPHSAEQIRQRAQDLG

LTLDLFQPFRDFEGVEEEQFLKNLHRLEEKFKLMNRLGIEMILLCSNVGTATINDDDLFV

EQLHRAADLAEKYNVKIAYEALAWGKFVNDFEHAHALVEKVNHKALGTCLDTFHILSRGW

ETDEVENIPAEKIFFVQLADAPKLSMDILSWSRHHRVFPGEGDFDLVKFMVHLAKTGYDG

PISLEIFNDSFRKAEVGRTAIDGLRSLRWLEDQTWHALNAEDRPSALELRALPEVAEPEG

VDFIEIATGRLGETIRVLHQLGFRLGGHHCSKQDYQVWTQGDVRIVVCDRGVTGAPTTIS

AMGFDTPDPEAAHARAELLRAQTIDRPHIEGEVDLKGVYAPDGVELFFAGPSPDGMPEWL

PEFGVEKQEAGLIEAIDHVNFAQPWQHFDEAVLFYTALMALETVREDEFPSPIGLVRNQV

MRSPNDAVRLLLSVAPEDGEQGDFLNAAYPEHIALATADIVAVAERARKRGLDFLPVPEN

YYDDVQARFDLPQEFLDTLKENHLLYDRDENGEFLHFYTRTLGTLFFEVVERRGGFAGWG

ETNAPVRLAAQYREVRDLERGIPN-
``` qsuD gene sequence
<SEQ ID NO: 134>
```
tgaacgacagtattctcctcggcctaatcggccagggcctcgacctatcgcgc accccccgcaatgcacgaggcggaaggcctcgcgcagggacgtgcgacggtgtacaggcgc atcgacacgcttgggtcgcgtgcttccgggcaagatttaaagacgcttctcgacgccgcc ctctaccttggcttcaacggcctgaacatcactcacccgtacaaacaagcagtattaccc ctgcttgacgaagtctccgaacaagccacccaactcggcgcagtgaatactgtcgttatc gacgccaccggccacaccaccggccacaacaccgacgtctccggatttggccgcggaatg gaagaaggcctcccaacgccaagctcgattccgtcgtgcaggtcggcgccggcggcgta ggaaacgcagtggcatacgccctggtcacccacggtgtgcagaaacttcaggtcgctgac ctcgacacttcccgcgcgcaggcactggcagatgtcatcaacaacgcagtcggccgtgaa gccgtcgtgggagtagacgcccgcggcatcgaagacgtcatcgccgccgccgacggagta gtcaacgcaaccccccatgggaatgccagcacaccccggcaccgcctttgatgtcagctgc ctcaccaaggatcactgggttggcgacgtcgtgtacatgcccatcgaaactgaacttctc aaagccgcccgtgccctcggctgcgaaaccctcgacggaacccgcatggcaatccaccaa
```

-continued

```
gccgtcgatgccttccgactgttcaccggcctcgaacccgacgtctcccgcatgcgggaa actttcctgtccctctaa
``` qsuD amino acid sequence

<SEQ ID NO: 135>

```
NDSILLGLIGQGLDLSRTPAMHEAEGLAQGRATVYRRIDTLGSRASGQDLKTL

LDAALYLGFNGLNITHPYKQAVLPLLDEVSEQATQLGAVNTVVIDATGHTTGHNTDVSGF

GRGMEEGLPNAKLDSVVQVGAGGVGNAVAYALVTHGVQKLQVADLDTSRAQALADVINNA

VGREAVVGVDARGIEDVIAAADGVVNATPMGMPAHPGTAFDVSCLTKDHWVGDVVYMPIE

TELLKAARALGCETLDGTRMAIHQAVDAFRLFTGLEPDVSRMRETFLSL-
``` hdpA gene sequence

<SEQ ID NO: 136>

```
atgcgtacatccattgccactgtttgtttgtccggaactcttgctgaaaagctg cgcgcagctgcagatgctggatttgatggtgtggaaatcttcgagcaggacttggtggtt tccccgcattcggcagagcagattcgtcagcgggctcaggatttgggattaaccctggat ctgttccagccgtttcgagatttcgaaggtgtggaagaagagcagtttctgaagaatctg caccgcttggaagagaagttcaagctgatgaacaggcttggcattgagatgatcttgttg tgttccaatgtgggcaccgcgaccatcaatgatgatgaccttttcgtggagcagttgcat cgtgcagcagatttggctgagaagtacaacgtcaagattgcttatgaagcgttggcgtgg ggcaagtttgtcaatgattttgagcatgcgcatgcacttgtggagaaggtgaatcacaag gcgctgggaacctgcttggatacgttccatattctttcccgtggttgggaaaccgacgag gtggagaacatccctgcggagaagatcttctttgttcagttagcggatgcgccgaagctg agcatggacattttgtcctggtcgcgtcaccaccgtgttttccctggtgaaggcgatttc gatctggtgaaattcatggttcatctggccaagacgggttatgatggcccgatttctttg gagatcttcaacgattccttccgcaaggccgaggttggtcgcaccgcgattgatgggttg cgttctttgcgttggttggaagatcagacctggcatgcgctaaatgctgaggatcgtcca agcgctcttgaactgcgtgcacttcctgaggtcgcggaacctgagggtgttgatttcatt gagatcgccactggacgtttgggtgagaccattcgggttcttcatcaattgggtttccgc ttgggtggtcatcactgcagtaagcaggattaccaggtatggacccagggcgatgtgcgc attgtggtgtgtgatcgtgggtcaccggggctccaaccacgatctctgcgatgggctttt gacacccccgatccagaagctgctcatgcccgtgcggaattgctgcgggctcagacaatt gatcgtccccacatcgagggcgaagttgacctaaaaggtgtgtacgcaccggatggggtg gagctgttttcgcggggccgagcccgatggaatgcccgagtggctgccggaattcggc gtcgaaaagcaagaagctggtctcattgaagccatcgaccacgtcaatttcgcccagccg tggcaacattttgatgaggcagtgctgttttacaccgcgctgatggcgttggagactgtg cgtgaggatgagttcccgagcccaattggtttggtgcgcaatcaggtgatgcgttcgccg aatgatgcggtgcggttgctgctcagcgtggcgcggaggacggtgagcagggagatttc ctcaacgcggcctaccggagcacattgcgttggccacggcggacatcgtggcggtggct gaacgtgcgcgcaaacgaggcctggatttcttgcccgtcccagagaattactacgacgat gtgcaggcgcgttttgatttgccgcaggaattcttggacacactcaaggaaaaccacctg ctttacgaccgcgacgagaacggcgaattcctccacttttacacccgcacgtttgggcacg ctgttcttcgaagtggtggaacgccgcggcggttttgcaggttggggcgaaacaaacgct ccggtgcggttggcggcgcagtatcgtgaggtgcgggacctcgagcggggaatcccaaac tag
``` hdpA amino acid sequence
<SEQ ID NO: 137>
MRTSIATVCLSGTLAEKLRAAADAGFDGVEIFEQDLVVSPHSAEQIRQRAQDLG

LTLDLFQPFRDFEGVEEEQFLKNLHRLEEKFKLMNRLGIEMILLCSNVGTATINDDDLFV

EQLHRAADLAEKYNVKIAYEALAWGKFVNDFEHAHALVEKVNHKALGTCLDTFHILSRGW

ETDEVENIPAEKIFFVQLADAPKLSMDILSWSRHHRVFPGEGDFDLVKFMVHLAKTGYDG

PISLEIFNDSFRKAEVGRTAIDGLRSLRWLEDQTWHALNAEDRPSALELRALPEVAEPEG

VDFIEIATGRLGETIRVLHQLGFRLGGHHCSKQDYQVWTQGDVRIVVCDRGVTGAPTTIS

AMGFDTPDPEAAHARAELLRAQTIDRPHIEGEVDLKGVYAPDGVELFFAGPSPDGMPEWL

PEFGVEKQEAGLIEAIDHVNFAQPWQHFDEAVLFYTALMALETVREDEFPSPIGLVRNQV

MRSPNDAVRLLLSVAPEDGEQGDFLNAAYPEHIALATADIVAVAERARKRGLDFLPVPEN

YYDDVQARFDLPQEFLDTLKENHLLYDRDENGEFLHFYTRTLGTLFFEVVERRGGFAGWG

ETNAPVRLAAQYREVRDLERGIPNaroK gene sequence
<SEQ ID NO: 138>
atggagcgtaatgaagtgaatgatcaaattcacttagatcatcaatcagatgac acctctgaatgctcctgcccgatcgtggttcttgtgggtttgccaggagctggaaaatcc accattggacgtcgattagcgcgcgccttaaacactgaactcgtcgactccgacgaactg attgagcgcgccaccggaaaagcctgtggcgccgtgttcagcgagctcggcgagccagcc ttccgcgagctcgaggccatccacgtggccgaagcactgaaatcctccggagtggtgagc ttgggaggcggatctgtgctgacagaatccacccgtgaactgctcaaaggccaggacgtg gtctggatcgacgtgccagtagaagaaggcatcaggcgcaccgcaaacgagcgttcccgc cccgtgctgcaagccgccgaccccgccgagcactaccgcaacctggtgaaagtgcgcacc ccgttgtacgaagaggtggcaacctaccgacttcgcaccaacaaccgcagcccccagcaa gtggtggcagcagtgttgcatcatctagaaatcgattaa aroK amino acid sequence
<SEQ ID NO: 139>
MERNEVNDQIHLDHQSDDTSECSCPIVVLVGLPGAGKSTIGRRLARALNTELVD

SDELIERATGKACGAVFSELGEPAFRELEAIHVAEALKSSGVVSLGGGSVLTESTRELLK

GQDVVWIDVPVEEGIRRTANERSRPVLQAADPAEHYRNLVKVRTPLYEEVATYRLRTNNR

SPQQVVAAVLHHLEIDaroB gene sequence
<SEQ ID NO: 140>
atgagcgcagtgcagattttcaacaccgtccacgtcaatggatcttcccctat gatgtccacattggttccggcctcaacgagctcattgttcagcgcgcagcggaatcaggc gcggagcaggtagcgattttgcaccagcccagcatggatgacattgcatccgagttggat gcagcactagtcgctgctggtttgaaggtcctgcaccttaatgttcccgatgcggaaaac ggcaagtccttggaagtagcggggcagtgctgggatgaattgggtggcgcagcattcggc cgccgcgatatcgtcatcggacttggtggcggtgctgccacagatctcgcgggattcgtc gctgctgcatggatgcgtggcgtgcgcgtcattcaggttccaaccaccttgttggccatg gtggacgctgcggtgggcggcaagactggcatcaataccgccgcaggcaagaaccttgtg ggcgcgttccacgagcctgacgcagtattcattgacaccgatcgcctagccacccctgcct gacgcggaaatcatcgcgggatccgccgaaatcatcaaaactggtttcatcgccgaccca gaaatcctgcgcctttacgaaactgatcccgcagcctgcctgaagaaagaagtcgaaggc tcccacctacctgaactgatttggcgctccgtcaccgtcaagggctccgtggtcggccaa

```
gacctcaaagaatctagcctgcgcgaaatcctcaactacggacacacctttgcccacgcc gtcgaactccgcgaaaacttccgctggcgccacggcaatgccgttgcagtgggcatgatg ttcatcgccaacctctcccacaagctcgggcttatcgacgcgcccctcctcgagcgccac cgctcaatcctggcggccatcggtctgcccacttcctacgaaggcggagccttcgacgag ctttacgacggtatgacccgcgacaagaaaaaccgcgacggcaacatccgcttcgtcgca ctgaccgccgtgggcgaggttacccgcattgaggggccctcaaaacaagatttacagagt gcttatgaggcaatcagccactaa
``` aroB amino acid sequence

<SEQ ID NO: 141>

```
MSAVQIFNTVHVNGSSPYDVHIGSGLNELIVQRAAESGAEQVAILHQPSMDDIA

SELDAALVAAGLKVLHLNVPDAENGKSLEVAGQCWDELGGAAFGRRDIVIGLGGGAATDL

AGFVAAAWMRGVRVIQVPTTLLAMVDAAVGGKTGINTAAGKNLVGAFHEPDAVFIDTDRL

ATLPDAEIIAGSAEIIKTGFIADPEILRLYETDPAACLKKEVEGSHLPELIWRSVTVKGS

VVGQDLKESSLREILNYGHTFAHAVELRENFRWRHGNAVAVGMMFIANLSHKLGLIDAPL

LERHRSILAAIGLPTSYEGGAFDELYDGMTRDKKNRDGNIRFVALTAVGEVTRIEGPSKQ

DLQSAYEAISH-
``` tkt gene sequence

<SEQ ID NO: 142>

```
gtggacaccaaggctgtagacactgttcgtgtcctcgctgcagacgctgtagaa aactgtggctccggccacccaggcaccgcaatgagcctggctccccttgcatacaccttg taccagcgggttatgaacgtagatccacaggacaccaactgggcaggccgtgaccgcttc gttcttcttgtggccactcctctttgacccagtacatccagctttacttgggtggattc ggccttgagatggatgacctgaaggctctgcgcacctgggattccttgaccccaggacac cctgagtaccgccacaccaagggcgttgagatcaccactggccctcttggccagggtctt gcatctgcagttggtatggccatggctgctcgtcgtgagcgtggcctattcgacccaacc gctgctgagggcgaatccccattcgaccaccacatctacgtcattgcttctgatggtgac ctgcaggaaggtgtcacctctgaggcatcctccatcgctggcacccagcagctgggcaac ctcatcgtgttctgggatgacaaccgcatctccatcgaagacaacactgagatcgctttc aacgaggacgttgttgctcgttacaaggcttacggctggcagaccattgaggttgaggct ggcgaggacgttgcagcaatcgaagctgcagtggctgaggctaagaaggacaccaagcga cctaccttcatccgcgttcgcaccatcatcggcttcccagctccaactatgatgaacacc ggtgctgtgcacggtgctgctcttggcgcagctgaggttgcagcaaccaagactgagctt ggattcgatcctgaggctcacttcgcgatcgacgatgaggttatcgctcacacccgctcc ctcgcagagcgcgctgcacagaagaaggctgcatggcaggtcaagttcgatgagtgggca gctgccaaccctgagaacaaggctctgttcgatcgcctgaactcccgtgagcttccagcg ggctacgctgacgagctcccaacatgggatgcagatgagaagggcgtcgcaactcgtaag gcttccgaggctgcacttcaggcactgggcaagaccttcctgagctgtggggcggttcc gctgacctcgcaggttccaacaacaccgtgatcaagggctccccttccttcggccctgag tccatctccaccgagacctggtctgctgagccttacggccgtaacctgcacttcggtatc cgtgagcacgctatgggatccatcctcaacggcatttccctccacggtggcacccgccca tacggcggaaccttcctcatcttctccgactacatgcgtcctgcagttcgtcttgcagct ctcatggagaccgacgcttactacgtctggacccacgactccatcggtctgggcgaagat ggcccaacccaccagcctgttgaaaccttggctgcactgcgcgccatcccaggtctgtcc
```

-continued

```
gtcctgcgtcctgcagatgcgaacgagaccgcccaggcttgggctgcagcacttgagtac aaggaaggccctaagggtcttgcactgacccgccagaacgttcctgttctggaaggcacc aaggagaaggctgctgaaggcgttcgccgcggtggctacgtcctggttgagggttccaag gaaaccccagatgtgatcctcatgggctccggctccgaggttcagcttgcagttaacgct gcgaaggctctggaagctgagggcgttgcagctcgcgttgtttccgttccttgcatggat tggttccaggagcaggacgcagagtacatcgagtccgttctgcctgcagctgtgaccgct cgtgtgtctgttgaagctggcatcgcaatgccttggtaccgcttcttgggcacccagggc cgtgctgtctcccttgagcacttcggtgcttctgcggattaccagaccctgtttgagaag ttcggcatcaccaccgatgcagtcgtggcagcggccaaggactccattaacggttaa
``` tkt amino acid sequence
<SEQ ID NO: 143>

```
VDTKAVDTVRVLAADAVENCGSGHPGTAMSLAPLAYTLYQRVMNVDPQDTNWAG

RDRFVLSCGHSSLTQYIQLYLGGFGLEMDDLKALRTWDSLTPGHPEYRHTKGVEITTGPL

GQGLASAVGMAMAARRERGLFDPTAAEGESPFDHHIYVIASDGDLQEGVTSEASSIAGTQ

QLGNLIVFWDDNRISIEDNTEIAFNEDVVARYKAYGWQTIEVEAGEDVAAIEAAVAEAKK

DTKRPTFIRVRTIIGFPAPTMMNTGAVHGAALGAAEVAATKTELGFDPEAHFAIDDEVIA

HTRSLAERAAQKKAAWQVKFDEWAAANPENKALFDRLNSRELPAGYADELPTWDADEKGV

ATRKASEAALQALGKTLPELWGGSADLAGSNNTVIKGSPSFGPESISTETWSAEPYGRNL

HFGIREHAMGSILNGISLHGGTRPYGGTFLIFSDYMRPAVRLAALMETDAYYVWTHDSIG

LGEDGPTHQPVETLAALRAIPGLSVLRPADANETAQAWAAALEYKEGPKGLALTRQNVPV

LEGTKEKAAEGVRRGGYVLVEGSKETPDVILMGSGSEVQLAVNAAKALEAEGVAARVVSV

PCMDWFQEQDAEYIESVLPAAVTARVSVEAGIAMPWYRFLGTQGRAVSLEHFGASADYQT

LFEKFGITTDAVVAAAKDSING-
``` metK gene sequence
<SEQ ID NO: 144>

```
gtggctcagccaaccgccgtccgtttgttcaccagtgaatctgtaactgaggga catccagacaaaatatgtgatgctatttccgataccattttggacgcgctgctcgaaaaa gatccgcagtcgcgcgtcgcagtggaaactgtggtcaccaccggaatcgtccatgttgtt ggcgaggtccgtaccagcgcttacgtagagatccctcaattagtccgcaacaagctcatc gaaatcggattcaactcctctgaggttggattcgacggacgcacctgtggcgtctcagta tccatcggtgagcagtcccaggaaatcgctgacggcgtggataactccgacgaagcccgc accaacggcgacgttgaagaagacgaccgcgcaggtgctggcgaccagggcctgatgttc ggctacgccaccaacgaaaccgaagagtacatgcctcttcctatcgcgttggcgcaccga ctgtcacgtcgtctgacccaggttcgtaaagagggcatcgttcctcacctgcgtccagac ggaaaaacccaggtcaccttcgcatacgatgcgcaagaccgccctagccacctggatacc gttgtcatctccacccagcacgacccagaagttgaccgtgcatggttggaaacccaactg cgcgaacacgtcattgattgggtaatcaaagacgcaggcattgaggatctggcaaccggt gagatcaccgtgttgatcaacccttcaggttccttcattctgggtggccccatgggtgat gcgggtctgaccggccgcaagatcatcgtggataccacggtggcatggctcgccatggt ggtggagcattctccggtaaggatccaagcaaggtggaccgctctgctgcatacgccatg cgttgggtagcaaagaacatcgtggcagcaggccttgctgatcgcgctgaagttcaggtt gcatacgccattggacgcgcaaagccagtcggactttacgttgaaacctttgacaccaac
```

```
aaggaaggcctgagcgacgagcagattcaggctgccgtgttggaggtctttgacctgcgt ccagcagcaattatccgtgagcttgatctgcttcgtccgatctacgctgacactgctgcc tacggccactttggtcgcactgatttggaccttccttgggaggctatcgaccgcgttgat gaacttcgcgcagccctcaagttggcctaa
``` metK amino acid sequence

<SEQ ID NO: 145>

```
VAQPTAVRLFTSESVTEGHPDKICDAISDTILDALLEKDPQSRVAVETVVTTGI

VHVVGEVRTSAYVEIPQLVRNKLIEIGFNSSEVGFDGRTCGVSVSIGEQSQEIADGVDNS

DEARTNGDVEEDDRAGAGDQGLMFGYATNETEEYMPLPIALAHRLSRRLTQVRKEGIVPH

LRPDGKTQVTFAYDAQDRPSHLDTVVISTQHDPEVDRAWLETQLREHVIDWVIKDAGIED

LATGEITVLINPSGSFILGGPMGDAGLTGRKIIVDTYGGMARHGGGAFSGKDPSKVDRSA

AYAMRWVAKNIVAAGLADRAEVQVAYAIGRAKPVGLYVETFDTNKEGLSDEQIQAAVLEV

FDLRPAAIIRELDLLRPIYADTAAYGHFGRTDLDLPWEAIDRVDELRAALKLA-
``` aroG gene sequence

<SEQ ID NO: 146>

```
atgagttctccagtctcactcgaaaacgcggcgtcaaccagcaacaagcgcgtc gtggcttttccacgagctgcctagccctacagatctcatcgccgcaaacccactgacacca aagcaggcttccaaggtggagcaggatcgccaggacatcgctgatatcttcgctggcgac gatgaccgcctcgttgtcgttgtgggaccttgctcagttcacgatcctgaagcagccatc gattacgcaaaccgcctggctccgctggcaaagcgccttgatcaggacctcaagattgtc atgcgcgtgtacttcgagaagcctcgcaccatcgtcggatggaagggattgatcaatgat cctcacctcaacgaaacctacgacatcccagagggcttgcgcattgcgcgcaaagtgctt atcgacgttgtgaaccttgatctcccagtcggctgcgaattcctcgaaccaaacagccct cagtactacgccgacactgtcgcatggggagcaatcggcgctcgtaccaccgaatctcag gtgcaccgccagctggcttctgggatgtctatgccaattggtttcaagaacggaactgac ggaaacatccaggttgcagtcgacgcggtacaggctgcccagaacccacacttcttcttc ggaacctccgacgacggcgcgctgagcgtcgtggagaccgcaggcaacagcaactcccac atcattttgcgcggcggtacctccggcccgaatcatgatgcagcttcggtggaggccgtc gtcgagaagcttggtgaaaacgctcgtctcatgatcgatgcttcccatgctaactccggc aaggatcatatccgacaggttgaggttgttcgtgaaatcgcagagcagatttctggcggt tctgaagctgtggctggaatcatgattgagtccttcctcgttggtggcgcacagaaccttt gatcctgcgaaattgcgcatcaatggcggtgaaggcctggtgtacggacagtctgtgacc gataagtgcatcgatattgacaccaccatcgatttgctcgctgagctggccgcagcagta agggaacgccgagcagcagccaagtaa
``` aroG amino acid sequence

<SEQ ID NO: 147>

```
MSSPVSLENAASTSNKRVVAFHELPSPTDLIAANPLTPKQASKVEQDRQDIADI

FAGDDDRLVVVVGPCSVHDPEAAIDYANRLAPLAKRLDQDLKIVMRVYFEKPRTIVGWKG

LINDPHLNETYDIPEGLRIARKVLIDVVNLDLPVGCEFLEPNSPQYYADTVAWGAIGART

TESQVHRQLASGMSMPIGFKNGTDGNIQVAVDAVQAAQNPHFFFGTSDDGALSVVETAGN

SNSHIILRGGTSGPNHDAASVEAVVEKLGENARLMIDASHANSGKDHIRQVEVVREIAEQ

ISGGSEAVAGIMIESFLVGGAQNLDPAKLRINGGEGLVYGQSVTDKCIDIDTTIDLLAEL

AAAVRERRAAAK
``` sahH gene sequence

<SEQ ID NO: 148> atggcacaggttatggacttcaaggttgccgatcttcactagcagaggcagga cgtcaccagattcgtcttgcagagtatgagatgccaggtctcatgcagttgcgcaaggaa ttcgcagacgagcagccttgaagggcgcccgaattgctggttctatccacatgacggtc cagaccgccgtgcttattgagaccctcactgctttgggcgctgaggttcgttgggcttcc tgcaacattttctccacccaggatgaggctgcagcggctatcgttgtcggctccggcacc gtcgaagagccagctggtgttccagtattcgcgtggaagggtgagtcactggaggagtac tggtggtgcatcaaccagatcttcagctggggcgatgagctgccaaacatgatcctcgac gacggcggtgacgccaccatggctgttattcgcggtcgcgaatacgagcaggctggtctg gttccaccagcagaggccaacgattccgatgagtacatcgcattcttgggcatgctgcgt gaggttcttgctgcagagcctggcaagtggggcaagatcgctgaggccgttaagggtgtc accgaggaaccaccaccggtgtgcaccgcctgtaccacttcgctgaagaaggcgtgctg cctttcccagcgatgaacgtcaacgacgctgtcaccaagtccaagtttgataacaagtac ggcacccgccactccctgatcgacggcatcaaccgcgccactgacatgctcatgggcggc aagaacgtgcttgtctgcggttacggcgatgtcggcaagggctgcgctgaggcttcgac ggccagggcgctcgcgtcaaggtcaccgaagctgacccaatcaacgctcttcaggctctg atggatggctactctgtggtcaccgttgatgaggccatcgaggacgccgacatcgtgatc accgcgaccggcaacaaggacatcatttccttcgagcagatgctcaagatgaaggatcac gctctgctgggcaacatcggtcactttgataatgagatcgatatgcattccctgttgcac cgcgacgacgtcacccgcaccacgatcaagccacaggtcgacgagttcaccttctccacc ggtcgctccatcatcgtcctgtccgaaggtcgcctgttgaaccttggcaacgccaccgga cacccatcatttgtcatgtccaactctttcgccgatcagaccattgcgcagatcgaactg ttccaaaacgaaggacagtacgagaacgaggtctaccgtctgcctaaggttctcgacgaa aaggtggcacgcatccacgttgaggctctcggcggtcagctcaccgaactgaccaaggag caggctgagtacatcggcgttgacgttgcaggcccattcaagccggagcactaccgctac taa sahH amino acid sequence

<SEQ ID NO: 149>

MAQVMDFKVADLSLAEAGRHQIRLAEYEMPGLMQLRKEFADEQPLKGARIAGSI

HMTVQTAVLIETLTALGAEVRWASCNIFSTQDEAAAAIVVGSGTVEEPAGVPVFAWKGES

LEEYWWCINQIFSWGDELPNMILDDGGDATMAVIRGREYEQAGLVPPAEANDSDEYIAFL

GMLREVLAAEPGKWGKIAEAVKGVTEETTTGVHRLYHFAEEGVLPFPAMNVNDAVTKSKF

DNKYGTRHSLIDGINRATDMLMGGKNVLVCGYGDVGKGCAEAFDGQGARVKVTEADPINA

LQALMDGYSVVTVDEAIEDADIVITATGNKDIISFEQMLKMKDHALLGNIGHFDNEIDMH

SLLHRDDVTRTTIKPQVDEFTFSTGRSIIVLSEGRLLNLGNATGHPSFVMSNSFADQTIA

QIELFQNEGQYENEVYRLPKVLDEKVARIHVEALGGQLTELTKEQAEYIGVDVAGPFKPE

HYRY aroG$^{S180F}$ gene sequence

<SEQ ID NO: 150> atgaattatcagaacgacgatttacgcatcaaagaaatcaaagagttacttcct cctgtcgcattgctggaaaaattccccgctactgaaaatgccgcgaatacggttgcccat gcccgaaaaagcgatccataagatcctgaaaggtaatgatgatcgcctgttggttgtgatt ggcccatgctcaattcatgatcctgtcgcggcaaaagagtatgccactcgcttgctggcg -continued

```
ctgcgtgaagagctgaaagatgagctggaaatcgtaatgcgcgtctattttgaaaagccg cgtaccacggtgggctggaaagggctgattaacgatccgcatatggataatagcttccag atcaacgacggtctgcgtatagcccgtaaattgctgcttgatattaacgacagcggtctg ccagcggcaggtgagtttctcgatatgatcacccacaatatctcgctgacctgatgagc tggggcgcaattggcgcacgtaccaccgaatcgcaggtgcaccgcgaactggcatcaggg cttttttgtccggtcggcttcaaaaatggcaccgacggtacgattaaagtggctatcgat gccattaatgccgccggtgcgccgcactgcttcctgtccgtaacgaaatgggggcattcg gcgattgtgaataccagcggtaacggcgattgccatatcattctgcgcggcggtaaagag cctaactacagcgcgaagcacgttgctgaagtgaaagaagggctgaacaaagcaggcctg ccagcacaggtgatgatcgatttcagccatgctaactcgtccaaacaattcaaaaagcag atggatgtttgtgctgacgtttgccagcagattgccggtggcgaaaaggccattattggc gtgatggtggaaagccatctggtggaaggcaatcagagcctcgagagcggggagccgctg gcctacggtaagagcatcaccgatgcctgcatcggctgggaagataccgatgctctgtta cgtcaactggcgaatgcagtaaaagcgcgtcgcgggtaa
``` aro<sup>GS18F</sup> amino acid sequence

<SEQ ID NO: 151>

MNYQNDDLRIKEIKELLPPVALLEKFPATENAANTVAHARKAIHKILKGNDDRL

LVVIGPCSIHDPVAAKEYATRLLALREELKDELEIVMRVYFEKPRTTVGWKGLINDPHMD

NSFQINDGLRIARKLLLDINDSGLPAAGEFLDMITPQYLADLMSWGAIGARTTESQVHRE

LASGLFCPVGFKNGTDGTIKVAIDAINAAGAPHCFLSVTKWGHSAIVNTSGNGDCHIILR

GGKEPNYSAKHVAEVKEGLNKAGLPAQVMIDFSHANSSKQFKKQMDVCADVCQQIAGGEK

AIIGVMVESHLVEGNQSLESGEPLAYGKSITDACIGWEDTDALLRQLANAVKARRG-aamt 2 gene sequence

<SEQ ID NO: 152>

```
ATGAGAATAGAGCGTGATCTCCACATGGCCACAGGGGACGGAGAAACTAGCTACACGAAA

AATTCTAGGATTCAAGAGAAAACTATGITTCAGATCAAGCCTGICCITGAGGAGGCCACA

AGAGCAGTATACACAGCTCTCCACCCTCAAACCATGGITGTTGCTGACTTAGGCTGCTCA

TCTGGGCCTAACACACTACGCTTCGTATCCGAGGTGATTGGCATCATAGCTCGCCATTGC

AAAGAATATGGCCGACAACATGACCACACACAGCTICAGTICTICCTGAATGACCTGCCC

GGAAACGACTTCAACAATCTCTTCCAGCTGATCCAGCAGTTCAATAAGTCGACGGCAATA

AACCACAAGAGTGAGGCAGCTGAGGCACTACCTCCTCCGTGCTATATCTCTGGGTTGCCT

GGCTCCTACTACACTAGGATCTTCCCTAGCGAAAGTGTTCACCTTTTCCATTCTTTGTTC

TGCCTTCAGTGGCGCTCTGAGGCACCAGAGGGCAACAAAAAAACATGCCTAGATATCTAC

ATCACAAAGACTATGTCACCGTCGATGGTGAAGTTGTTTCAACAACAGTTTCAGAAGGAT

TTCTCCCTCTTCCTCAGGCTACGCTACGAGGAACTCGTGTCCGGTGGCCAAATGGTTCTA

ACATTTATTGGAAGGAAGCATGAGAATGTGTTCACTGGAGAGTCTAACCATCTTTACGGA

TTGCTTGCGCAGTCACTGAAATCCCTAGTTGATGAGGGTCTTGTGGAGAAGGAAAAACTT

GAATCATTCTATTTACCAATGTATTCACCATCGGTTGGTGAAGTGGAGGCCATACTAAAG

CAAGTTGGGTTGTTCAACATGAATCATGTAAAAGTATTCCAGACAAATTGGGATCCCTAC

GATGACTTGGAAAGTGATGTTGTGCATAACAGTATTAGGAGCGGTGAAAATGTTGCTAAG

TGCCTACGAGCAGTTATGCAGCCGCTAGTCGCAAGCCAATTTGGAGAACCCATTCTCGAT

AAGTTATTCAAAGAGTACGCTCGCCGTGTTGCCAAACACCTTGAGAATGAGAAAACCAAG

CATGCTATTATTGTCCTATCCATCGAGAAAGCAATTCACCTGTGA
```

-continued aamt 2 amino acid sequence
<SEQ ID NO: 153>
MRIERDLHMATGDGETSYTKNSRIQEKTMFQIKPVLEEATRAVYTALHPQTMVVADLGCS

SGPNTLRFVSEVIGIIARHCKEYGRQHDHTQLQFFLNDLPGNDFNNLFQLIQQFNKSTAI

NHKSEAAEALPPPCYISGLPGSYYTRIFPSESVHLFHSLFCLQWRSEAPEGNKKTCLDIY

ITKTMSPSMVKLFQQQFQKDFSLFLRLRYEELVSGGQMVLIFIGRKHENVFTGESNHLYG

LLAQSLKSLVDEGLVEKEKLESFYLPMYSPSVGEVEAILKQVGLFNMNHVKVFQTNWDPY

DDLESDVVHNSIRSGENVAKCLRAVMQPLVASQFGEPILDKLFKEYARRVAKHLENEKTK

HAIIVLSIEKAIHL aamt 3 gene sequence
<SEQ ID NO: 154>
ATGCCGATGAGAATCGAGCGTGATCTCCACATGGCCACAGGGAACGGAGAAACTAGCTACACGAAAAACT

CTAGGATTCAGGAGAAAGTTATGTTTCAGATCAAGCCAGTCCTTGAGGAGGCCACTAGAGCAGCATACTC

AGCTCTCCTCCCTCAAACCATGGTCGTGGCCGACTTAGGCTGCTCATCGGGGCCTAACACACTGCGCTTC

GTCTCCGAGGTGATTGGCATCATAGCTCGCCATTGCAAAGAACACGACCGACGACATGACTACCCACAAC

TTCAGTTCTTCCTGAATGACCTGCCGGGAAACGACTTCAACAATCTCTTCCTACTCATCCAGCAGTTCAA

TAAGTCGATGGCAAGAAACCACAAGGGTGAGGCAGCCGAGGCACTGCCTCCGTGCTATATCTCTGGTTTG

CCAGGCTCCTTCTACACTAGGATCTTCCCTAGCGAAAGCGTTCACCTTTTCCACTCTTTGTTCTCCGTTC

ACTGGCACTCTCAGGCATCAGAACAACTAAAGGACACCAAAAATAAATGCTTAGATATCTACATCACAAA

GAATATGCCACCGTCGATGGTGAAGTTGTTTCAACAGCAGTTTGAGAAGGACTTCTCCCTCTTCCTCAAG

CTACGCTATGAGGAACTCGTGTCTGGTGGCCAAATGGTTCTAACATTTATTGGAAGAAAGCATGAGGATG

TGTTCACTGGAGAGTCCAACCATCTTTACGGATTGCTTGCGCAGTCACTGAAATCCCTAGTTGATGAGGG

TCTTGTGGAGAAAGAAAAACTTGAGTCATTCTATCTTCCGATCTACTCACCGTCGGTTGGTGAAGTGGAG

GCGATAGTGAAGCAAGTTGGGTTGTTCAACATGAATCATGTTAAAGTATTTGAGATAAATTGGGATCCCT

ACGGTGACTCAGAAGGTGATGATGTGCATGACAGTATTAGGAGCGGTGAAAATGTTGCTAAGTGCCTACG

AGCAGTTATGGAGCCGTTGGTTGCAAGCCAATTTGGAGAACACATACTCGACAAGTTATTCAAAGAGTAC

GCTCGTCGTGTTGCCAAACACCTTGAGAATGAGAAAACCAAGCATGCTATTCTTGTCCTATCCATCGAGA

AAGCAATAATTCATGTGTGA aamt 3 amino acid sequence
<SEQ ID NO: 155>
MPMRIERDLHMATGNGETSYTKNSRIQEKVMFQIKPVLEEATRAAYSALLPQTMVVADLG

CSSGPNTLRFVSEVIGIIARHCKEHDRRHDYPQLQFFLNDLPGNDFNNLFLLIQQFNKSM

ARNHKGEAAEALPPCYISGLPGSFYTRIFPSESVHLFHSLFSVHWHSQASEQLKDTKNKC

LDIYITKNMPPSMVKLFQQQFEKDFSLFLKLRYEELVSGGQMVLTFIGRKHEDVFTGESN

HLYGLLAQSLKSLVDEGLVEKEKLESFYLPIYSPSVGEVEAIVKQVGLFNMNHVKVFEIN

WDPYGDSEGDDVHDSIRSGENVAKCLRAVMEPLVASQFGEHILDKLFKEYARRVAKHLEN

EKTKHAILVLSIEKAIIHV 13-4. Host Strain Information
*Escherichia coli* str. K-12 substr. W3110
*Corynebacterium glutamicum* ATCC 13032

Although specific configurations of the present invention have been described in detail, those skilled in the art will appreciate that this detailed description is provided as preferred embodiments for illustrative purposes and should not be construed as limiting the scope of the present invention. Therefore, the substantial scope of the present invention is defined by the accompanying claims filed and equivalents thereto.

DESCRIPTION OF SYMBOLS

For Recombinant *E. Coli*
trpD, anthranilate phosphoribosyltransferase
aroK, shikimate kinase 1
pykF, pyruvate kinase I
pykA, pyruvate kinase II
aroG$^{fbr}$, feedback-resistant 3-deoxy-7-phosphoheptulonate synthase
metA$^{fbr}$, homoserine O-succinyltransferase
cysE$^{fbr}$, serine acetyltransferase trpE$^{fbr}$, anthranilate synthase subunit
ppsA, phosphoenolpyruvate synthetase
aroL, shikimate kinase 2
tktA, transketolase 1
metK, S-adenosylmethionine synthase
mtn, S-adenosylhomocysteine nucleosidase
luxS, S-ribosylhomocysteine lyase
For Recombinant *C. Glutamicum*
trpD, anthranilate phosphoribosyltransferase
qsuB, dehydroshikimate dehydratase
qsuD, quinate/shikimate dehydrogenase
hdpA, dihydroxyacetone phosphate phosphatase
aroK, shikimate kinase,
aroB, 3-dehydroquinate synthase
tkt, transketolase,
metK, S-adenosylmethionine synthase
aroG, 3-deoxy-7-phosphoheptulonate synthase
sahH, adenosylhomocysteinase
aroG$^{S180F}$, feedback-resistant 3-deoxy-7-phosphoheptulonate synthase

What is claimed is:

1. A recombinant bacterial or fungal microorganism that produces methyl anthranilate (MANT) from anthranilic acid (ANT), said bacterial or fungal microorganism comprising a gene encoding aamt1, aamt2, or aamt3.

2. The recombinant bacterial or fungal microorganism according to claim 1, wherein the aamt1 gene comprises SEQ ID NO: 1.

3. The recombinant bacterial or fungal microorganism according to claim 1, wherein the gene is codon-optimized for production of MANT in the recombinant bacterial or fungal microorganism.

4. The recombinant bacterial or fungal microorganism according to claim 1, wherein the gene is present along with a promoter selected from the group consisting of lac, lacUV5, trc, tac, trp, araBAD, T3, T5, T7, L10, 116, H30, H36, sod, tuf, eftu, Pm and Ptet.

5. The recombinant bacterial or fungal microorganism according to claim 1, wherein the bacterial or fungal microorganism is selected from the group consisting of *Escherichia coli*, *Corynebacterium* sp., *Bacillus* sp., *Lactobacillus* sp., *Lactococcus* sp., *Pseudomonas* sp., *Anacystis* sp., *Anabena* sp., *Chlorobium* sp., *Chloroflexus* sp., *Clostridium* sp., *Methanobacterium*, *Propionibacterium* sp., *Rhodopseudomonas* sp., *Rhodobacter* sp., *Rhodovulum* sp., *Streptococcus* sp., *Saccharomyces* sp. and *Aspergillus* sp.

6. The recombinant bacterial or fungal microorganism according to claim 1, wherein the recombinant bacterial or fungal microorganism is characterized in that
  at least one gene selected from the group consisting of trpD, pykA and pykF is deleted or inhibited;
  at least one feedback-resistant gene selected from the group consisting of aroGfbr, metA$^{fbr}$, cysE$^{fbr}$ and trpE-$^{fbr}$ is introduced or amplified; or
  at least one gene selected from the group consisting of ppsA, aroL, tktA, metK, mtn and luxS is introduced or amplified.

7. The recombinant bacterial or fungal microorganism according to claim 1, wherein the recombinant bacterial or fungal microorganism is characterized in that aroG$^{fbr}$, metA$^{fbr}$, cysE$^{fbr}$ and ppsA genes are introduced or amplified, and trpD and pykF genes are deleted or inhibited.

8. The recombinant bacterial or fungal microorganism according to claim 7, wherein the recombinant bacterial or fungal microorganism is characterized in that a tktA and/or metK gene is further introduced or amplified.

9. The recombinant bacterial or fungal microorganism according to claim 8, wherein the recombinant bacterial or fungal microorganism is *Escherichia coli* (*E. coli*).

10. The recombinant bacterial or fungal microorganism according to claim 1, wherein the recombinant bacterial or fungal microorganism is characterized in that at least one gene selected from the group consisting of trpD, qsuB, qsuD and hdpA is deleted or inhibited.

11. The recombinant bacterial or fungal microorganism according to claim 1, wherein the recombinant bacterial or fungal microorganism is characterized in that at least one gene selected from the group consisting of aroK, aroB, tkt, metK, aroG and sahH is introduced or amplified.

12. The recombinant bacterial or fungal microorganism according to claim 11, wherein the aroG gene is a feedback-resistant aroG gene.

13. The recombinant bacterial or fungal microorganism according to claim 1, wherein the recombinant bacterial or fungal microorganism is characterized in that aroG$^{S180F}$ and sahH genes are introduced or amplified, and trpD, qsuB, qsuD and hdpA genes are deleted or inhibited.

14. The recombinant bacterial or fungal microorganism according to claim 13, wherein the recombinant bacterial or fungal microorganism is *Corynebacterium glutamicum* (*C. glutamicum*).

15. A method of producing methyl anthranilate comprising:
  (a) culturing the recombinant bacterial or fungal microorganism according to claim 1 to produce methyl anthranilate; and
  (b) recovering the methyl anthranilate.

16. The method according to claim 15, wherein the culturing is carried out in a two-phase system comprising an aqueous phase and an organic phase.

17. The method according to claim 16, wherein the organic phase comprises tributyrin, a silicon oil, or 2-undecanone.

18. The method according to claim 16, wherein the culturing is carried out in a culture medium comprising methionine.

19. The method according to claim 16, wherein the recombinant microorganism is cultured in a medium supplemented with anthranilic acid.

* * * * *

UNITED STATES PATENT AND TRADEMARK OFFICE
CERTIFICATE OF CORRECTION

PATENT NO. : 10,837,005 B2
APPLICATION NO. : 16/792229
DATED : November 17, 2020
INVENTOR(S) : Sang Yup Lee et al.

Page 1 of 1

It is certified that error appears in the above-identified patent and that said Letters Patent is hereby corrected as shown below:

In the Claims

Column 206 Line 66: "116" should be -- I16 --.

Column 207 Line 19: "IuxS" should be -- luxS --.

Column 207 Line 25: "pykFgenes" should be -- pykF genes --.

Signed and Sealed this
Twenty-ninth Day of December, 2020

Andrei Iancu
*Director of the United States Patent and Trademark Office*

SEQUENCE LISTING

<160> NUMBER OF SEQ ID NOS: 161

<210> SEQ ID NO 1
<211> LENGTH: 1149
<212> TYPE: DNA
<213> ORGANISM: Artificial Sequence
<220> FEATURE:
<223> OTHER INFORMATION: Synthetic construct

<400> SEQUENCE: 1

```
atgccgatga gaatcgagcg tgatctccac atggccatag ggaacggaga aactagctac      60
acaaaaaatt ctaggattca agagaaagct atgtttcaga tgaagtcggt ccttgaggag     120
gccactagag cagtatgcac aactctcctc ccacaaacca tggttgtggc cgacttaggc     180
tgctcatcag ggcctaacac actgcgcttc gtcactgagg tgactagaat catagctcac     240
cattgcaagc tggagcacaa ccgacgacat gaccacctgc cgcagcttca gttctttctg     300
aatgacctgc ctggtaacga cttcaacaat ctcttccagc tcatcgagca gttcaataag     360
tcatcgacga cacacaaggg agatgcagca actgaggcac tacagcctcc ttgctatatc     420
tccggattgc cgggctccta ctacactagg atcttcccta gcgaaagcgt tcatcttttc     480
cactctctgt tctgccttca gtggcgctct caggcaccag agcaactgaa gggcacccaa     540
aaatcatgcc tagatatcta catcacaaag actatgtcac catcgatggt gaagttgttt     600
caacagcagt tcagaaagga cttctccctc ttcctcaggc tacgctatga ggaactcgtg     660
tctggtggcc aaatggttct aacatttatt ggaaggaagc atgaggatgt gttcactgga     720
gagtccaacc atctttacgg attgcttgcg cagtcactga atccctagt tgatgagggt       780 cttgtggaga agaaaaaact tgagtcattc tatcttccga tctactcacc gtcggttggt     840
gaagtggagg cgatagtgaa gcaacttggg ttgttcaaca tgaatcatgt taaagtattt     900
gagataaatt gggatcccta cgatgactca gaaggtgatg atgtgcataa cagtattgag     960
agtggtgaaa atgttgctaa gtgcctacgc gcagttatgc agccgctggt cgcaagccaa    1020
tttggagaac gcatactcga cgagttattc aaagagtacg ctcgccgtgt tgccaaacac    1080
cttgagaatg agaaaaccaa gcatgctgtt cttgtcctat ccatcgagaa agcaataatt    1140
catgtgtga                                                           1149
```

<210> SEQ ID NO 2
<211> LENGTH: 30
<212> TYPE: DNA
<213> ORGANISM: Artificial Sequence
<220> FEATURE:
<223> OTHER INFORMATION: Synthetic construct

<400> SEQUENCE: 2

```
agacaggaat tcatgccgat gcgtattgag                                       30
```

```
<210> SEQ ID NO 3
<211> LENGTH: 30
<212> TYPE: DNA
<213> ORGANISM: Artificial Sequence
<220> FEATURE:
<223> OTHER INFORMATION: Synthetic construct

<400> SEQUENCE: 3
agacagctgc agtcacacat ggataatcgc                              30

<210> SEQ ID NO 4
<211> LENGTH: 48
<212> TYPE: DNA
<213> ORGANISM: Artificial Sequence
<220> FEATURE:
<223> OTHER INFORMATION: Synthetic construct

<400> SEQUENCE: 4
agacaggaat tctcacacag gaaacagacc atgccgatgc gtattgag          48

<210> SEQ ID NO 5
<211> LENGTH: 30
<212> TYPE: DNA
<213> ORGANISM: Artificial Sequence
<220> FEATURE:
<223> OTHER INFORMATION: Synthetic construct

<400> SEQUENCE: 5
agacaggagc tctcacacat ggataatcgc                              30

<210> SEQ ID NO 6
<211> LENGTH: 40
<212> TYPE: DNA
<213> ORGANISM: Artificial Sequence
<220> FEATURE:
<223> OTHER INFORMATION: Synthetic construct

<400> SEQUENCE: 6
ttaaagagga gaaattaact atgccgatgc gtattgagcg                   40

<210> SEQ ID NO 7
<211> LENGTH: 40
<212> TYPE: DNA
<213> ORGANISM: Artificial Sequence
<220> FEATURE:
<223> OTHER INFORMATION: Synthetic construct

<400> SEQUENCE: 7
ctatcaacag gagtccaagc tcacacatgg ataatcgcct                   40

<210> SEQ ID NO 8
<211> LENGTH: 40
<212> TYPE: DNA
<213> ORGANISM: Artificial Sequence
<220> FEATURE:
<223> OTHER INFORMATION: Synthetic construct

<400> SEQUENCE: 8
aggcgattat ccatgtgtga gcttggactc ctgttgatag                   40

<210> SEQ ID NO 9
<211> LENGTH: 40
<212> TYPE: DNA
<213> ORGANISM: Artificial Sequence
<220> FEATURE:
<223> OTHER INFORMATION: Synthetic construct
```

<400> SEQUENCE: 9
cgctcaatac gcatcggcat agttaatttc tcctctttaa                                40

<210> SEQ ID NO 10
<211> LENGTH: 50
<212> TYPE: DNA
<213> ORGANISM: Artificial Sequence
<220> FEATURE:
<223> OTHER INFORMATION: Synthetic construct

<400> SEQUENCE: 10
gtgccaacat agtaagccag tatacactcc gtcataaaaa atttatttgc                     50

<210> SEQ ID NO 11
<211> LENGTH: 52
<212> TYPE: DNA
<213> ORGANISM: Artificial Sequence
<220> FEATURE:
<223> OTHER INFORMATION: Synthetic construct

<400> SEQUENCE: 11
tggccggggg actgttgggc gccatctcct tgattctcac caataaaaaa cg                  52

<210> SEQ ID NO 12
<211> LENGTH: 45
<212> TYPE: DNA
<213> ORGANISM: Artificial Sequence
<220> FEATURE:
<223> OTHER INFORMATION: Synthetic construct

<400> SEQUENCE: 12
tcacacagga aacagaccat atgaattatc agaacgacga tttac                          45

<210> SEQ ID NO 13
<211> LENGTH: 40
<212> TYPE: DNA
<213> ORGANISM: Artificial Sequence
<220> FEATURE:
<223> OTHER INFORMATION: Synthetic construct

<400> SEQUENCE: 13
gggtaccgag ctcgaattcc ttacccgcga cgcgctttta                                40

<210> SEQ ID NO 14
<211> LENGTH: 40
<212> TYPE: DNA
<213> ORGANISM: Artificial Sequence
<220> FEATURE:
<223> OTHER INFORMATION: Synthetic construct

<400> SEQUENCE: 14
taaaagcgcg tcgcgggtaa ggaattcgag ctcggtaccc                                40

<210> SEQ ID NO 15
<211> LENGTH: 40
<212> TYPE: DNA
<213> ORGANISM: Artificial Sequence
<220> FEATURE:
<223> OTHER INFORMATION: Synthetic construct

<400> SEQUENCE: 15
tcgtcgttct gataattcat atggtctgtt tcctgtgtga                                40

<210> SEQ ID NO 16
<211> LENGTH: 37
<212> TYPE: DNA
<213> ORGANISM: Artificial Sequence
<220> FEATURE:
<223> OTHER INFORMATION: Synthetic construct

<400> SEQUENCE: 16
ttcacacagg aaacagctat gaattatcag aacgacg                    37

<210> SEQ ID NO 17
<211> LENGTH: 40
<212> TYPE: DNA
<213> ORGANISM: Artificial Sequence
<220> FEATURE:
<223> OTHER INFORMATION: Synthetic construct

<400> SEQUENCE: 17
agcttatcga taccgtcgac ttacccgcga cgcgctttta                 40

<210> SEQ ID NO 18
<211> LENGTH: 40
<212> TYPE: DNA
<213> ORGANISM: Artificial Sequence
<220> FEATURE:
<223> OTHER INFORMATION: Synthetic construct

<400> SEQUENCE: 18
taaaagcgcg tcgcgggtaa gtcgacggta tcgataagct                 40

<210> SEQ ID NO 19
<211> LENGTH: 37
<212> TYPE: DNA
<213> ORGANISM: Artificial Sequence
<220> FEATURE:
<223> OTHER INFORMATION: Synthetic construct

<400> SEQUENCE: 19
cgtcgttctg ataattcata gctgtttcct gtgtgaa                    37

<210> SEQ ID NO 20
<211> LENGTH: 60
<212> TYPE: DNA
<213> ORGANISM: Artificial Sequence
<220> FEATURE:
<223> OTHER INFORMATION: Synthetic construct

<400> SEQUENCE: 20
cttgatatcg aattcctgca gcccggggac aggaaacaga ccatatgtcc tcacgtaaag    60

<210> SEQ ID NO 21
<211> LENGTH: 48
<212> TYPE: DNA
<213> ORGANISM: Artificial Sequence
<220> FEATURE:
<223> OTHER INFORMATION: Synthetic construct

<400> SEQUENCE: 21
accgcggtgg cggccgctct agaactagtg ttacagcagt tcttttgc        48

<210> SEQ ID NO 22
<211> LENGTH: 70
<212> TYPE: DNA
<213> ORGANISM: Artificial Sequence
<220> FEATURE:
<223> OTHER INFORMATION: Synthetic construct

<400> SEQUENCE: 22
gcatttcatt tttatggttt cgtttatacc gatggtttat gtggaaattg cgcgtcatac    60
acatacgatt                                                          70

<210> SEQ ID NO 23
<211> LENGTH: 70
<212> TYPE: DNA
<213> ORGANISM: Artificial Sequence
<220> FEATURE:
<223> OTHER INFORMATION: Synthetic construct

<400> SEQUENCE: 23
atgccgagtt ggttatacca aagcaccagc ggtgacgagc cattgttgga catggtctgt    60
ttcctgtgtg                                                          70

<210> SEQ ID NO 24
<211> LENGTH: 68
<212> TYPE: DNA
<213> ORGANISM: Artificial Sequence
<220> FEATURE:
<223> OTHER INFORMATION: Synthetic construct

<400> SEQUENCE: 24
ttatgtctgg tttataaaat gaaccttcaa ttttattttt tatgaaaaca gcatttcatt    60
tttatggt                                                            68

<210> SEQ ID NO 25
<211> LENGTH: 68
<212> TYPE: DNA
<213> ORGANISM: Artificial Sequence
<220> FEATURE:
<223> OTHER INFORMATION: Synthetic construct

<400> SEQUENCE: 25
tcatttcacc cagggaggca tttttgcccc caaccctgtc tacatcattc atgccgagtt    60
ggttatac                                                            68

<210> SEQ ID NO 26
<211> LENGTH: 71
<212> TYPE: DNA
<213> ORGANISM: Artificial Sequence
<220> FEATURE:
<223> OTHER INFORMATION: Synthetic construct

<400> SEQUENCE: 26
gaaagcaagt ttctcccatc cttctcaact taaagactaa gactgtcatg taggtgacac    60
tatagaacgc g                                                        71

<210> SEQ ID NO 27
<211> LENGTH: 70
<212> TYPE: DNA
<213> ORGANISM: Artificial Sequence
<220> FEATURE:
<223> OTHER INFORMATION: Synthetic construct

<400> SEQUENCE: 27
gatatacaaa ttaattcaca aaagcaatat tacaggacgt gaacagatgc tagtggatct    60
gatgggtacc                                                          70

<210> SEQ ID NO 28
<211> LENGTH: 70
<212> TYPE: DNA
<213> ORGANISM: Artificial Sequence
<220> FEATURE:
<223> OTHER INFORMATION: Synthetic construct

<400> SEQUENCE: 28
aggcaccacc actttcgtaa taccggattc gctttccggc agtgcgccca gaaagcaagt    60
ttctcccatc                                                          70

<210> SEQ ID NO 29
<211> LENGTH: 70
<212> TYPE: DNA
<213> ORGANISM: Artificial Sequence
<220> FEATURE:
<223> OTHER INFORMATION: Synthetic construct

<400> SEQUENCE: 29
attgcttctg gttatcgatt aaataaaaaa agcgcccatc agggcgcttc gatatacaaa    60
ttaattcaca                                                          70

<210> SEQ ID NO 30
<211> LENGTH: 84
<212> TYPE: DNA
<213> ORGANISM: Artificial Sequence
<220> FEATURE:
<223> OTHER INFORMATION: Synthetic construct

<400> SEQUENCE: 30
ttatttcatt cggatttcat gttcaagcaa cacctggttg tttcagtcaa cggagtatta    60
cattaggtga cactatagaa cgcg                                          84

<210> SEQ ID NO 31
<211> LENGTH: 80
<212> TYPE: DNA
<213> ORGANISM: Artificial Sequence
<220> FEATURE:
<223> OTHER INFORMATION: Synthetic construct

<400> SEQUENCE: 31
gttgaactat cattgaactg taggccggat gtggcgtttt cgccgcatcc ggcaacgtac    60
tagtggatct gatgggtacc                                               80

<210> SEQ ID NO 32
<211> LENGTH: 68
<212> TYPE: DNA
<213> ORGANISM: Artificial Sequence
<220> FEATURE:
<223> OTHER INFORMATION: Synthetic construct

<400> SEQUENCE: 32
cctaatctta tacgacatcc gaatgagatt aatttatcgc catcgcggcg ttatttcatt    60
cggatttc                                                            68

<210> SEQ ID NO 33
<211> LENGTH: 68
<212> TYPE: DNA
<213> ORGANISM: Artificial Sequence
<220> FEATURE:
<223> OTHER INFORMATION: Synthetic construct -continued

<400> SEQUENCE: 33
ggccttcgcc tgatgataag ttcaagtttg cttcagaata ttcgaaatct gttgaactat    60
cattgaac                                                              68

<210> SEQ ID NO 34
<211> LENGTH: 71
<212> TYPE: DNA
<213> ORGANISM: Artificial Sequence
<220> FEATURE:
<223> OTHER INFORMATION: Synthetic construct

<400> SEQUENCE: 34
agcgccctgg cacagacgat caattgttga ctgcatcaca caggaaacag accatgcaaa    60
cacaaaaacc g                                                          71

<210> SEQ ID NO 35
<211> LENGTH: 53
<212> TYPE: DNA
<213> ORGANISM: Artificial Sequence
<220> FEATURE:
<223> OTHER INFORMATION: Synthetic construct

<400> SEQUENCE: 35
tcatccgcca aaacagccaa gcttgcatgc ctgcatcaga agtctcctg tgc             53

<210> SEQ ID NO 36
<211> LENGTH: 55
<212> TYPE: DNA
<213> ORGANISM: Artificial Sequence
<220> FEATURE:
<223> OTHER INFORMATION: Synthetic construct

<400> SEQUENCE: 36
atcagtgcca acatagtaag ccagtataca ctccgtgagc tgttgacaat taatc          55

<210> SEQ ID NO 37
<211> LENGTH: 54
<212> TYPE: DNA
<213> ORGANISM: Artificial Sequence
<220> FEATURE:
<223> OTHER INFORMATION: Synthetic construct

<400> SEQUENCE: 37
ccgtggccgg gggactgttg ggcgccatct ccttggcaac gttcaaatcc gctc           54

<210> SEQ ID NO 38
<211> LENGTH: 43
<212> TYPE: DNA
<213> ORGANISM: Artificial Sequence
<220> FEATURE:
<223> OTHER INFORMATION: Synthetic construct

<400> SEQUENCE: 38
agacagaagc ttacaggaaa cagctatgcc gattcgtgtg ccg                       43

<210> SEQ ID NO 39
<211> LENGTH: 31
<212> TYPE: DNA
<213> ORGANISM: Artificial Sequence
<220> FEATURE:
<223> OTHER INFORMATION: Synthetic construct

<400> SEQUENCE: 39
agacagctgc agttaatcca gcgttggatt c                                    31

<210> SEQ ID NO 40
<211> LENGTH: 68
<212> TYPE: DNA
<213> ORGANISM: Artificial Sequence
<220> FEATURE:
<223> OTHER INFORMATION: Synthetic construct

<400> SEQUENCE: 40
cacatgaatc aacgctgga ttaactgcag cccggggaca ggaaacagct atgtcgtgtg    60
aagaactg    68

<210> SEQ ID NO 41
<211> LENGTH: 61
<212> TYPE: DNA
<213> ORGANISM: Artificial Sequence
<220> FEATURE:
<223> OTHER INFORMATION: Synthetic construct

<400> SEQUENCE: 41
aattggagct ccaccgcggt ggcggccgct ctagaactag tgttagatcc catccccata    60
c    61

<210> SEQ ID NO 42
<211> LENGTH: 70
<212> TYPE: DNA
<213> ORGANISM: Artificial Sequence
<220> FEATURE:
<223> OTHER INFORMATION: Synthetic construct

<400> SEQUENCE: 42
aggcgattat ccatgtgtga ctgcaggcat gacacaggaa acagaccata tggcaaaaca    60
cctttttacg    70

<210> SEQ ID NO 43
<211> LENGTH: 53
<212> TYPE: DNA
<213> ORGANISM: Artificial Sequence
<220> FEATURE:
<223> OTHER INFORMATION: Synthetic construct

<400> SEQUENCE: 43
ctctcatccg ccaaaacagc caagcttgca tgttacttca gaccggcagc atc    53

<210> SEQ ID NO 44
<211> LENGTH: 30
<212> TYPE: DNA
<213> ORGANISM: Artificial Sequence
<220> FEATURE:
<223> OTHER INFORMATION: Synthetic construct

<400> SEQUENCE: 44
agacaggaat tcatgccgat gcgtattgag    30

<210> SEQ ID NO 45
<211> LENGTH: 30
<212> TYPE: DNA
<213> ORGANISM: Artificial Sequence
<220> FEATURE:
<223> OTHER INFORMATION: Synthetic construct

<400> SEQUENCE: 45
agacagctgc agtcacacat ggataatcgc    30

<210> SEQ ID NO 46
<211> LENGTH: 30
<212> TYPE: DNA
<213> ORGANISM: Artificial Sequence
<220> FEATURE:
<223> OTHER INFORMATION: Synthetic construct

<400> SEQUENCE: 46
agacagggat ccatgccgat gcgtattgag                               30

<210> SEQ ID NO 47
<211> LENGTH: 32
<212> TYPE: DNA
<213> ORGANISM: Artificial Sequence
<220> FEATURE:
<223> OTHER INFORMATION: Synthetic construct

<400> SEQUENCE: 47
agacaggcgg ccgctcacac atggataatc gc                            32

<210> SEQ ID NO 48
<211> LENGTH: 48
<212> TYPE: DNA
<213> ORGANISM: Artificial Sequence
<220> FEATURE:
<223> OTHER INFORMATION: Synthetic construct

<400> SEQUENCE: 48
agacagggat ccatgcatca ccatcaccat catccgatgc gtattgag            48

<210> SEQ ID NO 49
<211> LENGTH: 32
<212> TYPE: DNA
<213> ORGANISM: Artificial Sequence
<220> FEATURE:
<223> OTHER INFORMATION: Synthetic construct

<400> SEQUENCE: 49
agacaggcgg ccgctcacac atggataatc gc                            32

<210> SEQ ID NO 50
<211> LENGTH: 20
<212> TYPE: DNA
<213> ORGANISM: Artificial Sequence
<220> FEATURE:
<223> OTHER INFORMATION: Synthetic construct

<400> SEQUENCE: 50
ctgctcaccg cgagtacgga                                          20

<210> SEQ ID NO 51
<211> LENGTH: 20
<212> TYPE: DNA
<213> ORGANISM: Artificial Sequence
<220> FEATURE:
<223> OTHER INFORMATION: Synthetic construct

<400> SEQUENCE: 51
ctggccaaga cgggttatga                                          20

<210> SEQ ID NO 52
<211> LENGTH: 20
<212> TYPE: DNA
<213> ORGANISM: Artificial Sequence
<220> FEATURE:
<223> OTHER INFORMATION: Synthetic construct

<400> SEQUENCE: 52
gcactgatta ctacccaaat                                           20

<210> SEQ ID NO 53
<211> LENGTH: 47
<212> TYPE: DNA
<213> ORGANISM: Artificial Sequence
<220> FEATURE:
<223> OTHER INFORMATION: Synthetic construct

<400> SEQUENCE: 53
tatagatatc cgcggtata ttaattaata taaacgcaga aaggccc              47

<210> SEQ ID NO 54
<211> LENGTH: 51
<212> TYPE: DNA
<213> ORGANISM: Artificial Sequence
<220> FEATURE:
<223> OTHER INFORMATION: Synthetic construct

<400> SEQUENCE: 54
tggatgatgg ggcgattcag gtatagatat cttgacaatt aatcatcggc t        51

<210> SEQ ID NO 55
<211> LENGTH: 44
<212> TYPE: DNA
<213> ORGANISM: Artificial Sequence
<220> FEATURE:
<223> OTHER INFORMATION: Synthetic construct

<400> SEQUENCE: 55
aaggtgttgc tgactcatac caggtataga tatcccgcgg tata                44

<210> SEQ ID NO 56
<211> LENGTH: 78
<212> TYPE: DNA
<213> ORGANISM: Artificial Sequence
<220> FEATURE:
<223> OTHER INFORMATION: Synthetic construct

<400> SEQUENCE: 56
ttgacaatta atcatcggct cgtataatgt gtggctgctc accgcgagta cggagtttta    60
gagctagaaa tagcaagt                                             78

<210> SEQ ID NO 57
<211> LENGTH: 78
<212> TYPE: DNA
<213> ORGANISM: Artificial Sequence
<220> FEATURE:
<223> OTHER INFORMATION: Synthetic construct

<400> SEQUENCE: 57
ttgacaatta atcatcggct cgtataatgt gtggctggcc aagacgggtt atgagtttta    60
gagctagaaa tagcaagt                                             78

<210> SEQ ID NO 58
<211> LENGTH: 78
<212> TYPE: DNA
<213> ORGANISM: Artificial Sequence
<220> FEATURE:
<223> OTHER INFORMATION: Synthetic construct

```
<400> SEQUENCE: 58
ttgacaatta atcatcggct cgtataatgt gtggcctcgc gcagggacgt gcgagtttta      60
gagctagaaa tagcaagt                                                   78

<210> SEQ ID NO 59
<211> LENGTH: 88
<212> TYPE: DNA
<213> ORGANISM: Artificial Sequence
<220> FEATURE:
<223> OTHER INFORMATION: Synthetic construct

<400> SEQUENCE: 59
tgtgtcgaac agcttctcgc gaactaataa aaaaggatt tgataggttt gctagattcc       60
gctggtactg gtggcgacgg tgccaaca                                        88

<210> SEQ ID NO 60
<211> LENGTH: 80
<212> TYPE: DNA
<213> ORGANISM: Artificial Sequence
<220> FEATURE:
<223> OTHER INFORMATION: Synthetic construct

<400> SEQUENCE: 60
tcagttagcg gatgcgccga agctgagcat ggacattttg ctttggagat cttcaacgat      60
tccttccgca aggccgaggt                                                 80

<210> SEQ ID NO 61
<211> LENGTH: 80
<212> TYPE: DNA
<213> ORGANISM: Artificial Sequence
<220> FEATURE:
<223> OTHER INFORMATION: Synthetic construct

<400> SEQUENCE: 61
ctggcaaatc tcaaaaagta gaaagcccaa aaatatgaac acaggcgcat cgacacgctt      60
gggtcgcgtg cttccgggca                                                 80

<210> SEQ ID NO 62
<211> LENGTH: 50
<212> TYPE: DNA
<213> ORGANISM: Artificial Sequence
<220> FEATURE:
<223> OTHER INFORMATION: Synthetic construct

<400> SEQUENCE: 62
agacagggat ccatgcatca ccatcaccat catcctatgc gtatcgaacg                50

<210> SEQ ID NO 63
<211> LENGTH: 32
<212> TYPE: DNA
<213> ORGANISM: Artificial Sequence
<220> FEATURE:
<223> OTHER INFORMATION: Synthetic construct

<400> SEQUENCE: 63
agacaggcgg ccgctcagac gtggatgata gc                                   32

<210> SEQ ID NO 64
<211> LENGTH: 201
<212> TYPE: DNA
<213> ORGANISM: Artificial Sequence
<220> FEATURE:
<223> OTHER INFORMATION: Synthetic construct
```

<400> SEQUENCE: 64
aaccctactt agctgccaat tattccgggc ttgtgacccg ctacccgata aataggtcgg        60
ctgaaaaatt tcgttgcaat atcaacaaaa aggcctatca ttgggaggtg tcgcaccaag       120
tacttttgcg aagcgccatc tgacggattt tcaaaagatg tatatgctcg gtgcggaaac       180
ctacgaaagg attttttacc c                                                 201

<210> SEQ ID NO 65
<211> LENGTH: 20
<212> TYPE: DNA
<213> ORGANISM: Artificial Sequence
<220> FEATURE:
<223> OTHER INFORMATION: Synthetic construct

<400> SEQUENCE: 65
aaccctactt agctgccaat                                                    20

<210> SEQ ID NO 66
<211> LENGTH: 22
<212> TYPE: DNA
<213> ORGANISM: Artificial Sequence
<220> FEATURE:
<223> OTHER INFORMATION: Synthetic construct

<400> SEQUENCE: 66
gggtaaaaaa tcctttcgta gg                                                 22

<210> SEQ ID NO 67
<211> LENGTH: 40
<212> TYPE: DNA
<213> ORGANISM: Artificial Sequence
<220> FEATURE:
<223> OTHER INFORMATION: Synthetic construct

<400> SEQUENCE: 67
ccaagcttgc atgcctgcag tttgggctca cacatttctg                              40

<210> SEQ ID NO 68
<211> LENGTH: 40
<212> TYPE: DNA
<213> ORGANISM: Artificial Sequence
<220> FEATURE:
<223> OTHER INFORMATION: Synthetic construct

<400> SEQUENCE: 68
attggcagct aagtagggtt cctctaaacc ttcgaatttc                              40

<210> SEQ ID NO 69
<211> LENGTH: 40
<212> TYPE: DNA
<213> ORGANISM: Artificial Sequence
<220> FEATURE:
<223> OTHER INFORMATION: Synthetic construct

<400> SEQUENCE: 69
tacgaaagga ttttttaccc atggagcgta atgaagtgaa                              40

<210> SEQ ID NO 70
<211> LENGTH: 40
<212> TYPE: DNA
<213> ORGANISM: Artificial Sequence
<220> FEATURE:
<223> OTHER INFORMATION: Synthetic construct

<400> SEQUENCE: 70
agctcggtac ccggggatcc taggttgcca cctcttcgta            40

<210> SEQ ID NO 71
<211> LENGTH: 42
<212> TYPE: DNA
<213> ORGANISM: Artificial Sequence
<220> FEATURE:
<223> OTHER INFORMATION: Synthetic construct

<400> SEQUENCE: 71
ccaagcttgc atgcctgcag aacactgaac tcgtcgactc cg         42

<210> SEQ ID NO 72
<211> LENGTH: 40
<212> TYPE: DNA
<213> ORGANISM: Artificial Sequence
<220> FEATURE:
<223> OTHER INFORMATION: Synthetic construct

<400> SEQUENCE: 72
attggcagct aagtagggtt ggggcacgtt gcctttcgct            40

<210> SEQ ID NO 73
<211> LENGTH: 40
<212> TYPE: DNA
<213> ORGANISM: Artificial Sequence
<220> FEATURE:
<223> OTHER INFORMATION: Synthetic construct

<400> SEQUENCE: 73
tacgaaagga ttttttaccc atgagcgcag tgcagatttt            40

<210> SEQ ID NO 74
<211> LENGTH: 40
<212> TYPE: DNA
<213> ORGANISM: Artificial Sequence
<220> FEATURE:
<223> OTHER INFORMATION: Synthetic construct

<400> SEQUENCE: 74
agctcggtac ccggggatcc aatactgcgt caggctcgtg            40

<210> SEQ ID NO 75
<211> LENGTH: 31
<212> TYPE: DNA
<213> ORGANISM: Artificial Sequence
<220> FEATURE:
<223> OTHER INFORMATION: Synthetic construct

<400> SEQUENCE: 75
agacaggaat tcatgaatta tcagaacgac g                     31

<210> SEQ ID NO 76
<211> LENGTH: 30
<212> TYPE: DNA
<213> ORGANISM: Artificial Sequence
<220> FEATURE:
<223> OTHER INFORMATION: Synthetic construct

<400> SEQUENCE: 76
agacagggat ccttacccgc gacgcgcttt                       30

<210> SEQ ID NO 77
<211> LENGTH: 50
<212> TYPE: DNA
<213> ORGANISM: Artificial Sequence
<220> FEATURE:
<223> OTHER INFORMATION: Synthetic construct

<400> SEQUENCE: 77
agacagggat ccatgcatca ccatcaccat catcctatgc gtatcgaacg          50

<210> SEQ ID NO 78
<211> LENGTH: 32
<212> TYPE: DNA
<213> ORGANISM: Artificial Sequence
<220> FEATURE:
<223> OTHER INFORMATION: Synthetic construct

<400> SEQUENCE: 78
agacaggcgg ccgctcagac gtggatgata gc          32

<210> SEQ ID NO 79
<211> LENGTH: 33
<212> TYPE: DNA
<213> ORGANISM: Artificial Sequence
<220> FEATURE:
<223> OTHER INFORMATION: Synthetic construct

<400> SEQUENCE: 79
agacaggaat tcatggctca gccaaccgcc gtc          33

<210> SEQ ID NO 80
<211> LENGTH: 32
<212> TYPE: DNA
<213> ORGANISM: Artificial Sequence
<220> FEATURE:
<223> OTHER INFORMATION: Synthetic construct

<400> SEQUENCE: 80
agacagctgc agttaggcca acttgagggc tg          32

<210> SEQ ID NO 81
<211> LENGTH: 60
<212> TYPE: DNA
<213> ORGANISM: Artificial Sequence
<220> FEATURE:
<223> OTHER INFORMATION: Synthetic construct

<400> SEQUENCE: 81
gttttcgccc cgaagaacgt tttccaatga tgagcacttt tgagctgttg acaattaatc          60

<210> SEQ ID NO 82
<211> LENGTH: 58
<212> TYPE: DNA
<213> ORGANISM: Artificial Sequence
<220> FEATURE:
<223> OTHER INFORMATION: Synthetic construct

<400> SEQUENCE: 82
cgtcaacacg ggataatacc gcgccacata gcagaacttt ttaggccaac ttgagggc          58

<210> SEQ ID NO 83
<211> LENGTH: 40
<212> TYPE: DNA
<213> ORGANISM: Artificial Sequence
<220> FEATURE:
<223> OTHER INFORMATION: Synthetic construct

<400> SEQUENCE: 83
ccaagcttgc atgcctgcag cgcaaatacc cacttaccga                                40

<210> SEQ ID NO 84
<211> LENGTH: 30
<212> TYPE: DNA
<213> ORGANISM: Artificial Sequence
<220> FEATURE:
<223> OTHER INFORMATION: Synthetic construct

<400> SEQUENCE: 84
aagagtaaaa gctgttggtg ttccttgatg                                          30

<210> SEQ ID NO 85
<211> LENGTH: 30
<212> TYPE: DNA
<213> ORGANISM: Artificial Sequence
<220> FEATURE:
<223> OTHER INFORMATION: Synthetic construct

<400> SEQUENCE: 85
caccaacagc ttttactctt gcctgaagcg                                          30

<210> SEQ ID NO 86
<211> LENGTH: 40
<212> TYPE: DNA
<213> ORGANISM: Artificial Sequence
<220> FEATURE:
<223> OTHER INFORMATION: Synthetic construct

<400> SEQUENCE: 86
agctcggtac ccggggatcc caccgaaaga aaggagaac                                40

<210> SEQ ID NO 87
<211> LENGTH: 40
<212> TYPE: DNA
<213> ORGANISM: Artificial Sequence
<220> FEATURE:
<223> OTHER INFORMATION: Synthetic construct

<400> SEQUENCE: 87
ccaagcttgc atgcctgcag ttctttcgga agaagaatcc                               40

<210> SEQ ID NO 88
<211> LENGTH: 30
<212> TYPE: DNA
<213> ORGANISM: Artificial Sequence
<220> FEATURE:
<223> OTHER INFORMATION: Synthetic construct

<400> SEQUENCE: 88
gatgttgatt cttgaacttg tgttggaaat                                          30

<210> SEQ ID NO 89
<211> LENGTH: 30
<212> TYPE: DNA
<213> ORGANISM: Artificial Sequence
<220> FEATURE:
<223> OTHER INFORMATION: Synthetic construct

<400> SEQUENCE: 89
caagttcaag aatcaacatc tggtttcccc                                          30

```
<210> SEQ ID NO 90
<211> LENGTH: 40
<212> TYPE: DNA
<213> ORGANISM: Artificial Sequence
<220> FEATURE:
<223> OTHER INFORMATION: Synthetic construct

<400> SEQUENCE: 90
agctcggtac ccggggatcc aggcaaagat gccctcgttt                    40

<210> SEQ ID NO 91
<211> LENGTH: 40
<212> TYPE: DNA
<213> ORGANISM: Artificial Sequence
<220> FEATURE:
<223> OTHER INFORMATION: Synthetic construct

<400> SEQUENCE: 91
ccaagcttgc atgcctgcag aggttattga gggcctgctc                    40

<210> SEQ ID NO 92
<211> LENGTH: 30
<212> TYPE: DNA
<213> ORGANISM: Artificial Sequence
<220> FEATURE:
<223> OTHER INFORMATION: Synthetic construct

<400> SEQUENCE: 92
attcacgctg aacgaccagg aaatggacga                               30

<210> SEQ ID NO 93
<211> LENGTH: 30
<212> TYPE: DNA
<213> ORGANISM: Artificial Sequence
<220> FEATURE:
<223> OTHER INFORMATION: Synthetic construct

<400> SEQUENCE: 93
cctggtcgtt cagcgtgaat cgatgcagtg                               30

<210> SEQ ID NO 94
<211> LENGTH: 40
<212> TYPE: DNA
<213> ORGANISM: Artificial Sequence
<220> FEATURE:
<223> OTHER INFORMATION: Synthetic construct

<400> SEQUENCE: 94
agctcggtac ccggggatcc aaaaagcccg caccctgatt                    40

<210> SEQ ID NO 95
<211> LENGTH: 68
<212> TYPE: DNA
<213> ORGANISM: Artificial Sequence
<220> FEATURE:
<223> OTHER INFORMATION: Synthetic construct

<400> SEQUENCE: 95
aaagcgcgtc gcgggtaagg atccgtcgac ctgcaagaag gagatatacc atggcacagg    60
ttatggac                                                      68

<210> SEQ ID NO 96
<211> LENGTH: 53
<212> TYPE: DNA
<213> ORGANISM: Artificial Sequence
```

```
<220> FEATURE:
<223> OTHER INFORMATION: Synthetic construct

<400> SEQUENCE: 96
tctctcatcc gccaaaacag ccaagcttgg ctgcattagt agcggtagtg ctc          53

<210> SEQ ID NO 97
<211> LENGTH: 40
<212> TYPE: DNA
<213> ORGANISM: Artificial Sequence
<220> FEATURE:
<223> OTHER INFORMATION: Synthetic construct

<400> SEQUENCE: 97
ccaagcttgc atgcctgcag gtacggtttt tgctaaatgc                         40

<210> SEQ ID NO 98
<211> LENGTH: 30
<212> TYPE: DNA
<213> ORGANISM: Artificial Sequence
<220> FEATURE:
<223> OTHER INFORMATION: Synthetic construct

<400> SEQUENCE: 98
ctacagaata aacaccattg tccctgtttt                                    30

<210> SEQ ID NO 99
<211> LENGTH: 30
<212> TYPE: DNA
<213> ORGANISM: Artificial Sequence
<220> FEATURE:
<223> OTHER INFORMATION: Synthetic construct

<400> SEQUENCE: 99
caatggtgtt tattctgtag gtcatggcat                                    30

<210> SEQ ID NO 100
<211> LENGTH: 40
<212> TYPE: DNA
<213> ORGANISM: Artificial Sequence
<220> FEATURE:
<223> OTHER INFORMATION: Synthetic construct

<400> SEQUENCE: 100
agctcggtac ccggggatcc tgtcggagat gagtccgatt                         40

<210> SEQ ID NO 101
<211> LENGTH: 382
<212> TYPE: PRT
<213> ORGANISM: Artificial Sequence
<220> FEATURE:
<223> OTHER INFORMATION: Synthetic construct

<400> SEQUENCE: 101

Met Pro Met Arg Ile Glu Arg Asp Leu His Met Ala Ile Gly Asn Gly
1               5                   10                  15

Glu Thr Ser Tyr Thr Lys Asn Ser Arg Ile Gln Glu Lys Ala Met Phe
            20                  25                  30

Gln Met Lys Ser Val Leu Glu Glu Ala Thr Arg Ala Val Cys Thr Thr
        35                  40                  45

Leu Leu Pro Gln Thr Met Val Val Ala Asp Leu Gly Cys Ser Ser Gly
    50                  55                  60

Pro Asn Thr Leu Arg Phe Val Thr Glu Val Thr Arg Ile Ile Ala His
65                  70                  75                  80
```

His Cys Lys Leu Glu His Asn Arg Arg His Asp His Leu Pro Gln Leu
                85                  90                  95

Gln Phe Phe Leu Asn Asp Leu Pro Gly Asn Asp Phe Asn Asn Leu Phe
            100                 105                 110

Gln Leu Ile Glu Gln Phe Asn Lys Ser Ser Thr Thr His Lys Gly Asp
        115                 120                 125

Ala Ala Thr Glu Ala Leu Gln Pro Pro Cys Tyr Ile Ser Gly Leu Pro
    130                 135                 140

Gly Ser Tyr Tyr Thr Arg Ile Phe Pro Ser Glu Ser Val His Leu Phe
145                 150                 155                 160

His Ser Leu Phe Cys Leu Gln Trp Arg Ser Gln Ala Pro Glu Gln Leu
                165                 170                 175

Lys Gly Thr Gln Lys Ser Cys Leu Asp Ile Tyr Ile Thr Lys Thr Met
            180                 185                 190

Ser Pro Ser Met Val Lys Leu Phe Gln Gln Gln Phe Gln Lys Asp Phe
        195                 200                 205

Ser Leu Phe Leu Arg Leu Arg Tyr Glu Glu Leu Val Ser Gly Gly Gln
    210                 215                 220

Met Val Leu Thr Phe Ile Gly Arg Lys His Glu Asp Val Phe Thr Gly
225                 230                 235                 240

Glu Ser Asn His Leu Tyr Gly Leu Leu Ala Gln Ser Leu Lys Ser Leu
                245                 250                 255

Val Asp Glu Gly Leu Val Glu Lys Glu Lys Leu Glu Ser Phe Tyr Leu
            260                 265                 270

Pro Ile Tyr Ser Pro Ser Val Gly Glu Val Glu Ala Ile Val Lys Gln
        275                 280                 285

Leu Gly Leu Phe Asn Met Asn His Val Lys Val Phe Glu Ile Asn Trp
    290                 295                 300

Asp Pro Tyr Asp Asp Ser Glu Gly Asp Asp Val His Asn Ser Ile Glu
305                 310                 315                 320

Ser Gly Glu Asn Val Ala Lys Cys Leu Arg Ala Val Met Glu Pro Leu
                325                 330                 335

Val Ala Ser Gln Phe Gly Glu Arg Ile Leu Asp Glu Leu Phe Lys Glu
            340                 345                 350

Tyr Ala Arg Arg Val Ala Lys His Leu Glu Asn Glu Lys Thr Lys His
        355                 360                 365

Ala Val Leu Val Leu Ser Ile Glu Lys Ala Ile Ile His Val
    370                 375                 380

<210> SEQ ID NO 102
<211> LENGTH: 1149
<212> TYPE: DNA
<213> ORGANISM: Artificial Sequence
<220> FEATURE:
<223> OTHER INFORMATION: Synthetic construct

<400> SEQUENCE: 102
atgccgatgc gtattgagcg cgacctgcac atggcgatcg gtaatggcga gaccagctac      60
accaagaaca gccgtatcca agaaaaagcg atgttccaga tgaaaagcgt gctggaggaa     120
gcgacccgtg cggtttgcac caccctgctg ccgcaaacca tggttgttgc ggacctgggt     180
tgcagcagcg gtccgaacac cctgcgtttt gtgaccgagg ttacccgtat cattgcgcac     240
cactgcaagc tggaacacaa ccgtcgtcac gatcacctgc cgcaactgca attctttctg     300
aacgacctgc cgggtaacga tttcaacaac ctgtttcaac tgatcgagca gttcaacaag     360

| | |
|---|---|
| agcagcacca cccataaagg tgatgcggcg accgaagcgc tgcaaccgcc gtgctacatc | 420 |
| agcggtctgc cgggtagcta ctatacccgt attttccga gcgagagcgt gcacctgttc | 480 |
| cacagcctgt tttgcctgca atggcgtagc caggcgccgg aacaactgaa gggtacccag | 540 |
| aagagctgcc tggacatcta cattaccaag accatgagcc cgagcatggt taaactgttc | 600 |
| cagcaacagt ttcagaagga tttcagcctg tttctgcgtc tgcgttatga ggaactggtg | 660 |
| agcggtggcc aaatggttct gaccttcatt ggtcgtaaac acgaggacgt gtttaccggt | 720 |
| gaaagcaacc acctgtatgg cctgctggcg cagagcctga gagcctggt ggatgagggc | 780 |
| ctggttgaga aggaaaaact ggaaagcttc tacctgccga tctatagccc gagcgtgggt | 840 |
| gaggttgaag cgattgttaa acaactgggc ctgttcaaca tgaaccacgt gaaggttttt | 900 |
| gagatcaact gggacccgta cgacgatagc gaaggtgacg atgtgcacaa cagcattgag | 960 |
| agcggcgaaa acgttgcgaa atgcctgcgt gcggtgatgg agccgctggt tgcgagccag | 1020 |
| ttcggcgaac gtatcctgga tgagctgttt aagaatatg cgcgtcgtgt ggcgaagcac | 1080 |
| ctggagaacg aaaagaccaa acacgcggtt ctggttctga gcattgaaaa ggcgattatc | 1140 |
| catgtgtga | 1149 |

<210> SEQ ID NO 103
<211> LENGTH: 1149
<212> TYPE: DNA
<213> ORGANISM: Artificial Sequence
<220> FEATURE:
<223> OTHER INFORMATION: Synthetic construct

<400> SEQUENCE: 103

| | |
|---|---|
| atgcctatgc gtatcgaacg tgacctccac atggctatcg gtaacggcga aacctcttac | 60 |
| accaaaaact ctcgtattca ggaaaaagcc atgttccaga tgaagtccgt tctggaagag | 120 |
| gccacccgcg cagtgtgcac caccctgctg ccacagacca tggttgttgc tgatctgggc | 180 |
| tgctcctccg gtccaaacac cctgcgcttc gtcaccgaag ttacccgcat catcgcacac | 240 |
| cactgcaagc tggagcacaa ccgtcgccac gaccacctgc acagctcca gttcttcctg | 300 |
| aacgatctgc aggcaacga cttcaacaac ctgttccagc tgatcgaaca gttcaacaag | 360 |
| tcctccacca cccacaaggg tgatgcagct accgaggcac tccagccacc atgctacatc | 420 |
| tccggcctgc caggttccta ctacacccgc atcttcccat ccgaatccgt gcacctgttc | 480 |
| cactccctgt tctgcctcca gtggcgctcc caggctccag agcagctgaa gggcacccag | 540 |
| aagtcctgcc tggatatcta catcaccaag accatgtccc catccatggt caagctgttc | 600 |
| cagcagcagt tccagaagga cttctcctg ttcctgcgcc tgcgctacga agagctggtg | 660 |
| tccggcggtc agatggtcct gaccttcatc ggccgcaagc acgaagatgt tttcaccggc | 720 |
| gagtccaacc acctgtacgg tctgctggct cagtccctga gtccctggt tgacgaaggt | 780 |
| ctggtggaaa aggagaagct ggagtccttc tacctgccaa tctactcccc atccgtgggc | 840 |
| gaagtcgagg ccatcgtgaa gcagctgggt ctgttcaaca tgaaccacgt taaggtgttc | 900 |
| gaaatcaact gggatccata cgatgactcc gagggcgatg acgtccacaa ctccatcgaa | 960 |
| tccggcgaga acgttgcaaa gtgcctgcgc gctgtcatgg aaccactggt tgcttcccag | 1020 |
| ttcggcgagc gcatcctgga cgaactgttc aaggagtacg ctcgtcgcgt cgccaagcac | 1080 |
| ctggaaaacg aaaaaccaa acacgcagtg cttgtgctgt ccattgaaaa ggctatcatc | 1140 |
| cacgtctga | 1149 |

<210> SEQ ID NO 104
<211> LENGTH: 1596
<212> TYPE: DNA
<213> ORGANISM: Artificial Sequence
<220> FEATURE:
<223> OTHER INFORMATION: Synthetic construct

<400> SEQUENCE: 104

```
atggctgaca ttctgctgct cgataatatc gactctttta cgtacaacct ggcagatcag      60
ttgcgcagca atgggcataa cgtggtgatt taccgcaacc atattccggc gcaaaccttc     120
attgaacgcc tggcgaccat gagcaatccg gtgctgatgc tttctcctgg ccccggtgtg     180
ccgagcgaag ccggttgtat gccggaactc ctcacccgct tgcgtggcaa gctgcccatt     240
attggcattt gcctcggaca tcaggcgatt gtcgaagctt acgggggcta tgtcggtcag     300
gcgggcgaaa ttctccacgg taaagcctcc agcattgaac atgacggtca ggcgatgttt     360
gccggattaa caaacccgct gccggtggcg cgttatcact cgctggttgg cagtaacatt     420
ccggccggtt taaccatcaa cgcccatttt aatggcatgg tgatggcagt acgtcacgat     480
gcggatcgcg tttgtggatt ccagttccat ccggaatcca ttctcaccac ccagggcgct     540
cgcctgctgg aacaaacgct ggcctgggcg cagcagaaac tagagccagc caacacgctg     600
caaccgattc tggaaaaact gtatcaggcg cagacgctta gccaacaaga aagccaccag     660
ctgtttttcag cggtggtgcg tggcgagctg aagccggaac aactggcggc ggcgctggtg     720
agcatgaaaa ttcgcggtga gcacccgaac gagatcgccg gggcagcaac cgcgctactg     780
gaaaacgcag cgccgttccc cgcgcccgat tatctgtttg ctgatatcgt cggtactggc     840
ggtgacggca gcaacagtat caatatttct accgccagtg cgtttgtcgc cgcggcctgt     900
gggctgaaag tggcgaaaca cggcaaccgt agcgtctcca gtaaatctgg ttcgtccgat     960
ctgctggcgg cgttcggtat taatcttgat atgaacgccg ataaatcgcg ccaggcgctg    1020
gatgagttag gtgtatgttt cctctttgcg ccgaagtatc acaccggatt ccgccacgcg    1080
atgccggttc gccagcaact gaaaacccgc accctgttca atgtgctggg ccattgatt     1140
aacccggcgc atccgccgct ggcgttaatt ggtgtttata gtccggaact ggtgctgccg    1200
attgccgaaa ccttgcgcgt gctggggtat caacgcgcgg cggtggtgca cagcggcggg    1260
atggatgaag tttcattaca cgcgccgaca atcgttgccg aactgcatga cggcgaaatt    1320
aaaagctatc agctcaccgc agaagacttt ggcctgacac cctaccacca ggagcaactg    1380
gcaggcggaa caccggaaga aaaccgtgac atttttaacac gtttgttaca aggtaaaggc    1440
gacgccgccc atgaagcagc cgtcgctgcg aacgtcgcca tgttaatgcg cctgcatggc    1500
catgaagatc tgcaagccaa tgcgcaaacc gttcttgagg tactgcgcag tggttccgct    1560
tacgacagag tcaccgcact ggcggcacga gggtaa                              1596
```

<210> SEQ ID NO 105
<211> LENGTH: 531
<212> TYPE: PRT
<213> ORGANISM: Artificial Sequence
<220> FEATURE:
<223> OTHER INFORMATION: Synthetics construct

<400> SEQUENCE: 105

```
Met Ala Asp Ile Leu Leu Leu Asp Asn Ile Asp Ser Phe Thr Tyr Asn
1               5                   10                  15

Leu Ala Asp Gln Leu Arg Ser Asn Gly His Asn Val Val Ile Tyr Arg
            20                  25                  30
```

-continued

Asn His Ile Pro Ala Gln Thr Leu Ile Glu Arg Leu Ala Thr Met Ser
        35                  40                  45

Asn Pro Val Leu Met Leu Ser Pro Gly Pro Gly Val Pro Ser Glu Ala
50                      55                  60

Gly Cys Met Pro Glu Leu Leu Thr Arg Leu Arg Gly Lys Leu Pro Ile
65                  70                  75                  80

Ile Gly Ile Cys Leu Gly His Gln Ala Ile Val Glu Ala Tyr Gly Gly
                85                  90                  95

Tyr Val Gly Gln Ala Gly Glu Ile Leu His Gly Lys Ala Ser Ser Ile
            100                 105                 110

Glu His Asp Gly Gln Ala Met Phe Ala Gly Leu Thr Asn Pro Leu Pro
        115                 120                 125

Val Ala Arg Tyr His Ser Leu Val Gly Ser Asn Ile Pro Ala Gly Leu
    130                 135                 140

Thr Ile Asn Ala His Phe Asn Gly Met Val Met Ala Val Arg His Asp
145                 150                 155                 160

Ala Asp Arg Val Cys Gly Phe Gln Phe His Pro Glu Ser Ile Leu Thr
                165                 170                 175

Thr Gln Gly Ala Arg Leu Leu Glu Gln Thr Leu Ala Trp Ala Gln Gln
            180                 185                 190

Lys Leu Glu Pro Ala Asn Thr Leu Gln Pro Ile Leu Glu Lys Leu Tyr
        195                 200                 205

Gln Ala Gln Thr Leu Ser Gln Gln Glu Ser His Gln Leu Phe Ser Ala
    210                 215                 220

Val Val Arg Gly Glu Leu Lys Pro Glu Gln Leu Ala Ala Ala Leu Val
225                 230                 235                 240

Ser Met Lys Ile Arg Gly Glu His Pro Asn Glu Ile Ala Gly Ala Ala
                245                 250                 255

Thr Ala Leu Leu Glu Asn Ala Ala Pro Phe Pro Arg Pro Asp Tyr Leu
            260                 265                 270

Phe Ala Asp Ile Val Gly Thr Gly Gly Asp Gly Ser Asn Ser Ile Asn
        275                 280                 285

Ile Ser Thr Ala Ser Ala Phe Val Ala Ala Cys Gly Leu Lys Val
    290                 295                 300

Ala Lys His Gly Asn Arg Ser Val Ser Ser Lys Ser Gly Ser Ser Asp
305                 310                 315                 320

Leu Leu Ala Ala Phe Gly Ile Asn Leu Asp Met Asn Ala Asp Lys Ser
                325                 330                 335

Arg Gln Ala Leu Asp Glu Leu Gly Val Cys Phe Leu Phe Ala Pro Lys
            340                 345                 350

Tyr His Thr Gly Phe Arg His Ala Met Pro Val Arg Gln Gln Leu Lys
        355                 360                 365

Thr Arg Thr Leu Phe Asn Val Leu Gly Pro Leu Ile Asn Pro Ala His
    370                 375                 380

Pro Pro Leu Ala Leu Ile Gly Val Tyr Ser Pro Glu Leu Val Leu Pro
385                 390                 395                 400

Ile Ala Glu Thr Leu Arg Val Leu Gly Tyr Gln Arg Ala Ala Val Val
                405                 410                 415

His Ser Gly Gly Met Asp Glu Val Ser Leu His Ala Pro Thr Ile Val
            420                 425                 430

Ala Glu Leu His Asp Gly Glu Ile Lys Ser Tyr Gln Leu Thr Ala Glu
        435                 440                 445

Asp Phe Gly Leu Thr Pro Tyr His Gln Glu Gln Leu Ala Gly Gly Thr
            450                 455                 460

Pro Glu Glu Asn Arg Asp Ile Leu Thr Arg Leu Leu Gln Gly Lys Gly
465                 470                 475                 480

Asp Ala Ala His Glu Ala Ala Val Ala Ala Asn Val Ala Met Leu Met
                485                 490                 495

Arg Leu His Gly His Glu Asp Leu Gln Ala Asn Ala Gln Thr Val Leu
            500                 505                 510

Glu Val Leu Arg Ser Gly Ser Ala Tyr Asp Arg Val Thr Ala Leu Ala
        515                 520                 525

Ala Arg Gly
    530

<210> SEQ ID NO 106
<211> LENGTH: 1443
<212> TYPE: DNA
<213> ORGANISM: Artificial Sequence
<220> FEATURE:
<223> OTHER INFORMATION: Synthetic construct

<400> SEQUENCE: 106
atgtccagaa ggcttcgcag aacaaaaatc gttaccacgt taggcccagc aacagatcgc      60
gataataatc ttgaaaaagt tatcgcggcg ggtgccaacg ttgtacgtat gaacttttct     120
cacggctcgc tgaagatca caaaatgcgc gcggataaag ttcgtgagat tgccgcaaaa     180
ctggggcgtc atgtggctat tctgggtgac ctccaggggc ccaaaatccg tgtatccacc     240 tttaagaag gcaaagtttt cctcaatatt ggggataaat tcctgctcga cgccaacctg     300
ggtaaaggtg aaggcgacaa agaaaaagtc ggtatcgact acaaaggcct gcctgctgac     360
gtcgtgcctg gtgacatcct gctgctggac gatggtcgcg tccagttaaa agtactggaa     420
gttcagggca tgaaagtgtt caccgaagtc accgtcggtg tcccctctc caacaataaa     480 ggtatcaaca aacttggcgg cggtttgtcg gctgaagcgc tgaccgaaaa agacaaagca     540
gacattaaga ctgcggcgtt gattggcgta gattacctgg ctgtctcctt cccacgctgt     600
ggcgaagatc tgaactatgc ccgtcgcctg cacgcgatg caggatgtga tgcgaaaatt     660
gttgccaagg ttgaacgtgc ggaagccgtt tgcagccagg atgcaatgga tgacatcatc     720
ctcgcctctg acgtggtaat ggttgcacgt ggcgacctcg tgtgtgaaat tggcgacccg     780
gaactggtcg gcattcagaa agcgttgatc cgtcgtgcgc gtcagctaaa ccgagcggta     840
atcacggcga cccagatgat ggagtcaatg attactaacc cgatgccgac gcgtgcagaa     900
gtcatggacg tagcaaacgc cgttctggat ggtactgacg ctgtgatgct gtctgcagaa     960
actgccgctg ggcagtatcc gtcagaaacc gttgcagcca tggcgcgcgt ttgcctgggt    1020
gcggaaaaaa tcccgagcat caacgtttct aaacaccgtc tggacgttca gttcgacaat    1080
gtggaagaag ctattgccat gtcagcaatg tacgcagcta accacctgaa aggcgttacg    1140
gcgatcatca ccatgaccga atcgggtcgt accgcgctga tgacctccg tatcagctct    1200 ggtctgccaa ttttcgccat gtcgcgccat gaacgtacgc tgaacctgac tgctctctat    1260
cgtggcgtta cgccggtgca ctttgatagc gctaatgacg gcgtagcagc tgccagcgaa    1320
gcggttaatc tgctgcgcga taaaggttac ttgatgtctg gtgacctggt gattgtcacc    1380
cagggcgacg tgatgagtac cgtgggttct actaatacca cgcgtatttt aacggtagag    1440
taa                                                                  1443

<210> SEQ ID NO 107
<211> LENGTH: 480
<212> TYPE: PRT
<213> ORGANISM: Artificial Sequence
<220> FEATURE:
<223> OTHER INFORMATION: Synthetic construct

<400> SEQUENCE: 107

```
Met Ser Arg Arg Leu Arg Arg Thr Lys Ile Val Thr Thr Leu Gly Pro
1               5                   10                  15

Ala Thr Asp Arg Asp Asn Asn Leu Glu Lys Val Ile Ala Ala Gly Ala
            20                  25                  30

Asn Val Val Arg Met Asn Phe Ser His Gly Ser Pro Glu Asp His Lys
        35                  40                  45

Met Arg Ala Asp Lys Val Arg Glu Ile Ala Ala Lys Leu Gly Arg His
    50                  55                  60

Val Ala Ile Leu Gly Asp Leu Gln Gly Pro Lys Ile Arg Val Ser Thr
65                  70                  75                  80

Phe Lys Glu Gly Lys Val Phe Leu Asn Ile Gly Asp Lys Phe Leu Leu
                85                  90                  95

Asp Ala Asn Leu Gly Lys Gly Glu Gly Asp Lys Glu Lys Val Gly Ile
            100                 105                 110

Asp Tyr Lys Gly Leu Pro Ala Asp Val Val Pro Gly Asp Ile Leu Leu
        115                 120                 125

Leu Asp Asp Gly Arg Val Gln Leu Lys Val Leu Glu Val Gln Gly Met
    130                 135                 140

Lys Val Phe Thr Glu Val Thr Val Gly Gly Pro Leu Ser Asn Asn Lys
145                 150                 155                 160

Gly Ile Asn Lys Leu Gly Gly Gly Leu Ser Ala Glu Ala Leu Thr Glu
                165                 170                 175

Lys Asp Lys Ala Asp Ile Lys Thr Ala Ala Leu Ile Gly Val Asp Tyr
            180                 185                 190

Leu Ala Val Ser Phe Pro Arg Cys Gly Glu Asp Leu Asn Tyr Ala Arg
        195                 200                 205

Arg Leu Ala Arg Asp Ala Gly Cys Asp Ala Lys Ile Val Ala Lys Val
    210                 215                 220

Glu Arg Ala Glu Ala Val Cys Ser Gln Asp Ala Met Asp Asp Ile Ile
225                 230                 235                 240

Leu Ala Ser Asp Val Val Met Val Ala Arg Gly Asp Leu Gly Val Glu
                245                 250                 255

Ile Gly Asp Pro Glu Leu Val Gly Ile Gln Lys Ala Leu Ile Arg Arg
            260                 265                 270

Ala Arg Gln Leu Asn Arg Ala Val Ile Thr Ala Thr Gln Met Met Glu
        275                 280                 285

Ser Met Ile Thr Asn Pro Met Pro Thr Arg Ala Glu Val Met Asp Val
    290                 295                 300

Ala Asn Ala Val Leu Asp Gly Thr Asp Ala Val Met Leu Ser Ala Glu
305                 310                 315                 320

Thr Ala Ala Gly Gln Tyr Pro Ser Glu Thr Val Ala Ala Met Ala Arg
                325                 330                 335

Val Cys Leu Gly Ala Glu Lys Ile Pro Ser Ile Asn Val Ser Lys His
            340                 345                 350

Arg Leu Asp Val Gln Phe Asp Asn Val Glu Glu Ala Ile Ala Met Ser
        355                 360                 365
```

```
Ala Met Tyr Ala Ala Asn His Leu Lys Gly Val Thr Ala Ile Ile Thr
        370                 375                 380

Met Thr Glu Ser Gly Arg Thr Ala Leu Met Thr Ser Arg Ile Ser Ser
385                 390                 395                 400

Gly Leu Pro Ile Phe Ala Met Ser Arg His Glu Arg Thr Leu Asn Leu
                405                 410                 415

Thr Ala Leu Tyr Arg Gly Val Thr Pro Val His Phe Asp Ser Ala Asn
            420                 425                 430

Asp Gly Val Ala Ala Ser Glu Ala Val Asn Leu Leu Arg Asp Lys
                435                 440                 445

Gly Tyr Leu Met Ser Gly Asp Leu Val Ile Val Thr Gln Gly Asp Val
        450                 455                 460

Met Ser Thr Val Gly Ser Thr Asn Thr Thr Arg Ile Leu Thr Val Glu
465                 470                 475                 480
```

<210> SEQ ID NO 108
<211> LENGTH: 1413
<212> TYPE: DNA
<213> ORGANISM: Artificial Sequence
<220> FEATURE:
<223> OTHER INFORMATION: Synthetic construct

<400> SEQUENCE: 108

```
atgaaaaaga ccaaaattgt ttgcaccatc ggaccgaaaa ccgaatctga agagatgtta      60
gctaaaatgc tggacgctgg catgaacgtt atgcgtctga acttctctca tggtgactat     120
gcagaacacg tcagcgcat tcagaatctg cgcaacgtga tgagcaaaac tggtaaaacc     180
ccgctatcc tgcttgatac caaaggtccg gaaatccgca ccatgaaact ggaaggcggt     240
aacgacgttt ctctgaaagc tggtcagacc tttactttca ccactgataa atctgttatc     300
ggcaacagcg aaatggttgc ggtaacgtat gaaggtttca ctactgacct gtctgttggc     360
aacaccgtac tggttgacga tggtctgatc ggtatggaag ttaccgccat gaaggtaac     420
aaagttatct gtaaagtgct gaacaacggt gacctgggcg aaaacaaagg tgtgaacctg     480
cctggcgttt ccattgctct gccagcactg gctgaaaaag acaaacagga cctgatcttt     540
ggttgcgaac aaggcgtaga cttgttgct gcttccttta ttcgtaagcg ttctgacgtt     600
atcgaaatcc gtgagcacct gaaagcgcac ggcggcgaaa acatccacat catctccaaa     660
atcgaaaacc aggaaggcct caacaacttc gacgaaatcc tcgaagcctc tgacggcatc     720
atggttgcgc gtggcgacct gggtgtagaa atcccggtag aagaagttat cttcgcccag     780
aagatgatga tcgaaaaatg tatccgtgca cgtaaagtcg ttatcactgc gacccagatg     840
ctggattcca tgatcaaaaa cccacgcccg actcgcgcag aagccggtga cgttgcaaac     900
gccatcctcg acggtactga cgcagtgatg ctgtctggtg aatccgcaaa aggtaaatac     960
ccgctggaag cggttttctat catggcgacc atctgcgaac gtaccgaccg cgtgatgaac    1020
agccgtctcg agttcaacaa tgacaaccgt aaactgcgca ttaccgaagc ggtatgccgt    1080
ggtgccgttg aaactgctga aaaactggat gctccgctga cgtggttgc tactcagggc    1140
ggtaaatctg ctcgcgcagt acgtaaatac ttcccggatg ccaccatcct ggcactgacc    1200
accaacgaaa aaacggctca tcagttggta ctgagcaaag cgttgtgcc gcagcttgtt    1260
aaagagatca cttctactga tgatttctac cgtctgggta agaactggc tctgcagagc    1320
ggtctggcac acaaaggtga cgttgtagtt atggtttctg gtgcactggt accgagcggc    1380
actactaaca ccgcatctgt tcacgtcctg taa                                 1413
```

-continued

```
<210> SEQ ID NO 109
<211> LENGTH: 470
<212> TYPE: PRT
<213> ORGANISM: Artificial Sequence
<220> FEATURE:
<223> OTHER INFORMATION: Synthetic construct

<400> SEQUENCE: 109

Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
            20                  25                  30

Leu Asn Phe Ser His Gly Asp Tyr Ala Glu His Gly Gln Arg Ile Gln
        35                  40                  45

Asn Leu Arg Asn Val Met Ser Lys Thr Gly Lys Thr Ala Ala Ile Leu
    50                  55                  60

Leu Asp Thr Lys Gly Pro Glu Ile Arg Thr Met Lys Leu Glu Gly Gly
65                  70                  75                  80

Asn Asp Val Ser Leu Lys Ala Gly Gln Thr Phe Thr Phe Thr Thr Asp
                85                  90                  95

Lys Ser Val Ile Gly Asn Ser Glu Met Val Ala Val Thr Tyr Glu Gly
            100                 105                 110

Phe Thr Thr Asp Leu Ser Val Gly Asn Thr Val Leu Val Asp Asp Gly
        115                 120                 125

Leu Ile Gly Met Glu Val Thr Ala Ile Glu Gly Asn Lys Val Ile Cys
    130                 135                 140

Lys Val Leu Asn Asn Gly Asp Leu Gly Glu Asn Lys Gly Val Asn Leu
145                 150                 155                 160

Pro Gly Val Ser Ile Ala Leu Pro Ala Leu Ala Glu Lys Asp Lys Gln
                165                 170                 175

Asp Leu Ile Phe Gly Cys Glu Gln Gly Val Asp Phe Val Ala Ala Ser
            180                 185                 190

Phe Ile Arg Lys Arg Ser Asp Val Ile Glu Ile Arg Glu His Leu Lys
        195                 200                 205

Ala His Gly Gly Glu Asn Ile His Ile Ile Ser Lys Ile Glu Asn Gln
    210                 215                 220

Glu Gly Leu Asn Asn Phe Asp Glu Ile Leu Glu Ala Ser Asp Gly Ile
225                 230                 235                 240

Met Val Ala Arg Gly Asp Leu Gly Val Glu Ile Pro Val Glu Glu Val
                245                 250                 255

Ile Phe Ala Gln Lys Met Met Ile Glu Lys Cys Ile Arg Ala Arg Lys
            260                 265                 270

Val Val Ile Thr Ala Thr Gln Met Leu Asp Ser Met Ile Lys Asn Pro
        275                 280                 285

Arg Pro Thr Arg Ala Glu Ala Gly Asp Val Ala Asn Ala Ile Leu Asp
    290                 295                 300

Gly Thr Asp Ala Val Met Leu Ser Gly Glu Ser Ala Lys Gly Lys Tyr
305                 310                 315                 320

Pro Leu Glu Ala Val Ser Ile Met Ala Thr Ile Cys Glu Arg Thr Asp
                325                 330                 335

Arg Val Met Asn Ser Arg Leu Glu Phe Asn Asn Asp Asn Arg Lys Leu
            340                 345                 350

Arg Ile Thr Glu Ala Val Cys Arg Gly Ala Val Glu Thr Ala Glu Lys
        355                 360                 365
```

Leu Asp Ala Pro Leu Ile Val Val Ala Thr Gln Gly Gly Lys Ser Ala
            370                 375                 380

Arg Ala Val Arg Lys Tyr Phe Pro Asp Ala Thr Ile Leu Ala Leu Thr
385                 390                 395                 400

Thr Asn Glu Lys Thr Ala His Gln Leu Val Leu Ser Lys Gly Val Val
                405                 410                 415

Pro Gln Leu Val Lys Glu Ile Thr Ser Thr Asp Phe Tyr Arg Leu
            420                 425                 430

Gly Lys Glu Leu Ala Leu Gln Ser Gly Leu Ala His Lys Gly Asp Val
            435                 440                 445

Val Val Met Val Ser Gly Ala Leu Val Pro Ser Gly Thr Thr Asn Thr
    450                 455                 460

Ala Ser Val His Val Leu
465                 470

<210> SEQ ID NO 110
<211> LENGTH: 1053
<212> TYPE: DNA
<213> ORGANISM: Artificial Sequence
<220> FEATURE:
<223> OTHER INFORMATION: Synthetic construct

<400> SEQUENCE: 110
atgaattatc agaacgacga tttacgcatc aaagaaatca agagttact tcctcctgtc        60 gcattgctgg aaaaattccc cgctactgaa aatgccgcga atacggttgc ccatgcccga      120
aaagcgatcc ataagatcct gaaaggtaat gatgatcgcc tgttggttgt gattggccca      180
tgctcaattc atgatcctgt cgcggcaaaa gagtatgcca ctcgcttgct ggcgctgcgt      240
gaagagctga agatgagct ggaaatcgta atgcgcgtct attttgaaaa gccgcgtacc        300
acggtgggct ggaaagggct gattaacgat ccgcatatgg ataatagctt ccagatcaac      360
gacggtctgc gtatagcccg taaattgctg cttgatatta cgacagcgg tctgccagcg       420 gcaggtgagt ttctcaatat gatcacccca caatatctcg ctgacctgat gagctggggc      480
gcaattggcg cacgtaccac cgaatcgcag gtgcaccgcg aactggcatc agggctttct     540
tgtccggtcg gcttcaaaaa tggcaccgac ggtacgatta agtggctat cgatgccatt       600 aatgccgccg gtgcgccgca ctgcttcctg tccgtaacga atgggggca ttcggcgatt       660 gtgaatacca gcggtaacgg cgattgccat atcattctgc gcggcggtaa agagcctaac      720
tacagcgcga agcacgttgc tgaagtgaaa gaagggctga acaaagcagg cctgccagca      780
caggtgatga tcgatttcag ccatgctaac tcgtccaaac aattcaaaaa gcagatggat      840
gtttgtgctg acgtttgcca gcagattgcc ggtggcgaaa aggccattat tggcgtgatg      900
gtggaaagcc atctggtgga aggcaatcag agcctcgaga gcggggagcc gctggcctac      960
ggtaagagca tcaccgatgc ctgcatcggc tggaagata ccgatgctct gttacgtcaa      1020
ctggcgaatg cagtaaaagc gcgtcgcggg taa                                  1053

<210> SEQ ID NO 111
<211> LENGTH: 350
<212> TYPE: PRT
<213> ORGANISM: Artificial Sequence
<220> FEATURE:
<223> OTHER INFORMATION: Synthetic construct

<400> SEQUENCE: 111

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
    50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
130                 135                 140

Leu Asn Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350

<210> SEQ ID NO 112
<211> LENGTH: 930
<212> TYPE: DNA
<213> ORGANISM: Artificial Sequence
<220> FEATURE:
<223> OTHER INFORMATION: Synthetic construct

<400> SEQUENCE: 112

```
atgccgattc gtgtgccgga cgagctaccc gccgtcaatt tcttgcgtga agaaaacgtc    60
tttgtgatga caacttcttg tgcgtctggt caggaaattc gtccacttaa ggttctgatc   120
cttaacctga tgccgaagaa gattgaaact gaaaatcagt ttctgcgcct gctttcaaac   180
tcacctttgc aggtcgatat tcagctgttg cgcatcgatt cccgtgaatc gcgcaacacg   240
cccgcagagc atctgaacaa cttctactgt aactttgaag atattcagga tcagaacttt   300
gacggtttga ttgtaactgg tgcgccgctg ggcctggtgg agtttaatga tgtcgcttac   360
tggccgcaga tcaaacaggt gctggagtgg tcgaaagatc acgtcacctc gacgctgttt   420
gtctgctggg cggtacaggc cgcgctcaat atcctctacg gcattcctaa gcaaactcgc   480
accgaaaaac tctctggcgt ttacgagcat catattctcc atcctcatgc gcttctgacg   540
cgtggctttg atgattcatt cctggcaccg cattcgcgct atgctgactt ccggcagcg    600
ttgattcgtg attacaccga tctggaaatt ctggcagaga cggaagaagg ggatgcatat   660
ctgtttgcca gtaaagataa gcgcattgcc tttgtgacgg ccatcccga  atatgatgcg   720
caaacgctgg cgcaggaatt tttccgcgat gtggaagccg actagaccc  ggatgtaccg   780
tataactatt tcccgcacaa tgatccgcaa aatacaccgc gagcgagctg gcgtagtcac   840
ggtaatttac tgtttaccaa ctggctcaac tattacgtct accagagcac gctatacgat   900
ctacggcaca tgaatccaac gctggattaa                                     930
```

<210> SEQ ID NO 113
<211> LENGTH: 309
<212> TYPE: PRT
<213> ORGANISM: Artificial Sequence
<220> FEATURE:
<223> OTHER INFORMATION: Synthetic construct

<400> SEQUENCE: 113

```
Met Pro Ile Arg Val Pro Asp Glu Leu Pro Ala Val Asn Phe Leu Arg
 1               5                  10                  15

Glu Glu Asn Val Phe Val Met Thr Thr Ser Cys Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190
```

```
Arg Tyr Ala Asp Phe Pro Ala Ala Leu Ile Arg Asp Tyr Thr Asp Leu
            195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ser Thr Leu Tyr Asp Leu Arg His Met
    290                 295                 300

Asn Pro Thr Leu Asp
305
```

<210> SEQ ID NO 114
<211> LENGTH: 822
<212> TYPE: DNA
<213> ORGANISM: Artificial Sequence
<220> FEATURE:
<223> OTHER INFORMATION: Synthetic construct

<400> SEQUENCE: 114

```
atgtcgtgtg aagaactgga aattgtctgg aacaatatta agccgaagc cagaacgctg    60 gcggactgtg agccaatgct ggccagtttt taccacgcga cgctactcaa gcacgaaaac   120
cttggcagtg cactgagcta catgctggcg aacaagctgt catcgccaat tatgcctgct   180
attgctatcc gtgaagtggt ggaagaagcc tacgccgctg acccggaaat gatcgcctct   240
gcggcctgtg atattcaggc ggtgcgtacc cgcgacccgg caagacccaa atactcaacc   300
ccgttgttat acctgaaggg ttttcatgcc ttgcaggcct atcgcatcgg tcactggttg   360
tggaatcagg ggcgtcgcgc actggcaatc tttctgcaaa accaggtttc tgtgacgttc   420
caggtcgata ttcacccggc agcaaaaatt ggtcgcggta tcatgcttga ccacgcgaca   480
ggcatcgtcg ttggtgaaac ggcggtgatt gaaaacgacg tatcgattct gcaatctgtg   540
acgcttggcg gtacgggtaa atctggtggt gaccgtcacc cgaaaattcg tgaaggtgtg   600
atgattggcg cgggcgcgaa aatcctcggc aatattgaag ttgggcgcgg cgcgaagatt   660
ggcgcaggtt ccgtggtgct gcaaccggtg ccgccgcata ccaccgccgc tggcgttccg   720
gctcgtattg tcggtaaacc agacagcgat aagccatcaa tggatatgga ccagcatttc   780
aacggtatta accatacatt tgagtatggg gatgggatct aa                      822
```

<210> SEQ ID NO 115
<211> LENGTH: 273
<212> TYPE: PRT
<213> ORGANISM: Artificial Sequence
<220> FEATURE:
<223> OTHER INFORMATION: Synthetic construct

<400> SEQUENCE: 115

```
Met Ser Cys Glu Glu Leu Glu Ile Val Trp Asn Asn Ile Lys Ala Glu
1               5                   10                  15

Ala Arg Thr Leu Ala Asp Cys Glu Pro Met Leu Ala Ser Phe Tyr His
            20                  25                  30
```

Ala Thr Leu Leu Lys His Glu Asn Leu Gly Ser Ala Leu Ser Tyr Met
        35                  40                  45

Leu Ala Asn Lys Leu Ser Ser Pro Ile Met Pro Ala Ile Ala Ile Arg
 50                  55                  60

Glu Val Glu Glu Ala Tyr Ala Ala Asp Pro Glu Met Ile Ala Ser
65                  70                  75                  80

Ala Ala Cys Asp Ile Gln Ala Val Arg Thr Arg Asp Pro Ala Arg Pro
                85                  90                  95

Lys Tyr Ser Thr Pro Leu Leu Tyr Leu Lys Gly Phe His Ala Leu Gln
            100                 105                 110

Ala Tyr Arg Ile Gly His Trp Leu Trp Asn Gln Gly Arg Arg Ala Leu
        115                 120                 125

Ala Ile Phe Leu Gln Asn Gln Val Ser Val Thr Phe Gln Val Asp Ile
    130                 135                 140

His Pro Ala Ala Lys Ile Gly Arg Gly Ile Met Leu Asp His Ala Thr
145                 150                 155                 160

Gly Ile Val Val Gly Glu Thr Ala Val Ile Glu Asn Asp Val Ser Ile
                165                 170                 175

Leu Gln Ser Val Thr Leu Gly Gly Thr Gly Lys Ser Gly Gly Asp Arg
            180                 185                 190

His Pro Lys Ile Arg Glu Gly Val Met Ile Gly Ala Gly Ala Lys Ile
        195                 200                 205

Leu Gly Asn Ile Glu Val Gly Arg Gly Ala Lys Ile Gly Ala Gly Ser
    210                 215                 220

Val Val Leu Gln Pro Val Pro Pro His Thr Thr Ala Ala Gly Val Pro
225                 230                 235                 240

Ala Arg Ile Val Gly Lys Pro Asp Ser Asp Lys Pro Ser Met Asp Met
                245                 250                 255

Asp Gln His Phe Asn Gly Ile Asn His Thr Phe Glu Tyr Gly Asp Gly
            260                 265                 270

Ile

<210> SEQ ID NO 116
<211> LENGTH: 1563
<212> TYPE: DNA
<213> ORGANISM: Artificial Sequence
<220> FEATURE:
<223> OTHER INFORMATION: Synthetic construct

<400> SEQUENCE: 116
atgcaaacac aaaaaccgac tctcgaactg ctaacctgcg aaggcgctta tcgcgacaat      60
cccaccgcgc ttttcacca gttgtgtggg gatcgtccgg caacgctgct gctggaattc     120
gcagatatcg acagcaaaga tgatttaaaa agcctgctgc tggtagacag tgcgctgcgc     180
attacagctt taggtgacac tgtcacaatc caggcacttt ccggcaacgg cgaagccctc     240
ctggcactac tggataacgc cctgcctgcg ggtgtggaaa gtgaacaatc accaaactgc     300
cgtgtgctgc gcttcccccc tgtcagtcca ctgctggatg aagacgcccg cttatgctcc     360
ctttcggttt ttgacgcttt ccgtttattg cagaatctgt tgaatgtacc gaaggaagaa     420
cgagaagcca tgttcttcgg cggcctgttc tcttatgacc ttgtggcggg atttgaagat     480
ttaccgcaac tgtcagcgga aaataactgc cctgatttct gttttatct cgctgaaacg     540 ctgatggtga ttgaccatca gaaaaaaagc acccgtattc aggccagcct gtttgctccg     600
aatgaagaag aaaaacaacg tctccactgct cgcctgaacg aactacgtca gcaactgacc     660

```
gaagccgcgc cgccgctgcc agtggtttcc gtgccgcata tgcgttgtga atgtaatcag    720
agcgatgaag agttcggtgg cgtagtgcgt ttgttgcaaa aagcgattcg cgctggagaa    780
attttccagg tggtgccatc tcgccgtttc tctctgccct gcccgtcacc gctggcggcc    840
tattacgtgc tgaaaaagag taatcccagc ccgtacatgt tttttatgca ggataatgat    900
ttcaccctat ttggcgcgtc gccggaaagc tcgctcaagt atgatgccac cagccgccag    960
attgagatct acccgattgc cggaacacgc ccacgcggtc gtcgcgccga tggttcactg   1020
gacagagatc tcgacagccg tattgaactg gaaatgcgta ccgatcataa agagctgtct   1080
gaacatctga tgctggttga tctcgcccgt aatgatctgg cacgcatttg acccccggc    1140
agccgctacg tcgccgatct caccaaagtt gaccgttatt cctatgtgat gcacctcgtc   1200
tctcgcgtag tcggcgaact gcgtcacgat cttgacgccc tgcacgctta tcgcgcctgt   1260
atgaatatgg ggacgttaag cggtgcgccg aaagtacgcg ctatgcagtt aattgccgag   1320
gcggaaggtc gtcgccgcgg cagctacggc ggcgcggtag gttatttcac cgcgcatggc   1380
gatctcgaca cctgcattgt gatccgctcg gcgctggtgg aaaacggtat cgccaccgtg   1440
caagcgggtg ctggtgtagt ccttgattct gttccgcagt cggaagccga cgaaacccgt   1500
aacaaagccc gcgctgtact gcgcgctatt gccaccgcgc atcatgcaca ggagactttc   1560
tga                                                                 1563

<210> SEQ ID NO 117
<211> LENGTH: 520
<212> TYPE: PRT
<213> ORGANISM: Artificial Sequence
<220> FEATURE:
<223> OTHER INFORMATION: Synthetic construct

<400> SEQUENCE: 117

Met Gln Thr Gln Lys Pro Thr Leu Glu Leu Leu Thr Cys Glu Gly Ala
1               5                   10                  15

Tyr Arg Asp Asn Pro Thr Ala Leu Phe His Gln Leu Cys Gly Asp Arg
            20                  25                  30

Pro Ala Thr Leu Leu Glu Phe Ala Asp Ile Asp Ser Lys Asp Asp
        35                  40                  45

Leu Lys Ser Leu Leu Leu Val Asp Ser Ala Leu Arg Ile Thr Ala Leu
    50                  55                  60

Gly Asp Thr Val Thr Ile Gln Ala Leu Ser Gly Asn Gly Glu Ala Leu
65                  70                  75                  80

Leu Ala Leu Leu Asp Asn Ala Leu Pro Ala Gly Val Glu Ser Glu Gln
                85                  90                  95

Ser Pro Asn Cys Arg Val Leu Arg Phe Pro Val Ser Pro Leu Leu
            100                 105                 110

Asp Glu Asp Ala Arg Leu Cys Ser Leu Ser Val Phe Asp Ala Phe Arg
        115                 120                 125

Leu Leu Gln Asn Leu Leu Asn Val Pro Lys Glu Glu Arg Glu Ala Met
    130                 135                 140

Phe Phe Gly Gly Leu Phe Ser Tyr Asp Leu Val Ala Gly Phe Glu Asp
145                 150                 155                 160

Leu Pro Gln Leu Ser Ala Glu Asn Asn Cys Pro Asp Phe Cys Phe Tyr
                165                 170                 175

Leu Ala Glu Thr Leu Met Val Ile Asp His Gln Lys Lys Ser Thr Arg
            180                 185                 190
```

```
Ile Gln Ala Ser Leu Phe Ala Pro Asn Glu Glu Lys Gln Arg Leu
            195                 200                 205
Thr Ala Arg Leu Asn Glu Leu Arg Gln Gln Leu Thr Glu Ala Ala Pro
    210                 215                 220
Pro Leu Pro Val Val Ser Val Pro His Met Arg Cys Glu Cys Asn Gln
225                 230                 235                 240
Ser Asp Glu Glu Phe Gly Gly Val Val Arg Leu Leu Gln Lys Ala Ile
                245                 250                 255
Arg Ala Gly Glu Ile Phe Gln Val Val Pro Ser Arg Arg Phe Ser Leu
            260                 265                 270
Pro Cys Pro Ser Pro Leu Ala Ala Tyr Tyr Val Leu Lys Lys Ser Asn
        275                 280                 285
Pro Ser Pro Tyr Met Phe Phe Met Gln Asp Asn Asp Phe Thr Leu Phe
    290                 295                 300
Gly Ala Ser Pro Glu Ser Ser Leu Lys Tyr Asp Ala Thr Ser Arg Gln
305                 310                 315                 320
Ile Glu Ile Tyr Pro Ile Ala Gly Thr Arg Pro Arg Gly Arg Arg Ala
                325                 330                 335
Asp Gly Ser Leu Asp Arg Asp Leu Asp Ser Arg Ile Glu Leu Glu Met
            340                 345                 350
Arg Thr Asp His Lys Glu Leu Ser Glu His Leu Met Leu Val Asp Leu
        355                 360                 365
Ala Arg Asn Asp Leu Ala Arg Ile Cys Thr Pro Gly Ser Arg Tyr Val
    370                 375                 380
Ala Asp Leu Thr Lys Val Asp Arg Tyr Ser Tyr Val Met His Leu Val
385                 390                 395                 400
Ser Arg Val Val Gly Glu Leu Arg His Asp Leu Asp Ala Leu His Ala
                405                 410                 415
Tyr Arg Ala Cys Met Asn Met Gly Thr Leu Ser Gly Ala Pro Lys Val
            420                 425                 430
Arg Ala Met Gln Leu Ile Ala Glu Ala Glu Gly Arg Arg Arg Gly Ser
        435                 440                 445
Tyr Gly Gly Ala Val Gly Tyr Phe Thr Ala His Gly Asp Leu Asp Thr
    450                 455                 460
Cys Ile Val Ile Arg Ser Ala Leu Val Glu Asn Gly Ile Ala Thr Val
465                 470                 475                 480
Gln Ala Gly Ala Gly Val Val Leu Asp Ser Val Pro Gln Ser Glu Ala
                485                 490                 495
Asp Glu Thr Arg Asn Lys Ala Arg Ala Val Leu Arg Ala Ile Ala Thr
            500                 505                 510
Ala His His Ala Gln Glu Thr Phe
        515                 520

<210> SEQ ID NO 118
<211> LENGTH: 2379
<212> TYPE: DNA
<213> ORGANISM: Artificial Sequence
<220> FEATURE:
<223> OTHER INFORMATION: Synthetic construct

<400> SEQUENCE: 118
atgtccaaca atggctcgtc accgctggtg ctttggtata accaactcgg catgaatgat      60
gtagacaggg ttgggggcaa aaatgcctcc ctgggtgaaa tgattactaa tctttccgga     120
atgggtgttt ccgttccgaa tggtttcgcc acaaccgccg acgcgtttaa ccagtttctg     180
```

| | |
|---|---|
| gaccaaagcg gcgtaaacca gcgcatttat gaactgctgg ataaaacgga tattgacgat | 240 |
| gttactcagc ttgcgaaagc gggcgcgcaa atccgccagt ggattatcga cactcccttc | 300 |
| cagcctgagc tggaaaacgc catccgcgaa gcctatgcac agctttccgc cgatgacgaa | 360 |
| aacgcctctt ttgcggtgcg ctcctccgcc accgcagaag atatgccgga cgcttctttt | 420 |
| gccggtcagc aggaaaacctt cctcaacgtt cagggttttg acgccgttct cgtggcagtg | 480 |
| aaacatgtat ttgcttctct gtttaacgat cgcgccatct cttatcgtgt gcaccagggt | 540 |
| tacgatcacc gtggtgtggc gctctccgcc ggtgttcaac ggatggtgcg ctctgacctc | 600 |
| gcatcatctg gcgtgatgtt ctccattgat accgaatccg gctttgacca ggtggtgttt | 660 |
| atcacttccg catggggcct tggtgagatg gtcgtgcagg gtgcggttaa cccggatgag | 720 |
| ttttacgtgc ataaaccgac actgcggcg aatcgcccgg ctatcgtgcg ccgcaccatg | 780 |
| gggtcgaaaa aaatccgcat ggtttacgcg ccgacccagg agcacggcaa gcaggttaaa | 840 |
| atcgaagacg taccgcagga acagcgtgac atcttctcgc tgaccaacga agaagtgcag | 900 |
| gaactggcaa acaggccgt acaaattgag aaacactacg gtcgcccgat ggatattgag | 960 |
| tgggcgaaag atggccacac cggtaaactg ttcattgtgc aggcgcgtcc ggaaaccgtg | 1020 |
| cgctcacgcg gtcaggtcat ggagcgttat acgctgcatt cacagggtaa gattatcgcc | 1080 |
| gaaggccgtg ctatcggtca tcgcatcggt gcgggtccgg tgaaagtcat ccatgacatc | 1140 |
| agcgaaatga accgcatcga acctggcgac gtgctggtta ctgacatgac cgacccggac | 1200 |
| tgggaaccga tcatgaagaa agcatctgcc atcgtcacca accgtggcgg tcgtacctgt | 1260 |
| cacgcggcga tcatcgctcg tgaactgggc attccggcgg tagtgggctg tggagatgca | 1320 |
| acagaacgga tgaaagacgg tgagaacgtc actgtttctt gtgccgaagg tgataccggt | 1380 |
| tacgtctatg cggagttgct ggaatttagc gtgaaaagct ccagcgtaga aacgatgccg | 1440 |
| gatctgccgt tgaaagtgat gatgaacgtc ggtaacccgg accgtgcttt cgacttcgcc | 1500 |
| tgcctaccga acgaaggcgt gggccttgcg cgtctggaat ttatcatcaa ccgtatgatt | 1560 |
| ggcgtccacc cacgcgcact gcttgagttt gacgatcagg aaccgcagtt gcaaaacgaa | 1620 |
| atccgcgaga tgatgaaagg ttttgattct ccgcgtgaat tttacgttgg tcgtctgact | 1680 |
| gaagggatcg cgacgctggg tgccgcgttt tatccgaagc gcgtcattgt ccgtctctct | 1740 |
| gatttaaat cgaacgaata tgccaacctg gtcggtggtg agcgttacga gccagatgaa | 1800 |
| gagaacccga tgctcggctt ccgtggcgcg ggccgctatg tttccgacag cttccgcgac | 1860 |
| tgtttcgcgc tggagtgtga agcagtgaaa cgtgtgcgca acgacatggg actgaccaac | 1920 |
| gttgagatca tgatcccgtt cgtgcgtacc gtagatcagg cgaaagcggt ggttgaagaa | 1980 |
| ctggcgcgtc aggggctgaa acgtggcgag aacgggctga aaatcatcat gatgtgtgaa | 2040 |
| atcccgtcca acgccttgct ggccgagcag ttcctcgaat atttcgacgg cttctcaatt | 2100 |
| ggctcaaacg atatgacgca gctggcgctc ggtctggacc gtgactccgg cgtggtgtct | 2160 |
| gaattgttcg atgagcgcaa cgatgcgtg aaagcactgc tgtcgatggc tatccgtgcc | 2220 |
| gcgaagaaac agggcaaata tgtcgggatt tgcggtcagg gtccgtccga ccacgaagac | 2280 |
| tttgccgcat ggttgatgga gaggggatc gatagcctgt ctctgaaccc ggacaccgtg | 2340 |
| gtgcaaacct ggttaagcct ggctgaactg aagaaataa | 2379 |

<210> SEQ ID NO 119
<211> LENGTH: 792
<212> TYPE: PRT
<213> ORGANISM: Artificial Sequence
<220> FEATURE:
<223> OTHER INFORMATION: Synthetic construct

<400> SEQUENCE: 119

```
Met Ser Asn Asn Gly Ser Ser Pro Leu Val Leu Trp Tyr Asn Gln Leu
1               5                   10                  15

Gly Met Asn Asp Val Asp Arg Val Gly Gly Lys Asn Ala Ser Leu Gly
            20                  25                  30

Glu Met Ile Thr Asn Leu Ser Gly Met Gly Val Ser Val Pro Asn Gly
        35                  40                  45

Phe Ala Thr Thr Ala Asp Ala Phe Asn Gln Phe Leu Asp Gln Ser Gly
    50                  55                  60

Val Asn Gln Arg Ile Tyr Glu Leu Leu Asp Lys Thr Asp Ile Asp Asp
65                  70                  75                  80

Val Thr Gln Leu Ala Lys Ala Gly Ala Gln Ile Arg Gln Trp Ile Ile
                85                  90                  95

Asp Thr Pro Phe Gln Pro Glu Leu Glu Asn Ala Ile Arg Glu Ala Tyr
            100                 105                 110

Ala Gln Leu Ser Ala Asp Asp Glu Asn Ala Ser Phe Ala Val Arg Ser
        115                 120                 125

Ser Ala Thr Ala Glu Asp Met Pro Asp Ala Ser Phe Ala Gly Gln Gln
    130                 135                 140

Glu Thr Phe Leu Asn Val Gln Gly Phe Asp Ala Val Leu Val Ala Val
145                 150                 155                 160

Lys His Val Phe Ala Ser Leu Phe Asn Asp Arg Ala Ile Ser Tyr Arg
                165                 170                 175

Val His Gln Gly Tyr Asp His Arg Gly Val Ala Leu Ser Ala Gly Val
            180                 185                 190

Gln Arg Met Val Arg Ser Asp Leu Ala Ser Ser Gly Val Met Phe Ser
        195                 200                 205

Ile Asp Thr Glu Ser Gly Phe Asp Gln Val Val Phe Ile Thr Ser Ala
    210                 215                 220

Trp Gly Leu Gly Glu Met Val Val Gln Gly Ala Val Asn Pro Asp Glu
225                 230                 235                 240

Phe Tyr Val His Lys Pro Thr Leu Ala Ala Asn Arg Pro Ala Ile Val
                245                 250                 255

Arg Arg Thr Met Gly Ser Lys Lys Ile Arg Met Val Tyr Ala Pro Thr
            260                 265                 270

Gln Glu His Gly Lys Gln Val Lys Ile Glu Asp Val Pro Gln Glu Gln
        275                 280                 285

Arg Asp Ile Phe Ser Leu Thr Asn Glu Glu Val Gln Glu Leu Ala Lys
    290                 295                 300

Gln Ala Val Gln Ile Glu Lys His Tyr Gly Arg Pro Met Asp Ile Glu
305                 310                 315                 320

Trp Ala Lys Asp Gly His Thr Gly Lys Leu Phe Ile Val Gln Ala Arg
                325                 330                 335

Pro Glu Thr Val Arg Ser Arg Gly Gln Val Met Glu Arg Tyr Thr Leu
            340                 345                 350

His Ser Gln Gly Lys Ile Ile Ala Glu Gly Arg Ala Ile Gly His Arg
        355                 360                 365

Ile Gly Ala Gly Pro Val Lys Val Ile His Asp Ile Ser Glu Met Asn
    370                 375                 380
```

```
Arg Ile Glu Pro Gly Asp Val Leu Val Thr Asp Met Thr Asp Pro Asp
385                 390                 395                 400

Trp Glu Pro Ile Met Lys Lys Ala Ser Ala Ile Val Thr Asn Arg Gly
                405                 410                 415

Gly Arg Thr Cys His Ala Ala Ile Ile Ala Arg Glu Leu Gly Ile Pro
            420                 425                 430

Ala Val Val Gly Cys Gly Asp Ala Thr Glu Arg Met Lys Asp Gly Glu
        435                 440                 445

Asn Val Thr Val Ser Cys Ala Glu Gly Asp Thr Gly Tyr Val Tyr Ala
    450                 455                 460

Glu Leu Leu Glu Phe Ser Val Lys Ser Ser Val Glu Thr Met Pro
465             470                 475                 480

Asp Leu Pro Leu Lys Val Met Met Asn Val Gly Asn Pro Asp Arg Ala
                485                 490                 495

Phe Asp Phe Ala Cys Leu Pro Asn Glu Gly Val Gly Leu Ala Arg Leu
            500                 505                 510

Glu Phe Ile Ile Asn Arg Met Ile Gly Val His Pro Arg Ala Leu Leu
        515                 520                 525

Glu Phe Asp Asp Gln Glu Pro Gln Leu Gln Asn Glu Ile Arg Glu Met
    530                 535                 540

Met Lys Gly Phe Asp Ser Pro Arg Glu Phe Tyr Val Gly Arg Leu Thr
545                 550                 555                 560

Glu Gly Ile Ala Thr Leu Gly Ala Ala Phe Tyr Pro Lys Arg Val Ile
                565                 570                 575

Val Arg Leu Ser Asp Phe Lys Ser Asn Glu Tyr Ala Asn Leu Val Gly
            580                 585                 590

Gly Glu Arg Tyr Glu Pro Asp Glu Asn Pro Met Leu Gly Phe Arg
        595                 600                 605

Gly Ala Gly Arg Tyr Val Ser Asp Ser Phe Arg Asp Cys Phe Ala Leu
    610                 615                 620

Glu Cys Glu Ala Val Lys Arg Val Arg Asn Asp Met Gly Leu Thr Asn
625                 630                 635                 640

Val Glu Ile Met Ile Pro Phe Val Arg Thr Val Asp Gln Ala Lys Ala
                645                 650                 655

Val Val Glu Glu Leu Ala Arg Gln Gly Leu Lys Arg Gly Glu Asn Gly
            660                 665                 670

Leu Lys Ile Ile Met Met Cys Glu Ile Pro Ser Asn Ala Leu Leu Ala
        675                 680                 685

Glu Gln Phe Leu Glu Tyr Phe Asp Gly Phe Ser Ile Gly Ser Asn Asp
    690                 695                 700

Met Thr Gln Leu Ala Leu Gly Leu Asp Arg Asp Ser Gly Val Val Ser
705                 710                 715                 720

Glu Leu Phe Asp Glu Arg Asn Asp Ala Val Lys Ala Leu Leu Ser Met
                725                 730                 735

Ala Ile Arg Ala Ala Lys Lys Gln Gly Lys Tyr Val Gly Ile Cys Gly
            740                 745                 750

Gln Gly Pro Ser Asp His Glu Asp Phe Ala Ala Trp Leu Met Glu Glu
        755                 760                 765

Gly Ile Asp Ser Leu Ser Leu Asn Pro Asp Thr Val Val Gln Thr Trp
    770                 775                 780

Leu Ser Leu Ala Glu Leu Lys Lys
785                 790
```

-continued

```
<210> SEQ ID NO 120
<211> LENGTH: 525
<212> TYPE: DNA
<213> ORGANISM: Artificial Sequence
<220> FEATURE:
<223> OTHER INFORMATION: Synthetic construct

<400> SEQUENCE: 120
atgacacaac ctcttttct gatcgggcct cggggctgtg gtaaaacaac ggtcggaatg      60
gcccttgccg attcgcttaa ccgtcggttt gtcgataccg atcagtggtt gcaatcacag     120
ctcaatatga cggtcgcgga gatcgtcgaa agggaagagt gggcgggatt tcgcgccaga    180
gaaacggcgg cgctggaagc ggtaactgcg ccatccaccg ttatcgctac aggcggcggc    240
attattctga cggaatttaa tcgtcacttc atgcaaaata cgggatcgt ggtttatttg     300 tgtgcgccag tatcagtcct ggttaaccga ctgcaagctg caccggaaga agatttacgg    360
ccaaccttaa cgggaaaacc gctgagcgaa gaagttcagg aagtgctgga gaacgcgat    420 gcgctatatc gcgaagttgc gcatattatc atcgacgcaa caaacgaacc cagccaggtg    480
atttctgaaa ttcgcagcgc cctggcacag acgatcaatt gttga                   525

<210> SEQ ID NO 121
<211> LENGTH: 174
<212> TYPE: PRT
<213> ORGANISM: Artificial Sequence
<220> FEATURE:
<223> OTHER INFORMATION: Synthetic construct

<400> SEQUENCE: 121

Met Thr Gln Pro Leu Phe Leu Ile Gly Pro Arg Gly Cys Gly Lys Thr
1               5                   10                  15

Thr Val Gly Met Ala Leu Ala Asp Ser Leu Asn Arg Arg Phe Val Asp
            20                  25                  30

Thr Asp Gln Trp Leu Gln Ser Gln Leu Asn Met Thr Val Ala Glu Ile
        35                  40                  45

Val Glu Arg Glu Glu Trp Ala Gly Phe Arg Ala Arg Glu Thr Ala Ala
    50                  55                  60

Leu Glu Ala Val Thr Ala Pro Ser Thr Val Ile Ala Thr Gly Gly Gly
65                  70                  75                  80

Ile Ile Leu Thr Glu Phe Asn Arg His Phe Met Gln Asn Asn Gly Ile
                85                  90                  95

Val Val Tyr Leu Cys Ala Pro Val Ser Val Leu Val Asn Arg Leu Gln
            100                 105                 110

Ala Ala Pro Glu Glu Asp Leu Arg Pro Thr Leu Thr Gly Lys Pro Leu
        115                 120                 125

Ser Glu Glu Val Gln Glu Val Leu Glu Glu Arg Asp Ala Leu Tyr Arg
    130                 135                 140

Glu Val Ala His Ile Ile Asp Ala Thr Asn Glu Pro Ser Gln Val
145                 150                 155                 160

Ile Ser Glu Ile Arg Ser Ala Leu Ala Gln Thr Ile Asn Cys
                165                 170

<210> SEQ ID NO 122
<211> LENGTH: 1992
<212> TYPE: DNA
<213> ORGANISM: Artificial Sequence
<220> FEATURE:
<223> OTHER INFORMATION: Synthetic construct
```

<400> SEQUENCE: 122

```
atgtcctcac gtaaagagct tgccaatgct attcgtgcgc tgagcatgga cgcagtacag    60
aaagccaaat ccggtcaccc gggtgcccct atgggtatgg ctgacattgc cgaagtcctg   120
tggcgtgatt tcctgaaaca caacccgcag aatccgtcct gggctgaccg tgaccgcttc   180
gtgctgtcca acggccacgg ctccatgctg atctacagcc tgctgcacct caccggttac   240
gatctgccga tggaagaact gaaaaacttc cgtcagctgc actctaaaac tccgggtcac   300
ccggaagtgg gttacaccgc tggtgtggaa accaccaccg gtccgctggg tcagggtatt   360
gccaacgcag tcggtatggc gattgcagaa aaaacgctgg cggcgcagtt taaccgtccg   420
ggccacgaca ttgtcgacca ctacacctac gccttcatgg gcgacggctg catgatggaa   480
ggcatctccc acgaagtttg ctctctggcg gtacgctgaa gctgggtaa actgattgca    540
ttctacgatg acaacggtat ttctatcgat ggtcacgttg aaggctggtt caccgacgac   600
accgcaatgc gtttcgaagc ttacggctgg cacgttattc gcgacatcga cggtcatgac   660
gcggcatcta tcaaacgcgc agtagaagaa gcgcgcgcag tgactgacaa accttccctg   720
ctgatgtgca aaaccatcat cggtttcggt tccccgaaca aagccggtac ccacgactcc   780
cacggtgcgc cgctgggcga cgctgaaatt gccctgaccc gcaacaact gggctggaaa    840
tatgcgccgt tcgaaatccc gtctgaaatc tatgctcagt gggatgcgaa agaagcaggc   900
caggcgaaag aatccgcatg gaacgagaaa ttcgctgctt acgcgaaagc ttatccgcag   960
gaagccgctg aatttacccg ccgtatgaaa ggcgaaatgc cgtctgactt cgacgctaaa  1020
gcgaaagagt tcatcgctaa actgcaggct aatccggcga aaatcgccag ccgtaaagcg  1080
tctcagaatg ctatcgaagc gttcggtccg ctgttgccgg aattcctcgg cggttctgct  1140
gacctggcgc cgtctaacct gaccctgtgg tctggttcta aagcaatcaa cgaagatgct  1200
gcgggtaact acatccacta cggtgttcgc gagttcggta tgaccgcgat tgctaacggt  1260
atctccctgc acggtggctt cctgccgtac acctccacct tcctgatgtt cgtggaatac  1320
gcacgtaacg ccgtacgtat ggctgcgctg atgaaacagc gtcaggtgat ggtttacacc  1380
cacgactcca tcggtctggg cgaagacggc ccgactcacc agccggttga gcaggtcgct  1440
tctctgcgcg taaccccgaa catgtctaca tggcgtccgt gtgaccaggt tgaatccgcg  1500
gtcgcgtgga aataccggtgt tgagcgtcag gacggcccga ccgcactgat cctctcccgt  1560
cagaacctgg cgcagcagga acgaactgaa gagcaactgg caaacatcgc gcgcggtggt  1620
tatgtgctga agactgcgc cggtcagccg gaactgattt tcatcgctac cggttcagaa   1680
gttgaactgc tgttgctgc ctacgaaaaa ctgactgccg aaggcgtgaa agcgcgcgtg  1740
gtgtccatgc cgtctaccga cgcatttgac aagcaggatg ctgcttaccg tgaatccgta  1800
ctgccgaaag cggttactgc acgcgttgct gtagaagcgg gtattgctga ctactggtac  1860
aagtatgttg gcctgaacgg tgctatcgtc ggtatgacca ccttcggtga atctgctccg  1920
gcagagctgc tgtttgaaga gttcggcttc actgttgata cgttgttgc gaaagcaaaa   1980
gaactgctgt aa                                                     1992
```

<210> SEQ ID NO 123
<211> LENGTH: 663
<212> TYPE: PRT
<213> ORGANISM: Artificial Sequence
<220> FEATURE:
<223> OTHER INFORMATION: Synthetic construct

<400> SEQUENCE: 123

```
Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Lys His Asn
        35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Thr Ala Met Arg Phe Glu Ala Tyr
        195                 200                 205

Gly Trp His Val Ile Arg Asp Ile Asp Gly His Asp Ala Ala Ser Ile
    210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
        275                 280                 285

Glu Ile Tyr Ala Gln Trp Asp Ala Lys Glu Ala Gly Gln Ala Lys Glu
    290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
            340                 345                 350

Ala Lys Ile Ala Ser Arg Lys Ala Ser Gln Asn Ala Ile Glu Ala Phe
        355                 360                 365

Gly Pro Leu Leu Pro Glu Phe Leu Gly Gly Ser Ala Asp Leu Ala Pro
    370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415
```

```
Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
        435                 440                 445

Ala Leu Met Lys Gln Arg Gln Val Met Val Tyr Thr His Asp Ser Ile
    450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
                485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
        515                 520                 525

Thr Glu Glu Gln Leu Ala Asn Ile Ala Arg Gly Gly Tyr Val Leu Lys
    530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
                565                 570                 575

Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
        595                 600                 605

Val Ala Val Glu Ala Gly Ile Ala Asp Tyr Trp Tyr Lys Tyr Val Gly
    610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
                645                 650                 655

Ala Lys Ala Lys Glu Leu Leu
            660

<210> SEQ ID NO 124
<211> LENGTH: 1155
<212> TYPE: DNA
<213> ORGANISM: Artificial Sequence
<220> FEATURE:
<223> OTHER INFORMATION: Synthetic construct

<400> SEQUENCE: 124
atggcaaaac acctttttac gtccgagtcc gtctctgaag gcatcctga caaaattgct      60 gaccaaattt ctgatgccgt tttagacgcg atcctcgaac aggatccgaa agcacgcgtt    120
gcttgcgaaa cctacgtaaa aaccggcatg gttttagttg gcggcgaaat caccaccagc    180
gcctgggtag acatcgaaga gatcacccgt aacaccgttc gcgaaattgg ctatgtgcat    240
tccgacatgg gctttgacgc taactcctgt gcggttctga cgctatcgg caaacagtct    300 cctgacatca accagggcgt tgaccgtgcc gatccgctgg aacagggcgc gggtgaccag    360
ggtctgatgt ttggctacgc aactaatgaa accgacgtgc tgatgccagc acctatcacc    420
tatgcacacc gtctggtaca gcgtcaggct gaagtgcgta aaaacggcac tctgccgtgg    480
ctgcgcccgg acgcgaaaag ccaggtgact tttcagtatg acgacggcaa atcgttggt    540 atcgatgctg tcgtgctttc cactcagcac tctgaagaga tcgaccagaa atcgctgcaa    600
gaagcggtaa tggaagagat catcaagcca attctgcccg ctgaatggct gacttctgcc    660
```

```
accaaattct tcatcaaccc gaccggtcgt ttcgttatcg gtggcccaat gggtgactgc    720
ggtctgactg gtcgtaaaat tatcgttgat acctacggcg gcatggcgcg tcacggtggc    780
ggtgcattct ctggtaaaga tccatcaaaa gtggaccgtt ccgcagccta cgcagcacgt    840
tatgtcgcga aaacatcgt tgctgctggc ctggccgatc gttgtgaaat tcaggtttcc     900
tacgcaatcg gcgtggctga accgacctcc atcatggtag aaactttcgg tactgagaaa    960
gtgccttctg aacaactgac cctgctggta cgtgagttct tcgacctgcg cccatacgt    1020 ctgattcaga tgctggatct gctgcacccg atctacaaag aaaccgcagc atacggtcac   1080
tttggtcgtg aacatttccc gtgggaaaaa accgacaaag cgcagctgct gcgcgatgct   1140
gccggtctga agtaa                                                    1155
```

<210> SEQ ID NO 125
<211> LENGTH: 384
<212> TYPE: PRT
<213> ORGANISM: Artificial Sequence
<220> FEATURE:
<223> OTHER INFORMATION: Synthetic construct

<400> SEQUENCE: 125

```
Met Ala Lys His Leu Phe Thr Ser Glu Ser Val Ser Glu Gly His Pro
1               5                   10                  15

Asp Lys Ile Ala Asp Gln Ile Ser Asp Ala Val Leu Asp Ala Ile Leu
            20                  25                  30

Glu Gln Asp Pro Lys Ala Arg Val Ala Cys Glu Thr Tyr Val Lys Thr
        35                  40                  45

Gly Met Val Leu Val Gly Gly Glu Ile Thr Thr Ser Ala Trp Val Asp
    50                  55                  60

Ile Glu Glu Ile Thr Arg Asn Thr Val Arg Glu Ile Gly Tyr Val His
65                  70                  75                  80

Ser Asp Met Gly Phe Asp Ala Asn Ser Cys Ala Val Leu Ser Ala Ile
                85                  90                  95

Gly Lys Gln Ser Pro Asp Ile Asn Gln Gly Val Asp Arg Ala Asp Pro
            100                 105                 110

Leu Glu Gln Gly Ala Gly Asp Gln Gly Leu Met Phe Gly Tyr Ala Thr
        115                 120                 125

Asn Glu Thr Asp Val Leu Met Pro Ala Pro Ile Thr Tyr Ala His Arg
    130                 135                 140

Leu Val Gln Arg Gln Ala Glu Val Arg Lys Asn Gly Thr Leu Pro Trp
145                 150                 155                 160

Leu Arg Pro Asp Ala Lys Ser Gln Val Thr Phe Gln Tyr Asp Asp Gly
                165                 170                 175

Lys Ile Val Gly Ile Asp Ala Val Val Leu Ser Thr Gln His Ser Glu
            180                 185                 190

Glu Ile Asp Gln Lys Ser Leu Gln Glu Ala Val Met Glu Glu Ile Ile
        195                 200                 205

Lys Pro Ile Leu Pro Ala Glu Trp Leu Thr Ser Ala Thr Lys Phe Phe
    210                 215                 220

Ile Asn Pro Thr Gly Arg Phe Val Ile Gly Pro Met Gly Asp Cys
225                 230                 235                 240

Gly Leu Thr Gly Arg Lys Ile Ile Val Asp Thr Tyr Gly Gly Met Ala
                245                 250                 255

Arg His Gly Gly Gly Ala Phe Ser Gly Lys Asp Pro Ser Lys Val Asp
            260                 265                 270
```

-continued

```
Arg Ser Ala Ala Tyr Ala Ala Arg Tyr Val Ala Lys Asn Ile Val Ala
            275                 280                 285

Ala Gly Leu Ala Asp Arg Cys Glu Ile Gln Val Ser Tyr Ala Ile Gly
        290                 295                 300

Val Ala Glu Pro Thr Ser Ile Met Val Glu Thr Phe Gly Thr Glu Lys
305                 310                 315                 320

Val Pro Ser Glu Gln Leu Thr Leu Leu Val Arg Glu Phe Phe Asp Leu
                325                 330                 335

Arg Pro Tyr Gly Leu Ile Gln Met Leu Asp Leu Leu His Pro Ile Tyr
            340                 345                 350

Lys Glu Thr Ala Ala Tyr Gly His Phe Gly Arg Glu His Phe Pro Trp
        355                 360                 365

Glu Lys Thr Asp Lys Ala Gln Leu Leu Arg Asp Ala Ala Gly Leu Lys
    370                 375                 380
```

<210> SEQ ID NO 126
<211> LENGTH: 699
<212> TYPE: DNA
<213> ORGANISM: Artificial Sequence
<220> FEATURE:
<223> OTHER INFORMATION: Synthetic construct

<400> SEQUENCE: 126

```
atgaaaatcg gcatcattgg tgcaatggaa gaagaagtta cgctgctgcg tgacaaaatc      60
gaaaaccgtc aaactatcag tctcggcggt tgcgaaatct ataccggcca actgaatgga     120
accgaggttg cgcttctgaa atcgggcatc ggtaaagtcg ctgcggcgct gggtgccact     180
ttgctgttgg aacactgcaa gccagatgtg attattaaca ccggttctgc cggtggcctg     240
gcaccaacgt tgaaagtggg cgatatcgtt gtctcggacg aagcacgtta tcacgacgcg     300
gatgtcacgg catttggtta tgaataccgg tcagttaccag gctgtccggc aggctttaaa     360
gctgacgata aactgatcgc tgccgctgag gcctgcattg ccgaactgaa tcttaacgct     420
gtacgtggcc tgattgttag cggcgacgct ttcatcaacg ttctgttgg tctggcgaaa     480
atccgccaca acttcccaca ggccattgct gtagagatgg aagcgacggc aatcgcccat     540
gtctgccaca atttcaacgt cccgtttgtt gtcgtacgcg ccatctccga cgtggccgat     600
caacagtctc atcttagctt cgatgagttc ctggctgttg ccgctaaaca gtccagcctg     660
atggttgagt cactggtgca gaaacttgca catggctaa                             699
```

<210> SEQ ID NO 127
<211> LENGTH: 232
<212> TYPE: PRT
<213> ORGANISM: Artificial Sequence
<220> FEATURE:
<223> OTHER INFORMATION: Synthetic construct

<400> SEQUENCE: 127

```
Met Lys Ile Gly Ile Ile Gly Ala Met Glu Glu Glu Val Thr Leu Leu
1               5                   10                  15

Arg Asp Lys Ile Glu Asn Arg Gln Thr Ile Ser Leu Gly Gly Cys Glu
            20                  25                  30

Ile Tyr Thr Gly Gln Leu Asn Gly Thr Glu Val Ala Leu Leu Lys Ser
        35                  40                  45

Gly Ile Gly Lys Val Ala Ala Ala Leu Gly Ala Thr Leu Leu Leu Glu
    50                  55                  60

His Cys Lys Pro Asp Val Ile Ile Asn Thr Gly Ser Ala Gly Gly Leu
65                  70                  75                  80
```

```
Ala Pro Thr Leu Lys Val Gly Asp Ile Val Ser Asp Glu Ala Arg
            85                  90                  95

Tyr His Asp Ala Asp Val Thr Ala Phe Gly Tyr Glu Tyr Gly Gln Leu
        100                 105                 110

Pro Gly Cys Pro Ala Gly Phe Lys Ala Asp Asp Lys Leu Ile Ala Ala
        115                 120                 125

Ala Glu Ala Cys Ile Ala Glu Leu Asn Leu Asn Ala Val Arg Gly Leu
    130                 135                 140

Ile Val Ser Gly Asp Ala Phe Ile Asn Gly Ser Val Gly Leu Ala Lys
145                 150                 155                 160

Ile Arg His Asn Phe Pro Gln Ala Ile Ala Val Glu Met Glu Ala Thr
                165                 170                 175

Ala Ile Ala His Val Cys His Asn Phe Asn Val Pro Phe Val Val Val
            180                 185                 190

Arg Ala Ile Ser Asp Val Ala Asp Gln Gln Ser His Leu Ser Phe Asp
        195                 200                 205

Glu Phe Leu Ala Val Ala Ala Lys Gln Ser Ser Leu Met Val Glu Ser
    210                 215                 220

Leu Val Gln Lys Leu Ala His Gly
225                 230

<210> SEQ ID NO 128
<211> LENGTH: 516
<212> TYPE: DNA
<213> ORGANISM: Artificial Sequence
<220> FEATURE:
<223> OTHER INFORMATION: Synthetic construct

<400> SEQUENCE: 128
atgccgttgt tagatagctt cacagtcgat catacccgga tggaagcgcc tgcagttcgg      60
gtggcgaaaa caatgaacac cccgcatggc gacgcaatca ccgtgttcga tctgcgcttc     120
tgcgtgccga caaagaagt gatgccagaa agagggatcc ataccctgga gcacctgttt     180
gctggtttta tgcgtaacca tcttaacggt aatggtgtag agattatcga tatctcgcca     240
atgggctgcc gcaccggttt ttatatgagt ctgattggta cgccagatga gcagcgtgtt     300
gctgatgcct ggaaagcggc aatggaagac gtgctgaaag tgcaggatca gaatcagatc     360
ccggaactga acgtctacca gtgtggcact taccagatgc actcgttgca ggaagcgcag     420
gatattgcgc gtagcattct ggaacgtgac gtacgcatca acagcaacga gaactggca     480 ctgccgaaag agaagttgca ggaactgcac atctag                              516

<210> SEQ ID NO 129
<211> LENGTH: 171
<212> TYPE: PRT
<213> ORGANISM: Artificial Sequence
<220> FEATURE:
<223> OTHER INFORMATION: Synthetic construct

<400> SEQUENCE: 129

Met Pro Leu Leu Asp Ser Phe Thr Val Asp His Thr Arg Met Glu Ala
1               5                   10                  15

Pro Ala Val Arg Val Ala Lys Thr Met Asn Thr Pro His Gly Asp Ala
            20                  25                  30

Ile Thr Val Phe Asp Leu Arg Phe Cys Val Pro Asn Lys Glu Val Met
        35                  40                  45
```

Pro Glu Arg Gly Ile His Thr Leu Glu His Leu Phe Ala Gly Phe Met
    50                  55                  60

Arg Asn His Leu Asn Gly Asn Gly Val Glu Ile Ile Asp Ile Ser Pro
65                  70                  75                  80

Met Gly Cys Arg Thr Gly Phe Tyr Met Ser Leu Ile Gly Thr Pro Asp
                85                  90                  95

Glu Gln Arg Val Ala Asp Ala Trp Lys Ala Ala Met Glu Asp Val Leu
            100                 105                 110

Lys Val Gln Asp Gln Asn Gln Ile Pro Glu Leu Asn Val Tyr Gln Cys
        115                 120                 125

Gly Thr Tyr Gln Met His Ser Leu Gln Glu Ala Gln Asp Ile Ala Arg
    130                 135                 140

Ser Ile Leu Glu Arg Asp Val Arg Ile Asn Ser Asn Glu Glu Leu Ala
145                 150                 155                 160

Leu Pro Lys Glu Lys Leu Gln Glu Leu His Ile
                165                 170

<210> SEQ ID NO 130
<211> LENGTH: 1047
<212> TYPE: DNA
<213> ORGANISM: Artificial Sequence
<220> FEATURE:
<223> OTHER INFORMATION: Synthetic construct

<400> SEQUENCE: 130
atgacttctc cagcaacact gaaagttctc aacgcctact ggataaaccc cactccaacc    60
ctggaggagg caattgaggt gttcaccccg ctgaccgtgg gtgaatacga tgacgtgcac   120
atcgcagcgc tgcttgccac catccgtact cgcggtgagc agttcgctga tattgccggc   180
gctgccaagg cgttcctcgc ggcggctcgt ccgttcccga ttactggcgc aggtttgcta   240
gattccgctg gtactggtgg cgacggtgcc aacaccatca acatcaccac cggcgcatcc   300
ctgatcgcag catccggtgg agtgaagctg gttaagcacg caaccgttc ggtgagctcc   360 aagtccggct ccgccgatgt gctggaagcg ctgaatattc ctttgggcct tgatgtggat   420
cgtgctgtga gtggttcga agcgtccaac ttcaccttcc tgttcgcacc tgcgtacaac   480
cctgcgattg cgcatgtgca gccggttcgc caggcgctga aattccccac catcttcaac   540
acgcttggac cattgctgtc ccggcgcgc ccggagcgtc agatcatggg cgtgccaat   600 gccaatcatg gacagctcat cgccgaggtc ttccgcgagt gggccgtac acgcgcgctt   660 gttgtgcatg gcgcaggcac cgatgagatc gcagtccacg gcaccacctt ggtgtgggag   720
cttaaagaag acggcaccat cgagcattac accatcgagc ctgaggacct tggccttggc   780
cgctacaccc ttgaggatct cgtaggtggc ctcggcactg agaacgccga agctatgcgc   840
gctactttcg cgggcaccgg ccctgatgca caccgtgatg cgttggctgc gtccgcaggt   900
gcgatgttct acctcaacgg cgatgtcgac tccttgaaag atggtgcaca aaaggcgctt   960
tccttgcttg ccgacggcac cacccaggca tggttggcca agcacgaaga gatcgattac  1020
tcagaaaagg agtcttccaa tgactag                                     1047

<210> SEQ ID NO 131
<211> LENGTH: 348
<212> TYPE: PRT
<213> ORGANISM: Artificial Sequence
<220> FEATURE:
<223> OTHER INFORMATION: Synthetic construct

<400> SEQUENCE: 131

| | | | | | | | | | | | | | | | |
|---|---|---|---|---|---|---|---|---|---|---|---|---|---|---|---|
|Met|Thr|Ser|Pro|Ala|Thr|Leu|Lys|Val|Leu|Asn|Ala|Tyr|Leu|Asp|Asn|
|1| | | |5| | | | |10| | | | |15| |

Pro Thr Pro Thr Leu Glu Glu Ala Ile Glu Val Phe Thr Pro Leu Thr
            20                  25                  30

Val Gly Glu Tyr Asp Asp Val His Ile Ala Ala Leu Leu Ala Thr Ile
        35                  40                  45

Arg Thr Arg Gly Glu Gln Phe Ala Asp Ile Ala Gly Ala Ala Lys Ala
50                  55                  60

Phe Leu Ala Ala Ala Arg Pro Phe Pro Ile Thr Gly Ala Gly Leu Leu
65                  70                  75                  80

Asp Ser Ala Gly Thr Gly Gly Asp Gly Ala Asn Thr Ile Asn Ile Thr
            85                  90                  95

Thr Gly Ala Ser Leu Ile Ala Ala Ser Gly Gly Val Lys Leu Val Lys
            100                 105                 110

His Gly Asn Arg Ser Val Ser Ser Lys Ser Gly Ser Ala Asp Val Leu
            115                 120                 125

Glu Ala Leu Asn Ile Pro Leu Gly Leu Asp Val Asp Arg Ala Val Lys
            130                 135                 140

Trp Phe Glu Ala Ser Asn Phe Thr Phe Leu Phe Ala Pro Ala Tyr Asn
145                 150                 155                 160

Pro Ala Ile Ala His Val Gln Pro Val Arg Gln Ala Leu Lys Phe Pro
                165                 170                 175

Thr Ile Phe Asn Thr Leu Gly Pro Leu Leu Ser Pro Ala Arg Pro Glu
            180                 185                 190

Arg Gln Ile Met Gly Val Ala Asn Ala Asn His Gly Gln Leu Ile Ala
            195                 200                 205

Glu Val Phe Arg Glu Leu Gly Arg Thr Arg Ala Leu Val Val His Gly
            210                 215                 220

Ala Gly Thr Asp Glu Ile Ala Val His Gly Thr Thr Leu Val Trp Glu
225                 230                 235                 240

Leu Lys Glu Asp Gly Thr Ile Glu His Tyr Thr Ile Glu Pro Glu Asp
                245                 250                 255

Leu Gly Leu Gly Arg Tyr Thr Leu Glu Asp Leu Val Gly Gly Leu Gly
            260                 265                 270

Thr Glu Asn Ala Glu Ala Met Arg Ala Thr Phe Ala Gly Thr Gly Pro
            275                 280                 285

Asp Ala His Arg Asp Ala Leu Ala Ala Ser Ala Gly Ala Met Phe Tyr
290                 295                 300

Leu Asn Gly Asp Val Asp Ser Leu Lys Asp Gly Ala Gln Lys Ala Leu
305                 310                 315                 320

Ser Leu Leu Ala Asp Gly Thr Thr Gln Ala Trp Leu Ala Lys His Glu
                325                 330                 335

Glu Ile Asp Tyr Ser Glu Lys Glu Ser Ser Asn Asp
            340                 345

<210> SEQ ID NO 132
<211> LENGTH: 1857
<212> TYPE: DNA
<213> ORGANISM: Artificial Sequence
<220> FEATURE:
<223> OTHER INFORMATION: Synthetic construct

<400> SEQUENCE: 132

```
atgcgtacat ccattgccac tgtttgtttg tccggaactc ttgctgaaaa gctgcgcgca      60
gctgcagatg ctggatttga tggtgtggaa atcttcgagc aggacttggt ggtttccccg     120
cattcggcag agcagattcg tcagcgggct caggatttgg gattaaccct ggatctgttc     180
cagccgtttc gagatttcga aggtgtggaa gaagagcagt ttctgaagaa tctgcaccgc     240
ttggaagaga agttcaagct gatgaacagg cttggcattg agatgatctt gttgtgttcc     300
aatgtgggca ccgcgaccat caatgatgat gaccttttcg tggagcagtt gcatcgtgca     360
gcagatttgg ctgagaagta aacgtcaag attgcttatg aagcgttggc gtggggcaag      420
tttgtcaatg attttgagca tgcgcatgca cttgtggaga aggtgaatca aaggcgctg       480
ggaacctgct tggatacgtt ccatattctt tcccgtggtt gggaaaccga cgaggtggag     540
aacatccctg cggagaagat cttctttgtt cagttagcgg atgcgccgaa gctgagcatg     600
gacattttgt cctggtcgcg tcaccaccgt gttttccctg gtgaaggcga tttcgatctg     660
gtgaaattca tggttcatct ggccaagacg ggttatgatg cccgatttc tttgagatc       720
ttcaacgatt ccttccgcaa ggccgaggtt ggtcgcaccg cgattgatgg gttgcgttct     780
ttgcgttggt tggaagatca gacctggcat gcgctaaatg ctgaggatcg tccaagcgct     840
cttgaactgc gtgcacttcc tgaggtcgcg gaacctgagg tgttgatttt cattgagatc     900
gccactggac gtttgggtga gaccattcgg gttcttcatc aattgggttt ccgcttgggt     960
ggtcatcact gcagtaagca ggattaccag gtatggaccc agggcgatgt gcgcattgtg    1020
gtgtgtgatc gtggggtcac cggggctcca accacgatct ctgcgatggg cttttgacacc   1080
cccgatccag aagctgctca tgcccgtgcg gaattgctgc gggctcagac aattgatcgt    1140
ccccacatcg agggcgaagt tgacctaaaa ggtgtgtacg caccgatgg ggtggagctg      1200
ttttcgcgg ggccgagccc cgatggaatg cccgagtggc tgccggaatt cggcgtcgaa     1260
aagcaagaag ctggtctcat tgaagccatc gaccacgtca atttcgccca gccgtggcaa    1320
cattttgatg aggcagtgct gttttacacc gcgctgatgg cgttggagac tgtgcgtgag    1380
gatgagttcc cgagcccaat tggtttggtg cgcaatcagg tgatgcgttc gccgaatgat    1440
gcggtgcggt tgctgctcag cgtggcgccg gaggacggtg agcagggaga tttcctcaac    1500
gcggcctacc cggagcacat tgcgttggcc acggcggaca tcgtggcggt ggctgaacgt    1560
gcgcgcaaac gaggcctgga tttcttgccc gtcccagaga attactacga cgatgtgcag    1620
gcgcgttttg atttgccgca ggaattcttg gacacactca aggaaaacca cctgctttac    1680
gaccgcgacg agaacggcga attcctccac ttttacaccc gcacgttggg cacgctgttc    1740
ttcgaagtgg tggaacgccg cggcggtttt gcaggttggg gcgaaacaaa cgctccggtg    1800
cggttggcgg cgcagtatcg tgaggtgcgg gacctcgagc ggggaatccc aaactag       1857
```

<210> SEQ ID NO 133
<211> LENGTH: 618
<212> TYPE: PRT
<213> ORGANISM: Artificial Sequence
<220> FEATURE:
<223> OTHER INFORMATION: Synthetic construct

<400> SEQUENCE: 133

```
Met Arg Thr Ser Ile Ala Thr Val Cys Leu Ser Gly Thr Leu Ala Glu
1               5                   10                  15

Lys Leu Arg Ala Ala Ala Asp Ala Gly Phe Asp Gly Val Glu Ile Phe
            20                  25                  30
```

-continued

```
Glu Gln Asp Leu Val Val Ser Pro His Ser Ala Glu Gln Ile Arg Gln
             35                  40                  45

Arg Ala Gln Asp Leu Gly Leu Thr Leu Asp Leu Phe Gln Pro Phe Arg
 50                  55                  60

Asp Phe Glu Gly Val Glu Glu Gln Phe Leu Lys Asn Leu His Arg
 65                  70                  75                  80

Leu Glu Glu Lys Phe Lys Leu Met Asn Arg Leu Gly Ile Glu Met Ile
                 85                  90                  95

Leu Leu Cys Ser Asn Val Gly Thr Ala Thr Ile Asn Asp Asp Leu
                100                 105                 110

Phe Val Glu Gln Leu His Arg Ala Ala Asp Leu Ala Glu Lys Tyr Asn
                115                 120                 125

Val Lys Ile Ala Tyr Glu Ala Leu Ala Trp Gly Lys Phe Val Asn Asp
    130                 135                 140

Phe Glu His Ala His Ala Leu Val Glu Lys Val Asn His Lys Ala Leu
145                 150                 155                 160

Gly Thr Cys Leu Asp Thr Phe His Ile Leu Ser Arg Gly Trp Glu Thr
                165                 170                 175

Asp Glu Val Glu Asn Ile Pro Ala Glu Lys Ile Phe Phe Val Gln Leu
                180                 185                 190

Ala Asp Ala Pro Lys Leu Ser Met Asp Ile Leu Ser Trp Ser Arg His
    195                 200                 205

His Arg Val Phe Pro Gly Glu Gly Asp Phe Asp Leu Val Lys Phe Met
    210                 215                 220

Val His Leu Ala Lys Thr Gly Tyr Asp Gly Pro Ile Ser Leu Glu Ile
225                 230                 235                 240

Phe Asn Asp Ser Phe Arg Lys Ala Glu Val Gly Arg Thr Ala Ile Asp
                245                 250                 255

Gly Leu Arg Ser Leu Arg Trp Leu Glu Asp Gln Thr Trp His Ala Leu
                260                 265                 270

Asn Ala Glu Asp Arg Pro Ser Ala Leu Glu Leu Arg Ala Leu Pro Glu
    275                 280                 285

Val Ala Glu Pro Glu Gly Val Asp Phe Ile Glu Ile Ala Thr Gly Arg
    290                 295                 300

Leu Gly Glu Thr Ile Arg Val Leu His Gln Leu Gly Phe Arg Leu Gly
305                 310                 315                 320

Gly His His Cys Ser Lys Gln Asp Tyr Gln Val Trp Thr Gln Gly Asp
                325                 330                 335

Val Arg Ile Val Val Cys Asp Arg Gly Val Thr Gly Ala Pro Thr Thr
                340                 345                 350

Ile Ser Ala Met Gly Phe Asp Thr Pro Asp Pro Glu Ala Ala His Ala
                355                 360                 365

Arg Ala Glu Leu Leu Arg Ala Gln Thr Ile Asp Arg Pro His Ile Glu
    370                 375                 380

Gly Glu Val Asp Leu Lys Gly Val Tyr Ala Pro Asp Gly Val Glu Leu
385                 390                 395                 400

Phe Phe Ala Gly Pro Ser Pro Asp Gly Met Pro Glu Trp Leu Pro Glu
                405                 410                 415

Phe Gly Val Glu Lys Gln Glu Ala Gly Leu Ile Glu Ala Ile Asp His
                420                 425                 430

Val Asn Phe Ala Gln Pro Trp Gln His Phe Asp Glu Ala Val Leu Phe
    435                 440                 445
```

Tyr Thr Ala Leu Met Ala Leu Glu Thr Val Arg Glu Asp Glu Phe Pro
            450                 455                 460

Ser Pro Ile Gly Leu Val Arg Asn Gln Val Met Arg Ser Pro Asn Asp
465                 470                 475                 480

Ala Val Arg Leu Leu Leu Ser Val Ala Pro Glu Asp Gly Glu Gln Gly
                485                 490                 495

Asp Phe Leu Asn Ala Ala Tyr Pro Glu His Ile Ala Leu Ala Thr Ala
            500                 505                 510

Asp Ile Val Ala Val Ala Glu Arg Ala Arg Lys Arg Gly Leu Asp Phe
        515                 520                 525

Leu Pro Val Pro Glu Asn Tyr Tyr Asp Asp Val Gln Ala Arg Phe Asp
530                 535                 540

Leu Pro Gln Glu Phe Leu Asp Thr Leu Lys Glu Asn His Leu Leu Tyr
545                 550                 555                 560

Asp Arg Asp Glu Asn Gly Glu Phe Leu His Phe Tyr Thr Arg Thr Leu
                565                 570                 575

Gly Thr Leu Phe Phe Glu Val Val Glu Arg Arg Gly Gly Phe Ala Gly
            580                 585                 590

Trp Gly Glu Thr Asn Ala Pro Val Arg Leu Ala Ala Gln Tyr Arg Glu
        595                 600                 605

Val Arg Asp Leu Glu Arg Gly Ile Pro Asn
610                 615

<210> SEQ ID NO 134
<211> LENGTH: 852
<212> TYPE: DNA
<213> ORGANISM: Artificial Sequence
<220> FEATURE:
<223> OTHER INFORMATION: Synthetic construct

<400> SEQUENCE: 134
atgaacgaca gtattctcct cggcctaatc ggccagggcc tcgacctatc gcgcaccccc    60
gcaatgcacg aggcggaagg cctcgcgcag ggacgtgcga cggtgtacag gcgcatcgac   120
acgcttgggt cgcgtgcttc cgggcaagat ttaaagacgc ttctcgacgc cgccctctac   180
cttggcttca acggcctgaa catcactcac ccgtacaaac aagcagtatt accccctgctt   240 gacgaagtct ccgaacaagc cacccaactc ggcgcagtga atactgtcgt tatcgacgcc   300
accggccaca ccaccggcca caacaccgac gtctccggat ttggccgcgg aatggaagaa   360
ggcctcccca cgccaagctc gattccgtc gtgcaggtcg gcgccggcgg cgtaggaaac   420
gcagtggcat acgccctggt cacccacggt gtgcagaaac ttcaggtcgc tgacctcgac   480
acttcccgcg cgcaggcact ggcagatgtc atcaacaacg cagtcggccg tgaagccgtc   540
gtgggagtag acgccgcgg catcgaagac gtcatcgccg ccgccgacgg agtagtcaac   600 gcaacccca tgggaatgcc agcacacccc ggcaccgcct ttgatgtcag ctgcctcacc   660
aaggatcact gggttggcga cgtcgtgtac atgcccatcg aaactgaact tctcaaagcc   720
gcccgtgccc tcggctgcga aaccctcgac ggaacccgca tggcaatcca ccaagccgtc   780
gatgccttcc gactgttcac cggcctcgaa cccgacgtct cccgcatgcg ggaaactttc   840
ctgtccctct aa                                                       852

<210> SEQ ID NO 135
<211> LENGTH: 283
<212> TYPE: PRT
<213> ORGANISM: Artificial Sequence
<220> FEATURE:
<223> OTHER INFORMATION: Synthetic construct

<400> SEQUENCE: 135

Met Asn Asp Ser Ile Leu Leu Gly Leu Ile Gly Gln Gly Leu Asp Leu
1               5                   10                  15

Ser Arg Thr Pro Ala Met His Glu Ala Glu Gly Leu Ala Gln Gly Arg
            20                  25                  30

Ala Thr Val Tyr Arg Arg Ile Asp Thr Leu Gly Ser Arg Ala Ser Gly
        35                  40                  45

Gln Asp Leu Lys Thr Leu Leu Asp Ala Ala Leu Tyr Leu Gly Phe Asn
    50                  55                  60

Gly Leu Asn Ile Thr His Pro Tyr Lys Gln Ala Val Leu Pro Leu Leu
65                  70                  75                  80

Asp Glu Val Ser Glu Gln Ala Thr Gln Leu Gly Ala Val Asn Thr Val
                85                  90                  95

Val Ile Asp Ala Thr Gly His Thr Thr Gly His Asn Thr Asp Val Ser
            100                 105                 110

Gly Phe Gly Arg Gly Met Glu Glu Gly Leu Pro Asn Ala Lys Leu Asp
        115                 120                 125

Ser Val Val Gln Val Gly Ala Gly Val Gly Asn Ala Val Ala Tyr
    130                 135                 140

Ala Leu Val Thr His Gly Val Gln Lys Leu Gln Val Ala Asp Leu Asp
145                 150                 155                 160

Thr Ser Arg Ala Gln Ala Leu Ala Asp Val Ile Asn Asn Ala Val Gly
                165                 170                 175

Arg Glu Ala Val Val Gly Val Asp Ala Arg Gly Ile Glu Asp Val Ile
            180                 185                 190

Ala Ala Ala Asp Gly Val Val Asn Ala Thr Pro Met Gly Met Pro Ala
        195                 200                 205

His Pro Gly Thr Ala Phe Asp Val Ser Cys Leu Thr Lys Asp His Trp
    210                 215                 220

Val Gly Asp Val Val Tyr Met Pro Ile Glu Thr Glu Leu Leu Lys Ala
225                 230                 235                 240

Ala Arg Ala Leu Gly Cys Glu Thr Leu Asp Gly Thr Arg Met Ala Ile
                245                 250                 255

His Gln Ala Val Asp Ala Phe Arg Leu Phe Thr Gly Leu Glu Pro Asp
            260                 265                 270

Val Ser Arg Met Arg Glu Thr Phe Leu Ser Leu
        275                 280

<210> SEQ ID NO 136
<211> LENGTH: 1857
<212> TYPE: DNA
<213> ORGANISM: Artificial Sequence
<220> FEATURE:
<223> OTHER INFORMATION: Synthetic construct

<400> SEQUENCE: 136
atgcgtacat ccattgccac tgtttgtttg tccggaactc ttgctgaaaa gctgcgcgca      60
gctgcagatg ctggatttga tggtgtggaa atcttcgagc aggacttggt ggtttccccg     120
cattcggcag agcagattcg tcagcgggct caggatttgg gattaaccct ggatctgttc     180
cagccgtttc gagatttcga aggtgtggaa gaagagcagt tcctgaagaa tctgcaccgc     240
ttggaagaga agttcaagct gatgaacagg cttggcattg agatgatctt ggtgtgttcc     300

```
aatgtgggca ccgcgaccat caatgatgat gacctttttcg tggagcagtt gcatcgtgca    360
gcagatttgg ctgagaagta caacgtcaag attgcttatg aagcgttggc gtggggcaag    420
tttgtcaatg attttgagca tgcgcatgca cttgtggaga aggtgaatca caggcgctg     480
ggaacctgct tggatacgtt ccatattctt tcccgtggtt gggaaaccga cgaggtggag    540
aacatccctg cggagaagat cttctttgtt cagttagcgg atgcgccgaa gctgagcatg    600
gacattttgt cctggtcgcg tcaccaccgt gttttccctg gtgaaggcga tttcgatctg    660
gtgaaattca tggttcatct ggccaagacg ggttatgatg gcccgatttc tttggagatc    720
ttcaacgatt ccttccgcaa ggccgaggtt ggtcgcaccg cgattgatgg gttgcgttct    780
ttgcgttggt tggaagatca gacctggcat gcgctaaatg ctgaggatcg tccaagcgct    840
cttgaactgc gtgcacttcc tgaggtcgcg gaacctgagg gtgttgattt cattgagatc    900
gccactggac gtttgggtga gaccattcgg gttcttcatc aattgggttt ccgcttgggt    960
ggtcatcact gcagtaagca ggattaccag gtatggaccc agggcgatgt gcgcattgtg   1020
gtgtgtgatc gtgggggtcac cggggctcca accacgatct ctgcgatggg ctttgacacc   1080
cccgatccag aagctgctca tgcccgtgcg gaattgctgc gggctcagac aattgatcgt   1140
ccccacatcg agggcgaagt tgacctaaaa ggtgtgtacg caccgatgg ggtggagctg    1200
ttttcgcgg ggccgagccc cgatggaatg cccgagtggc tgccggaatt cggcgtcgaa    1260
aagcaagaag ctggtctcat tgaagccatc gaccacgtca atttcgccca gccgtggcaa   1320
cattttgatg aggcagtgct gttttacacc gcgctgatgg cgttggagac tgtgcgtgag    1380
gatgagttcc cgagcccaat tggtttggtg cgcaatcagg tgatgcgttc gccgaatgat    1440
gcggtgcggt tgctgctcag cgtggcgccg gaggacggtg agcagggaga tttcctcaac    1500
gcggcctacc cggagcacat tgcgttggcc acggcggaca tcgtggcggt ggctgaacgt    1560
gcgcgcaaac gaggcctgga tttcttgccc gtcccagaga attactacga cgatgtgcag    1620
gcgcgttttg atttgccgca ggaattcttg gacacactca aggaaaacca cctgctttac    1680
gaccgcgacg agaacggcga attcctccac ttttacaccc gcacgttggg cacgctgttc    1740
ttcgaagtgg tggaacgccg cggcggtttt gcaggttggg gcgaaacaaa cgctccggtg    1800
cggttggcgg cgcagtatcg tgaggtgcgg gacctcgagc ggggaatccc aaactag       1857
```

<210> SEQ ID NO 137
<211> LENGTH: 618
<212> TYPE: PRT
<213> ORGANISM: Artificial Sequence
<220> FEATURE:
<223> OTHER INFORMATION: Synthetic construct

<400> SEQUENCE: 137

```
Met Arg Thr Ser Ile Ala Thr Val Cys Leu Ser Gly Thr Leu Ala Glu
1               5                   10                  15

Lys Leu Arg Ala Ala Ala Asp Ala Gly Phe Asp Gly Val Glu Ile Phe
            20                  25                  30

Glu Gln Asp Leu Val Val Ser Pro His Ser Ala Glu Gln Ile Arg Gln
        35                  40                  45

Arg Ala Gln Asp Leu Gly Leu Thr Leu Asp Leu Phe Gln Pro Phe Arg
    50                  55                  60

Asp Phe Glu Gly Val Glu Glu Glu Gln Phe Leu Lys Asn Leu His Arg
65                  70                  75                  80

Leu Glu Glu Lys Phe Lys Leu Met Asn Arg Leu Gly Ile Glu Met Ile
                85                  90                  95
```

```
Leu Leu Cys Ser Asn Val Gly Thr Ala Thr Ile Asn Asp Asp Leu
            100                 105                 110

Phe Val Glu Gln Leu His Arg Ala Ala Asp Leu Ala Glu Lys Tyr Asn
        115                 120                 125

Val Lys Ile Ala Tyr Glu Ala Leu Ala Trp Gly Lys Phe Val Asn Asp
    130                 135                 140

Phe Glu His Ala His Ala Leu Val Glu Lys Val Asn His Lys Ala Leu
145                 150                 155                 160

Gly Thr Cys Leu Asp Thr Phe His Ile Leu Ser Arg Gly Trp Glu Thr
                165                 170                 175

Asp Glu Val Glu Asn Ile Pro Ala Glu Lys Ile Phe Phe Val Gln Leu
            180                 185                 190

Ala Asp Ala Pro Lys Leu Ser Met Asp Ile Leu Ser Trp Ser Arg His
        195                 200                 205

His Arg Val Phe Pro Gly Glu Gly Asp Phe Asp Leu Val Lys Phe Met
    210                 215                 220

Val His Leu Ala Lys Thr Gly Tyr Asp Gly Pro Ile Ser Leu Glu Ile
225                 230                 235                 240

Phe Asn Asp Ser Phe Arg Lys Ala Glu Val Gly Arg Thr Ala Ile Asp
                245                 250                 255

Gly Leu Arg Ser Leu Arg Trp Leu Glu Asp Gln Thr Trp His Ala Leu
            260                 265                 270

Asn Ala Glu Asp Arg Pro Ser Ala Leu Glu Leu Arg Ala Leu Pro Glu
        275                 280                 285

Val Ala Glu Pro Glu Gly Val Asp Phe Ile Glu Ile Ala Thr Gly Arg
    290                 295                 300

Leu Gly Glu Thr Ile Arg Val Leu His Gln Leu Gly Phe Arg Leu Gly
305                 310                 315                 320

Gly His His Cys Ser Lys Gln Asp Tyr Gln Val Trp Thr Gln Gly Asp
                325                 330                 335

Val Arg Ile Val Val Cys Asp Arg Gly Val Thr Gly Ala Pro Thr Thr
            340                 345                 350

Ile Ser Ala Met Gly Phe Asp Thr Pro Asp Pro Glu Ala Ala His Ala
        355                 360                 365

Arg Ala Glu Leu Leu Arg Ala Gln Thr Ile Asp Arg Pro His Ile Glu
    370                 375                 380

Gly Glu Val Asp Leu Lys Gly Val Tyr Ala Pro Asp Gly Val Glu Leu
385                 390                 395                 400

Phe Phe Ala Gly Pro Ser Pro Asp Gly Met Pro Glu Trp Leu Pro Glu
                405                 410                 415

Phe Gly Val Glu Lys Gln Glu Ala Gly Leu Ile Glu Ala Ile Asp His
            420                 425                 430

Val Asn Phe Ala Gln Pro Trp Gln His Phe Asp Glu Ala Val Leu Phe
        435                 440                 445

Tyr Thr Ala Leu Met Ala Leu Glu Thr Val Arg Glu Asp Glu Phe Pro
    450                 455                 460

Ser Pro Ile Gly Leu Val Arg Asn Gln Val Met Arg Ser Pro Asn Asp
465                 470                 475                 480

Ala Val Arg Leu Leu Leu Ser Val Ala Pro Glu Asp Gly Glu Gln Gly
                485                 490                 495

Asp Phe Leu Asn Ala Ala Tyr Pro Glu His Ile Ala Leu Ala Thr Ala
            500                 505                 510
```

Asp Ile Val Ala Val Ala Glu Arg Ala Arg Lys Arg Gly Leu Asp Phe
            515                 520                 525

Leu Pro Val Pro Glu Asn Tyr Tyr Asp Asp Val Gln Ala Arg Phe Asp
        530                 535                 540

Leu Pro Gln Glu Phe Leu Asp Thr Leu Lys Glu Asn His Leu Leu Tyr
545                 550                 555                 560

Asp Arg Asp Glu Asn Gly Glu Phe Leu His Phe Tyr Thr Arg Thr Leu
                565                 570                 575

Gly Thr Leu Phe Phe Glu Val Val Glu Arg Arg Gly Gly Phe Ala Gly
            580                 585                 590

Trp Gly Glu Thr Asn Ala Pro Val Arg Leu Ala Ala Gln Tyr Arg Glu
        595                 600                 605

Val Arg Asp Leu Glu Arg Gly Ile Pro Asn
    610                 615

<210> SEQ ID NO 138
<211> LENGTH: 573
<212> TYPE: DNA
<213> ORGANISM: Artificial Sequence
<220> FEATURE:
<223> OTHER INFORMATION: Synthetic construct

<400> SEQUENCE: 138

```
atggagcgta atgaagtgaa tgatcaaatt cacttagatc atcaatcaga tgacacctct      60
gaatgctcct gcccgatcgt ggttcttgtg ggtttgccag gagctggaaa atccaccatt     120
ggacgtcgat tagcgcgcgc cttaaacact gaactcgtcg actccgacga actgattgag     180
cgcgccaccg gaaaagcctg tggcgccgtg ttcagcgagc tcggcgagcc agccttccgc     240
gagctcgagg ccatccacgt ggccgaagca ctgaaatcct ccggagtggt gagcttggga     300
ggcggatctg tgctgacaga atccacccgt gaactgctca aaggccagga cgtggtctgg     360
atcgacgtgc agtagaaga aggcatcagg cgcaccgcaa acgagcgttc ccgccccgtg      420
ctgcaagccg ccgaccccgc cgagcactac cgcaacctgg tgaaagtgcg caccccgttg     480
tacgaagagg tggcaaccta ccgacttcgc accaacaacc gcagccccca gcaagtggtg     540
gcagcagtgt tgcatcatct agaaatcgat taa                                  573
```

<210> SEQ ID NO 139
<211> LENGTH: 190
<212> TYPE: PRT
<213> ORGANISM: Artificial Sequence
<220> FEATURE:
<223> OTHER INFORMATION: Synthetic construct

<400> SEQUENCE: 139

Met Glu Arg Asn Glu Val Asn Asp Gln Ile His Leu Asp His Gln Ser
1               5                   10                  15

Asp Asp Thr Ser Glu Cys Ser Cys Pro Ile Val Val Leu Val Gly Leu
            20                  25                  30

Pro Gly Ala Gly Lys Ser Thr Ile Gly Arg Arg Leu Ala Arg Ala Leu
        35                  40                  45

Asn Thr Glu Leu Val Asp Ser Asp Glu Leu Ile Glu Arg Ala Thr Gly
    50                  55                  60

Lys Ala Cys Gly Ala Val Phe Ser Glu Leu Gly Glu Pro Ala Phe Arg
65                  70                  75                  80

```
Glu Leu Glu Ala Ile His Val Ala Glu Ala Leu Lys Ser Ser Gly Val
                85                  90                  95

Val Ser Leu Gly Gly Gly Ser Val Leu Thr Glu Ser Thr Arg Glu Leu
            100                 105                 110

Leu Lys Gly Gln Asp Val Val Trp Ile Asp Val Pro Val Glu Glu Gly
        115                 120                 125

Ile Arg Arg Thr Ala Asn Glu Arg Ser Arg Pro Val Leu Gln Ala Ala
    130                 135                 140

Asp Pro Ala Glu His Tyr Arg Asn Leu Val Lys Val Arg Thr Pro Leu
145                 150                 155                 160

Tyr Glu Glu Val Ala Thr Tyr Arg Leu Arg Thr Asn Asn Arg Ser Pro
                165                 170                 175

Gln Gln Val Val Ala Ala Val Leu His His Leu Glu Ile Asp
            180                 185                 190
```

<210> SEQ ID NO 140
<211> LENGTH: 1098
<212> TYPE: DNA
<213> ORGANISM: Artificial Sequence
<220> FEATURE:
<223> OTHER INFORMATION: Synthetic construct

<400> SEQUENCE: 140

```
atgagcgcag tgcagatttt caacaccgtc cacgtcaatg gatcttcccc ctatgatgtc      60
cacattggtt ccggcctcaa cgagctcatt gttcagcgcg cagcggaatc aggcgcggag     120
caggtagcga ttttgcacca gcccagcatg gatgacattg catccgagtt ggatgcagca     180
ctagtcgctg ctggtttgaa ggtcctgcac cttaatgttc ccgatgcgga aaacggcaag     240
tccttggaag tagcggggca gtgctgggat gaattgggtg gcgcagcatt cggccgccgc     300
gatatcgtca tcggacttgg tggcggtgct gccacagatc tcgcgggatt cgtcgctgct     360
gcatggatgc gtggcgtgcg cgtcattcag gttccaacca ccttgttggc catggtggac     420
gctgcggtgg cggcaagac tggcatcaat accgccgcag gcaagaacct tgtgggcgcg     480
ttccacgagc ctgacgcagt attcattgac accgatcgcc tagccaccct gcctgacgcg     540
gaaatcatcg cgggatccgc cgaaatcatc aaaactggtt tcatcgccga cccagaaatc     600
ctgcgccttt acgaaactga tcccgcagcc tgcctgaaga agaagtcga aggctcccac     660
ctacctgaac tgatttggcg ctccgtcacc gtcaagggct ccgtggtcgg ccaagacctc     720
aaagaatcta gcctgcgcga atcctcaac tacggacaca cctttgccca cgccgtcgaa     780
ctccgcgaaa acttccgctg gcgccacggc aatgccgttg cagtgggcat gatgttcatc     840
gccaacctct cccacaagct cgggcttatc gacgcgcccc tcctcgagcg ccaccgctca     900
atcctggcgg ccatcggtct gcccacttcc tacgaaggcg gagccttcga cgagctttac     960
gacggtatga cccgcgacaa gaaaaaccgc gacggcaaca tccgcttcgt cgcactgacc    1020
gccgtgggcg aggttacccg cattgagggg ccctcaaaac aagatttaca gagtgcttat    1080
gaggcaatca gccactaa                                                  1098
```

<210> SEQ ID NO 141
<211> LENGTH: 365
<212> TYPE: PRT
<213> ORGANISM: Artificial Sequence
<220> FEATURE:
<223> OTHER INFORMATION: Synthetic construct

<400> SEQUENCE: 141

| | | | | | | | | | | | | | | | |
|---|---|---|---|---|---|---|---|---|---|---|---|---|---|---|---|
|Met|Ser|Ala|Val|Gln|Ile|Phe|Asn|Thr|Val|His|Val|Asn|Gly|Ser|Ser|
|1| | | |5| | | | |10| | | | |15| |
|Pro|Tyr|Asp|Val|His|Ile|Gly|Ser|Gly|Leu|Asn|Glu|Leu|Ile|Val|Gln|
| | | |20| | | | |25| | | | |30| | |
|Arg|Ala|Ala|Glu|Ser|Gly|Ala|Glu|Gln|Val|Ala|Ile|Leu|His|Gln|Pro|
| | | |35| | | | |40| | | | |45| | |
|Ser|Met|Asp|Asp|Ile|Ala|Ser|Glu|Leu|Asp|Ala|Ala|Leu|Val|Ala|Ala|
| |50| | | | |55| | | | |60| | | | |
|Gly|Leu|Lys|Val|Leu|His|Leu|Asn|Val|Pro|Asp|Ala|Glu|Asn|Gly|Lys|
|65| | | | |70| | | | |75| | | | |80|
|Ser|Leu|Glu|Val|Ala|Gly|Gln|Cys|Trp|Asp|Glu|Leu|Gly|Gly|Ala|Ala|
| | | | |85| | | | |90| | | | |95| |
|Phe|Gly|Arg|Arg|Asp|Ile|Val|Ile|Gly|Leu|Gly|Gly|Ala|Ala|Ala|Thr|
| | | |100| | | | |105| | | | |110| | |
|Asp|Leu|Ala|Gly|Phe|Val|Ala|Ala|Ala|Trp|Met|Arg|Gly|Val|Arg|Val|
| | | |115| | | | |120| | | | |125| | |
|Ile|Gln|Val|Pro|Thr|Thr|Leu|Leu|Ala|Met|Val|Asp|Ala|Ala|Val|Gly|
| |130| | | | |135| | | | |140| | | | |
|Gly|Lys|Thr|Gly|Ile|Asn|Thr|Ala|Ala|Gly|Lys|Asn|Leu|Val|Gly|Ala|
|145| | | | |150| | | | |155| | | | |160|
|Phe|His|Glu|Pro|Asp|Ala|Val|Phe|Ile|Asp|Thr|Asp|Arg|Leu|Ala|Thr|
| | | |165| | | | |170| | | | |175| | |
|Leu|Pro|Asp|Ala|Glu|Ile|Ile|Ala|Gly|Ser|Ala|Glu|Ile|Ile|Lys|Thr|
| | | |180| | | | |185| | | | |190| | |
|Gly|Phe|Ile|Ala|Asp|Pro|Glu|Ile|Leu|Arg|Leu|Tyr|Glu|Thr|Asp|Pro|
| |195| | | | |200| | | | |205| | | | |
|Ala|Ala|Cys|Leu|Lys|Lys|Glu|Val|Glu|Gly|Ser|His|Leu|Pro|Glu|Leu|
| |210| | | | |215| | | | |220| | | | |
|Ile|Trp|Arg|Ser|Val|Thr|Val|Lys|Gly|Ser|Val|Val|Gly|Gln|Asp|Leu|
|225| | | | |230| | | | |235| | | | |240|
|Lys|Glu|Ser|Ser|Leu|Arg|Glu|Ile|Leu|Asn|Tyr|Gly|His|Thr|Phe|Ala|
| | | | |245| | | | |250| | | | |255| |
|His|Ala|Val|Glu|Leu|Arg|Glu|Asn|Phe|Arg|Trp|Arg|His|Gly|Asn|Ala|
| | | |260| | | | |265| | | | |270| | |
|Val|Ala|Val|Gly|Met|Met|Phe|Ile|Ala|Asn|Leu|Ser|His|Lys|Leu|Gly|
| | |275| | | | |280| | | | |285| | | |
|Leu|Ile|Asp|Ala|Pro|Leu|Leu|Glu|Arg|His|Arg|Ser|Ile|Leu|Ala|Ala|
| |290| | | | |295| | | | |300| | | | |
|Ile|Gly|Leu|Pro|Thr|Ser|Tyr|Glu|Gly|Gly|Ala|Phe|Asp|Glu|Leu|Tyr|
|305| | | | |310| | | | |315| | | | |320|
|Asp|Gly|Met|Thr|Arg|Asp|Lys|Lys|Asn|Arg|Asp|Gly|Asn|Ile|Arg|Phe|
| | | |325| | | | |330| | | | |335| | |
|Val|Ala|Leu|Thr|Ala|Val|Gly|Glu|Val|Thr|Arg|Ile|Glu|Gly|Pro|Ser|
| | | |340| | | | |345| | | | |350| | |
|Lys|Gln|Asp|Leu|Gln|Ser|Ala|Tyr|Glu|Ala|Ile|Ser|His|
| | | |355| | | | |360| | | | |365|

<210> SEQ ID NO 142
<211> LENGTH: 2031
<212> TYPE: DNA
<213> ORGANISM: Artificial Sequence
<220> FEATURE:
<223> OTHER INFORMATION: Synthetic construct

<400> SEQUENCE: 142

```
gtggacacca aggctgtaga cactgttcgt gtcctcgctg cagacgctgt agaaaactgt    60
ggctccggcc acccaggcac cgcaatgagc ctggctcccc ttgcatacac cttgtaccag   120
cgggttatga acgtagatcc acaggacacc aactgggcag gccgtgaccg cttcgttctt   180
tcttgtggcc actcctcttt gacccagtac atccagcttt acttgggtgg attcggcctt   240
gagatggatg acctgaaggc tctgcgcacc tgggattcct tgaccccagg acaccctgag   300
taccgccaca ccaagggcgt tgagatcacc actggccctc ttggccaggg tcttgcatct   360
gcagttggta tggccatggc tgctcgtcgt gagcgtggcc tattcgaccc aaccgctgct   420
gagggcgaat ccccattcga ccaccacatc tacgtcattg cttctgatgg tgacctgcag   480
gaaggtgtca cctctgaggc atcctccatc gctggcaccc agcagctggg caacctcatc   540
gtgttctggg atgacaaccg catctccatc gaagacaaca ctgagatcgc tttcaacgag   600
gacgttgttg ctcgttacaa ggcttacggc tggcagacca ttgaggttga ggctggcgag   660
gacgttgcag caatcgaagc tgcagtggct gaggctaaga aggacaccaa gcgacctacc   720
ttcatccgcg ttcgcaccat catcggcttc ccagctccaa ctatgatgaa caccggtgct   780
gtgcacggtg ctgctcttgg cgcagctgag gttgcagcaa ccaagactga gcttggattc   840
gatcctgagg ctcacttcgc gatcgacgat gaggttatcg ctcacacccg ctccctcgca   900
gagcgcgctg cacagaagaa ggctgcatgg caggtcaagt tcgatgagtg ggcagctgcc   960
aaccctgaga caaggctct gttcgatcgc ctgaactccc gtgagcttcc agcgggctac  1020
gctgacgagc tcccaacatg ggatgcagat gagaagggcg tcgcaactcg taaggcttcc  1080
gaggctgcac ttcaggcact gggcaagacc cttcctgagc tgtggggcgg ttccgctgac  1140
ctcgcaggtt ccaacaacac cgtgatcaag ggctcccctt ccttcggccc tgagtccatc  1200
tccaccgaga cctggtctgc tgagccttac ggccgtaacc tgcacttcgg tatccgtgag  1260
cacgctatgg gatccatcct caacggcatt tccctccacg gtggcacccg cccatacggc  1320
ggaaccttcc tcatcttctc cgactacatg cgtcctgcag ttcgtcttgc agctctcatg  1380
gagaccgacg cttactacgt ctggacccac gactccatcg gtctgggcga agatggccca  1440
acccaccagc ctgttgaaac cttggctgca ctgcgcgcca tcccaggtct gtccgtcctg  1500
cgtcctgcag atgcgaacga gaccgcccag gcttgggctg cagcacttga gtacaaggaa  1560
ggccctaagg gtcttgcact gacccgccag aacgttcctg ttctggaagg caccaaggag  1620
aaggctgctg aaggcgttcg ccgcggtggc tacgtcctgg ttgagggttc caaggaaacc  1680
ccagatgtga tcctcatggg ctccggctcc gaggttcagc ttgcagttaa cgctgcgaag  1740
gctctggaag ctgagggcgt tgcagctcgc gttgtttccg ttccttgcat ggattggttc  1800
caggagcagg acgcagagta catcgagtcc gttctgcctg cagctgtgac cgctcgtgtg  1860
tctgttgaag ctggcatcgc aatgccttgg taccgcttct tgggcaccca gggccgtgct  1920
gtctcccttg agcacttcgg tgcttctgcg gattaccaga ccctgtttga agttcggc   1980
atcaccaccg atgcagtcgt ggcagcggcc aaggactcca ttaacggtta a           2031
```

<210> SEQ ID NO 143
<211> LENGTH: 676
<212> TYPE: PRT
<213> ORGANISM: Artificial Sequence
<220> FEATURE:
<223> OTHER INFORMATION: Synthetic construct

<400> SEQUENCE: 143

```
Val Asp Thr Lys Ala Val Asp Thr Val Arg Val Leu Ala Ala Asp Ala
1               5                   10                  15
Val Glu Asn Cys Gly Ser Gly His Pro Gly Thr Ala Met Ser Leu Ala
            20                  25                  30
Pro Leu Ala Tyr Thr Leu Tyr Gln Arg Val Met Asn Val Asp Pro Gln
        35                  40                  45
Asp Thr Asn Trp Ala Gly Arg Asp Arg Phe Val Leu Ser Cys Gly His
    50                  55                  60
Ser Ser Leu Thr Gln Tyr Ile Gln Leu Tyr Leu Gly Gly Phe Gly Leu
65                  70                  75                  80
Glu Met Asp Asp Leu Lys Ala Leu Arg Thr Trp Asp Ser Leu Thr Pro
                85                  90                  95
Gly His Pro Glu Tyr Arg His Thr Lys Gly Val Glu Ile Thr Thr Gly
            100                 105                 110
Pro Leu Gly Gln Gly Leu Ala Ser Ala Val Gly Met Ala Met Ala Ala
        115                 120                 125
Arg Arg Glu Arg Gly Leu Phe Asp Pro Thr Ala Ala Glu Gly Glu Ser
    130                 135                 140
Pro Phe Asp His His Ile Tyr Val Ile Ala Ser Asp Gly Asp Leu Gln
145                 150                 155                 160
Glu Gly Val Thr Ser Glu Ala Ser Ser Ile Ala Gly Thr Gln Gln Leu
                165                 170                 175
Gly Asn Leu Ile Val Phe Trp Asp Asp Asn Arg Ile Ser Ile Glu Asp
            180                 185                 190
Asn Thr Glu Ile Ala Phe Asn Glu Asp Val Val Ala Arg Tyr Lys Ala
        195                 200                 205
Tyr Gly Trp Gln Thr Ile Glu Val Glu Ala Gly Glu Asp Val Ala Ala
    210                 215                 220
Ile Glu Ala Ala Val Ala Glu Ala Lys Lys Asp Thr Lys Arg Pro Thr
225                 230                 235                 240
Phe Ile Arg Val Arg Thr Ile Ile Gly Phe Pro Ala Pro Thr Met Met
                245                 250                 255
Asn Thr Gly Ala Val His Gly Ala Ala Leu Gly Ala Ala Glu Val Ala
            260                 265                 270
Ala Thr Lys Thr Glu Leu Gly Phe Asp Pro Glu Ala His Phe Ala Ile
        275                 280                 285
Asp Asp Glu Val Ile Ala His Thr Arg Ser Leu Ala Glu Arg Ala Ala
    290                 295                 300
Gln Lys Lys Ala Ala Trp Gln Val Lys Phe Asp Glu Trp Ala Ala Ala
305                 310                 315                 320
Asn Pro Glu Asn Lys Ala Leu Phe Asp Arg Leu Asn Ser Arg Glu Leu
                325                 330                 335
Pro Ala Gly Tyr Ala Asp Glu Leu Pro Thr Trp Asp Ala Asp Glu Lys
            340                 345                 350
Gly Val Ala Thr Arg Lys Ala Ser Glu Ala Ala Leu Gln Ala Leu Gly
        355                 360                 365
Lys Thr Leu Pro Glu Leu Trp Gly Gly Ser Ala Asp Leu Ala Gly Ser
    370                 375                 380
Asn Asn Thr Val Ile Lys Gly Ser Pro Ser Phe Gly Pro Glu Ser Ile
385                 390                 395                 400
Ser Thr Glu Thr Trp Ser Ala Glu Pro Tyr Gly Arg Asn Leu His Phe
                405                 410                 415
```

```
Gly Ile Arg Glu His Ala Met Gly Ser Ile Leu Asn Gly Ile Ser Leu
                420                 425                 430

His Gly Gly Thr Arg Pro Tyr Gly Gly Thr Phe Leu Ile Phe Ser Asp
            435                 440                 445

Tyr Met Arg Pro Ala Val Arg Leu Ala Ala Leu Met Glu Thr Asp Ala
        450                 455                 460

Tyr Tyr Val Trp Thr His Asp Ser Ile Gly Leu Gly Glu Asp Gly Pro
465                 470                 475                 480

Thr His Gln Pro Val Glu Thr Leu Ala Ala Leu Arg Ala Ile Pro Gly
                485                 490                 495

Leu Ser Val Leu Arg Pro Ala Asp Ala Asn Glu Thr Ala Gln Ala Trp
            500                 505                 510

Ala Ala Ala Leu Glu Tyr Lys Glu Gly Pro Lys Gly Leu Ala Leu Thr
        515                 520                 525

Arg Gln Asn Val Pro Val Leu Glu Gly Thr Lys Glu Lys Ala Ala Glu
530                 535                 540

Gly Val Arg Arg Gly Gly Tyr Val Leu Val Glu Gly Ser Lys Glu Thr
545                 550                 555                 560

Pro Asp Val Ile Leu Met Gly Ser Gly Ser Glu Val Gln Leu Ala Val
                565                 570                 575

Asn Ala Ala Lys Ala Leu Glu Ala Glu Gly Val Ala Ala Arg Val Val
            580                 585                 590

Ser Val Pro Cys Met Asp Trp Phe Gln Glu Gln Asp Ala Glu Tyr Ile
        595                 600                 605

Glu Ser Val Leu Pro Ala Ala Val Thr Ala Arg Val Ser Val Glu Ala
610                 615                 620

Gly Ile Ala Met Pro Trp Tyr Arg Phe Leu Gly Thr Gln Gly Arg Ala
625                 630                 635                 640

Val Ser Leu Glu His Phe Gly Ala Ser Ala Asp Tyr Gln Thr Leu Phe
                645                 650                 655

Glu Lys Phe Gly Ile Thr Thr Asp Ala Val Val Ala Ala Ala Lys Asp
            660                 665                 670

Ser Ile Asn Gly
        675

<210> SEQ ID NO 144
<211> LENGTH: 1224
<212> TYPE: DNA
<213> ORGANISM: Artificial Sequence
<220> FEATURE:
<223> OTHER INFORMATION: Synthetic construct

<400> SEQUENCE: 144
gtggctcagc caaccgccgt ccgtttgttc accagtgaat ctgtaactga gggacatcca      60
gacaaaatat gtgatgctat ttccgatacc attttggacg cgctgctcga aaaagatccg     120
cagtcgcgcg tcgcagtgga aactgtggtc accaccggaa tcgtccatgt tgttggcgag     180
gtccgtacca gcgcttacgt agagatccct caattagtcc gcaacaagct catcgaaatc     240
ggattcaact cctctgaggt tggattcgac ggacgcacct gtggcgtctc agtatccatc     300
ggtgagcagt cccaggaaat cgctgacggc gtggataact ccgacgaagc ccgcaccaac     360
ggcgacgttg aagaagacga ccgcgcaggt gctggcgacc agggcctgat gttcggctac     420
gccaccaacg aaaccgaaga gtacatgcct cttcctatcg cgttggcgca ccgactgtca     480
cgtcgtctga cccaggttcg taaagagggc atcgttcctc acctgcgtcc agacggaaaa     540
```

```
acccaggtca ccttcgcata cgatgcgcaa gaccgcccta gccacctgga taccgttgtc    600
atctccaccc agcacgaccc agaagttgac cgtgcatggt tggaaaccca actgcgcgaa    660
cacgtcattg attgggtaat caaagacgca ggcattgagg atctggcaac cggtgagatc    720
accgtgttga tcaacccttc aggttccttc attctgggtg gccccatggg tgatgcgggt    780
ctgaccggcc gcaagatcat cgtggatacc tacggtggca tggctcgcca tggtggtgga    840
gcattctccg gtaaggatcc aagcaaggtg gaccgctctg ctgcatacgc catgcgttgg    900
gtagcaaaga acatcgtggc agcaggcctt gctgatcgcg ctgaagttca ggttgcatac    960
gccattggac gcgcaaagcc agtcggactt tacgttgaaa cctttgacac caacaaggaa   1020
ggcctgagcg acgagcagat tcaggctgcc gtgttggagg tctttgacct gcgtccagca   1080
gcaattatcc gtgagcttga tctgcttcgt ccgatctacg ctgacactgc tgcctacggc   1140
cactttggtc gcactgattt ggaccttcct tgggaggcta tcgaccgcgt tgatgaactt   1200
cgcgcagccc tcaagttggc ctaa                                          1224
```

```
<210> SEQ ID NO 145
<211> LENGTH: 407
<212> TYPE: PRT
<213> ORGANISM: Artificial Sequence
<220> FEATURE:
<223> OTHER INFORMATION: Synthetic construct

<400> SEQUENCE: 145

Val Ala Gln Pro Thr Ala Val Arg Leu Phe Thr Ser Glu Ser Val Thr
1               5                   10                  15

Glu Gly His Pro Asp Lys Ile Cys Asp Ala Ile Ser Asp Thr Ile Leu
            20                  25                  30

Asp Ala Leu Leu Glu Lys Asp Pro Gln Ser Arg Val Ala Val Glu Thr
        35                  40                  45

Val Val Thr Thr Gly Ile Val His Val Gly Glu Val Arg Thr Ser
    50                  55                  60

Ala Tyr Val Glu Ile Pro Gln Leu Val Arg Asn Lys Leu Ile Glu Ile
65                  70                  75                  80

Gly Phe Asn Ser Ser Glu Val Gly Phe Asp Gly Arg Thr Cys Gly Val
                85                  90                  95

Ser Val Ser Ile Gly Glu Gln Ser Gln Glu Ile Ala Asp Gly Val Asp
            100                 105                 110

Asn Ser Asp Glu Ala Arg Thr Asn Gly Asp Val Glu Glu Asp Asp Arg
        115                 120                 125

Ala Gly Ala Gly Asp Gln Gly Leu Met Phe Gly Tyr Ala Thr Asn Glu
    130                 135                 140

Thr Glu Glu Tyr Met Pro Leu Pro Ile Ala Leu Ala His Arg Leu Ser
145                 150                 155                 160

Arg Arg Leu Thr Gln Val Arg Lys Glu Gly Ile Val Pro His Leu Arg
                165                 170                 175

Pro Asp Gly Lys Thr Gln Val Thr Phe Ala Tyr Asp Ala Gln Asp Arg
            180                 185                 190

Pro Ser His Leu Asp Thr Val Val Ile Ser Thr Gln His Asp Pro Glu
        195                 200                 205

Val Asp Arg Ala Trp Leu Glu Thr Gln Leu Arg Glu His Val Ile Asp
    210                 215                 220

Trp Val Ile Lys Asp Ala Gly Ile Glu Asp Leu Ala Thr Gly Glu Ile
225                 230                 235                 240
```

```
Thr Val Leu Ile Asn Pro Ser Gly Ser Phe Ile Leu Gly Gly Pro Met
                245                 250                 255

Gly Asp Ala Gly Leu Thr Gly Arg Lys Ile Ile Val Asp Thr Tyr Gly
            260                 265                 270

Gly Met Ala Arg His Gly Gly Ala Phe Ser Gly Lys Asp Pro Ser
        275                 280                 285

Lys Val Asp Arg Ser Ala Ala Tyr Ala Met Arg Trp Val Ala Lys Asn
    290                 295                 300

Ile Val Ala Ala Gly Leu Ala Asp Arg Ala Glu Val Gln Val Ala Tyr
305                 310                 315                 320

Ala Ile Gly Arg Ala Lys Pro Val Gly Leu Tyr Val Glu Thr Phe Asp
                325                 330                 335

Thr Asn Lys Glu Gly Leu Ser Asp Glu Gln Ile Gln Ala Ala Val Leu
            340                 345                 350

Glu Val Phe Asp Leu Arg Pro Ala Ala Ile Ile Arg Glu Leu Asp Leu
        355                 360                 365

Leu Arg Pro Ile Tyr Ala Asp Thr Ala Ala Tyr Gly His Phe Gly Arg
    370                 375                 380

Thr Asp Leu Asp Leu Pro Trp Glu Ala Ile Asp Arg Val Asp Glu Leu
385                 390                 395                 400

Arg Ala Ala Leu Lys Leu Ala
                405

<210> SEQ ID NO 146
<211> LENGTH: 1101
<212> TYPE: DNA
<213> ORGANISM: Artificial Sequence
<220> FEATURE:
<223> OTHER INFORMATION: Synthetic construct

<400> SEQUENCE: 146
atgagttctc cagtctcact cgaaaacgcg gcgtcaacca gcaacaagcg cgtcgtggct       60
ttccacgagc tgcctagccc tacagatctc atcgccgcaa acccactgac accaaagcag      120
gcttccaagg tggagcagga tcgccaggac atcgctgata tcttcgctgg cgacgatgac      180
cgcctcgttg tcgttgtggg accttgctca gttcacgatc ctgaagcagc catcgattac      240
gcaaaccgcc tggctccgct ggcaaagcgc cttgatcagg acctcaagat tgtcatgcgc      300
gtgtacttcg agaagcctcg caccatcgtc ggatggaagg gattgatcaa tgatcctcac      360
ctcaacgaaa cctacgacat cccagagggc ttgcgcattg cgcgcaaagt gcttatcgac      420
gttgtgaacc ttgatctccc agtcggctgc gaattcctcg aaccaaacag ccctcagtac      480
tacgccgaca ctgtcgcatg gggagcaatc ggcgctcgta ccaccgaatc tcaggtgcac      540
cgccagctgg cttctgggat gtctatgcca attggtttca gaacggaac tgacggaaac      600 atccaggttg cagtcgacgc ggtacaggct gcccagaacc cacacttctt cttcggaacc      660
tccgacgacg gcgcgctgag cgtcgtggag accgcaggca acagcaactc ccacatcatt      720
ttgcgcggcg gtacctccgg cccgaatcat gatgcagctt cggtggaggc cgtcgtcgag      780
aagcttggtg aaaacgctcg tctcatgatc gatgcttccc atgctaactc cggcaaggat      840
catatccgac aggttgaggt tgttcgtgaa atcgcagagc agatttctgg cggttctgaa      900
gctgtggctg gaatcatgat tgagtccttc ctcgttggtg gcgcacagaa ccttgatcct      960
```

```
gcgaaattgc gcatcaatgg cggtgaaggc ctggtgtacg gacagtctgt gaccgataag    1020
tgcatcgata ttgacaccac catcgatttg ctcgctgagc tggccgcagc agtaagggaa    1080
cgccgagcag cagccaagta a                                              1101
```

<210> SEQ ID NO 147
<211> LENGTH: 366
<212> TYPE: PRT
<213> ORGANISM: Artificial Sequence
<220> FEATURE:
<223> OTHER INFORMATION: Synthetic construct

<400> SEQUENCE: 147

```
Met Ser Ser Pro Val Ser Leu Glu Asn Ala Ala Ser Thr Ser Asn Lys
1               5                   10                  15

Arg Val Val Ala Phe His Glu Leu Pro Ser Pro Thr Asp Leu Ile Ala
            20                  25                  30

Ala Asn Pro Leu Thr Pro Lys Gln Ala Ser Lys Val Glu Gln Asp Arg
        35                  40                  45

Gln Asp Ile Ala Asp Ile Phe Ala Gly Asp Asp Arg Leu Val Val
    50                  55                  60

Val Val Gly Pro Cys Ser Val His Asp Pro Glu Ala Ala Ile Asp Tyr
65                  70                  75                  80

Ala Asn Arg Leu Ala Pro Leu Ala Lys Arg Leu Asp Gln Asp Leu Lys
                85                  90                  95

Ile Val Met Arg Val Tyr Phe Glu Lys Pro Arg Thr Ile Val Gly Trp
            100                 105                 110

Lys Gly Leu Ile Asn Asp Pro His Leu Asn Glu Thr Tyr Asp Ile Pro
        115                 120                 125

Glu Gly Leu Arg Ile Ala Arg Lys Val Leu Ile Asp Val Val Asn Leu
    130                 135                 140

Asp Leu Pro Val Gly Cys Glu Phe Leu Glu Pro Asn Ser Pro Gln Tyr
145                 150                 155                 160

Tyr Ala Asp Thr Val Ala Trp Gly Ala Ile Gly Ala Arg Thr Thr Glu
                165                 170                 175

Ser Gln Val His Arg Gln Leu Ala Ser Gly Met Ser Met Pro Ile Gly
            180                 185                 190

Phe Lys Asn Gly Thr Asp Gly Asn Ile Gln Val Ala Val Asp Ala Val
        195                 200                 205

Gln Ala Ala Gln Asn Pro His Phe Phe Phe Gly Thr Ser Asp Asp Gly
    210                 215                 220

Ala Leu Ser Val Val Glu Thr Ala Gly Asn Ser Asn Ser His Ile Ile
225                 230                 235                 240

Leu Arg Gly Gly Thr Ser Gly Pro Asn His Asp Ala Ala Ser Val Glu
                245                 250                 255

Ala Val Val Glu Lys Leu Gly Glu Asn Ala Arg Leu Met Ile Asp Ala
            260                 265                 270

Ser His Ala Asn Ser Gly Lys Asp His Ile Arg Gln Val Glu Val Val
        275                 280                 285

Arg Glu Ile Ala Glu Gln Ile Ser Gly Gly Ser Glu Ala Val Ala Gly
    290                 295                 300

Ile Met Ile Glu Ser Phe Leu Val Gly Gly Ala Gln Asn Leu Asp Pro
305                 310                 315                 320

Ala Lys Leu Arg Ile Asn Gly Gly Glu Gly Leu Val Tyr Gly Gln Ser
                325                 330                 335
```

```
Val Thr Asp Lys Cys Ile Asp Ile Asp Thr Thr Ile Asp Leu Leu Ala
        340                 345                 350

Glu Leu Ala Ala Ala Val Arg Glu Arg Arg Ala Ala Ala Lys
        355                 360                 365
```

<210> SEQ ID NO 148
<211> LENGTH: 1437
<212> TYPE: DNA
<213> ORGANISM: Artificial Sequence
<220> FEATURE:
<223> OTHER INFORMATION: Synthetic construct

<400> SEQUENCE: 148

| | | | | | |
|---|---|---|---|---|---|
| atggcacagg | ttatggactt | caaggttgcc | gatctttcac | tagcagaggc | aggacgtcac | 60 |
| cagattcgtc | ttgcagagta | tgagatgcca | ggtctcatgc | agttgcgcaa | ggaattcgca | 120 |
| gacgagcagc | ctttgaaggg | cgcccgaatt | gctggttcta | tccacatgac | ggtccagacc | 180 |
| gccgtgctta | ttgagaccct | cactgctttg | ggcgctgagg | ttcgttgggc | ttcctgcaac | 240 |
| atttctcca | cccaggatga | ggctgcagcg | gctatcgttg | tcggctccgg | caccgtcgaa | 300 |
| gagccagctg | gtgttccagt | attcgcgtgg | aagggtgagt | cactggagga | gtactggtgg | 360 |
| tgcatcaacc | agatcttcag | ctggggcgat | gagctgccaa | acatgatcct | cgacgacggc | 420 |
| ggtgacgcca | ccatggctgt | tattcgcggt | cgcgaatacg | agcaggctgg | tctggttcca | 480 |
| ccagcagagg | ccaacgattc | cgatgagtac | atcgcattct | gggcatgct | gcgtgaggtt | 540 |
| cttgctgcag | agcctggcaa | gtggggcaag | atcgctgagg | ccgttaaggg | tgtcaccgag | 600 |
| gaaaccacca | ccggtgtgca | ccgcctgtac | cacttcgctg | aagaaggcgt | gctgcctttc | 660 |
| ccagcgatga | acgtcaacga | cgctgtcacc | aagtccaagt | ttgataacaa | gtacggcacc | 720 |
| cgccactccc | tgatcgacgg | catcaaccgc | gccactgaca | tgctcatggg | cggcaagaac | 780 |
| gtgcttgtct | gcggttacgg | cgatgtcggc | aagggctgcg | ctgaggcttt | cgacggccag | 840 |
| ggcgctcgcg | tcaaggtcac | cgaagctgac | ccaatcaacg | ctcttcaggc | tctgatggat | 900 |
| ggctactctg | tggtcaccgt | tgatgaggcc | atcgaggacg | ccgacatcgt | gatcaccgcg | 960 |
| accggcaaca | aggacatcat | tccttcgag | cagatgctca | agatgaagga | tcacgctctg | 1020 |
| ctgggcaaca | tcggtcactt | tgataatgag | atcgatatgc | attccctgtt | gcaccgcgac | 1080 |
| gacgtcaccc | gcaccacgat | caagccacag | gtcgacgagt | tcaccttctc | caccggtcgc | 1140 |
| tccatcatcg | tcctgtccga | aggtcgcctg | ttgaaccttg | caacgccac | cggacaccca | 1200 |
| tcatttgtca | tgtccaactc | tttcgccgat | cagaccattg | cgcagatcga | actgttccaa | 1260 |
| aacgaaggac | agtacgagaa | cgaggtctac | cgtctgccta | aggttctcga | cgaaaaggtg | 1320 |
| gcacgcatcc | acgttgaggc | tctcggcggt | cagctcaccg | aactgaccaa | ggagcaggct | 1380 |
| gagtacatcg | gcgttgacgt | tgcaggccca | ttcaagccgg | agcactaccg | ctactaa | 1437 |

<210> SEQ ID NO 149
<211> LENGTH: 478
<212> TYPE: PRT
<213> ORGANISM: Artificial Sequence
<220> FEATURE:
<223> OTHER INFORMATION: Synthetic construct

<400> SEQUENCE: 149

```
Met Ala Gln Val Met Asp Phe Lys Val Ala Asp Leu Ser Leu Ala Glu
1               5                   10                  15

Ala Gly Arg His Gln Ile Arg Leu Ala Glu Tyr Glu Met Pro Gly Leu
            20                  25                  30
```

```
Met Gln Leu Arg Lys Glu Phe Ala Asp Glu Gln Pro Leu Lys Gly Ala
         35                  40                  45
Arg Ile Ala Gly Ser Ile His Met Thr Val Gln Thr Ala Val Leu Ile
 50                  55                  60
Glu Thr Leu Thr Ala Leu Gly Ala Glu Val Arg Trp Ala Ser Cys Asn
 65                  70                  75                  80
Ile Phe Ser Thr Gln Asp Glu Ala Ala Ala Ile Val Gly Ser
                 85                  90                  95
Gly Thr Val Glu Glu Pro Ala Gly Val Pro Val Phe Ala Trp Lys Gly
             100                 105                 110
Glu Ser Leu Glu Glu Tyr Trp Trp Cys Ile Asn Gln Ile Phe Ser Trp
             115                 120                 125
Gly Asp Glu Leu Pro Asn Met Ile Leu Asp Asp Gly Asp Ala Thr
 130                 135                 140
Met Ala Val Ile Arg Gly Arg Glu Tyr Glu Gln Ala Gly Leu Val Pro
 145                 150                 155                 160
Pro Ala Glu Ala Asn Asp Ser Asp Glu Tyr Ile Ala Phe Leu Gly Met
                 165                 170                 175
Leu Arg Glu Val Leu Ala Ala Glu Pro Gly Lys Trp Gly Lys Ile Ala
             180                 185                 190
Glu Ala Val Lys Gly Val Thr Glu Glu Thr Thr Thr Gly Val His Arg
             195                 200                 205
Leu Tyr His Phe Ala Glu Glu Gly Val Leu Pro Phe Pro Ala Met Asn
         210                 215                 220
Val Asn Asp Ala Val Thr Lys Ser Lys Phe Asp Asn Lys Tyr Gly Thr
 225                 230                 235                 240
Arg His Ser Leu Ile Asp Gly Ile Asn Arg Ala Thr Asp Met Leu Met
                 245                 250                 255
Gly Gly Lys Asn Val Leu Val Cys Gly Tyr Gly Asp Val Gly Lys Gly
                 260                 265                 270
Cys Ala Glu Ala Phe Asp Gly Gln Gly Ala Arg Val Lys Val Thr Glu
             275                 280                 285
Ala Asp Pro Ile Asn Ala Leu Gln Ala Leu Met Asp Gly Tyr Ser Val
 290                 295                 300
Val Thr Val Asp Glu Ala Ile Glu Asp Ala Asp Ile Val Ile Thr Ala
 305                 310                 315                 320
Thr Gly Asn Lys Asp Ile Ile Ser Phe Glu Gln Met Leu Lys Met Lys
                 325                 330                 335
Asp His Ala Leu Leu Gly Asn Ile Gly His Phe Asp Asn Glu Ile Asp
             340                 345                 350
Met His Ser Leu Leu His Arg Asp Asp Val Thr Arg Thr Thr Ile Lys
             355                 360                 365
Pro Gln Val Asp Glu Phe Thr Phe Ser Thr Gly Arg Ser Ile Ile Val
             370                 375                 380
Leu Ser Glu Gly Arg Leu Leu Asn Leu Gly Asn Ala Thr Gly His Pro
 385                 390                 395                 400
Ser Phe Val Met Ser Asn Ser Phe Ala Asp Gln Thr Ile Ala Gln Ile
                 405                 410                 415
Glu Leu Phe Gln Asn Glu Gly Gln Tyr Glu Asn Glu Val Tyr Arg Leu
             420                 425                 430
Pro Lys Val Leu Asp Glu Lys Val Ala Arg Ile His Val Glu Ala Leu
             435                 440                 445
```

Gly Gly Gln Leu Thr Glu Leu Thr Lys Glu Gln Ala Glu Tyr Ile Gly
        450                 455                 460

Val Asp Val Ala Gly Pro Phe Lys Pro Glu His Tyr Arg Tyr
465                 470                 475

<210> SEQ ID NO 150
<211> LENGTH: 1053
<212> TYPE: DNA
<213> ORGANISM: Artificial Sequence
<220> FEATURE:
<223> OTHER INFORMATION: Synthetic construct

<400> SEQUENCE: 150
atgaattatc agaacgacga tttacgcatc aaagaaatca agagttact tcctcctgtc      60
gcattgctgg aaaaattccc cgctactgaa aatgccgcga atacggttgc ccatgcccga     120
aaagcgatcc ataagatcct gaaaggtaat gatgatcgcc tgttggttgt gattggccca     180
tgctcaattc atgatcctgt cgcggcaaaa gagtatgcca ctcgcttgct ggcgctgcgt     240
gaagagctga agatgagct ggaaatcgta atgcgcgtct attttgaaaa gccgcgtacc     300
acggtgggct ggaaagggct gattaacgat ccgcatatgg ataatagctt ccagatcaac     360
gacggtctgc gtatagcccg taaattgctg cttgatatta cgacagcgg tctgccagcg     420
gcaggtgagt ttctcgatat gatcacccca caatatctcg ctgacctgat gagctggggc     480
gcaattggcg cacgtaccac cgaatcgcag gtgcaccgcg aactggcatc agggcttttt     540
tgtccggtcg gcttcaaaaa tggcaccgac ggtacgatta agtggctat cgatgccatt     600
aatgccgccg gtgcgccgca ctgcttcctg tccgtaacga aatgggggca ttcggcgatt     660
gtgaatacca gcggtaacgg cgattgccat atcattctgc gcggcggtaa agagcctaac     720
tacagcgcga agcacgttgc tgaagtgaaa gaagggctga caaagcagg cctgccagca     780
caggtgatga tcgatttcag ccatgctaac tcgtccaaac aattcaaaaa gcagatggat     840
gtttgtgctg acgtttgcca gcagattgcc ggtggcgaaa aggccattat ggcgtgatg     900
gtggaaagcc atctggtgga aggcaatcag agcctcgaga gcggggagcc gctggcctac     960
ggtaagagca tcaccgatgc ctgcatcggc tgggaagata ccgatgctct gttacgtcaa    1020
ctggcgaatg cagtaaaagc gcgtcgcggg taa                                 1053

<210> SEQ ID NO 151
<211> LENGTH: 350
<212> TYPE: PRT
<213> ORGANISM: Artificial Sequence
<220> FEATURE:
<223> OTHER INFORMATION: Synthetic construct

<400> SEQUENCE: 151

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
    50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

```
Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
    130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Phe Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
    210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
    290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350

<210> SEQ ID NO 152
<211> LENGTH: 1125
<212> TYPE: DNA
<213> ORGANISM: Artificial Sequence
<220> FEATURE:
<223> OTHER INFORMATION: Synthetic construct

<400> SEQUENCE: 152
atgagaatag agcgtgatct ccacatggcc acaggggacg agaaactag ctacacgaaa      60 aattctagga ttcaagagaa aactatgttt cagatcaagc ctgtccttga ggaggccaca     120
agagcagtat acacagctct ccaccctcaa accatggttg ttgctgactt aggctgctca     180
tctgggccta acacactacg cttcgtatcc gaggtgattg gcatcatagc tcgccattgc     240
aaagaatatg gccgacaaca tgaccacaca cagcttcagt tcttcctgaa tgacctgccc     300
ggaaacgact tcaacaatct cttccagctg atccagcagt tcaataagtc gacggcaata     360
aaccacaaga gtgaggcagc tgaggcacta cctcctccgt gctatatctc tgggttgcct     420
ggctcctact acactaggat cttccctagc gaaagtgttc accttttcca ttctttgttc     480
tgccttcagt ggcgctctga ggcaccagag gcaacaaaa aaacatgcct agatatctac     540
atcacaaaga ctatgtcacc gtcgatggtg aagttgtttc aacaacagtt tcagaaggat     600 ttctcccctct tcctcaggct acgctacgag gaactcgtgt ccggtggcca aatggttcta     660
```

```
acatttattg gaaggaagca tgagaatgtg ttcactggag agtctaacca tctttacgga      720
ttgcttgcgc agtcactgaa atccctagtt gatgagggtc ttgtggagaa ggaaaaactt      780
gaatcattct atttaccaat gtattcacca tcggttggtg aagtggaggc catactaaag      840
caagttgggt tgttcaacat gaatcatgta aaagtattcc agacaaattg ggatccctac      900
gatgacttgg aaagtgatgt tgtgcataac agtattagga gcggtgaaaa tgttgctaag      960
tgcctacgag cagttatgca gccgctagtc gcaagccaat ttggagaacc cattctcgat     1020
aagttattca agagtacgc tcgccgtgtt gccaaacacc ttgagaatga aaaaccaag      1080 catgctatta ttgtcctatc catcgagaaa gcaattcacc tgtga                    1125
```

<210> SEQ ID NO 153
<211> LENGTH: 374
<212> TYPE: PRT
<213> ORGANISM: Artificial Sequence
<220> FEATURE:
<223> OTHER INFORMATION: Synthetic construct

<400> SEQUENCE: 153

```
Met Arg Ile Glu Arg Asp Leu His Met Ala Thr Gly Asp Gly Glu Thr
1               5                   10                  15

Ser Tyr Thr Lys Asn Ser Arg Ile Gln Glu Lys Thr Met Phe Gln Ile
            20                  25                  30

Lys Pro Val Leu Glu Glu Ala Thr Arg Ala Val Tyr Thr Ala Leu His
        35                  40                  45

Pro Gln Thr Met Val Val Ala Asp Leu Gly Cys Ser Ser Gly Pro Asn
    50                  55                  60

Thr Leu Arg Phe Val Ser Glu Val Ile Gly Ile Ala Arg His Cys
65                  70                  75                  80

Lys Glu Tyr Gly Arg Gln His Asp His Thr Gln Leu Gln Phe Leu
                85                  90                  95

Asn Asp Leu Pro Gly Asn Asp Phe Asn Asn Leu Phe Gln Leu Ile Gln
            100                 105                 110

Gln Phe Asn Lys Ser Thr Ala Ile Asn His Lys Ser Glu Ala Ala Glu
        115                 120                 125

Ala Leu Pro Pro Pro Cys Tyr Ile Ser Gly Leu Pro Gly Ser Tyr Tyr
    130                 135                 140

Thr Arg Ile Phe Pro Ser Glu Ser Val His Leu Phe His Ser Leu Phe
145                 150                 155                 160

Cys Leu Gln Trp Arg Ser Glu Ala Pro Glu Gly Asn Lys Lys Thr Cys
                165                 170                 175

Leu Asp Ile Tyr Ile Thr Lys Thr Met Ser Pro Ser Met Val Lys Leu
            180                 185                 190

Phe Gln Gln Gln Phe Gln Lys Asp Phe Ser Leu Phe Leu Arg Leu Arg
        195                 200                 205

Tyr Glu Glu Leu Val Ser Gly Gly Gln Met Val Leu Thr Phe Ile Gly
    210                 215                 220

Arg Lys His Glu Asn Val Phe Thr Gly Glu Ser Asn His Leu Tyr Gly
225                 230                 235                 240

Leu Leu Ala Gln Ser Leu Lys Ser Leu Val Asp Glu Gly Leu Val Glu
                245                 250                 255

Lys Glu Lys Leu Glu Ser Phe Tyr Leu Pro Met Tyr Ser Pro Ser Val
            260                 265                 270
```

Gly Glu Val Glu Ala Ile Leu Lys Gln Val Gly Leu Phe Asn Met Asn
            275                 280                 285

His Val Lys Val Phe Gln Thr Asn Trp Asp Pro Tyr Asp Asp Leu Glu
        290                 295                 300

Ser Asp Val Val His Asn Ser Ile Arg Ser Gly Glu Asn Val Ala Lys
305                 310                 315                 320

Cys Leu Arg Ala Val Met Gln Pro Leu Val Ala Ser Gln Phe Gly Glu
            325                 330                 335

Pro Ile Leu Asp Lys Leu Phe Lys Glu Tyr Ala Arg Arg Val Ala Lys
            340                 345                 350

His Leu Glu Asn Glu Lys Thr Lys His Ala Ile Ile Val Leu Ser Ile
        355                 360                 365

Glu Lys Ala Ile His Leu
    370

<210> SEQ ID NO 154
<211> LENGTH: 1140
<212> TYPE: DNA
<213> ORGANISM: Artificial Sequence
<220> FEATURE:
<223> OTHER INFORMATION: Synthetic construct

<400> SEQUENCE: 154
atgccgatga gaatcgagcg tgatctccac atggccacag ggaacggaga aactagctac     60
acgaaaaact ctaggattca ggagaaagtt atgtttcaga tcaagccagt ccttgaggag    120
gccactagag cagcatactc agctctcctc cctcaaacca tggtcgtggc cgacttaggc    180
tgctcatcgg ggcctaacac actgcgcttc gtctccgagg tgattggcat catagctcgc    240
cattgcaaag aacacgaccg acgacatgac tacccacaac ttcagttctt cctgaatgac    300
ctgccgggaa acgacttcaa caatctcttc ctactcatcc agcagttcaa taagtcgatg    360
gcaagaaacc acaagggtga ggcagccgag gcactgcctc cgtgctatat ctctggtttg    420
ccaggctcct tctacactag gatcttccct agcgaaagcg ttcaccttt ccactctttg     480 ttctccgttc actggcactc tcaggcatca gaacaactaa aggacaccaa aaataaatgc    540
ttagatatct acatcacaaa gaatatgcca ccgtcgatgg tgaagttgtt caacagcag    600 tttgagaagg acttctccct cttcctcaag ctacgctatg aggaactcgt gtctggtggc    660
caaatggttc taacatttat tggaagaaag catgaggatg tgttcactgg agagtccaac    720
catctttacg gattgcttgc gcagtcactg aaatccctag ttgatgaggg tcttgtggag    780
aaagaaaaac ttgagtcatt ctatcttccg atctactcac cgtcggttgg tgaagtggag    840
gcgatagtga agcaagttgg gttgttcaac atgaatcatg ttaaagtatt tgagataaat    900
tgggatccct acggtgactc agaaggtgat gatgtgcatg acagtattag gagcggtgaa    960
aatgttgcta agtgcctacg agcagttatg gagccgttgg ttgcaagcca atttggagaa   1020
cacatactcg acaagttatt caaagagtac gctcgtcgtg ttgccaaaca ccttgagaat   1080
gagaaaacca agcatgctat tcttgtccta tccatcgaga aagcaataat tcatgtgtga   1140

<210> SEQ ID NO 155
<211> LENGTH: 379
<212> TYPE: PRT
<213> ORGANISM: Artificial Sequence
<220> FEATURE:
<223> OTHER INFORMATION: Synthetic construct

<400> SEQUENCE: 155

Met Pro Met Arg Ile Glu Arg Asp Leu His Met Ala Thr Gly Asn Gly
1               5                   10                  15

Glu Thr Ser Tyr Thr Lys Asn Ser Arg Ile Gln Glu Lys Val Met Phe
            20                  25                  30

Gln Ile Lys Pro Val Leu Glu Ala Thr Arg Ala Ala Tyr Ser Ala
        35                  40                  45

Leu Leu Pro Gln Thr Met Val Val Ala Asp Leu Gly Cys Ser Ser Gly
    50                  55                  60

Pro Asn Thr Leu Arg Phe Val Ser Glu Val Ile Gly Ile Ile Ala Arg
65                  70                  75                  80

His Cys Lys Glu His Asp Arg Arg His Asp Tyr Pro Gln Leu Gln Phe
                85                  90                  95

Phe Leu Asn Asp Leu Pro Gly Asn Asp Phe Asn Leu Phe Leu Leu
                100                 105                 110

Ile Gln Gln Phe Asn Lys Ser Met Ala Arg Asn His Lys Gly Glu Ala
        115                 120                 125

Ala Glu Ala Leu Pro Pro Cys Tyr Ile Ser Gly Leu Pro Gly Ser Phe
    130                 135                 140

Tyr Thr Arg Ile Phe Pro Ser Glu Ser Val His Leu Phe His Ser Leu
145                 150                 155                 160

Phe Ser Val His Trp His Ser Gln Ala Ser Glu Gln Leu Lys Asp Thr
                165                 170                 175

Lys Asn Lys Cys Leu Asp Ile Tyr Ile Thr Lys Asn Met Pro Pro Ser
                180                 185                 190

Met Val Lys Leu Phe Gln Gln Phe Glu Lys Asp Phe Ser Leu Phe
        195                 200                 205

Leu Lys Leu Arg Tyr Glu Glu Leu Val Ser Gly Gly Gln Met Val Leu
210                 215                 220

Thr Phe Ile Gly Arg Lys His Glu Asp Val Phe Thr Gly Glu Ser Asn
225                 230                 235                 240

His Leu Tyr Gly Leu Leu Ala Gln Ser Leu Lys Ser Leu Val Asp Glu
            245                 250                 255

Gly Leu Val Glu Lys Glu Lys Leu Glu Ser Phe Tyr Leu Pro Ile Tyr
            260                 265                 270

Ser Pro Ser Val Gly Glu Val Glu Ala Ile Val Lys Gln Val Gly Leu
            275                 280                 285

Phe Asn Met Asn His Val Lys Val Phe Glu Ile Asn Trp Asp Pro Tyr
290                 295                 300

Gly Asp Ser Glu Gly Asp Asp Val His Asp Ser Ile Arg Ser Gly Glu
305                 310                 315                 320

Asn Val Ala Lys Cys Leu Arg Ala Val Met Glu Pro Leu Val Ala Ser
                325                 330                 335

Gln Phe Gly Glu His Ile Leu Asp Lys Leu Phe Lys Glu Tyr Ala Arg
            340                 345                 350

Arg Val Ala Lys His Leu Glu Asn Glu Lys Thr Lys His Ala Ile Leu
            355                 360                 365

Val Leu Ser Ile Glu Lys Ala Ile Ile His Val
        370                 375

<210> SEQ ID NO 156
<211> LENGTH: 35
<212> TYPE: DNA
<213> ORGANISM: Artificial Sequence

```
<220> FEATURE:
<223> OTHER INFORMATION: Synthetic construct

<400> SEQUENCE: 156
ttgacggcta gctcagtcct aggtacagtg ctagc                                35

<210> SEQ ID NO 157
<211> LENGTH: 35
<212> TYPE: DNA
<213> ORGANISM: Artificial Sequence
<220> FEATURE:
<223> OTHER INFORMATION: Synthetic construct

<400> SEQUENCE: 157
tttacagcta gctcagtcct aggtattatg ctagc                                35

<210> SEQ ID NO 158
<211> LENGTH: 35
<212> TYPE: DNA
<213> ORGANISM: Artificial Sequence
<220> FEATURE:
<223> OTHER INFORMATION: Synthetic construct

<400> SEQUENCE: 158
ttgacggcta gctcagtcct aggtattgtg ctagc                                35

<210> SEQ ID NO 159
<211> LENGTH: 35
<212> TYPE: DNA
<213> ORGANISM: Artificial Sequence
<220> FEATURE:
<223> OTHER INFORMATION: Synthetic construct

<400> SEQUENCE: 159
tttacggcta gctcagtcct aggtactatg ctagc                                35

<210> SEQ ID NO 160
<211> LENGTH: 35
<212> TYPE: DNA
<213> ORGANISM: Artificial Sequence
<220> FEATURE:
<223> OTHER INFORMATION: Synthetic construct

<400> SEQUENCE: 160
tttatggcta gctcagtcct aggtacaatg ctagc                                35

<210> SEQ ID NO 161
<211> LENGTH: 35
<212> TYPE: DNA
<213> ORGANISM: Artificial Sequence
<220> FEATURE:
<223> OTHER INFORMATION: Synthetic construct

<400> SEQUENCE: 161
ttgacagcta gctcagtcct agggattgtg ctagc                                35
```